US012636347B2

(12) United States Patent
Wei

(10) Patent No.: US 12,636,347 B2
(45) Date of Patent: *May 26, 2026

(54) RECOMBINANT INTERFERON WITH CHANGED SPATIAL CONFIGURATION

(71) Applicant: SUPERLAB FAR EAST LIMITED, Tortola (VG)

(72) Inventor: Guangwen Wei, Chengdu (CN)

( * ) Notice: Subject to any disclaimer, the term of this patent is extended or adjusted under 35 U.S.C. 154(b) by 889 days.

This patent is subject to a terminal disclaimer.

(21) Appl. No.: 17/548,598

(22) Filed: Dec. 13, 2021

(65) Prior Publication Data

US 2022/0339255 A1  Oct. 27, 2022

Related U.S. Application Data

(63) Continuation of application No. 16/038,704, filed on Jul. 18, 2018, now abandoned, which is a continuation of application No. 14/759,410, filed as application No. PCT/CN2014/000019 on Jan. 7, 2014, now abandoned.

(60) Provisional application No. 61/779,711, filed on Mar. 13, 2013, provisional application No. 61/749,570, filed on Jan. 7, 2013.

(51) Int. Cl.
| | |
|---|---|
| A61K 38/21 | (2006.01) |
| A61K 9/00 | (2006.01) |
| A61K 31/5377 | (2006.01) |
| A61K 31/7068 | (2006.01) |
| A61K 33/243 | (2019.01) |
| A61K 38/39 | (2006.01) |
| A61K 45/06 | (2006.01) |
| A61M 11/00 | (2006.01) |

(52) U.S. Cl.
CPC ............ *A61K 38/21* (2013.01); *A61K 9/0014* (2013.01); *A61K 9/0019* (2013.01); *A61K 9/0073* (2013.01); *A61K 31/5377* (2013.01); *A61K 31/7068* (2013.01); *A61K 33/243* (2019.01); *A61K 38/39* (2013.01); *A61K 45/06* (2013.01); *A61M 11/00* (2013.01)

(58) Field of Classification Search
None
See application file for complete search history.

(56) References Cited

U.S. PATENT DOCUMENTS

| | | | | |
|---|---|---|---|---|
| 10,874,716 B2 * | 12/2020 | Wei | .................... | A61K 33/243 |
| 12,109,250 B2 * | 10/2024 | Wei | ........................ | A61P 19/08 |

OTHER PUBLICATIONS

Castro et al. "Interferon-Based Biopharmaceuticals: Overview on the Production, Purification, and Formulation" Vaccines 9:328. (Year: 2021).*

* cited by examiner

*Primary Examiner* — Sudhakar Katakam
*Assistant Examiner* — Zachary J Miknis
(74) *Attorney, Agent, or Firm* — LAW OFFICES OF ALBERT WAI-KIT CHAN, PLLC

(57) ABSTRACT

The present invention provides methods for treating tumors in subjects by using a recombinant interferon (rSIFN-co), and optionally, methods for treating solid tumors, such as lung cancer, among others, with or without prior surgery, and as a first line or second line monotherapy or in combination with one or more other anti-tumor therapies. The present invention further provides non-surgical methods for eliminating tumors or reducing tumor sizes in subjects, and/or preventing postoperative tumor recurrence and/or metastases in subjects by using the recombinant interferon (rSIFN-co) which comprises a unique spatial configuration, alone or in conjunction with radiotherapy, chemotherapy, and/or one or more anti-tumor drugs such as biological agents, targeted drugs, small molecules, Traditional Chinese Medicine (TCM) and the like.

20 Claims, 29 Drawing Sheets
Specification includes a Sequence Listing.

SEQ ID NO:4
SEQ ID NO:5

Figure 18

| | Date | Amount of drawn pleural effusion (ml) | Interval (day) |
|---|---|---|---|
| Before the treatment | 2006-2-22 | 800 | |
| | 2006-2-24 | 800 | 2 |
| | 2006-3-2 | 400 | 6 |
| | 2006-3-6 | 400 | 2 |
| | 2006-3-10 | 500 | 4 |
| Start administration | 2006-3-9 | | |
| After the treatment | 2006-3-28 | 520 | 22 |
| | 2006-4-11 | 430 | 14 |
| | 2006-4-29 | 400 | 18 |
| | 2006-6-5 | 350 | 36 |

SEQUENCE LISTING

<160> NUMBER OF SEQ ID NOS: 5

<210> SEQ ID NO 1
<211> LENGTH: 167
<212> TYPE: PRT
<213> ORGANISM: Artificial Sequence
<220> FEATURE:
<223> OTHER INFORMATION: Amino acid sequence of recombinant interferon

<400> SEQUENCE: 1

Met Cys Asp Leu Pro Gln Thr His Ser Leu Gly Asn Arg Arg Ala Leu
1               5                   10                  15

Ile Leu Leu Ala Gln Met Arg Arg Ile Ser Pro Phe Ser Cys Leu Lys
            20                  25                  30

Asp Arg His Asp Phe Gly Phe Pro Gln Glu Glu Phe Asp Gly Asn Gln
        35                  40                  45

Phe Gln Lys Ala Gln Ala Ile Ser Val Leu His Glu Met Ile Gln Gln
    50                  55                  60

Thr Phe Asn Leu Phe Ser Thr Lys Asp Ser Ser Ala Ala Trp Asp Glu
65                  70                  75                  80

Ser Leu Leu Glu Lys Phe Tyr Thr Glu Leu Tyr Gln Gln Leu Asn Asp
                85                  90                  95

Leu Glu Ala Cys Val Ile Gln Glu Val Gly Val Glu Glu Thr Pro Leu
            100                 105                 110

Met Asn Val Asp Ser Ile Leu Ala Val Lys Lys Tyr Phe Gln Arg Ile
        115                 120                 125

Thr Leu Tyr Leu Thr Glu Lys Lys Tyr Ser Pro Cys Ala Trp Glu Val
    130                 135                 140

Val Arg Ala Glu Ile Met Arg Ser Phe Ser Leu Ser Thr Asn Leu Gln
145                 150                 155                 160

Glu Arg Leu Arg Arg Lys Glu
                165

<210> SEQ ID NO 2
<211> LENGTH: 504
<212> TYPE: DNA
<213> ORGANISM: Artificial Sequence
<220> FEATURE:
<223> OTHER INFORMATION: Nucleotide sequence encoding recombinant
     interferon

<400> SEQUENCE: 2
atgtgcgacc tgccgcagac ccactccctg ggtaaccgtc gtgctctgat cctgctggct        60
cagatgcgtc gtatctcccc gttctcctgc ctgaaagacc gtcacgactt cggtttcccg       120
caggaagaat tcgacggtaa ccagttccag aaagctcagg ctatctccgt tctgcacgaa       180
atgatccagc agaccttcaa cctgttctcc accaaagact cctccgctgc ttgggacgaa       240
tccctgctgg aaaaattcta caccgaactg taccagcagc tgaacgacct ggaagcttgc       300
gttatccagg aagttggtgt tgaagaaacc ccgctgatga acgttgactc catcctggct       360
gttaaaaaat acttccagcg tatcaccctg tacctgaccg aaaaaaaata ctccccgtgc       420
gcttgggaag ttgttcgtgc tgaaatcatg cgttccttct ccctgtccac caacctgcag       480
gaacgtctgc gtcgtaaaga ataa                                              504

<210> SEQ ID NO 3
<211> LENGTH: 504
<212> TYPE: DNA
<213> ORGANISM: Artificial Sequence
<220> FEATURE:
<223> OTHER INFORMATION: Nucleotide sequence encoding recombinant
      interferon

<400> SEQUENCE: 3
tacacgctgg acggcgtctg ggtgagggac ccattggcag cacgagacta ggacgaccga     60
gtctacgcag catagagggg caagaggacg gactttctgg cagtgctgaa gccaaagggc    120
gtccttctta agctgccatt ggtcaaggtc tttcgagtcc gatagaggca agacgtgctt    180
tactaggtcg tctggaagtt ggacaagagg tggtttctga ggaggcgacg aaccctgctt    240
agggacgacc tttttaagat gtggcttgac atggtcgtcg acttgctgga ccttcgaacg    300
caataggtcc ttcaaccaca acttctttgg ggcgactact tgcaactgag gtaggaccga    360
caatttttta tgaaggtcgc atagtgggac atggactggc ttttttttat gaggggcacg    420
cgaacccttc aacaagcacg actttagtac gcaaggaaga gggacaggtg gttggacgtc    480
cttgcagacg cagcatttct tatt                                          504

<210> SEQ ID NO 4
<211> LENGTH: 166
<212> TYPE: PRT
<213> ORGANISM: Artificial Sequence
<220> FEATURE:
<223> OTHER INFORMATION: Amino acid sequence of recombinant interferon

<400> SEQUENCE: 4

Cys Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Cys Leu Lys Asp
                20                  25                  30

Arg His Asp Phe Gly Phe Pro Gln Glu Glu Phe Asp Gly Asn Gln Phe
            35                  40                  45

Gln Lys Ala Gln Ala Ile Ser Val Leu His Glu Met Ile Gln Gln Thr
        50                  55                  60

Phe Asn Leu Phe Ser Thr Lys Asp Ser Ser Ala Ala Trp Asp Glu Ser
65                  70                  75                  80

Leu Leu Glu Lys Phe Tyr Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Val Asp Ser Ile Leu Ala Val Lys Lys Tyr Phe Gln Arg Ile Thr
        115                 120                 125

Leu Tyr Leu Thr Glu Lys Lys Tyr Ser Pro Cys Ala Trp Glu Val Val
        130                 135                 140

Arg Ala Glu Ile Met Arg Ser Phe Ser Leu Ser Thr Asn Leu Gln Glu
145                 150                 155                 160

Arg Leu Arg Arg Lys Glu
                165

<210> SEQ ID NO 5
<211> LENGTH: 165
<212> TYPE: PRT
<213> ORGANISM: Artificial Sequence
<220> FEATURE:
<223> OTHER INFORMATION: Amino acid sequence of recombinant interferon
      alpha-2b

<400> SEQUENCE: 5

Cys Asp Leu Pro Gln Thr His Ser Leu Gly Ser Arg Arg Thr Leu Met

-continued

```
1               5                    10                   15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
            85                  90                  95

Ala Cys Val Ile Gln Gly Val Gly Val Thr Glu Thr Pro Leu Met Asn
            100                 105                 110

Arg Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
            165
```

RECOMBINANT INTERFERON WITH CHANGED SPATIAL CONFIGURATION

CROSS-REFERENCE TO RELATED APPLICATIONS

This application is a continuation application of U.S. Ser. No. 16/038,704, filed Jul. 18, 2018, which is a filed continuation application of U.S. Ser. No. 14/759,410, filed Jul. 7, 2015, which is the National Stage of International Application No. PCT/CN2014/000019, filed Jan. 7, 2014, which claims benefit of U.S. Ser. No. 61/749,570, filed Jan. 7, 2013, and U.S. Ser. No. 61/779,711, filed Mar. 13, 2013. The entire contents and disclosures of the preceding applications are incorporated by reference into this application.

FIELD OF THE INVENTION

The present invention relates to methods for treating tumors in subjects by using recombinant interferon, and to methods for treating solid tumors, including lung cancers in subjects. The present invention further relates to non-surgical methods for eliminating tumors or reducing the sizes of tumors in subjects, or preventing postoperative tumor recurrence and/or metastases and/or prolonging tumor free survival in subjects by using a recombinant interferon (rSIFN-co) with changed spatial configuration, either alone, or in conjunction with radiotherapy, chemotherapy, and/or anti-tumor drugs such as biological agents, targeted drugs and the like.

BACKGROUND OF THE INVENTION

Cancer is one of the major causes of death in people around the world. The total number of cases worldwide continues to increase. According to the statistics of the world health organization (WHO), it is estimated that the global cancer deaths will be increased by 45% (from 7,900,000 to 11,500,000) from 2007 to 2030, and the new cases of cancer will zoom from 11,300,000 in 2007 to 15,500,000 in 2030 in the same period, wherein the incidence rate and the death rate of the lung cancer ranks first in the global malignant tumors. According to the statistical data, the amount of the worldwide new cases of lung cancer every year is more than 3,000,000 and increases continuously (see Gray, J. et al. Chest, 2007, 132, 56S-68S). The number of deaths caused by lung cancer is more than 1,300,000 around the world every year, which is more than the sum of the number of cancer-related deaths caused by other three common cancers (breast cancer, prostate cancer and colorectal cancer).

The classic methods for treating cancer include surgical therapy, radiotherapy and chemotherapy. However, the surgical therapy is not suitable for all types of solid tumors. The surgical therapy may not eliminate cancer cells thoroughly due to metastatic lesions and the like, so as not to achieve the purpose of cure. Radiotherapy is only suitable for the tumors situated at positions that are sensitive to rays, take muscles as tumor beds and have better blood circulation, and the radiotherapy may accidentally injure normal cells to cause various side effects, so as to affect the quality of life of the patients. The effect of the chemotherapy as the systemic treatment means is determined by the types and the states of cancers. Chemotherapy can suppress the growth and the spread of the cancers more especially, and same with the radiotherapy, the chemotherapy can also accidentally injure normal cells to affect the quality of life of the patients.

Surgical therapy can be performed to eliminate tumors, improve the quality of life and provide time for follow-up treatment for some early or medium-term solid tumor patients; but for some advanced patients with metastasized solid tumors, the treatment methods in the prior art are only chemotherapy, radiotherapy or combining the chemotherapy, radiotherapy and other treatment methods when the quality of life is obviously affected and life is even threatened, these treatment methods are not ideal in effects and cannot achieve the purpose of eliminating the tumors and completely alleviating the condition of the patients.

According to the mass data, the existing methods for treating cancer, in particular, chemotherapy, cannot obtain the satisfied treatment effect for advanced lung cancer patients, and the number of complete remission (CR) cases is few and is even zero. For example, in the clinical trial of 78 cases which employed cis-platinum for combining Navelbine, Gemzar and Taxotere, respectively, to treat advanced non-small cell lung cancers, no complete remission appeared in any case (see Song, Y. et al, Journal of Modern Oncology, 2005, 13(4), 494-496); however, in the clinical observation of 1155 cases which employed four chemotherapy protocols (Cisplatin+Paclitaxel, Cisplatin+Gemcitabine, Cisplatin+Docetaxel, and Carboplatin+Paclitaxel) for treating the advanced non-small cell lung cancers, complete response was observed, but the complete response (CR) rate was less than 1% (see Schiller, J. H. et al. N Engl J Med, 2002, 346(2), 92-98); and in a random, double-blind, control and multicenter III-stage clinical research which employed recombinant human endostatin for combining NP to treat the advanced non-small cell lung cancers, the 486 evaluable cases in the test group and the control group yielded no cases of complete remission (see Wang, J. W. et al, Chinese Journal of Lung Cancer, 2005, 8(4), 283-290).

In the recent 20 years, due to the in depth research on the cell biology, molecular biology, tumor immunology and the like and the development of the bio-engineering technology, the biotherapy has become the important treatment means for cancer treatment after surgical therapy, radiotherapy and chemotherapy has been performed.

Since Isaacs and Lindenmann discovered interferon (IFN), interferon has been widely researched. Interferon (IFN) is a kind of soluble protein produced by a variety of cells which has many important biological functions, including anti-viral, anti-tumor, and immunoregulatory functions. Interferons can be divided into type I, type II, and type III interferons according to the differences in the types of producing cells, receptors and biological activities, etc. Type I IFNs, which are mostly induced by viruses and synthetic double-stranded RNA, are also known as anti-viral interferons. There are three forms of type I interferons: interferon-alpha or alpha-interferon (IFNα), interferon-beta (INFβ) and interferon omega (IFNω).

In recent years, many companies in the world have engaged in the research of interferon. For example, U.S. Pat. Nos. 4,695,623 and 4,897,471 disclosed new types of human interferon polypeptides which possessed amino acid sequences containing the common or predominant amino acids found in naturally occurring α-interferon polypeptides. One new type of interferon was named IFN-con (consensus interferon α). Compared with leukocyte interferon or other type I interferons, studies have shown that recombinant IFN-con has higher anti-viral, anti-proliferative and natural killer cell activities in vitro. By the end of 1997, the FDA had approved the use of human IFN-con, which was produced by US Amgen and sold under the brand name INFERGEN® (interferon alfacon-1), for clinical treatment of hepatitis C.

It is generally known that the amino acid sequence of a protein can determine the three-dimensional structure of the protein and further determine the functionality thereof. However, in recent years, evidence shows that synonymous mutation(s) of the nucleotide sequence encoding the protein (that is, codon mutation(s) with no change in the amino acid sequence of the encoded protein) can affect the spatial structure and the function of the encoded protein, namely, the nucleotide sequence with synonymous mutation(s) can express and generate proteins with different final spatial structure and different function compared with the wild type protein (see Sarfaty, C. K. et al. Science, 2007, 315:525-528).

A recombinant interferon (rSIFN-co) which has enhanced therapeutic effects, smaller side effects and can be used in a larger doses was disclosed in U.S. Pat. Nos. 7,364,724, 7,585,647, 8,114,395, CN 1740197 A, CN 101001644 A, US 2009/0123417, US 2011/0158941 and WO 2011072487A1. This recombinant interferon, rSIFN-co, has the same amino acid sequence as that of INFERGEN®, but the encoding nucleotide sequences of this recombinant interferon, rSIFN-co, and that of INFERGEN® are different (i.e. synonymous mutations exists in the nucleotide sequence encoding the recombinant interferon, rSIFN-co), resulting in changes in spatial configuration of the recombinant interferon, rSIFN-co, and qualitative changes in its biological efficacy.

SUMMARY OF THE INVENTION

One of the objects of the present invention is to provide new methods for treating tumors in subjects by using the recombinant interferon, rSIFN-co encoded by the nucleotide sequence of SEQ ID NO: 2. Another one of the objects of the present invention is to provide new methods for treating lung cancers in subjects by using the recombinant interferon encoded by the nucleotide sequence of SEQ ID NO: 2 (hereafter also be referred to as recombinant super-compound interferon or rSIFN-co).

The present invention is illustrated by the various embodiments described below. However, the present invention is not limited by these illustrative embodiments and should be interpreted to include those embodiments taught by the description herein and as understood by persons skilled in the art. Illustrative examples of the various embodiments of the present invention include:

In one aspect, the present invention provides:

(1) A method for treating a tumor in a subject, comprising administering to the subject a recombinant interferon encoded by SEQ ID NO: 2.

(2) The method of (1), wherein the tumor in the subject comprises a metastasized tumor.

(3) The method of (1) or (2), wherein the subject is an early, medium-term, or advanced cancer patient, optionally, the subject is a medium-term, or advanced cancer patient, further optionally, the subject is an advanced cancer patient.

(4) The method of (1) or (2), wherein the subject is a stage 0, I, II, III, or IV cancer patient, optionally, the subject is a stage III or stage IV cancer patient.

(5) The method of any one of (1)-(4), wherein the tumor is a cancer or a solid tumor that is indicated or appropriate for surgery.

(6) The method of any one of (1)-(4), wherein the tumor is a cancer or a solid tumor that is not indicated nor appropriate for surgery.

(7) The method of any one of (1)-(5), wherein the tumor is a tumor that is capable of being resected.

(8) The method of any one of (1)-(4) and (6), wherein the tumor is a tumor that is not capable of being resected.

(9) The method of (7) or (8), wherein the tumor is resected by a surgical resection.

(10) The method of any one of (1)-(9), wherein the tumor is a solid tumor.

(11) The method of (10), wherein the solid tumor comprises one or more of: lung cancer, liver cancer, hepatocellular carcinoma (HCC), esophageal cancer, cholangiocarcinoma, gallbladder carcinoma, stomach cancer, abdominal cancer, gastrointestinal cancer, gastric cancer, pancreatic cancer, renal cell carcinoma, renal cancer, bone cancer, breast cancer, ovarian cancer, uterine cancer, cervical cancer, endometrial cancer, colorectal cancer, colon cancer, rectal cancer, bladder cancer, superficial bladder cancer, prostate cancer, adrenal tumors, squamous cell carcinoma, neuroma, malignant neuroma, myoepithelial carcinoma, synovial sarcoma, rhabdomyosarcoma, gastrointestinal interstitial cell tumor, skin cancer, basal cell carcinoma, malignant melanoma, thyroid cancer, nasopharyngeal carcinoma, hemangioma, epidermoid carcinoma, head and neck cancer, glioma, or Kaposi's sarcoma.

(12) The method of (11), wherein the solid tumor comprises lung cancer, optionally, the lung cancer comprises small cell lung cancer (SCLC), non small cell lung cancer (NSCLC), or both.

(13) The method of any one of (1)-(4), wherein the tumor is a non-solid tumor.

(14) The method of (13), wherein the non-solid tumor comprises one or more of: leukemia, acute leukemia, chronic leukemia, chronic myelocytic leukemia, acute myelogenous leukemia, chronic myelogenous leukemia, chronic lymphocytic leukemia, acute lymphoblastic leukemia, T-cell leukemia, hairy cell leukemia, polycythemia, myelodysplastic syndrome, multiple myeloma, lymphadenoma, Hodgkin's lymphoma, and Non-Hodgkin's lymphoma.

(15) The method of any one of (1)-(14), wherein the recombinant interferon is administered to the subject by at least one of: systemic administration, local administration, and topical administration.

(16) The method of any one of (1)-(15), wherein the recombinant interferon is administered to the subject by an administration route, the administration route comprises one or more of: oral, rectal, sublingual, intravenous, intra-arterial, intramuscular, subcutaneous, intrabone, intracutaneous, intra-articular, intraperitoneal, intrathecal, intracerebral, vaginal, percutaneous, transdermal, epidermal, transmucosal, transocular, pulmonary, nasal, abdominal, intrapleural, intraventricular, pericardial, inhalation, intratumoral, uterine, infiltration, and intravesical administration.

(17) The method of any one of (1)-(16), wherein an effective amount of recombinant interferon encoded by the nucleotide sequence of SEQ ID NO: 2 is administered to the subject, optionally, the effective amount is a therapeutically effective amount.

(18) The method of any one of (1)-(17), wherein the recombinant interferon is administered to the subject in a single dose in a range of about 2 μg to about 2000 μg, optionally, the recombinant interferon is administered to the subject in a single dose in a range of about 4 µg to about 1500 µg, further optionally, the recombinant interferon is administered to the subject in a single dose in a range of about 9 µg to about 1000 µg.

(19) The method of any one of (1)-(18), wherein the recombinant interferon is administered in one or more treatment cycles, optionally, the more treatment cycles comprises 2, 3, 4, 5, 6, 7, 8, 9, 10 treatment cycles, further optionally, the number of treatment cycles comprises more than 10 treatment cycles.

(20) The method of (19), wherein the duration of the treatment cycle is at least about 1 day, about 2 days, about 3 days, about 4 days, about 5 days, about 6 days, about 7 days, about 8 days, about 9 days, about 10 days, about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, or about 6 years and the like, or optionally, the recombinant interferon can be administered for a long time, including over the life time of the subject; or the duration of recombinant interferon treatment can also be about 1 day to about 6 years, about 1 week to about 4 years, about 2 weeks to about 3 years, about 1 month to about 1 year, or about 2 months to about 9 months and the like.

(21) The method of (19) or (20), wherein the time interval between any two adjacent treatment cycles of the more treatment cycles is at least about 2 days, about 3 days, about 4 days, about 5 days, about 6 days, about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, or about 6 years and the like; or optionally the time interval can be about 2 days to about 6 years, about 4 days to about 3 years, about 1 week to about 1 year, about 2 months to about 9 months, or about 3 months to about 6 months and the like.

(22) The method of any one of (1)-(21), wherein the recombinant interferon is administered to the subject as monotherapy.

(23) The method of any one of (1)-(21), further comprising at least one other anti-cancer therapy administered to the subject, optionally, the at least one other anti-cancer therapy is administered to the subject before, simultaneously, and/or after administration of the recombinant interferon.

(24) The method of (23), wherein the at least one other anti-cancer therapy comprises at least one of: chemotherapy, radiotherapy, surgical therapy, interventional therapy, biotherapy, gene therapy, ablation therapy, immunotherapy, targeted therapy, and traditional Chinese medicine therapy.

(25) The method of (24), wherein the at least one other anti-cancer therapy comprises at least one of: chemotherapy, radiotherapy, surgical therapy, targeted therapy, and biotherapy.

(26) The method of (25), wherein the at least one other anti-cancer therapy comprises at least one of: chemotherapy and radiotherapy.

(27) The method of any one of (24)-(26), wherein the chemotherapy is administered as first-line chemotherapy, optionally, one or more chemotherapeutic drugs used in the first-line chemotherapy comprise platinum compounds, such as Cisplatin.

(28) The method of any one of (24)-(27), wherein the targeted therapy comprises at least one of: Gefitinib, Erlotinib, and recombinant human endostatin.

(29) The method of any one of (1)-(28), wherein the therapies eliminate the tumor or reduce the size of the tumor as compared to the tumor before treatment.

(30) The method of (29), wherein the reduced size of the tumor converts the tumor to a resectable tumor.

(31) The method of (30), wherein the tumor is indicated for a surgical resection.

(32) The method of any one of (1)-(28), wherein the tumor, such as cancer or solid tumor, that is not earlier indicated nor appropriate for surgery becomes one that is indicated or appropriate for surgery.

(33) The method of (32), further comprising surgery to resect the tumor.

(34) The method of any one of (30)-(31) and (33), further comprising administering to the subject the recombinant interferon after resecting the tumor, to prevent tumor recurrence and/or metastasis, or to prolong or maintain a tumor-free status, optionally, a prophylactically effective amount of the recombinant interferon is administered to the subject to prevent tumor recurrence and/or metastasis, and/or to prolong or maintain a tumor-free status.

(35) A method for treating tumor in a subject, comprising administering to the subject a recombinant interferon encoded by SEQ ID NO: 2, and at least one other anti-cancer therapy, wherein the at least one other anti-cancer therapy is administered to the subject before, simultaneously, and/or after administration of the recombinant interferon, and wherein the tumor is a cancer or solid tumor that is not indicated nor appropriate for surgery, or the tumor is a solid tumor that cannot be resected, and the combination of the recombinant interferon and the at least one other anti-cancer therapy eliminate the tumor or reduce the size of the tumor compared to the tumor before treatment.

(36) The method of embodiment 35, wherein the subject is a medium-term, advanced cancer patient, or stage III or stage IV cancer patient, optionally, the subject is an advanced, or stage III or stage IV cancer patient.

(37) The method of any one of (1)-(29) and (35)-(36), wherein the therapies are the non-surgical therapies.

In another aspect, another embodiment of the present invention provides:

(1) A method for preventing tumor recurrence and/or metastasis or prolonging or maintaining a tumor-free status in a subject with a tumor after at least one anti-cancer therapy, comprising administering to the subject a recombinant interferon encoded by SEQ ID NO: 2.

(2) The method of (1), wherein the tumor in the subject comprises a metastasized tumor.

(3) The method of (1) or (2), wherein the subject is an early, medium-term, or advanced cancer patient.

(4) The method of (1) or (2), wherein the subject is a stage 0, I, II, III, or IV cancer patient.

(5) The method of any one of (1)-(4), wherein the tumor is a cancer or solid tumor that is indicated or appropriate for surgery.

(6) The method of any one of (1)-(4), wherein the tumor is a cancer or solid tumor that is not indicated nor appropriate for surgery.

(7) The method of any one of (1)-(4), wherein the tumor is a tumor that is capable of being resected.

(8) The method of any one of (1)-(4), wherein the tumor is a tumor that is not capable of being resected.

(9) The method of (7) or (8), wherein the tumor is resected by a surgical resection.

(10) The method of any one of (1)-(9), wherein the tumor is a solid tumor.

(11) The method of (10), wherein the solid tumor comprises one or more of: lung cancer, liver cancer, hepatocellular carcinoma (HCC), esophageal cancer, cholangiocarcinoma, gallbladder carcinoma, stomach cancer, abdominal cancer, gastrointestinal cancer, gastric cancer, pancreatic cancer, renal cell carcinoma, renal cancer, bone cancer, breast cancer, ovarian cancer, uterine cancer, cervical cancer, endometrial cancer, colorectal cancer, colon cancer, rectal cancer, bladder cancer, superficial bladder cancer, prostate cancer, adrenal tumors, squamous cell carcinoma, neuroma, malignant neuroma, myoepithelial carcinoma, synovial sarcoma, rhabdomyosarcoma, gastrointestinal interstitial cell tumor, skin cancer, basal cell carcinoma, malignant melanoma, thyroid cancer, nasopharyngeal carcinoma, hemangioma, epidermoid carcinoma, head and neck cancer, glioma, or Kaposi's sarcoma.

(12) The method of (11), wherein the solid tumor comprises lung cancer, optionally, the lung cancer comprises small cell lung cancer (SCLC), non small cell lung cancer (NSCLC), or both.

(13) The method of any one of (1)-(4), wherein the tumor comprises a non-solid tumor.

(14) The method of (13), wherein the non-solid tumor comprises one or more of: leukemia, acute leukemia, chronic leukemia, chronic myelocytic leukemia, acute myelogenous leukemia, chronic myelogenous leukemia, chronic lymphocytic leukemia, acute lymphoblastic leukemia, T-cell leukemia, hairy cell leukemia, polycythemia, myelodysplastic syndrome, multiple myeloma, lymphadenoma, Hodgkin's lymphoma, and Non-Hodgkin's lymphoma.

(15) The method of any one of (1)-(14), wherein the recombinant interferon is administered to the subject by at least one of: systemic administration, local administration, and topical administration.

(16) The method of any one of (1)-(15), wherein the recombinant interferon is administered to the subject by an administration route, the administration route comprises one or more of: oral, rectal, sublingual, intravenous, intra-arterial, intramuscular, subcutaneous, intra-bone, intracutaneous, intra-articular, intraperitoneal, intrathecal, intracerebral, vaginal, percutaneous, transdermal, epidermal, transmucosal, transocular, pulmonary, nasal, abdominal, intrapleural, intraventricular, pericardial, inhalation, intratumoral, uterine, infiltration, and intravesical administration.

(17) The method of any one of (1)-(16), wherein an effective amount of recombinant interferon encoded by the nucleotide sequence of SEQ ID NO: 2 is administered to the subject, optionally, the effective amount is a prophylactically effective amount.

(18) The method of any one of (1)-(17), wherein the recombinant interferon is administered to the subject in a single dose in the range of about 2 μg to about 2000 μg, optionally, the recombinant interferon is administered to the subject in a single dose in the range of about 4 μg to about 1500 μg, more optionally, the recombinant interferon is administered to the subject in a single dose in the range of about 9 μg to about 1000 μg.

(19) The method of any one of (1)-(18), wherein the recombinant interferon is administered in one or more prevention cycles, optionally, the more prevention cycles comprises 2, 3, 4, 5, 6, 7, 8, 9, or 10 prevention cycles, or optionally, more than 10 prevention cycles.

(20) The method of (19), wherein the duration of each prevention cycle is at least about 1 day, about 2 days, about 3 days, about 4 days, about 5 days, about 6 days, about 7 days, about 8 days, about 9 days, about 10 days, about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, or about 6 years and the like, or the recombinant interferon can be administered for a long time, including over the life time of the subject; or the duration can also be about 1 day to about 6 years, about 1 week to about 4 years, about 2 weeks to about 3 years, about 1 month to about 1 year, or about 2 months to about 9 months and the like.

(21) The method of (19) or (20), wherein the time interval between any two adjacent prevention cycles of the more prevention cycles is at least about 2 days, about 3 days, about 4 days, about 5 days, about 6 days, about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, or about 6 years and the like; or the time interval can also be about 2 days to about 6 years, about 4 days to about 3 years, about 1 week to about 1 year, about 2 months to about 9 months, or about 3 months to about 6 months and the like.

(22) The method of any one of (1)-(21), wherein the at least one anti-cancer therapy comprises at least one of: chemotherapy, radiotherapy, surgical therapy, interventional therapy, biotherapy, gene therapy, ablation therapy, immunotherapy, targeted therapy, and traditional Chinese medicine therapy, optionally, the at least one anti-cancer therapy comprises at least one of: chemotherapy, radiotherapy, surgical therapy, and biotherapy.

(23) The method of (22), wherein the at least one anti-cancer therapy comprises surgical therapy.

(24) The method of (23), wherein the recombinant interferon is administered to the operative site of the surgical therapy.

(25) The method of (24), wherein the recombinant interferon is administered to the operative site by topical or local administration.

(26) The method of (24) or (25), wherein the recombinant interferon is administered to the operative site by an administration route, the administration route comprises one or more of: infiltration administration, intrapleural administration, abdominal administration, pericardial administration, uterine administration, intravesical administration, intratumoral administration, pulmonary administration, nasal administration, percutaneous administration, transdermal administration, epidermal administration, and transmucosal administration.

(27) The method of (26), wherein the intrapleural administration, abdominal administration, pericardial administration, uterine administration, or intravesical administration comprises intrapleural perfusion administration, abdominal perfusion administration, pericardial perfusion administration, uterine perfusion administration, or intravesical perfusion administration, respectively.

(28) The method of (26), wherein the intratumoral administration comprises intratumoral injection.

(29) The method of (26), wherein the pulmonary administration or nasal administration comprises pulmonary inhalation administration or nasal inhalation administration, respectively.

(30) The method of (26), wherein the percutaneous administration, transdermal administration, epidermal administration, or transmucosal administration comprises percutaneous spray administration, transdermal spray administration, epidermal spray administration, or transmucosal spray administration, respectively.

(31) The method of any one of (25)-(30), wherein the recombinant interferon is further administered to the subject by systemic administration before, simultaneously, and/or after the topical or local administration of the recombinant interferon.

(32) The method of (31), wherein the systemic administration comprises at least one of: subcutaneous and intramuscular administration, optionally, the protocols in (24)-(32) also apply to the above-specified method for treatment of tumor in a subject.

(33) The method of any one of (1)-(32), wherein the recombinant interferon is administered to the subject as monotherapy.

In another aspect, another embodiment of the present invention provides:

(1) A non-surgical method for eliminating a tumor in a subject or reducing the size of a tumor in a subject, comprising administering to the subject a recombinant interferon encoded by SEQ ID NO: 2.

(2) The method of (1), wherein the tumor is a cancer or a solid tumor that is indicated or appropriate for surgery.

(3) The method of (1), wherein the tumor is a cancer or a solid tumor that is not indicated nor appropriate for surgery.

(4) The method of (1), wherein the tumor is a tumor that is capable of being resected.

(5) The method of (1), wherein the tumor is a tumor that is not capable of being resected.

(6) The method of (4) or (5), wherein the tumor is resected by a surgical resection.

(7) The method of any one of (1)-(6), wherein the subject is an early, medium-term, or advanced cancer patient, optionally, the subject is a medium-term, or advanced cancer patient, or further optionally, the subject is an advanced cancer patient.

(8) The method of any one of (1)-(6), wherein the subject is a stage 0, I, II, III, or IV cancer patient, optionally, the subject is a stage III or IV cancer patient.

(9) The method of any one of (1)-(8), wherein the subject is a medium-term, or advanced cancer patient, or a stage III or stage IV cancer patient, optionally, the subject is an advanced, or stage III or stage IV cancer patient.

(10) The method of any one of (1)-(9), wherein the tumor is a solid tumor.

(11) The method of (10), wherein the solid tumor comprises one or more of: lung cancer, liver cancer, hepatocellular carcinoma (HCC), esophageal cancer, cholangiocarcinoma, gallbladder carcinoma, stomach cancer, abdominal cancer, gastrointestinal cancer, gastric cancer, pancreatic cancer, renal cell carcinoma, renal cancer, bone cancer, breast cancer, ovarian cancer, uterine cancer, cervical cancer, endometrial cancer, colorectal cancer, colon cancer, rectal cancer, bladder cancer, superficial bladder cancer, prostate cancer, adrenal tumors, squamous cell carcinoma, neuroma, malignant neuroma, myoepithelial carcinoma, synovial sarcoma, rhabdomyosarcoma, gastrointestinal interstitial cell tumor, skin cancer, basal cell carcinoma, malignant melanoma, thyroid cancer, nasopharyngeal carcinoma, hemangioma, epidermoid carcinoma, head and neck cancer, glioma, or Kaposi's sarcoma.

(12) The method of (11), wherein the solid tumor comprises lung cancer, optionally, the lung cancer comprises small cell lung cancer (SCLC), non small cell lung cancer (NSCLC), or both.

(13) The method of any one of (1)-(12), wherein the recombinant interferon is administered to the subject by at least one of: systemic administration, local administration, and topical administration, optionally, the recombinant interferon is administered to the subject by topical or local administration, further optionally, the recombinant interferon is administered to the subject by local administration.

(14) The method of any one of (1)-(13), wherein the recombinant interferon is administered to the subject by an administration route, the administration route comprises one or more of: infiltration administration, intrapleural administration, abdominal administration, pericardial administration, uterine administration, intravesical administration, intratumoral administration, pulmonary administration, nasal administration, percutaneous administration, transdermal administration, epidermal administration, and transmucosal administration.

(15) The method of (14), wherein the intratumoral administration comprises intratumoral injection.

(16) The method of (15), wherein the recombinant interferon is administered in an amount in a range of: about 60 µg to about 600 µg, optionally about 60 µg to about 500 µg, further optionally, about 80 µg to about 400 µg, still optionally about 100 µg to about 250 µg, by one intratumoral injection.

(17) The method of (15) or (16), wherein the recombinant interferon is administered by intratumoral injection once every about 1 day to about 10 days, optionally, every about 1 day to about 7 days, such as every about 1, 2, 3, 4, 5, 6, or 7 days.

(18) The method of any one of (14)-(17), wherein the protocol of intratumoral administration is as follows: the recombinant interferon is administered by intratumoral injection once every about 1 day for about 4 to about 8 times, and then the recombinant interferon is administered by intratumoral injection once every about 3 days to about 5 days for about 4 to about 8 times, and then the recombinant interferon is administered by intratumoral injection once every about 7 days, the intratumoral administration is stopped when the tumor disappears or becomes too small to conduct the intratumoral injection.

(19) The method of (14), wherein the intrapleural administration, abdominal administration, pericardial administration, uterine administration, or intravesical administration comprises intrapleural perfusion administration, abdominal perfusion administration, pericardial perfusion administration, uterine perfusion administration, or intravesical perfusion administration, respectively.

(20) The method of (14), wherein the pulmonary administration, or nasal administration comprises pulmonary inhalation administration, or nasal inhalation administration, respectively.

(21) The method of (14), wherein the percutaneous administration, transdermal administration, epidermal administration, or transmucosal administration comprises percutaneous spray administration, transdermal spray administration, epidermal spray administration, or transmucosal spray administration, respectively.

(22) The method of any one of (13)-(21), wherein the recombinant interferon is further administered to the subject by systemic administration, and/or at least one other therapeutic drug is administered to the subject by topical, local and/or systemic administration before, simultaneously, and/or after the topical or local administration of the recombinant interferon.

(23) The method of (22), wherein the recombinant interferon is further administered to the subject by systemic administration, and/or at least one other therapeutic drug is administered to the subject by topical, local and/or systemic administration simultaneously and/or after the topical or local administration of the recombinant interferon.

(24) The method of (22) or (23), wherein the at least one other therapeutic drug comprises at least one antitumor drug.

(25) The method of (24), wherein the at least one antitumor drug comprises one or more chemotherapeutic drugs, targeted drugs, and/or biological drugs.

(26) The method of (25), wherein the one or more chemotherapeutic drugs comprise platinum compounds, such as Cisplatin.

(27) The method of (25), wherein one or more targeted drugs comprise Gefitinib, Erlotinib, and/or recombinant human endostatin.

In another aspect, another embodiment of the present invention provides:

(1) A method for eliminating or reducing the pleural effusion, ascites, and/or pericardial effusion in a subject with tumor, comprising administering to the subject a recombinant interferon encoded by SEQ ID NO: 2.

(2) The method of (1), wherein the tumor is a cancer or a solid tumor that is indicated or is appropriate for surgery.

(3) The method of (1), wherein the tumor is a cancer or a solid tumor that is not indicated nor appropriate for surgery.

(4) The method of (1), wherein the tumor is a tumor that is capable of being resected.

(5) The method of (1), wherein the tumor is a tumor that is not capable of being resected.

(6) The method of (4) or (5), wherein the tumor is resected by a surgical resection.

(7) The method of any one of (1)-(6), wherein the subject is an early, medium-term, or advanced cancer patient, optionally, the subject is a medium-term, or advanced cancer patient, or further optionally, the subject is an advanced cancer patient.

(8) The method of any one of (1)-(6), wherein the subject is a stage 0, I, II, III, or IV cancer patient, optionally, the subject is a stage III or stage IV cancer patient.

(9) The method of any one of (1)-(8), wherein the subject is a medium-term, or advanced cancer patient, or stage III or stage IV cancer patient, optionally, the subject is an advanced, or stage III or stage IV cancer patient.

(10) The method of any one of (1)-(9), wherein the tumor is a solid tumor.

(11) The method of (10), wherein the solid tumor comprises one or more of: lung cancer, liver cancer, hepatocellular carcinoma (HCC), esophageal cancer, cholangiocarcinoma, gallbladder carcinoma, stomach cancer, abdominal cancer, gastrointestinal cancer, gastric cancer, pancreatic cancer, renal cell carcinoma, renal cancer, bone cancer, breast cancer, ovarian cancer, uterine cancer, cervical cancer, endometrial cancer, colorectal cancer, colon cancer, rectal cancer, bladder cancer, superficial bladder cancer, prostate cancer, adrenal tumors, squamous cell carcinoma, neuroma, malignant neuroma, myoepithelial carcinoma, synovial sarcoma, rhabdomyosarcoma, gastrointestinal interstitial cell tumor, skin cancer, basal cell carcinoma, malignant melanoma, thyroid cancer, nasopharyngeal carcinoma, hemangioma, epidermoid carcinoma, head and neck cancer, glioma, or Kaposi's sarcoma.

(12) The method of (11), wherein the solid tumor comprises lung cancer, optionally, the lung cancer comprises small cell lung cancer (SCLC), non small cell lung cancer (NSCLC), or both.

(13) The method of any one of (1)-(12), wherein the pleural effusion is a malignant pleural effusion, the ascites is a malignant ascites, and/or the pericardial effusion is a malignant pericardial effusion.

(14) The method of any one of (1)-(13), wherein the recombinant interferon is administered to the subject by at least one of: systemic administration, local administration, and topical administration, optionally, by topical and local administration, further optionally, by local administration.

(15) The method of any one of (1)-(14), wherein the recombinant interferon is administered to the subject by an administration route, the administration route comprises one or more of: infiltration administration, intrapleural administration, abdominal administration, and pericardial administration.

(16) The method of any one of (1)-(15), wherein the administration is conducted by perfusion.

(17) The method of any one of (14)-(16), wherein the recombinant interferon is administered in an amount in a range of about 30 μg to about 2000 μg, optionally, about 100 μg to about 1500 μg, further optionally, about 150 μg to about 1000 μg, still further optionally, about 200 μg to about 800 μg, still optionally, about 200 μg to about 400 μg by one topical or local administration.

(18) The method of any one of (14)-(17), wherein the recombinant interferon is administered by topical or local administration once every about 1 to about 10 days, optionally every about 1 to about 7 days, such as every about 1, 2, 3, 4, 5, 6, or 7 days.

(19) The method of any one of (14)-(18), wherein the recombinant interferon is further administered to the subject by systemic administration, and at least one other therapeutic drug is administered to the subject by topical, local and/or systemic administration before, simultaneously, and/or after the topical or local administration of the recombinant interferon.

(20) The method of (19), wherein the recombinant interferon is further administered to the subject by systemic administration, and at least one other therapeutic drug is administered to the subject by topical, local and/or systemic administration simultaneously and/or after the topical or local administration of the recombinant interferon.

(21) The method of (19) or (20), wherein the at least one other therapeutic drug comprises an antitumor drug.

(22) The method of (21), wherein the antitumor drug comprises at least one of: chemotherapeutic drug, targeted drug, and biological drug.

(23) The method of (22), wherein the at least one chemotherapeutic drug comprises at least one platinum compounds, such as Cisplatin.

(24) The method of (22), wherein at least one targeted drug comprises at least one of: Gefitinib, Erlotinib, and recombinant human endostatin.

(25) The method of any one of (1)-(24), wherein the therapies eliminate the tumor or reduce the size of the tumor compared to the tumor before treatment.

(26) The method of any one of (1)-(25), wherein the therapies are the non-surgical therapies.

In another aspect, another embodiment of the present invention provides:

(1) A method for treating tumor in a subject, comprising topically or locally administering to the tumor lesions of the subject a recombinant interferon encoded by SEQ ID NO: 2.

(2) The method of (1), wherein the tumor lesions comprise metastatic tumor lesions.

(3) A method for eliminating or reducing metastatic tumor lesions in a subject, comprising topically or locally administering to the metastatic tumor lesions of the subject a recombinant interferon encoded by SEQ ID NO: 2.

(4) The method of any one of (1)-(3), wherein the tumor lesions comprise at least one of: bone lesions, muscular lesions, subcutaneous tissue lesions, prostatic lesions and lymph node lesions, and the tumor metastatic lesions comprise at least one of: bone metastatic lesions, muscular metastatic lesions, subcutaneous tissue metastatic lesions, prostatic metastatic lesions, and lymph node metastatic lesions, optionally, the tumor metastatic lesions comprise bone metastatic lesions.

(5) The method of any one of (1)-(4), wherein the subject is a medium-term, advanced, or stage III or stage IV cancer patient, optionally, the subject is an advanced, or stage III or stage IV cancer patient.

(6) The method of any one of (1)-(4), wherein the tumor or the metastatic tumor lesions comprise a cancer or a solid tumor that is not indicated nor appropriate for surgery.

(7) The method of any one of (1)-(6), wherein the topical or local administration comprises at least one of: infiltration administration, percutaneous administration, transdermal administration, epidermal administration and transmucosal administration, optionally, the topical and local administration comprises transdermal administration, or infiltration administration.

(8) The method of (7), wherein the infiltration administration comprises one or more of: percutaneous infiltration administration, epidermal infiltration administration, transdermal infiltration administration, and transmucosal infiltration administration.

(9) The method of (7), wherein the percutaneous administration, transdermal administration, epidermal administration, or transmucosal administration comprises percutaneous spray administration, transdermal spray administration, epidermal spray administration, or transmucosal spray administration, respectively.

(10) The method of any one of (1)-(9), wherein the recombinant interferon is administered in an amount in a range of about 2 µg to about 2000 µg, optionally about 4 µg to about 1500 µg, further optionally about 9 µg to about 1000 µg by one topical or local administration.

(11) The method of any one of (1)-(10), wherein the recombinant interferon is administered to the subject by topical or local administration about 1, 2, 3, 4, 5, 6, 7, 8, or more times per day, or the recombinant interferon is administered to the subject by topical or local administration once at the time interval of every about 2, 3, 4, 5, 6, 7, 8, 9, 10, 11, 12, 13, 14, 15, 16, 17, 18, 19, 20, or 21 days, every month, every 2 months, or a longer time.

(12) The method of any one of (7)-(11), wherein the recombinant interferon is administered in an amount in a range of about 6 µg to about 100 µg, optionally about 10 µg to about 40 µg, further optionally about 20 µg to about 40 µg by one spray administration when the topical or local administration is conducted by spray administration.

(13) The method of (12), wherein the recombinant interferon is administered by spray administration about 1 to about 6 times, such as about 1, 2, 3, 4, 5, or 6 times, per day.

(14) The method of any one of (1)-(13), wherein the recombinant interferon and/or one or more other therapeutic drugs are administered to the subject by systemic administration before, simultaneously, and/or after the topical or local administration of the recombinant interferon.

(15) The method of (14), wherein the systemic administration comprises subcutaneous and/or intramuscular administration.

(16) The method of (15), wherein the subcutaneous administration comprises subcutaneous injection.

(17) The method of (15), wherein the intramuscular administration comprises intramuscular injection.

(18) The method of any one of (15)-(17), wherein the recombinant interferon is administered one or more times by subcutaneous administration and/or intramuscular administration at an induction dose in the range of about 2 µg to about 10 µg each time, optionally, about 4 µg to about 10 µg each time, more optionally about 4.5 µg to about 9 µg each time, such as about 4.5 µg each time or about 9 µg each time, and then the recombinant interferon is administered more times by subcutaneous administration and/or intramuscular administration at a therapeutic dose of about 10 µg to about 70 µg each time, optionally about 12 µg to about 50 µg each time, more optionally about 12 µg to about 30 µg each time.

(19) The method of (18), wherein the time interval between administration of induction dose and administration of therapeutic dose is about 1 day to about 1 month, optionally about 1 day to about 1 week, further optionally about 1 day to about 3 days, comprising such as about 1 day, about 2 days, about 3 days, about 4 days, about 5 days, about 6 days, about 7 days, about 8 days, about 9 days, about 10 days, about 1 week, about 2 weeks, about 3 weeks, or about 1 month.

(20) The method of (18) or (19), wherein the recombinant interferon is administered once every about 1 day to about 10 days, optionally every about 1 day to about 7 days, further optionally every about 1 to about 2 days, comprising such as every about 1, 2, 3, 4, 5, 6, 7, 8, 9, or 10 days when the recombinant interferon is administered more times at an induction dose.

(21) The method of any one of (18)-(20), wherein the recombinant interferon is administered at a therapeutic dose once every about 1 day to about 10 days, optionally every about 1 day to about 7 days, further optionally every about 1 to about 2 days, comprising such as every about 1, 2, 3, 4, 5, 6, 7, 8, 9, or 10 days.

(22) The method of any one of (18)-(21), wherein the duration of administration of induction dose and therapeutic dose is at least: about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, or about 6 years and the like, or the recombinant interferon can be administered for a long time, including over the life time of the subject.

(23) The method of any one of (1)-(22), wherein the recombinant interferon is administered to the subject as monotherapy.

(24) The method of any one of (1)-(22), further comprising at least one other anti-cancer therapy administered to the subject, optionally, the at least one other anti-cancer therapy is administered to the subject before, simultaneously, and/or after administration of the recombinant interferon.

(25) The method of (24), wherein the at least one other anti-cancer therapy comprises one or more of: chemotherapy, radiotherapy, surgical therapy, interventional therapy, biotherapy, gene therapy, ablation therapy, immunotherapy, targeted therapy, and traditional Chinese medicine therapy.

(26) The method of any one of (1)-(25), wherein the recombinant interferon therapy and/or at least one other anti-cancer therapy eliminate the tumor or tumor metastatic lesions or reduce the size of the tumor or tumor metastatic lesions compared to the tumor or tumor metastatic lesions before treatment.

(27) A method for eliminating or reducing the bone metastatic lesions of tumor in a subject, comprising administering to the subject a recombinant interferon encoded by SEQ ID NO: 2 by topical or local administration, wherein the topical or local administration comprises transdermal administration and/or infiltration administration, optionally, the recombinant interferon is administered to the bone metastatic lesions of tumor of the subject.

(28) A method for eliminating or reducing the bone lesions of tumor such as bone metastatic lesions of tumor, muscular lesions of tumor such as muscular metastatic lesions of tumor, subcutaneous tissue lesions of tumor such as subcutaneous tissue metastatic lesions of tumor, prostatic lesions of tumor such as prostatic metastatic lesions of tumor, and/or lymph node lesions of tumor such as lymph node metastatic lesions of tumor in a subject, comprising administering to the subject a recombinant interferon encoded by SEQ ID NO: 2 by any administration route through the skin, so that eliminating or reducing the bone lesions of tumor such as bone metastatic lesions of tumor, muscular lesions of tumor such as muscular metastatic lesions of tumor, subcutaneous tissue lesions of tumor such as subcutaneous tissue metastatic lesions of tumor, prostatic lesions of tumor such as prostatic metastatic lesions of tumor, and/or lymph node lesions of tumor such as lymph node metastatic lesions of tumor, optionally, the recombinant interferon is administered to the metastatic lesions of tumor of the subject.

(29) The method of any one of (1)-(28), wherein the therapies are non-surgical therapies.

In another aspect, another embodiment of the present invention provides:

(1) A method for treating lung cancer in a subject, comprising administering to the subject a recombinant interferon encoded by SEQ ID NO: 2.

(2) The method of (1), wherein the lung cancer comprises small cell lung cancer (SCLC), non small cell lung cancer (NSCLC), or both.

(3) The method of (1) or (2), wherein the lung cancer in the subject comprises a metastasized tumor.

(4) The method of any one of (1)-(3), wherein the subject is an early, medium-term, or advanced cancer patient, optionally, the subject is a medium-term, or advanced cancer patient, further optionally, the subject is an advanced cancer patient.

(5) The method of any one of (1)-(3), wherein the subject is a stage 0, I, II, III, or IV cancer patient, optionally, the subject is an stage III or stage IV cancer patient.

(6) The method of any one of (1)-(5), wherein the lung cancer comprises a lung cancer that is indicated or appropriate for surgery.

(7) The method of any one of (1)-(5), wherein the lung cancer comprises a lung cancer that is not indicated nor appropriate for surgery.

(8) The method of any one of (1)-(5), wherein the lung cancer comprises a lung cancer that is capable of being resected.

(9) The method of any one of (1)-(5), wherein the lung cancer comprises a lung cancer that is not capable of being resected.

(10) The method of (8) or (9), wherein the lung cancer is resected by a surgical resection.

(11) The method of any one of (1)-(10), wherein an effective amount of recombinant interferon encoded by the nucleotide sequence of SEQ ID NO: 2 is administered to the subject, optionally, the effective amount is a therapeutically effective amount.

(12) The method of any one of (1)-(11), wherein the recombinant interferon is administered to the subject by at least one of: systemic administration, topical administration, and local administration.

(13) The method of any one of (1)-(12), wherein the recombinant interferon is administered to the subject by an administration route, the administration route comprises one or more of: oral, rectal, sublingual, intravenous, intra-arterial, intramuscular, subcutaneous, intrabone, intracutaneous, intra-articular, intraperitoneal, intrathecal, intracerebral, vaginal, percutaneous, transdermal, epidermal, transmucosal, transocular, pulmonary, nasal, abdominal, intrapleural, intraventricular, pericardial, inhalation, intratumoral, uterine, infiltration, and intravesical administration.

(14) The method of any one of (1)-(13), wherein the recombinant interferon is administered to the subject by subcutaneous administration and/or intramuscular administration.

(15) The method of (14), wherein the subcutaneous administration comprises subcutaneous injection.

(16) The method of (14), wherein the intramuscular administration comprises intramuscular injection.

(17) The method of any one of (14)-(16), wherein the recombinant interferon is administered in an amount in a range of about 2 μg to about 70 μg by one subcutaneous and/or intramuscular administration.

(18) The method of (17), wherein the recombinant interferon is administered in an amount in a range of about 4 μg to about 50 μg by one subcutaneous and/or intramuscular administration.

(19) The method of (18), wherein the recombinant interferon is administered in an amount in a range of about 4 μg to about 30 μg by one subcutaneous and/or intramuscular administration.

(20) The method of any one of (14)-(19), wherein the recombinant interferon is administered by subcutaneous and/or intramuscular administration once every about 1 to about 7 days.

(21) The method of (20), wherein the recombinant interferon is administered by subcutaneous and/or intramuscular administration once every about 1 to about 2 days.

(22) The method of any one of (1)-(21), wherein the recombinant interferon is administered to the subject by inhalation administration.

(23) The method of (22), wherein the recombinant interferon is administered by pulmonary and/or nasal inhalation.

(24) The method of (22) or (23), wherein the inhalation administration comprises dry powder inhalation and/or aerosol inhalation.

(25) The method of any one of (22)-(24), wherein the recombinant interferon is administered in an amount in a range of about 100 μg to about 2000 μg, optionally about 100 μg to about 1500 μg by one inhalation administration.

(26) The method of (25), wherein the recombinant interferon is administered in an amount in a range of about 150 μg to about 800 μg by one inhalation administration.

(27) The method of (26), wherein the recombinant interferon is administered in an amount in a range of about 200 μg to about 600 μg by one inhalation administration.

(28) The method of any one of (22)-(27), wherein the recombinant interferon is administered by inhalation administration once every about 1 to about 3 days.

(29) The method of (28), wherein the recombinant interferon is administered by inhalation administration once every about 1 day.

(30) The method of any one of (1)-(29), wherein the subject has the pleural effusion, ascites, and/or pericardial effusion.

(31) The method of (30), wherein the pleural effusion comprises a malignant pleural effusion, the ascites comprises a malignant ascites, and/or the pericardial effusion comprises a malignant pericardial effusion.

(32) The method of (30) or (31), wherein the recombinant interferon is administered to the subject by intrapleural administration, abdominal administration, and/or pericardial administration.

(33) The method of (32), wherein the intrapleural administration comprises intrapleural perfusion.

(34) The method of (32), wherein the abdominal administration comprises abdominal perfusion.

(35) The method of (32), wherein the pericardial administration comprises pericardial perfusion.

(36) The method of any one of (32)-(35), wherein the recombinant interferon is administered in an amount in a range of about 30 μg to about 2000 μg, optionally about 100 μg to about 1500 μg, further optionally about 150 μg to about 1000 μg, still optionally about 200 μg to about 800 μg by one intrapleural, abdominal, and/or pericardial administration.

(37) The method of (36), wherein the recombinant interferon is administered in an amount in a range of about 200 μg to about 400 μg by one intrapleural, abdominal, and/or pericardial administration.

(38) The method of any one of (32)-(37), wherein the recombinant interferon is administered by intrapleural, abdominal, and/or pericardial administration once every about 1 to about 10 days, optionally every about 1 to about 7 days, such as every about 1, 2, 3, 4, 5, 6, or 7 days.

(39) The method of any one of (1)-(13), wherein the recombinant interferon is administered to the subject by intratumoral administration.

(40) The method of (39), wherein the intratumoral administration comprises intratumoral injection.

(41) The method of (39) or (40), wherein the recombinant interferon is administered in an amount in a range of about 60 μg to about 600 μg, optionally about 60 μg to about 500 μg by one intratumoral administration.

(42) The method of (41), wherein the recombinant interferon is administered in an amount in a range of about 80 μg to about 400 μg by one intratumoral administration.

(43) The method of (42), wherein the recombinant interferon is administered in an amount in a range of about 100 μg to about 250 μg by one intratumoral administration.

(44) The method of any one of (39)-(43), wherein the recombinant interferon is administered by intratumoral administration once every about 1 day to about 10 days, optionally every about 1 day to about 7 days such as every about 1, 2, 3, 4, 5, 6, or 7 days.

(45) The method of any one of (39)-(44), wherein the protocol of intratumoral administration is as follow: the recombinant interferon is administered by intratumoral injection once every about 1 day for about 4 to about 8 times, and then the recombinant interferon is administered by intratumoral injection once every about 3 days to about 5 days for about 4 to about 8 times, and then the recombinant interferon is administered by intratumoral injection once every about 7 days, the intratumoral administration is stopped when the tumor disappears or becomes too small to conduct the intratumoral injection.

(46) The method of any one of (1)-(45), wherein the lung cancer in the subject comprises tumor metastasis in at least one of: skin, mucosa, superficial lymph nodes, and subcutaneous tissue.

(47) The method of (46), wherein the recombinant interferon is administered to the subject by spray administration.

(48) The method of (47), wherein the spray administration comprises at least one of: percutaneous spray administration, transdermal spray administration, epidermal spray administration, and transmucosal spray administration.

(49) The method of (47) or (48), wherein the recombinant interferon is administered in an amount in a range of about 6 μg to about 100 μg by one spray administration.

(50) The method of (49), wherein the recombinant interferon is administered in an amount in a range of about 10 μg to about 40 μg, optionally about 20 μg to about 40 μg by one spray administration.

(51) The method of any one of (47)-(50), wherein the recombinant interferon is administered by spray administration about 1 to about 6 times such as about 1, 2, 3, 4, 5, or 6 times per day.

(52) The method of any one of (1)-(51), wherein the recombinant interferon is administered to the subject by an administration route, the administration route comprises at least one of: subcutaneous administration, intramuscular administration, inhalation administration, infiltration administration, intrapleural administration, abdominal administration, pericardial administration, intratumoral administration, and spray administration.

(53) The method of any one of (1)-(52), wherein the recombinant interferon is administered to the subject as monotherapy.

(54) The method of any one of (1)-(52), further comprising at least one other anti-cancer therapy administered to the subject, optionally, the at least one other anti-cancer therapy is administered to the subject before, simultaneously, and/or after administration of the recombinant interferon.

(55) The method of (54), wherein the at least one other anti-cancer therapy comprises at least one of: chemotherapy, radiotherapy, surgical therapy, interventional therapy, biotherapy, gene therapy, ablation therapy, immunotherapy, targeted therapy, and traditional Chinese medicine therapy.

(56) The method of (55), wherein the at least one other anti-cancer therapy comprises chemotherapy.

(57) The method of (56), wherein the chemotherapy is the first-line chemotherapy.

(58) The method of (57), wherein at least one chemotherapeutic drugs used for the first-line chemotherapy comprise platinum compounds, such as Cisplatin.

(59) The method of (55), wherein the at least one other anti-cancer therapy comprises radiotherapy.

(60) The method of (59), wherein the radiotherapy comprises head gamma knife therapy when the lung cancer metastasizes to brain.

(61) The method of (55), wherein the at least one other anti-cancer therapy comprises surgical therapy.

(62) The method of (55), wherein the at least one other anti-cancer therapy comprises targeted therapy.

(63) The method of (62), wherein the targeted therapy comprises administering Gefitinib, Erlotinib, and/or recombinant human endostatin.

(64) The method of (55), wherein the at least one other anti-cancer therapy comprises biotherapy.

(65) The method of any one of (1)-(64), wherein the recombinant interferon is administered in at least one treatment cycle, optionally, the at least one treatment cycle comprises 2, 3, 4, 5, 6, 7, 8, 9, or 10 treatment cycles, or optionally, more than 10 treatment cycles.

(66) The method of (65), wherein the duration of the treatment cycle is at least about 1 day, about 2 days, about 3 days, about 4 days, about 5 days, about 6 days, about 7 days, about 8 days, about 9 days, about 10 days, about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, or about 6 years and the like, or the recombinant interferon can be administered for a long time, including over the life time of the subject; or the duration can also be about 1 day to about 6 years, about 1 week to about 4 years, about 2 weeks to about 3 years, about 1 month to about 1 year, or about 2 months to about 9 months and the like.

(67) The method of (65) or (66), wherein the time interval between any two adjacent treatment cycles of the more treatment cycles is at least about 2 days, about 3 days, about 4 days, about 5 days, about 6 days, about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, or about 6 years and the like; or the time interval can also be about 2 days to about 6 years, about 4 days to about 3 years, about 1 week to about 1 year, about 2 months to about 9 months, or about 3 months to about 6 months and the like.

(68) The method of any one of (1)-(67), wherein the therapies eliminate the tumor of the lung or reduce the size of the tumor of the lung compared to the tumor size before treatment.

(69) A method for treating lung cancer in a subject, comprising administering to the subject a recombinant interferon encoded by SEQ ID NO: 2 and one or more chemotherapeutic drugs in two or more treatment cycles, and then administering to the subject a recombinant interferon encoded by SEQ ID NO: 2 and one or more targeted drugs in one or more treatment cycles.

(70) The method of (69), wherein the therapies eliminate the tumor of the lung or reduce the size of the tumor of the lung compared to the tumor size before treatment.

(71) The method of (69) or (70), wherein the one or more chemotherapeutic drugs comprise platinum compounds, such as Cisplatin.

(72) The method of any one of (69)-(71), wherein the one or more targeted drugs comprise Gefitinib, Erlotinib, and/or recombinant human endostatin.

(73) The method of any one of (69)-(72), wherein an effective amount of recombinant interferon, encoded by the nucleotide sequence of SEQ ID NO: 2, is administered to the subject, optionally, the effective amount is a therapeutically effective amount.

(74) The method of any one of (1)-(73), wherein the therapies are the non-surgical therapies.

In another aspect, another embodiment of the present invention provides:

(1) A method for treating lung cancer in a subject, comprising administering to the subject a recombinant interferon encoded by SEQ ID NO: 2 by subcutaneous administration and/or intramuscular administration, wherein the recombinant interferon is administered in an amount in a range of about 2 µg to about 70 µg, optionally about 4 µg to about 50 µg, further optionally about 4 µg to about 30 µg by one subcutaneous administration and/or intramuscular administration, the recombinant interferon is administered by subcutaneous administration and/or intramuscular administration once every about 1 to about 7 days, optionally every about 1 to about 2 days, lasting at least about 1 day, about 2 days, about 3 days, about 4 days, about 5 days, about 6 days, about 7 days, about 8 days, about 9 days, about 10 days, about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, or about 6 years and the like, or the recombinant interferon can be administered for a long time, including over the life time of the subject; or the duration can also be about 1 day to about 6 years, about 1 week to about 4 years, about 2 weeks to about 3 years, about 1 month to about 1 year, or about 2 months to about 9 months and the like.

(2) The method of (1), wherein the lung cancer comprises small cell lung cancer (SCLC), non small cell lung cancer (NSCLC), or both.

(3) The method of (1) or (2), wherein the lung cancer in the subject comprises a metastasized tumor.

(4) The method of any one of (1)-(3), wherein the subject is an early, medium-term, or advanced cancer patient, optionally, the subject is a medium-term, or advanced cancer patient, further optionally, the subject is an advanced cancer patient.

(5) The method of any one of (1)-(3), wherein the subject is a stage 0, I, II, III, or IV cancer patient, optionally, the subject is a stage III or IV cancer patient.

(6) The method of any one of (1)-(5), wherein the lung cancer is a lung cancer that is indicated or appropriate for surgery.

(7) The method of any one of (1)-(5), wherein the lung cancer is a lung cancer that is not indicated nor appropriate for surgery.

(8) The method of any one of (1)-(5), wherein the lung cancer is a lung cancer that is capable of being resected.

(9) The method of any one of (1)-(5), wherein the lung cancer is a lung cancer that is not capable of being resected.

(10) The method of (8) or (9), wherein the lung cancer is resected by a surgical resection.

(11) The method of any one of (1)-(10), wherein the subcutaneous administration comprises subcutaneous injection.

(12) The method of any one of (1)-(10), wherein the intramuscular administration comprises intramuscular injection.

(13) The method of any one of (1)-(12), further comprising administering to the subject the recombinant interferon by inhalation administration.

(14) The method of (13), wherein the inhalation administration is conducted before, simultaneously, and/or after the subcutaneous administration and/or intramuscular administration.

(15) The method of (13) or (14), wherein the inhalation administration comprises pulmonary and/or nasal inhalation administration.

(16) The method of any one of (13)-(15), wherein the inhalation administration comprises aerosol inhalation.

(17) The method of any one of (13)-(16), wherein the recombinant interferon is administered in an amount in a range of about 100 μg to about 2000 μg, optionally about 100 μg to about 1500 μg, further optionally about 150 μg to about 800 μg, still optionally about 200 μg to about 600 μg by one inhalation administration, the recombinant interferon is administered by inhalation administration once every about 1 day to about 3 days, optionally every about 1 day, lasting at least about 1 day, about 2 days, about 3 days, about 4 days, about 5 days, about 6 days, about 7 days, about 8 days, about 9 days, about 10 days, about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, or about 6 years and the like, or the recombinant interferon can be administered for a long time, including over the life time of the subject; or the duration can also be about 1 day to about 6 years, about 1 week to about 4 years, about 2 weeks to about 3 years, about 1 month to about 1 year, or about 2 months to about 9 months and the like.

(18) The method of any one of (1)-(17), further comprising administering to the subject the recombinant interferon by intratumoral administration.

(19) The method of (18), wherein the intratumoral administration is conducted before, simultaneously, and/or after the subcutaneous administration and/or intramuscular administration.

(20) The method of (18), wherein the intratumoral administration is conducted before, simultaneously, and/or after the inhalation administration.

(21) The method of any one of (18)-(20), wherein the intratumoral administration comprises intratumoral injection.

(22) The method of any one of (18)-(21), wherein the recombinant interferon is administered in an amount in a range of about 60 μg to about 600 μg, optionally about 60 μg to about 500 μg, further optionally about 80 μg to about 400 μg, still further optionally about 100 μg to about 250 μg by one intratumoral administration, and the recombinant interferon is administered by intratumoral administration once every about 1 day to about 10 days, optionally every about 1 day to about 7 days such as every about 1, 2, 3, 4, 5, 6, or 7 days, the duration of the intratumoral administration is at least about 1 day, about 2 days, about 3 days, about 4 days, about 5 days, about 6 days, about 7 days, about 8 days, about 9 days, about 10 days, about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, or about 6 years and the like, or the recombinant interferon can be administered for a long time, including over the life time of the subject; or the duration can also be about 1 day to about 6 years, about 1 week to about 4 years, about 2 weeks to about 3 years, about 1 month to about 1 year, or about 2 months to about 9 months and the like.

(23) The method of any one of (18)-(22), wherein the protocol of intratumoral administration is as follows: the recombinant interferon is administered by intratumoral injection once every about 1 day for about 4 to about 8 times, and then the recombinant interferon is administered by intratumoral injection once every about 3 days to about 5 days for about 4 to about 8 times, and then the recombinant interferon is administered by intratumoral injection once every about 7 days, the intratumoral administration is stopped when the tumor disappears or becomes too small to conduct the intratumoral injection.

(24) The method of any one of (1)-(23), wherein the subject has the pleural effusion, ascites, and/or pericardial effusion.

(25) The method of (24), wherein the pleural effusion is a malignant pleural effusion, the ascites is a malignant ascites, and/or the pericardial effusion is a malignant pericardial effusion.

(26) The method of (24) or (25), wherein the recombinant interferon is administered to the subject by an administration route, the administration route comprises at least one of: intrapleural administration, abdominal administration, and pericardial administration.

(27) The method of (26), wherein the intrapleural administration comprises intrapleural perfusion.

(28) The method of (26), wherein the abdominal administration comprises abdominal perfusion.

(29) The method of (26), wherein the pericardial administration comprises pericardial perfusion.

(30) The method of any one of (26)-(29), wherein the recombinant interferon is administered in an amount in a range of about 30 μg to about 2000 μg, optionally about 100 μg to about 1500 μg, further optionally about 150 μg to about 1000 μg, still optionally about 200 μg to about 800 μg by one intrapleural, abdominal, and/or pericardial administration.

(31) The method of (30), wherein the recombinant interferon is administered in an amount in a range of about 200 μg to about 400 μg by one intrapleural, abdominal, and/or pericardial administration.

(32) The method of any one of (26)-(31), wherein the recombinant interferon is administered by intrapleural, abdominal, and/or pericardial administration once every about 1 day to about 10 days, optionally every about 1 day to about 7 days, such as every about 1, 2, 3, 4, 5, 6, or 7 days.

(33) The method of any one of (1)-(32), wherein the lung cancer in the subject comprises tumor metastasis in at least one of: skin, mucosa, superficial lymph nodes, and subcutaneous tissue.

(34) The method of (33), wherein the recombinant interferon is administered to the subject by spray administration.

(35) The method of (34), wherein the spray administration comprises at least one of: percutaneous spray administration, transdermal spray administration, epidermal spray administration, and transmucosal spray administration.

(36) The method of (34) or (35), wherein the recombinant interferon is administered in an amount in a range of about 6 μg to about 100 μg by one spray administration.

(37) The method of (36), wherein the recombinant interferon is administered in an amount of about 10 μg to about 40 μg, optionally about 20 μg to about 40 μg by one spray administration.

(38) The method of any one of (34)-(37), wherein the recombinant interferon is administered by spray administration about 1 to about 6 times per day, such as about 1, 2, 3, 4, 5, or 6 times per day.

(39) The method of any one of (1)-(38), wherein the recombinant interferon is administered to the subject as monotherapy.

(40) The method of any one of (1)-(38), further comprising at least one other anti-cancer therapy administered to the subject, optionally, the at least one other anti-cancer therapy is administered to the subject before, simultaneously, and/or after administration of the recombinant interferon.

(41) The method of (40), wherein the at least one other anti-cancer therapy comprises one or more of: chemotherapy, radiotherapy, surgical therapy, interventional therapy, biotherapy, gene therapy, ablation therapy, immunotherapy, targeted therapy, and traditional Chinese medicine therapy.

(42) The method of (41), wherein the at least one other anti-cancer therapy comprises chemotherapy.

(43) The method of (42), wherein the chemotherapy is the first-line chemotherapy.

(44) The method of (43), wherein one or more chemotherapeutic drugs used for the first-line chemotherapy comprise platinum compounds, such as Cisplatin.

(45) The method of (41), wherein the at least one other anti-cancer therapy comprises radiotherapy.

(46) The method of (45), wherein the radiotherapy comprises head gamma knife therapy when the lung cancer metastasizes to brain.

(47) The method of (41), wherein the at least one other anti-cancer therapy comprises surgical therapy.

(48) The method of (41), wherein the at least one other anti-cancer therapy comprises targeted therapy.

(49) The method of (48), wherein the targeted therapy comprises administering Gefitinib, Erlotinib, and/or recombinant human endostatin.

(50) The method of (41), wherein the at least one other anti-cancer therapy comprises biotherapy.

(51) The method of any one of (1)-(50), wherein the therapies eliminate the tumor or reduce the size of the tumor or the number of tumor metastasis compared to the tumor before treatment.

(52) The method of any one of (1)-(51), wherein the therapies are the non-surgical therapies.

In another aspect, another embodiment of the present invention provides:

(1) A method for treating lung cancer in a subject, comprising administering to the subject a recombinant interferon encoded by SEQ ID NO: 2 by subcutaneous administration and/or intramuscular administration, wherein the recombinant interferon is administered one or more times by subcutaneous administration and/or intramuscular administration at an induction dose in a range of about 2 μg to about 10 μg each time, optionally about 4 μg to about 10 μg each time, further optionally about 4.5 μg to about 9 μg each time, such as about 4.5 μg each time or about 9 μg each time, and then the recombinant interferon is administered more times by subcutaneous administration and/or intramuscular administration at a therapeutic dose in a range of about 10 μg to about 70 μg each time, optionally about 12 μg to about 50 μg each time, further optionally about 12 μg to about 30 μg each time.

(2) The method of (1), wherein the lung cancer comprises small cell lung cancer (SCLC), non small cell lung cancer (NSCLC), or both.

(3) The method of (1) or (2), wherein the tumor in the subject comprises a metastasized tumor.

(4) The method of any one of (1)-(3), wherein the subject is an early, medium-term, or advanced cancer patient, optionally, the subject is a medium-term, or advanced cancer patient, further optionally, the subject is an advanced cancer patient.

(5) The method of any one of (1)-(3), wherein the subject is a stage 0, I, II, III, or IV cancer patient, optionally, the subject is a stage III or IV cancer patient.

(6) The method of any one of (1)-(5), wherein the lung cancer is a lung cancer that is indicated or appropriate for surgery.

(7) The method of any one of (1)-(5), wherein the lung cancer is a lung cancer that is not indicated nor appropriate for surgery.

(8) The method of any one of (1)-(5), wherein the lung cancer is a lung cancer that is capable of being resected.

(9) The method of any one of (1)-(5), wherein the lung cancer is a lung cancer that is not capable of being resected.

(10) The method of (8) or (9), wherein the lung cancer is resected by a surgical resection.

(11) The method of any one of (1)-(10), wherein the subcutaneous administration comprises subcutaneous injection.

(12) The method of any one of (1)-(10), wherein the intramuscular administration comprises intramuscular injection.

(13) The method of any one of (1)-(12), wherein the time interval between administration of induction dose and administration of therapeutic dose is about 1 day to about 1 month, optionally about 1 day to about 1 week, further optionally about 1 day to about 3 days, comprising such as about 1 day, about 2 days, about 3 days, about 4 days, about 5 days, about 6 days, about 7 days, about 8 days, about 9 days, about 10 days, about 1 week, about 2 weeks, about 3 weeks, or about 1 month.

(14) The method of any one of (1)-(13), the recombinant interferon is administered once every about 1 day to about 10 days, optionally every about 1 day to about 7 days, further optionally every about 1 to about 2 days, comprising such as every about 1, 2, 3, 4, 5, 6, 7, 8, 9, or 10 days when the recombinant interferon is administered more times at an induction dose.

(15) The method of any one of (1)-(14), wherein the recombinant interferon is administered at a therapeutic dose once every about 1 day to about 10 days, optionally every about 1 day to about 7 days, further optionally every about 1 to about 2 days, comprising such as every about 1, 2, 3, 4, 5, 6, 7, 8, 9, or 10 days.

(16) The method of any one of (1)-(15), wherein the duration of administration of induction dose and therapeutic dose is at least about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, or about 6 years and the like, or the recombinant interferon can be administered for a long time, including over the life time of the subject.

(17) The method of any one of (1)-(16), further comprising administering to the subject the recombinant interferon by inhalation administration.

(18) The method of (17), wherein the inhalation administration is conducted before, simultaneously, and/or after the subcutaneous administration and/or intramuscular administration.

(19) The method of (17) or (18), wherein the inhalation administration comprises pulmonary and/or nasal inhalation administration.

(20) The method of any one of (17)-(19), wherein the inhalation administration comprises aerosol inhalation.

(21) The method of any one of (17)-(20), wherein the recombinant interferon is administered in an amount in a range of about 100 µg to about 2000 µg, optionally about 100 µg to about 1500 µg, further optionally about 150 µg to about 800 µg, still further optionally about 200 µg to about 600 µg by one inhalation administration, the recombinant interferon is administered by inhalation administration once every about 1 day to about 3 days, optionally every about 1 day, lasting at least about 1 day, about 2 days, about 3 days, about 4 days, about 5 days, about 6 days, about 7 days, about 8 days, about 9 days, about 10 days, about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, or about 6 years and the like, or the recombinant interferon can be administered for a long time, including over the life time of the subject; or the duration can also be about 1 day to about 6 years, about 1 week to about 4 years, about 2 weeks to about 3 years, about 1 month to about 1 year, or about 2 months to about 9 months and the like.

(22) The method of any one of (1)-(21), further comprising administering to the subject the recombinant interferon by intratumoral administration.

(23) The method of (22), wherein the intratumoral administration is conducted before, simultaneously, and/or after the subcutaneous administration and/or intramuscular administration.

(24) The method of (22), wherein the intratumoral administration is conducted before, simultaneously, and/or after the inhalation administration.

(25) The method of any one of (22)-(24), wherein the intratumoral administration comprises intratumoral injection.

(26) The method of any one of (22)-(25), wherein the recombinant interferon is administered in an amount in a range of about 60 µg to about 600 µg, optionally about 60 µg to about 500 µg, further optionally about 80 µg to about 400 µg, still further optionally about 100 µg to about 250 µg by one intratumoral administration, and the recombinant interferon is administered by intratumoral administration once every about 1 day to about 10 days, optionally every about 1 day to about 7 days such as every about 1, 2, 3, 4, 5, 6, or 7 days, the duration of the intratumoral administration is at least about 1 day, about 2 days, about 3 days, about 4 days, about 5 days, about 6 days, about 7 days, about 8 days, about 9 days, about 10 days, about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, or about 6 years and the like, or the recombinant interferon can be administered for a long time, including over the life time of the subject; or the duration can also be about 1 day to about 6 years, about 1 week to about 4 years, about 2 weeks to about 3 years, about 1 month to about 1 year, or about 2 months to about 9 months and the like.

(27) The method of any one of (22)-(26), wherein the protocol of intratumoral administration is as follows: the recombinant interferon is administered by intratumoral injection once every about 1 day for about 4 to about 8 times, and then the recombinant interferon is administered by intratumoral injection once every about 3 days to about 5 days for about 4 to about 8 times, and then the recombinant interferon is administered by intratumoral injection once every about 7 days, the intratumoral administration is stopped when the tumor disappears or becomes too small to conduct the intratumoral injection.

(28) The method of any one of (1)-(27), wherein the subject has the pleural effusion, ascites, and/or pericardial effusion.

(29) The method of (28), wherein the pleural effusion is a malignant pleural effusion, the ascites is a malignant ascites, and/or the pericardial effusion is a malignant pericardial effusion.

(30) The method of (28) or (29), wherein the recombinant interferon is administered to the subject by an administration route, the administration route comprises at least one of: intrapleural administration, abdominal administration, and pericardial administration.

(31) The method of (30), wherein the intrapleural administration comprises intrapleural perfusion.

(32) The method of (30), wherein the abdominal administration comprises abdominal perfusion.

(33) The method of (30), wherein the pericardial administration comprises pericardial perfusion.

(34) The method of any one of (30)-(33), wherein the recombinant interferon is administered in an amount in a range of about 30 μg to about 2000 μg, optionally about 100 μg to about 1500 μg, further optionally about 150 μg to about 1000 μg, still optionally about 200 μg to about 800 μg by one intrapleural administration, abdominal administration, and/or pericardial administration.

(35) The method of (34), wherein the recombinant interferon is administered in an amount in a range of about 200 μg to about 400 μg by one intrapleural administration, abdominal administration, and/or pericardial administration.

(36) The method of any one of (30)-(35), wherein the recombinant interferon is administered by intrapleural administration, abdominal administration, and/or pericardial administration once every about 1 day to about 10 days, optionally every about 1 day to about 7 days, such as every about 1, 2, 3, 4, 5, 6, or 7 days.

(37) The method of any one of (1)-(36), wherein the lung cancer in the subject comprises tumor metastasis in at least one of: skin, mucosa, superficial lymph nodes, and subcutaneous tissue.

(38) The method of (37), wherein the recombinant interferon is administered to the subject by spray administration.

(39) The method of (38), wherein the spray administration comprises at least one of: percutaneous spray administration, transdermal spray administration, epidermal spray administration, and transmucosal spray administration.

(40) The method of (38) or (39), wherein the recombinant interferon is administered in an amount in a range of about 6 μg to about 100 μg by one spray administration.

(41) The method of (40), wherein the recombinant interferon is administered in an amount in a range of about 10 μg to about 40 μg, optionally about 20 μg to about 40 μg by one spray administration.

(42) The method of any one of (38)-(41), wherein the recombinant interferon is administered by spray administration about 1 to about 6 times per day, such as about 1, 2, 3, 4, 5, or 6 times per day.

(43) The method of any one of (1)-(42), wherein the recombinant interferon is administered to the subject as monotherapy.

(44) The method of any one of (1)-(42), further comprising at least one other anti-cancer therapy administered to the subject, optionally, the at least one other anti-cancer therapy is administered to the subject before, simultaneously, and/or after administration of the recombinant interferon.

(45) The method of (44), wherein the at least one other anti-cancer therapy comprises one or more of: chemotherapy, radiotherapy, surgical therapy, interventional therapy, biotherapy, gene therapy, ablation therapy, immunotherapy, targeted therapy, and traditional Chinese medicine therapy.

(46) The method of (45), wherein the at least one other anti-cancer therapy comprises chemotherapy.

(47) The method of (46), wherein the chemotherapy is the first-line chemotherapy.

(48) The method of (47), wherein one or more chemotherapeutic drugs are used for the first-line chemotherapy and comprise platinum compounds, such as Cisplatin.

(49) The method of (45), wherein the at least one other anti-cancer therapy comprises radiotherapy.

(50) The method of (49), wherein the radiotherapy comprises head gamma knife therapy when the lung cancer metastasizes to brain.

(51) The method of (45), wherein the at least one other anti-cancer therapy comprises surgical therapy.

(52) The method of (45), wherein the at least one other anti-cancer therapy comprises targeted therapy.

(53) The method of (52), wherein the targeted therapy comprises administering Gefitinib, Erlotinib, and/or recombinant human endostatin.

(54) The method of (45), wherein the at least one other anti-cancer therapy comprises biotherapy.

(55) The method of any one of (1)-(54), wherein the therapies eliminate the tumor of the lung or reduce the size of the tumor of the lung compared to the tumor size before treatment.

(56) The method of any one of (1)-(55), wherein the therapies are the non-surgical therapies.

In another aspect, another embodiment of the present invention provides:

(1) A method for treating cancer in a subject, wherein the cancer originates from lung cancer in the subject and metastasizes to brain, comprising administering to the subject a recombinant interferon encoded by SEQ ID NO: 2, wherein the recombinant interferon is administered one or more times by subcutaneous administration and/or intramuscular administration at an induction dose in a range of about 2 μg to about 10 μg each time, optionally about 4 μg to about 10 μg each time, further optionally about 4.5 μg to about 9 μg each time, such as about 4.5 μg each time or about 9 μg each time, and then the recombinant interferon is administered more times by subcutaneous administration and/or intramuscular administration at a therapeutic dose in a range of about 10 μg to about 70 μg each time, optionally about 12 μg to about 50 μg each time, further optionally about 12 μg to about 30 μg each time, and the recombinant interferon is administered to the subject by inhalation administration before, simultaneously, and/or after the subcutaneous administration and/or intramuscular administration, the recombinant interferon is administered in an amount in a range of about 100 μg to about 2000 μg, optionally about 100 μg to about 1500 μg, further optionally about 150 μg to about 800 μg, still further optionally about 200 μg to about 600 μg by one inhalation administration, and the recombinant interferon is administered by inhalation administration once every about 1 day to about 3 days, optionally every about 1 day.

(2) The method of (1), wherein the subject is a medium-term, advanced, or stage III or stage IV cancer patient, optionally, the subject is an advanced, or stage III or stage IV cancer patient.

(3) The method of (1) or (2), wherein the cancer is a cancer that is not indicated nor appropriate for surgery.

(4) The method of (1) or (2), wherein the tumor is a tumor that is not capable of being resected.

(5) The method of (4), wherein the tumor is resected by a surgical resection.

(6) The method of any one of (1)-(5), wherein the subcutaneous administration comprises subcutaneous injection.

(7) The method of any one of (1)-(5), wherein the intramuscular administration comprises intramuscular injection.

(8) The method of any one of (1)-(7), wherein the inhalation administration comprises pulmonary and/or nasal inhalation administration.

(9) The method of any one of (1)-(8), wherein the inhalation administration comprises aerosol inhalation.

(10) The method of any one of (1)-(9), wherein the time interval between administration of induction dose and administration of therapeutic dose is about 1 day to about 1 month, optionally about 1 day to about 1 week, further optionally about 1 day to about 3 days, comprising such as about 1 day, about 2 days, about 3 days, about 4 days, about 5 days, about 6 days, about 7 days, about 8 days, about 9 days, about 10 days, about 1 week, about 2 weeks, about 3 weeks, or about 1 month.

(11) The method of any one of (1)-(10), wherein the recombinant interferon is administered once every about 1 day to about 10 days, optionally every about 1 day to about 7 days, further optionally every about 1 to about 2 days, comprising such as every about 1, 2, 3, 4, 5, 6, 7, 8, 9, or 10 days when the recombinant interferon is administered more times at an induction dose.

(12) The method of any one of (1)-(11), wherein the recombinant interferon is administered at a therapeutic dose once every about 1 day to about 10 days, optionally every about 1 day to about 7 days, further optionally every about 1 to about 2 days, comprising such as every about 1, 2, 3, 4, 5, 6, 7, 8, 9, or 10 days.

(13) The method of any one of (1)-(12), wherein the duration of administration of induction dose and therapeutic dose is at least about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, or about 6 years and the like, or the recombinant interferon can be administered for a long time, including over the life time of the subject.

(14) The method of any one of (1)-(13), wherein the duration of the inhalation administration is at least about 1 day, about 2 days, about 3 days, about 4 days, about 5 days, about 6 days, about 7 days, about 8 days, about 9 days, about 10 days, about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, or about 6 years and the like, or the recombinant interferon can be administered for a long time, including over the life time of the subject; or the duration can also be about 1 day to about 6 years, about 1 week to about 4 years, about 2 weeks to about 3 years, about 1 month to about 1 year, or about 2 months to about 9 months and the like.

(15) The method of any one of (1)-(14), wherein the recombinant interferon is administered to the subject as monotherapy.

(16) The method of any one of (1)-(15), further comprising at least one other anti-cancer therapy administered to the subject, optionally, the at least one other anti-cancer therapy is administered to the subject before, simultaneously, and/or after administration of the recombinant interferon.

(17) The method of (16), wherein the at least one other anti-cancer therapy comprises one or more of: chemotherapy, radiotherapy, surgical therapy, interventional therapy, biotherapy, gene therapy, ablation therapy, immunotherapy, targeted therapy, and traditional Chinese medicine therapy.

(18) The method of (17), wherein the chemotherapy is the first-line chemotherapy, optionally, one or more chemotherapeutic drugs are used for the first-line chemotherapy and comprise platinum compounds, such as Cisplatin.

(19) The method of (17), wherein the targeted therapy comprises administering Gefitinib, Erlotinib, and/or recombinant human endostatin.

(20) The method of (17), wherein the at least one other anti-cancer therapy comprises radiotherapy.

(21) The method of (20), wherein the radiotherapy comprises gamma knife therapy.

(22) The method of (21), wherein the gamma knife therapy comprises head gamma knife therapy.

(23) The method of any one of (1)-(22), wherein the therapies eliminate the tumor or reduce the size of the tumor compared to the tumor before treatment.

(24) The method of any one of (1)-(23), wherein the therapies are the non-surgical therapies.

In another aspect, another embodiment of the present invention provides:

(1) A method for treating cancer in a subject, wherein the cancer originates from lung cancer in the subject and metastasizes to bone or liver, comprising administering to the subject a recombinant interferon encoded by SEQ ID NO: 2, wherein the recombinant interferon is administered one or more times by subcutaneous administration and/or intramuscular administration at an induction dose in a range of about 2 μg to about 10 μg each time, optionally about 4 μg to about 10 μg each time, further optionally about 4.5 μg to about 9 μg each time, such as about 4.5 μg each time or about 9 μg each time, and then the recombinant interferon is administered more times by subcutaneous administration and/or intramuscular administration at a therapeutic dose of about 10 μg-about 70 μg each time, optionally about 12 μg to about 50 μg each time, further optionally about 12 μg to about 30 μg each time.

(2) The method of (1), wherein the subject is a medium-term, advanced, or stage III or stage IV cancer patient, optionally, the subject is an advanced, or stage III or stage IV cancer patient.

(3) The method of (1) or (2), wherein the cancer is a cancer that is not indicated nor appropriate for surgery.

(4) The method of (1) or (2), wherein the tumor is a tumor that is not capable of being resected.

(5) The method of (4), wherein the tumor is resected by a surgical resection.

(6) The method of any one of (1)-(5), wherein the subcutaneous administration comprises subcutaneous injection.

(7) The method of any one of (1)-(5), wherein the intramuscular administration comprises intramuscular injection.

(8) The method of any one of (1)-(7), wherein the time interval between administration of induction dose and administration of therapeutic dose is about 1 day to about 1 month, optionally about 1 day to about 1 week, further optionally about 1 day to about 3 days, comprising such as about 1 day, about 2 days, about 3 days, about 4 days, about 5 days, about 6 days, about 7 days, about 8 days, about 9 days, about 10 days, about 1 week, about 2 weeks, about 3 weeks, or about 1 month.

(9) The method of any one of (1)-(8), wherein the recombinant interferon is administered once every about 1 day to about 10 days, optionally every about 1 day to about 7 days, further optionally every about 1 to about 2 days, comprising such as every about 1, 2, 3, 4, 5, 6, 7, 8, 9, or 10 days when the recombinant interferon is administered more times at an induction dose.

(10) The method of any one of (1)-(9), wherein the recombinant interferon is administered at a therapeutic dose once every about 1 day to about 10 days, optionally every about 1 day to about 7 days, further optionally every about 1 to about 2 days, comprising such as every about 1, 2, 3, 4, 5, 6, 7, 8, 9, or 10 days.

(11) The method of any one of (1)-(10), wherein the duration of administration of induction dose and therapeutic dose is at least about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, or about 6 years and the like, or the recombinant interferon can be administered for a long time, including over the life time of the subject.

(12) The method of any one of (1)-(11), further comprising administering to the subject the recombinant interferon by inhalation administration.

(13) The method of (12), wherein the inhalation administration is conducted before, simultaneously, and/or after the subcutaneous administration and/or intramuscular administration.

(14) The method of (12) or (13), wherein the inhalation administration comprises pulmonary and/or nasal inhalation administration.

(15) The method of any one of (12)-(14), wherein the inhalation administration comprises aerosol inhalation.

(16) The method of any one of (12)-(15), wherein the recombinant interferon is administered in an amount in a range of about 100 μg to about 2000 μg, optionally about 100 μg to about 1500 μg, further optionally about 150 μg to about 800 μg, still further optionally about 200 μg to about 600 μg by one inhalation administration, the recombinant interferon is administered by inhalation administration once every about 1 day to about 3 days, optionally every about 1 day, and the duration of the inhalation administration is at least about 1 day, about 2 days, about 3 days, about 4 days, about 5 days, about 6 days, about 7 days, about 8 days, about 9 days, about 10 days, about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, or about 6 years and the like, or the recombinant interferon can be administered for a long time, including over the life time of the subject; or the duration can also be about 1 day to about 6 years, about 1 week to about 4 years, about 2 weeks to about 3 years, about 1 month to about 1 year, or about 2 months to about 9 months and the like.

(17) The method of any one of (1)-(16), wherein the recombinant interferon is administered to the subject as monotherapy.

(18) The method of any one of (1)-(16), further comprising at least one other anti-cancer therapy administered to the subject, optionally, the at least one other anti-cancer therapy is administered to the subject before, simultaneously, and/or after administration of the recombinant interferon.

(19) The method of (18), wherein the at least one other anti-cancer therapy comprises one or more of: chemotherapy, radiotherapy, surgical therapy, interventional therapy, biotherapy, gene therapy, ablation therapy, immunotherapy, targeted therapy, and traditional Chinese medicine therapy.

(20) The method of (19), wherein the at least one other anti-cancer therapy comprises chemotherapy.

(21) The method of (20), wherein the chemotherapy is first-line chemotherapy.

(22) The method of (21), wherein one or more chemotherapeutic drugs are used for the first-line chemotherapy and comprise platinum compounds, such as Cisplatin.

(23) The method of (19), wherein the at least one other anti-cancer therapy comprises targeted therapy.

(24) The method of (23), wherein the targeted therapy comprises administering Gefitinib, Erlotinib, and/or recombinant human endostatin.

(25) The method of (19), wherein the at least one other anti-cancer therapy comprises biotherapy.

(26) The method of any one of (1)-(25), wherein the therapies eliminate the tumor or reduce the size of the tumor compared to the tumor before treatment.

(27) The method of any one of (1)-(26), wherein the therapies are the non-surgical therapies.

In another aspect, another embodiment of the present invention provides:

(1) A method for treating cancer in a subject, wherein the cancer originates from lung cancer in the subject and metastasizes to lymph nodes, comprising administering to the subject a recombinant interferon encoded by SEQ ID NO: 2, wherein the recombinant interferon is administered one or more times by subcutaneous administration and/or intramuscular administration at an induction dose in a range of about 2 μg to about 10 μg each time, optionally about 4 μg to about 10 μg each time, further optionally about 4.5 μg to about 9 μg each time, such as about 4.5 μg each time or about 9 μg each time, and then the recombinant interferon is administered more times by subcutaneous administration and/or intramuscular administration at a therapeutic dose of about 10 μg to about 70 μg each time, optionally about 12 μg to about 50 μg each time, further optionally about 12 μg to about 30 μg each time, and the recombinant interferon is administered to the tumor and/or the lymph nodes metastases by topical or local administration before, simultaneously, and/or after the subcutaneous administration and/or intramuscular administration.

(2) The method of (1), wherein the subject is a medium-term, advanced, or stage III or stage IV cancer patient, optionally, the subject is an advanced, or stage III or stage IV cancer patient.

(3) The method of (1) or (2), wherein the cancer is a cancer that is not indicated nor appropriate for surgery.

(4) The method of (1) or (2), wherein the tumor is a tumor that is not capable of being resected.

(5) The method of (4), wherein the tumor is resected by a surgical resection.

(6) The method of any one of (1)-(5), wherein the subcutaneous administration comprises subcutaneous injection.

(7) The method of any one of (1)-(5), wherein the intramuscular administration comprises intramuscular injection.

(8) The method of any one of (1)-(7), wherein the time interval between administration of induction dose and administration of therapeutic dose is about 1 day to about 1 month, optionally about 1 day to about 1 week, further optionally about 1 day to about 3 days, comprising such as about 1 day, about 2 days, about 3 days, about 4 days, about 5 days, about 6 days, about 7 days, about 8 days, about 9 days, about 10 days, about 1 week, about 2 weeks, about 3 weeks, or about 1 month.

(9) The method of any one of (1)-(8), wherein the recombinant interferon is administered once every about 1 day to about 10 days, optionally every about 1 day to about 7 days, further optionally every about 1 to about 2 days, comprising such as every about 1, 2, 3, 4, 5, 6, 7, 8, 9, or 10 days when the recombinant interferon is administered more times at an induction dose.

(10) The method of any one of (1)-(9), wherein the recombinant interferon is administered at a therapeutic dose once every about 1 day to about 10 days, optionally every about 1 day to about 7 days, further optionally every about 1 to about 2 days, comprising such as every about 1, 2, 3, 4, 5, 6, 7, 8, 9, or 10 days.

(11) The method of any one of (1)-(10), wherein the duration of administration of induction dose and therapeutic dose is at least about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, or about 6 years and the like, or the recombinant interferon can be administered for a long time, including over the life time of the subject.

(12) The method of any one of (1)-(11), wherein the local administration comprises intratumoral administration when the lymph nodes are the deep lymph nodes.

(13) The method of (12), wherein the intratumoral administration comprises intratumoral injection.

(14) The method of (12) or (13), wherein the recombinant interferon is administered in an amount in a range of about 60 µg to about 600 µg, optionally about 60 µg to about 500 µg, further optionally about 80 µg to about 400 µg, still further optionally about 100 µg to about 250 µg by one intratumoral administration, and the recombinant interferon is administered by intratumoral administration once every about 1 day to about 10 days, optionally every about 1 day to about 7 days such as every about 1, 2, 3, 4, 5, 6, or 7 days, the duration of the intratumoral administration is at least about 1 day, about 2 days, about 3 days, about 4 days, about 5 days, about 6 days, about 7 days, about 8 days, about 9 days, about 10 days, about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, or about 6 years and the like, or the recombinant interferon can be administered for a long time, including over the life time of the subject; or the duration can also be about 1 day to about 6 years, about 1 week to about 4 years, about 2 weeks to about 3 years, about 1 month to about 1 year, or about 2 months to about 9 months and the like.

(15) The method of any one of (12)-(14), wherein the protocol of intratumoral administration is as follow: the recombinant interferon is administered by intratumoral injection once every about 1 day for about 4 to about 8 times, and then the recombinant interferon is administered by intratumoral injection once every about 3 days to about 5 days for about 4 to about 8 times, and then the recombinant interferon is administered by intratumoral injection once every about 7 days, the intratumoral administration is stopped when the tumor and/or metastasized lymph nodes are disappeared or become too small to conduct the intratumoral injection.

(16) The method of any one of (1)-(11), wherein the topical or local administration comprises at least one of: infiltration administration, percutaneous administration, transdermal administration, epidermal administration, and transmucosal administration when the lymph nodes are superficial lymph nodes.

(17) The method of (16), wherein the local administration comprises infiltration administration.

(18) The method of (17), wherein the infiltration administration is conducted by perfusion.

(19) The method of (16), wherein the percutaneous administration, transdermal administration, epidermal administration, or transmucosal administration comprises percutaneous spray administration, transdermal spray administration, epidermal spray administration, or transmucosal spray administration, respectively.

(20) The method of (19), wherein the recombinant interferon is administered in an amount in a range of about 6 µg to about 100 µg by one spray administration.

(21) The method of (20), wherein the recombinant interferon is administered in an amount of about 10 µg to about 40 µg, optionally about 20 µg to about 40 µg by one spray administration.

(22) The method of any one of (19)-(21), wherein the recombinant interferon is administered by spray administration about 1 to about 6 times such as about 1, 2, 3, 4, 5, or 6 times per day.

(23) The method of any one of (1)-(22), wherein the recombinant interferon is administered to the subject as monotherapy.

(24) The method of any one of (1)-(22), further comprising at least one other anti-cancer therapy administered to the subject, optionally, the at least one other anti-cancer therapy is administered to the subject before, simultaneously, and/or after administration of the recombinant interferon.

(25) The method of (24), wherein the at least one other anti-cancer therapy comprises one or more of: chemotherapy, radiotherapy, surgical therapy, interventional therapy, biotherapy, gene therapy, ablation therapy, immunotherapy, targeted therapy, and traditional Chinese medicine therapy.

(26) The method of (25), wherein the at least one other anti-cancer therapy comprises chemotherapy.

(27) The method of (26), wherein the chemotherapy is first-line chemotherapy.

(28) The method of (27), wherein one or more chemotherapeutic drugs are used for the first-line chemotherapy and comprise platinum compounds, such as Cisplatin.

(29) The method of (25), wherein the at least one other anti-cancer therapy comprises targeted therapy.

(30) The method of (29), wherein the targeted therapy comprises administering Gefitinib, Erlotinib, and/or recombinant human endostatin.

(31) The method of (25), wherein the at least one other anti-cancer therapy comprises biotherapy.

(32) The method of any one of (1)-(31), wherein the therapies eliminate the tumor or reduce the size of the tumor compared to the tumor before treatment.

(33) The method of any one of (1)-(32), wherein the therapies are the non-surgical therapies.

In another aspect, another embodiment of the present invention provides:

(1) A method for treating lung cancer in a subject, wherein the subject has pleural effusion, ascites and/or pericardial effusion, comprising administering to the subject a recombinant interferon encoded by SEQ ID NO: 2 by topical or local administration.

(2) The method of (1), wherein the subject is a medium-term, advanced, or stage III or stage IV cancer patient, optionally, the subject is an advanced, or stage III or stage IV cancer patient.

(3) The method of (1) or (2), wherein the lung cancer is a lung cancer that is not indicated nor appropriate for surgery.

(4) The method of (1) or (2), wherein the lung cancer is a lung cancer that is not capable of being resected.

(5) The method of (4), wherein the tumor is resected by a surgical resection.

(6) The method of any one of (1)-(5), wherein the pleural effusion is a malignant pleural effusion, the ascites is a malignant ascites, and/or the pericardial effusion is a malignant pericardial effusion.

(7) The method of any one of (1)-(6), wherein the local administration comprises at least one of: infiltration administration, intrapleural administration, abdominal administration, and pericardial administration.

(8) The method of (7), wherein the local administration is conducted by perfusion.

(9) The method of (8), wherein the recombinant interferon is administered in an amount in a range of about 30 μg to about 2000 μg, optionally about 100 μg to about 1500 μg, further optionally about 150 μg to about 1000 μg, still optionally about 200 μg to about 800 μg, still further optionally about 200 μg to about 400 μg by one perfusion administration.

(10) The method of (8) or (9), wherein the recombinant interferon is administered by perfusion administration once every about 1 to about 10 days, optionally every about 1 to about 7 days, such as every about 1, 2, 3, 4, 5, 6, or 7 days.

(11) The method of (10), wherein the recombinant interferon is administered by perfusion administration once every about 1 day, lasting about 4 to about 6 times.

(12) The method of any one of (1)-(11), wherein the recombinant interferon is administered to the subject by systemic administration before, simultaneously, and/or after the topical or local administration.

(13) The method of (12), wherein the systemic administration comprises subcutaneous and/or intramuscular administration.

(14) The method of (13), wherein the subcutaneous administration comprises subcutaneous injection.

(15) The method of (13), wherein the intramuscular administration comprises intramuscular injection.

(16) The method of any one of (13)-(15), wherein the recombinant interferon is administered one or more times by subcutaneous administration and/or intramuscular administration at an induction dose in a range of about 2 μg to about 10 μg each time, optionally about 4 μg to about 10 μg each time, further optionally about 4.5 μg to about 9 μg each time, such as about 4.5 μg each time or about 9 μg each time, and then the recombinant interferon is administered more times by subcutaneous administration and/or intramuscular administration at a therapeutic dose of about 10 μg to about 70 μg each time, optionally about 12 μg to about 50 μg each time, further optionally about 12 μg to about 30 μg each time.

(17) The method of (16), wherein the time interval between administration of induction dose and administration of therapeutic dose is about 1 day to about 1 month, optionally about 1 day to about 1 week, further optionally about 1 day to about 3 days, comprising such as about 1 day, about 2 days, about 3 days, about 4 days, about 5 days, about 6 days, about 7 days, about 8 days, about 9 days, about 10 days, about 1 week, about 2 weeks, about 3 weeks, or about 1 month.

(18) The method of (16) or (17), wherein the recombinant interferon is administered once every about 1 day to about 10 days, optionally every about 1 day to about 7 days, further optionally every about 1 to about 2 days, comprising such as every about 1, 2, 3, 4, 5, 6, 7, 8, 9, or 10 days when the recombinant interferon is administered more times at an induction dose.

(19) The method of any one of (16)-(18), wherein the recombinant interferon is administered at a therapeutic dose once every about 1 day to about 10 days, optionally every about 1 day to about 7 days, further optionally every about 1 to about 2 days, comprising such as every about 1, 2, 3, 4, 5, 6, 7, 8, 9, or 10 days.

(20) The method of any one of (16)-(19), wherein the duration of administration of induction dose and therapeutic dose is at least about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, or about 6 years and the like, or the recombinant interferon can be administered for a long time, including over the life time of the subject.

(21) The method of any one of (1)-(20), wherein other therapeutic drugs are further administered by topical, local and/or systemic administration

(22) The method of (21), wherein the other therapeutic drugs comprise antitumor drugs.

(23) The method of (22), wherein the antitumor drugs comprise one or more chemotherapeutic drugs, targeted drugs, or biological drugs.

(24) The method of (23), wherein one or more chemotherapeutic drugs comprise platinum compounds, such as Cisplatin.

(25) The method of (23), wherein one or more targeted drugs comprise Gefitinib, Erlotinib, and/or recombinant human endostatin

(26) The method of any one of (1)-(25), wherein the therapies eliminate the tumor or reduce the size of the tumor compared to the tumor size before treatment.

(27) The method of any one of (1)-(26), wherein the therapies are the non-surgical therapies.

More specifically, in one embodiment, in any one of the methods of the present invention mentioned above, the tumor is a solid tumor; optionally, the solid tumor comprises one or more of: lung cancer, liver cancer, hepatocellular carcinoma (HCC), esophageal cancer, cholangiocarcinoma, gallbladder carcinoma, stomach cancer, abdominal cancer, gastrointestinal cancer, gastric cancer, pancreatic cancer, renal cell carcinoma, renal cancer, bone cancer, breast cancer, ovarian cancer, uterine cancer, cervical cancer, endometrial cancer, colorectal cancer, colon cancer, rectal cancer, bladder cancer, superficial bladder cancer, prostate cancer, adrenal tumors, squamous cell carcinoma, neuroma, malignant neuroma, myoepithelial carcinoma, synovial sarcoma, rhabdomyosarcoma, gastrointestinal interstitial cell tumor, skin cancer, basal cell carcinoma, malignant melanoma, thyroid cancer, nasopharyngeal carcinoma, hemangioma, epidermoid carcinoma, head and neck cancer, glioma, or Kaposi's sarcoma.

In any one of methods of the present invention mentioned above, the tumor is a tumor such as cancer or solid tumor without indications for surgery or not indicated or appropriate for surgery; and/or the subject is a medium-term, advanced cancer patient, or III or IV stage cancer patient, optionally, the subject is an advanced, or III or IV stage cancer patient.

In any one of methods of the present invention mentioned above, the recombinant interferon is administered to the subject as monotherapy; or, further comprising one or more other anti-cancer therapies administered to the subject, optionally, other anti-cancer therapies are administered to the subject before, simultaneously, and/or after administration of the recombinant interferon. Optionally, the other anti-cancer therapies comprise one or more of: chemotherapy, radiotherapy, surgical therapy, interventional therapy, biotherapy, gene therapy, ablation therapy, immunotherapy, targeted therapy, and traditional Chinese medicine therapy.

And, in another aspect, another embodiment of the present invention also provides:

(1) A method of treating a tumor in a subject comprising administering to the subject a recombinant interferon that comprises an anti-tumor effect as a first line monotherapy.

(2) The method of (1), wherein the tumor comprises one of: lung cancer, uterine cancer, cervical cancer, and pancreatic cancer.

(3) The method of (2), wherein the lung cancer comprises non-small cell lung cancer.

(4) The method of (1), wherein the tumor is not a kidney cancer.

(5) A method of treating a tumor in a subject comprising administering to the subject a recombinant interferon that comprises an antitumor effect as a second line monotherapy.

(6) The method of (5), wherein the tumor comprises one of: lung cancer, colorectal cancer, malignant melanoma, ovarian cancer, cervical cancer, liver cancer, breast cancer, gastrointestinal cancer, prostate cancer, neuroma, and squamous cell carcinoma.

(7) The method of (6), wherein the colorectal cancer comprises colon cancer.

(8) The method of (6), wherein the colorectal cancer comprises rectal cancer.

(9) The method of (6), wherein the lung cancer comprises non-small cell lung cancer.

(10) The method of (6), wherein the liver cancer comprises HCC.

(11) The method of (6), wherein the gastrointestinal cancer comprises gastric cancer.

(12) A method of treating a tumor in a subject comprising administering to the subject a recombinant interferon that comprises an anti-tumor effect as a first line therapy in combination with one or more other anti-cancer therapy.

(13) The method of (12), wherein the tumor comprises one of: lung cancer, prostate cancer, and lymphoma.

(14) The method of (13), wherein the lung cancer comprises at least one of non-small cell lung cancer and small cell lung cancer.

(15) The method of (12), wherein the tumor is not an ovarian cancer.

(16) A method of treating a tumor in a subject comprising administering to the subject a recombinant interferon that comprises an anti-tumor effect as a second line therapy in combination with one or more other anti-cancer therapies.

(17) The method of (16), wherein the tumor comprises one of: lung cancer, lymphoma, cervical cancer, and cholangioadenocarcinoma.

(18) The method of (17), wherein the lung cancer comprises at least one of non-small cell lung cancer and small cell lung cancer.

(19) The method of (17), wherein the lymphoma is non-Hodgkins lymphoma.

(20) The method of any of (12), (13), (14), (15), (16), (17), (18), or (19), wherein the one or more other anti-cancer therapies comprise at least one of: radiotherapy, small molecule therapy, chemotherapy, biologics therapy, TCM, and surgery.

(21) The method of (20), wherein the small molecule in the small molecule therapy comprises Getifinib.

(22) The method of (20), wherein the biologics therapy comprises treatment with at least one of: a recombinant protein and isolated cells.

(23) The method of (22), wherein the recombinant protein comprises Endostar.

(24) The method of (22), wherein the isolated cells comprises at least one of: stem cells and NK cells.

(25) The method of (20), wherein the recombinant interferon is administered after surgical treatment of cancer.

(26) The method of any of (20)-(24), wherein the recombinant interferon is administered prior to surgical treatment of cancer.

(27) The method of any of (1)-(26), wherein the recombinant interferon is administered by at least one of the following routes: systemically and locally.

(28) The method of any of (1)-(26), wherein the recombinant interferon is administered by at least one of the following routes: intramuscularly, intraperitoneally, intravenously, intra-arterially, intratumorally, by injection into lymph nodes, topically, locally on the tumor, intranasally, subcutaneously, by spraying, by inhalation, by perfusion, and by infusion.

(29) The method of any of (1)-(28), wherein the recombinant interferon comprises rSIFN-co.

(30) The method of (29), wherein the recombinant interferon is administered at a dose in a range of about 2 μg to about 2500 μg per treatment.

(31) The method of (29), wherein recombinant interferon is administered at a dose in a range of about 9 μg to about 2100 μg per treatment.

(32) The method of (29), wherein recombinant interferon is administered at a dose of one or more of the following doses: 2 μg, 4 μg, 9 μg, 13.5 μg, 15 μg, 18 μg, 21 μg, 24 μg, 25.5 μg, 180 μg, 189 μg, 198 μg, 200 μg, 207 μg, 210 μg, 240 μg, 252 μg, 273 μg, 300 μg, 315 μg, 400 μg, 500 μg, 600 μg, 1000 μg, 2000 μg, 2100 μg.

(33) The method of any of (1)-(32), wherein the recombinant interferon comprises a specified activity.

(34) The method of (33), wherein the recombinant interferon comprises an activity in the range of about $4.4 \times 10^8$ IU/mg to about $1.0 \times 10^9$ IU/mg, and optionally greater than $5.5 \times 10^8$ IU/mg.

(35) A method of preventing tumor recurrence in a subject comprising administering an amount of a recombinant interferon that comprises an amino acid sequence that is encoded by a nucleic acid sequence comprising the sequence of SEQ ID NO: 2 after surgery, chemotherapy, radiotherapy, cryoablation, radiofrequency ablation, biologics therapy, intervention therapy, and/or rSIFN-co therapy, whereby the recombinant interferon is administered after tumor bulk in the subject has been reduced.

(36) A method of prolonging tumor-free survival in a subject comprising administering an amount of a recombinant interferon that comprises an amino acid sequence that is encoded by a nucleic acid sequence comprising the sequence of SEQ ID NO: 2 after surgery, chemotherapy, radiotherapy, cryoablation, radiofrequency ablation, biologics therapy, intervention therapy, and/or rSIFN-co therapy, whereby the recombinant interferon is administered after tumor bulk in the subject has been reduced.

BRIEF DESCRIPTION OF THE DRAWINGS

FIGS. 4A and 4B shows the treatment situation of patient 2, wherein FIG. 4A shows a PET/CT imaging diagnosis before rSIFN-co medication, and an arrow indicates the lesion; and FIG. 4B shows a PET/CT imaging diagnosis after rSIFN-co medication, and an arrow indicates the state of the original lesion after treatment.

FIGS. 5A, 5B, 6A and 6B show the treatment situation of patient 3, wherein FIG. 5A shows a lung CT image before rSIFN-co medication, and an arrow indicates the lesion; FIG. 5B shows head and chest CT imaging diagnoses after rSIFN-co medication, and an arrow indicates the state of the original lesion after treatment; FIG. 6A shows a brain CT image before rSIFN-co medication, and an arrow indicates the lesion; and FIG. 6B shows head and chest imaging diagnoses after rSIFN-co medication, and an arrow indicates the state of the original lesion after treatment.

FIGS. 7A, 7B, 8A and 8B show the treatment situation of patient 4, wherein FIGS. 7A and 8A show imaging diagnoses before rSIFN-co medication: as shown in PET/CT after chemotherapy, arrows in the FIGS. 7A and 8A indicate the lesions; and FIGS. 7B and 8B show imaging diagnoses after rSIFN-co medication: as shown in PET/CT, an arrow indicates the state of the original lesion after treatment.

FIGS. 9A, 9B, 10A and 10B and FIGS. 11A and 11B show the treatment situation of patient 5, wherein FIGS. 9A, 10A and 11A show imaging diagnoses before rSIFN-co medication: as shown in PET/CT, and arrows in the FIGS. 9A, 10A and 11A show the lesions; and FIGS. 9B, 10B and 11B show imaging diagnoses after rSIFN-co medication: as shown in PET/CT, and arrows in the FIGS. 9B, 10B and 11B show the states of the original lesions after treatment.

FIGS. 12A and 12B shows the treatment situation of patient 6, wherein FIG. 12A shows a chest CT imaging diagnosis before rSIFN-co medication, and an arrow shows the original lesion; and FIG. 12B shows a CT imaging diagnosis after rSIFN-co medication, and an arrow shows the state of the original lesion after treatment.

FIGS. 13A, 13B, 14A and 14B show the treatment situation of patient 7, wherein FIGS. 13A and 14A show CT imaging diagnoses before rSIFN-co medication, and arrows show the original lesions; and FIGS. 13B and 14B show CT imaging diagnoses after rSIFN-co medication, and arrows show the states of the original lesions after treatment.

FIGS. 15A, 15B, 16A and 16B show the treatment situation of patient 8, wherein FIGS. 15A and 16A show CT imaging diagnoses before rSIFN-co medication, and arrows show the original lesions; and FIGS. 15B and 16B show CT imaging diagnoses after rSIFN-co medication, and arrows show the states of the original lesions after treatment.

FIGS. 17A and 17B shows the treatment situation of patient 9, wherein FIG. 17A shows a CT imaging diagnosis before rSIFN-co medication, and an arrow shows the original lesion; and FIG. 17B shows a CT imaging diagnosis after rSIFN-co medication, and an arrow shows the state of the original lesion after treatment.

FIGS. 18, 19A and 19B show the treatment situation of patient 10, wherein the FIG. 18 shows pleural effusion change before and after the treatment; FIG. 19A shows a chest CT imaging diagnosis before rSIFN-co medication, and an arrow shows the original lesion; and FIG. 19B shows a chest CT imaging diagnosis after rSIFN-co medication, and an arrow shows the state of the original lesion after treatment.

FIGS. 20, 21A, 21B, 22A, 22B, 23A and 23B show the treatment situation of patient 11, wherein FIG. 20 shows the biopsy of patient before treatment, FIGS. 21A, 22A and 23A show PET/CT imaging diagnoses before rSIFN-co medication, and arrows show the original lesions; and FIGS. 21B, 22B and 23B show PET/CT imaging diagnoses after rSIFN-co medication, and arrows show the states of the original lesions after treatment.

FIGS. 24A and 24B shows the treatment situation of patient 12, wherein FIG. 24A shows a CT image at the beginning of the medicine administration, and an arrow shows the original lesion; and FIG. 24B shows an imaging diagnosis after rSIFN-co medication, and an arrow shows the state of the original lesion after treatment.

FIGS. 25A and 25B shows the treatment situation of patient 13, wherein FIG. 25A shows a CT image at the early stage of the treatment, and an arrow shows suspicious lesions of inferior lobe of right lung; and FIG. 25B shows a chest CT image at the later stage of the treatment, and an arrow shows the state of original suspicious lesions of inferior lobe of right lung after treatment.

FIGS. 26A and 26B shows the treatment situation of patient 14, wherein FIG. 26A shows a CT image at the beginning of the medicine administration (after surgery), and an arrow shows the original lesion; and FIG. 26B shows a CT image at the later stage of the treatment, and an arrow shows the state of the original lesion after treatment.

FIGS. 27A and 27B shows the treatment situation of patient 15, wherein FIG. 27A shows a pelvic cavity MRI imaging diagnosis before rSIFN-co medication, and an arrow shows the original lesion; and FIG. 27B shows a pelvic cavity MRI imaging diagnosis after rSIFN-co medication, and an arrow shows the state of the original lesion after treatment.

FIGS. 29A and 29B shows the treatment situation of the patient 16, wherein FIG. 29A shows a PEC/CT imaging diagnosis before rSIFN-co medication, and an arrow shows the original lesion; and FIG. 29B shows a PEC/CT imaging diagnosis after rSIFN-co medication, and an arrow show the state of the original lesion after treatment.

DETAILED DESCRIPTION OF THE INVENTION

Figure 1:
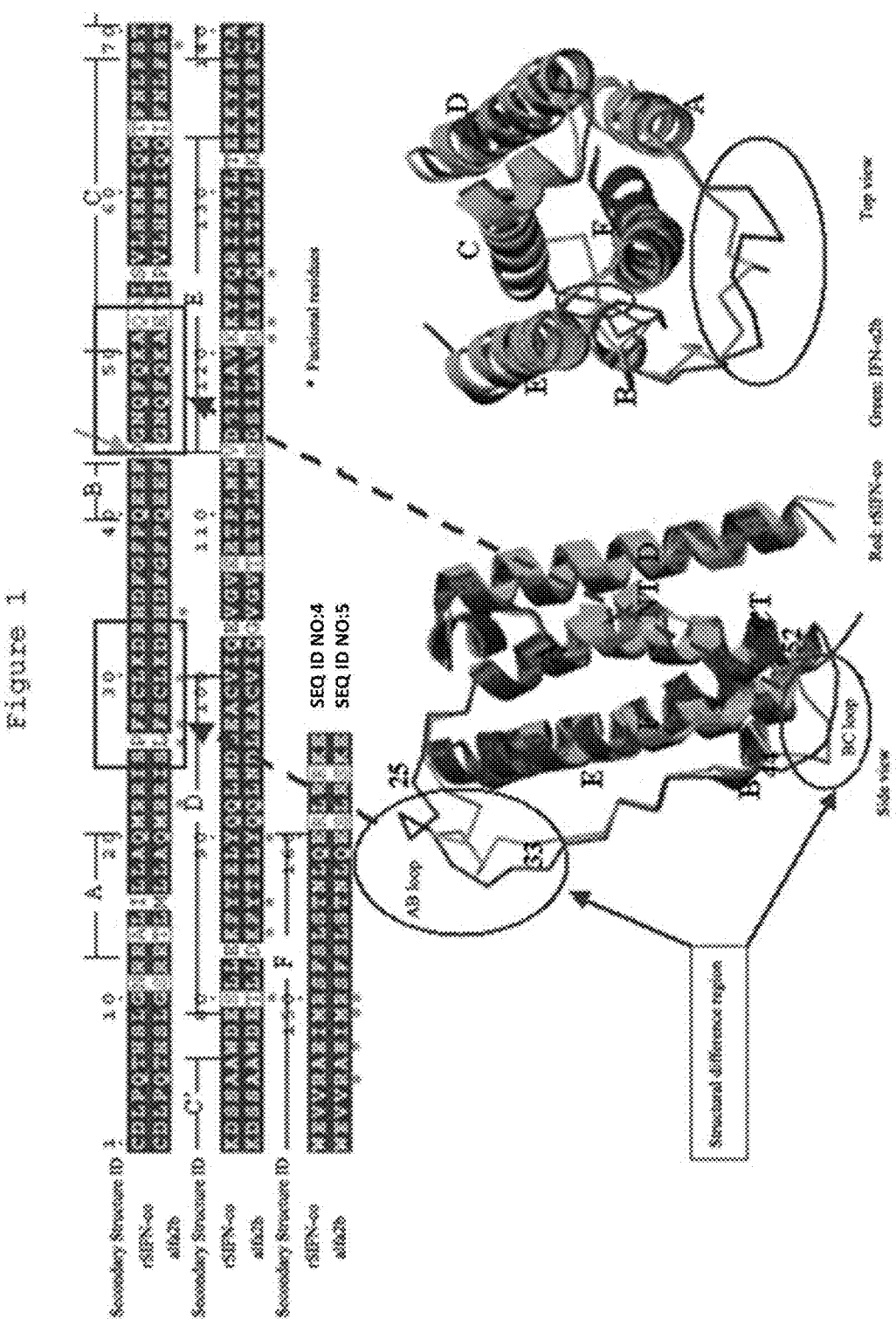
FIG. 1 shows the comparative difference in the structures of the present recombinant interferon (rSIFN-co) and IFN-α2b, wherein in a side view and a top view in the FIG. 1, the red shows rSIFN-co, the green shows IFN-α2b, the red is black in a black and white print drawing, and the green is grey in the black and white print drawing.

The inventor found that rSIFN-co can be advantageously used to control cancer, either alone or in combination with other anti-cancer therapies, as a first line or second line monotherapy or in combination with other treatment modalities. The advantages are: Firstly, the recombinant interferon (rSIFN-co) has broad-spectrum anti-tumor effects, which is effective to treat both solid tumors and non-solid tumors. At the same time, rSIFN-co has good synergetic effect with existing treatment means such as surgical therapy, chemotherapy, radiotherapy, other biotherapies and other anti-tumor drugs. Secondly, rSIFN-co has low toxicity, which means that little or no harm to normal cells has been observed when rSIFN-co is used in large doses. Thirdly, rSIFN-co is convenient to use and can be directly applied to tumors located in any part of the body. Thus, rSIFN-co can be used by subcutaneous or intramuscular injection to control systemic progression of tumor, by intrapleural or abdominal perfusion to eliminate effusion and intrapleural or abdominal tumors, by topical or local injection to eliminate primary or metastatic tumors, and by infiltration (transdermal) administration to treat tumor lesions in bone, skin, muscle, prostate and the like. Also, rSIFN-co can be administered by aerosol inhalation or by nasal spray.

According to the above advantages of rSIFN-co, its effective rate on tumors, as a monotherapy and as one element of a combination therapy, is not lower than 90%. With regard to early or medium-term cancer cases, rSIFN-co can be used after surgery in place of chemotherapy and effectively prevent recurrence and tumor metastasis or prolong the period of disease-free survival; with regard to advanced cancer cases or cancer cases that are not indicated for surgery, rSIFN-co can be used to eliminate or reduce the size of tumors without surgery; with regard to tumors that are not indicated for surgery, rSIFN-co can be used to transform the tumors into ones for which surgery is possible, that is, turning a non-resectable tumor into a resectable tumor, thereby creating conditions appropriate for surgery. Therefore, rSIFN-co, alone or in combination with other one or more anti-tumor therapy, is capable of controlling cancer in a large number of instances.

1. The Recombinant Interferon (rSIFN-co) and Preparation Method Thereof

In one aspect, the amino acid sequence of the present recombinant interferon, as well as the nucleotide sequence encoding the same (together with a termination codon), are shown below as SEQ ID NO:1 and SEQ ID NO:2, respectively. These sequences are also referenced in U.S. Pat. Nos. 7,585,647; 7,364,724; 8,114,395 and 8,287,852:

```
        M    C    D    L    P    Q      T    H    S    L    G    N    R      R    A    L      I    L    L    A

1 ATGTGCGACC TGCCGCAGAC CCACTCCCTG GGTAACCGTC GTGCTCTGAT CCTGCTGGCT

TACACGCTGG ACGGCGTCTG GGTGAGGGAC CCATTGGCAG CACGAGACTA GGACGACCGA

Q    M    R    R    I    S    P      F    S    C      L    K    D      R    H    D      F    G    F    P
 61 CAGATGCGTC GTATCTCCCC GTTCTCCTGC CTGAAAGACC GTCACGACTT CGGTTTCCCG

GTCTACGCAG CATAGAGGGG CAAGAGGACG GACTTTCTGG CAGTGCTGAA GCCAAAGGGC

Q    E    E    F    D    G    N      Q    F    Q      K    A    Q      A    I    S      V    L    H    E
121 CAGGAAGAAT TCGACGGTAA CCAGTTCCAG AAAGCTCAGG CTATCTCCGT TCTGCACGAA

GTCCTTCTTA AGCTGCCATT GGTCAAGGTC TTTCGAGTCC GATAGAGGCA AGACGTGCTT
```

-continued

```
    M   I   Q   Q   T   F   N   L   F   S   T   K   D   S   S   A   A   W   D   E

181 ATGATCCAGC AGACCTTCAA CCTGTTCTCC ACCAAAGACT CCTCCGCTGC TTGGGACGAA

TACTAGGTCG TCTGGAAGTT GGACAAGAGG TGGTTTCTGA GGAGGCGACG AACCCTGCTT

S   L   L   E   K   F   Y   T   E   L   Y   Q   Q   L   N   D   L   E   A   C

241 TCCCTGCTGG AAAAATTCTA CACCGAACTG TACCAGCAGC TGAACGACCT GGAAGCTTGC

AGGGACGACC TTTTTAAGAT GTGGCTTGAC ATGGTCGTCG ACTTGCTGGA CCTTCGAACG

V   I   Q   E   V   G   V   E   E   T   P   L   M   N   V   D   S   I   L   A

301 GTTATCCAGG AAGTTGGTGT TGAAGAAACC CCGCTGATGA ACGTTGACTC CATCCTGGCT

CAATAGGTCC TTCAACCACA ACTTCTTTGG GGCGACTACT TGCAACTGAG GTAGGACCGA

V   K   K   Y   F   Q   R   I   T   L   Y   L   T   E   K   K   Y   S   P   C

361 GTTAAAAAAT ACTTCCAGCG TATCACCCTG TACCTGACCG AAAAAAAATA CTCCCCGTGC

CAATTTTTTA TGAAGGTCGC ATAGTGGGAC ATGGACTGGC TTTTTTTTAT GAGGGGCACG

A   W   E   V   V   R   A   E   I   M   R   S   F   S   L   S   T   N   L   Q

421 GCTTGGGAAG TTGTTCGTGC TGAAATCATG CGTTCCTTCT CCCTGTCCAC CAACCTGCAG

CGAACCCTTC AACAAGCACG ACTTTAGTAC GCAAGGAAGA GGGACAGGTG GTTGGACGTC

E   R   L   R   R   K   E   (SEQ ID NO: 1)

481 GAACGTCTGC GTCGTAAAGA ATAA (SEQ ID NO: 2)

CTTGCAGACG CAGCATTTCT TATT (SEQ ID NO: 3)
```

Figure 2:
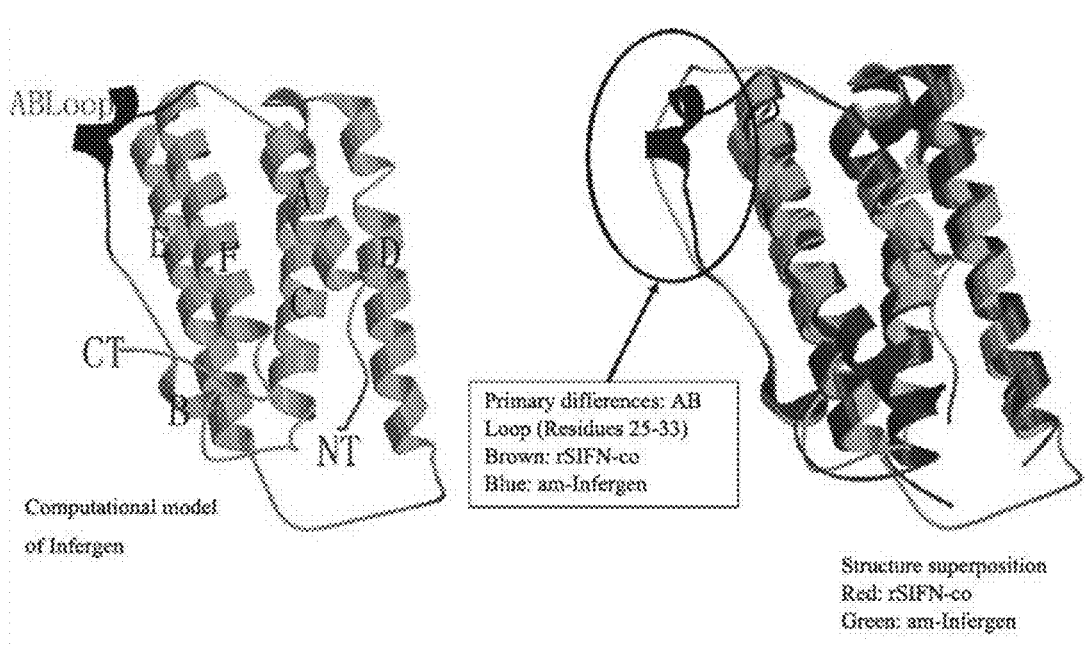
FIG. 2 shows the comparative difference of the three-dimensional structure of the recombinant interferon rSIFN-co of the present invention and the computation model structure of INFERGEN® (being indicated as am-Infergen or Infergen) of the US Amgen, wherein in a circle in the right drawing, a thin line in yellow is rSIFN-co, and a thick spiral in blue is am-Infergen. Meanwhile, in the right drawing, the red shows rSIFN-co, and the green shows am-Infergen, wherein the red is black in the black and white print drawing, and the green is grey in the black and white print drawing.

Compared with the IFN-α2b as published and the interferon such as interferon alfacon-1 (INFERGEN®), which has the amino acid sequence of SEQ ID NO: 1, but is not encoded by the nucleotide sequence of SEQ ID NO: 2, the three-dimensional structure of the present recombinant interferon (rSIFN-co) is different from the three-dimensional structure of IFN-α2b (see FIG. 1, wherein in the side view and the top view in the FIG. 1, the red represents rSIFN-co, the green represents IFN-α2b, the red is black in the black-and-white print drawing, and the green is grey in the black-and-white print drawing) and the computation model structure of the interferon alfacon-1 (see KORN, AP, Journal of Interferon Research 1994, 14:1-9). According to the comparison result between the present recombinant interferon and the interferon alfacon-1, there are obvious differences between the AB loops of the two, and their BC loops also cannot overlap completely (see FIG. 2).

In addition, after intramuscular injection of the present recombinant interferon into subjects whose BMI ranged from about 18 to about 23, the time of blood sample collection was plotted against the concentration of 2-5A oligonucleotidase (also referred to as 2', 5'-OAS) in the serum of the subjects. The chart generally shows a two-peak pattern, and the resulting area under the curve of this chart is significantly greater than that of interferon alfacon-1 (INFERGEN®) after injection under the same conditions. Furthermore, the half-life period of this recombinant interferon is longer than that of interferon alfacon-1 (INFERGEN®) after injection into the body (see CN 1740197A; Zeng, J. P. et al. Modern Preventive Medicine, 2008, 35(5), 982-984).

The experimental results have also confirmed that the present recombinant interferon is more effective than any interferon used clinically at present (including interferon alfacon-1 (INFERGEN®)). For example, for HBV, the present recombinant interferon is capable of not only inhibiting DNA replication of HBV, but also inhibiting secretion of both hepatitis B surface antigen (HBsAg) and hepatitis B e antigen (HBeAg). The efficiency of inhibiting DNA replication of hepatitis B core antigen (HBcAg) by this interferon is about twice that of interferon alfacon-1 (INFERGEN®). The in vitro pharmacodynamics of the present recombinant interferon shows that it is capable of not only inhibiting the DNA replication of HBV, but also inhibiting secretion of both hepatitis B surface antigen and hepatitis B e antigen. The cytotoxicity of the present recombinant interferon is only ⅛ that of the current clinically used interferons, but its antiviral activity is as much as 5-20 times greater; meanwhile, the biological responses of the present recombinant interferon is more effective, more broad-spectrum and longer lasting in the human body (see CN 1740197A).

Furthermore, with respect to prevention of viral diseases or treatment of tumor, the present recombinant interferon shows higher antiviral activity and less side effects compared with any other interferons (including interferon alfacon-1 (INFERGEN®)). For example, this recombinant interferon possesses not only an antiviral activity 20 times as great as that of the interferons currently in clinical use, but also a more effective inhibiting tumor cell growth or promoting apoptosis function compared with recombinant human interferon α.

Thus, the present recombinant interferon has a different spatial configuration, enhanced biologic activities and/or different pharmacokinetics characteristics as compared with the interferon such as interferon alfacon-1 (INFERGEN®), which has the amino acid sequence of SEQ ID NO: 1, but is not encoded by the nucleotide sequence of SEQ ID NO: 2.

Therefore, in some embodiments, the present recombinant interferon has the amino acid sequence of SEQ ID NO:

1, such as consisting of the amino acid sequence of SEQ ID NO: 1. In some embodiments, the present recombinant interferon is encoded by the nucleotide sequence of SEQ ID NO: 2. In some embodiments, the present recombinant interferon has the amino acid sequence of SEQ ID NO: 1, and is encoded by the nucleotide sequence of SEQ ID NO: 2. Further, the recombinant interferon comprises the amino acid sequence of SEQ ID NO: 1, and is encoded by the nucleotide sequence of SEQ ID NO: 2. Still further, the recombinant interferon is consisted of the amino acid sequence of SEQ ID NO: 1, and is encoded by the nucleotide sequence of SEQ ID NO: 2.

In some embodiments, in comparison with interferon such as interferon alfacon-1 (INFERGEN®), which has the amino acid sequence of SEQ ID NO: 1, but is not encoded by the nucleotide sequence of SEQ ID NO: 2, the present recombinant interferon has a changed spatial configuration and/or enhanced biologic activities and/or different pharmacokinetics characteristics. For example, the present recombinant interferon has a changed spatial configuration and enhanced biologic activities, changed spatial configuration and different pharmacokinetics characteristics, or changed spatial configuration, enhanced biologic activities and different pharmacokinetics characteristics. The enhanced biological activities include: enhanced antiviral activity, enhanced tumor cell growth inhibition or proapoptotic effect, less side effects and/or could be used in large dose (e.g. each dose>10 million IU). For example, the enhanced biological activities can be enhanced antiviral activity and/or enhanced tumor cell (such as breast cancer cell or cervical cancer cell) growth inhibition or proapoptotic effect (see Zheng, J. et al. J Sichuan Univ (Med Sci Edi), 2010, 41(1), 29-34; Chen, Y, et al. J Sichuan Univ (Med Sci Edi), 2008, 39(5), 715-718). The different pharmacokinetics characteristics include: after intramuscular injection of the recombinant interferon in subjects whose BMI ranged from about 18 to about 23, the time of blood sample collection was plotted against the concentration of 2-5A oligonucleotidase in the serum of the subjects, and the resulting area under the curve of this chart is significantly greater and/or the half-life of this recombinant interferon in the body is longer than those of the interferon such as interferon alfacon-1 (INFERGEN®), which has the amino acid sequence of SEQ ID NO: 1, but is not encoded by the nucleotide sequence of SEQ ID NO: 2 after injection under the same conditions.

In some embodiments, the present recombinant interferon has the amino acid sequence of SEQ ID NO: 1, and is encoded by the nucleotide sequence of SEQ ID NO: 2, wherein the recombinant interferon has increased inhibitory activities on the expression of hepatitis B surface antigen (HBsAg) and hepatitis B e antigen (HBeAg) of Hepatitis B Virus as compared to an interferon such as interferon alfacon-1 (INFERGEN®), which has the amino acid sequence of SEQ ID NO: 1, but is not encoded by the nucleotide sequence of SEQ ID NO: 2.

In another aspect, the recombinant interferon (rSIFN-co) used in the present invention can be produced by the methods disclosed in, for example, U.S. Pat. Nos. 7,364,724, 7,585,647, 8,114,395, CN 1740197 A, CN 101001644 A, US 2009/0123417, US 2011/0158941 and WO 2011072487A1. In a specific embodiment, the present recombinant interferon can be produced by the method comprising the following steps: introducing a nucleotide sequence comprising SEQ ID NO: 2 that encodes the recombinant interferon into an isolated host cell; culturing the host cell under appropriate condition for expression of the recombinant interferon; and harvesting the recombinant interferon, wherein the recombinant interferon has an amino acid sequence of SEQ ID NO: 1, and the recombinant interferon inhibits secretion of hepatitis B surface antigen (HBsAg) and hepatitis B e antigen (HBeAg) of Hepatitis B Virus. Further, the host cell is *Escherichia coli*, such as *Escherichia coli* LGM 194. Further, the nucleotide sequence comprising SEQ ID NO: 2 is under the control of the promoter $P_{BAD}$. Further, the harvesting step comprises extraction of the interferon from the fermentation broth, collection of the inclusion bodies, denaturation and renaturation of the harvested interferon. Still further, the harvesting step also comprises separation and purification of the recombinant interferon.

The person skilled in the art can prepare intramuscular injection dosage form, spray dosage form, or inhalation dosage form and the like of the present recombinant interferon with reference to the contents of the following part D with title of Pharmaceutical composition and administration route.

The specific activity of the present recombinant interferon is in a range of about $4.4 \times 10^8$ IU/mg to about $1.0 \times 10^9$ IU/mg, and optionally greater than $5.5 \times 10^8$ IU/mg. Such specific activity is the ratio of the biological activity and the content of protein. The biological activity is measured by a method well-known by the person skilled in the art such as the biological activity measurement method for the interferon (i.e. the cell lesion inhibition method) published in the Appendix X C in Chinese Pharmacopoeia (the third book), Edition 2010; and the content of the protein is measured by a method well-known by the person skilled in the art such as the second method (i.e. the Lowry method) of protein measurement method published in the Appendix VI B in Chinese Pharmacopoeia (the third book), Edition 2010.

2. Therapeutic Uses

The inventor has found that the present recombinant interferon (rSIFN-co) can be effectively used for treating tumors, in particular, solid tumors such as lung cancers and the like. Monotherapy using the present recombinant interferon, rSIFN-co, can suppress the growth of the tumors in patients, reduce the size of tumors in the patients effectively, even non-surgically directly eliminate tumors in the patients, reduce and even eliminate malignant pleural effusion, malignant ascites and/or malignant pericardial effusion, reduce tumor markers, effectively prolong the survival and/or tumor-free survival of the tumor patients and prevent postoperative cancer recurrence and/or metastasis of the tumor in the patients, and effectively treat advanced cancer patients and the cancer patients that are not indicated or appropriate for surgery. Combining other anti-cancer therapies such as one or more of chemotherapy, radiotherapy, surgical therapy, or targeted therapy, the present recombinant interferon can effectively eliminate the tumors of the patients so as to achieve the effect of cure in some embodiments. In addition, compared with existing interferons such as INFERGEN®, the present recombinant interferon has less side effects, so that it can be used in larger doses.

A. Diseases and Conditions

The diseases and conditions suitable for the treatment and/or prevention method of the invention include tumors. As used herein, the term "tumor" refers to all uncontrolled and malignant neoplastic cell growth and proliferation as well as all cancerous cells and tissues, and abnormally or aberrantly proliferative cells. In some embodiments, the tumors include malignant tumors. As used herein, the term "cancer" refers to physiological conditions of mammal generally characterized by unregulated cell growth and/or proliferation. In the context, the terms "cancer" and "malignant tumor" can be used interchangeably.

In some embodiments, the tumors include solid tumors and non-solid tumors, optionally, the solid tumors. As used herein, the term "solid tumor" refers to the abnormal growth or caking of tissues, and generally does not include cyst or liquid areas. As used herein, the term "non-solid tumor" refers to neoplasia of the hemopoietic system, such as lymphoma, myeloma and leukemia, or neoplasia without solid formation generally and with spread substantially.

In some embodiment, the solid tumors include but not limited to lung cancer, liver cancer, hepatocellular carcinoma (HCC), esophageal cancer, cholangiocarcinoma, gallbladder carcinoma, stomach cancer, abdominal cancer, gastrointestinal cancer, gastric cancer, pancreatic cancer, renal cell carcinoma, renal cancer, bone cancer, breast cancer, ovarian cancer, uterine cancer, cervical cancer, endometrial cancer, colorectal cancer, colon cancer, rectal cancer, bladder cancer, superficial bladder cancer, prostate cancer, adrenal tumors, squamous cell carcinoma, neuroma, malignant neuroma, myoepithelial carcinoma, synovial sarcoma, rhabdomyosarcoma, gastrointestinal interstitial cell tumor, skin cancer, basal cell carcinoma, malignant melanoma, thyroid cancer, nasopharyngeal carcinoma, hemangioma, epidermoid carcinoma, head and neck cancer, glioma, or Kaposi's sarcoma.

In some embodiments, the non-solid tumors include but not limited to leukemia, acute leukemia, chronic leukemia, chronic myelocytic leukemia, acute myelogenous leukemia, chronic myelogenous leukemia, chronic lymphocytic leukemia, acute lymphoblastic leukemia, T-cell leukemia, hairy cell leukemia, polycythemia, myelodysplastic syndrome, multiple myeloma, lymphadenoma, Hodgkin's lymphoma, and Non-Hodgkin's lymphoma.

In some embodiments, the tumors are lung tumors, and include but not limited to abnormally proliferative or aberrantly proliferative lung cells and/or malignant lung tumor. As used herein, the term "lung tumor" refers to any lung tumors, therefore, such tumors can be primary lung tumors and/or metastatic lung tumors, for example, the tumors are formed in a way that tumors at other positions are metastasized to the lung through various metastasis modes. The lung tumors can be benign (non-carcinous), preinvasive lesion (precancerous lesion), or malignant (carcinous) lung tumors, such as lung cancers.

In a specific embodiment, the lung tumors are the lung cancers, and include but not limited to small cell lung cancer (SCLC) and non-small cell lung cancer (NSCLC). As used herein, the term "lung cancer" refers to all types of lung cancers, and include but not limited to small cell lung cancer (SCLC) and the non-small cell lung cancer (NSCLC, including but not limited to adenocarcinoma, squamous cell carcinoma, large cell carcinoma, adenosquamous carcinoma and sarcomatoid carcinoma). Further, the SCLC includes but not limited to complex small cell lung cancer; and the NSCLC includes but not limited to adenocarcinoma, squamous cell carcinoma, large cell carcinoma, adenosquamous carcinoma, sarcomatoid carcinoma, carcinoid and salivary gland cancer. As used herein, the term "complex small cell lung cancer" refers to one lung cancer, wherein the ingredients of the non-small cell lung cancer, such as large cell carcinoma, are mixed in the small cell lung cancer.

In an embodiment, the lung tumors are preinvasive lesion (precancerous lesion), and include but not limited to squamous epithelial dysplasia of the lung, lung carcinoma in situ, atypical adenomatous hyperplasia of the lung, and diffuse and idiopathic neuroendocrine cell proliferation of the lung. In one embodiment, the metastatic lung tumors are the tumors formed in a way that breast cancer, colorectal cancer, stomach cancer, pancreatic cancer, renal cancer, malignant melanoma, prostate cancer, liver cancer, thyroid cancer and adrenal tumors and the like are metastasized to the lung.

In some embodiments, the tumors are metastasized, and such metastasis can be in situ and in the distance. As used herein and related to cancers or malignant tumors, the term "metastasis" refers to the spread of cancers or malignant tumors from the in-situ position to other in-vivo positions. Cancer cells can separate from in-situ tumors, penetrate into lymphatic vessels and blood vessels, and then grow in distant lesions in normal tissues at other in-vivo positions through blood circulation. The metastasis can be in situ or at the distance. The lung tumors such as lung cancers can metastasize to lymph nodes, brain, central nervous system, bone, liver, adrenal, skin, intestine, thyroid, ovary, prostate and the like. Therefore, the present recombinant interferon can be used for treating these metastasized tumors such as metastasized lung cancers; particularly, the present recombinant interferon can relieve the symptoms caused by partial stress and invasion of the lung cancers to adjacent tissues, and treat the distant metastasis of the lung cancers. The symptoms caused by the partial stress and invasion of the lung cancers include but not limited to dyscatabrosis caused by the metastasis and hyperplasia of lymph node around esophagus as well as dyspnea caused by the spread of tumors through the lung parenchyma lymphatic vessels. The distant metastases of the lung cancers include but not limited to brain metastases of the lung cancers, central nervous system metastases of the lung cancers, bone metastases of the lung cancers, liver metastases of the lung cancers, adrenal metastases of the lung cancers, and other metastases such as skin metastases, thyroid metastases, ovary metastases, prostate metastases and the like of the lung cancers.

In some embodiments, the tumors can be multiple primary cancers, for example, in the condition that the tumors are the lung cancers, such lung cancers can be multiple primary lung cancers such as the multiple primary lung cancers at different pulmonary segments or pulmonary lobes. As used herein, the term "multiple primary cancers" refers to more than two kinds of multiple primary malignant tumors that are formed at the same time or successively on a same body. Such multiple primary malignant tumors must be confirmed to be malignant and non-external metastasis tumors by histology. As used herein, the term "multiple primary lung cancers" refers to more than two multiple primary malignant tumors which are identical in histology and independent in existence, do not have metastasis between each other, and are generated at different pulmonary segments or pulmonary lobes.

The disease suitable for the treatment and/or prevention method of the invention also includes cancer emergencies, for example advanced cancer emergencies such as pleural effusion, ascites and/or pericardial effusion. In some embodiments, the pleural effusion, ascites and/or pericardial effusion are malignant pleural effusion, malignant ascites and/or malignant pericardial effusion. In some embodiments, the malignant pleural effusion can be caused by pleural primary tumors or pleural metastasized tumors, and is the common emergencies in the advanced lung cancers. The pleural primary tumors include malignant and diffuse mesothelioma, and the pleural metastasized tumors are originated from lung cancer, breast cancer, lymphoma, ovarian cancer, endometrial cancer, cervical cancer, stomach cancer, colorectal cancer, pancreatic cancer, bladder cancer, liver cancer and the like. In some embodiments, the malignant pericardial effusion can be caused by lung cancer, breast cancer and the like. For example, the malignant pericardial effusion can be caused in a way that the lung cancer can be metastasized or can directly invade pericardium, which is also the common expression of the advanced lung cancers. In some embodiments, the malignant ascites can be caused by malignant tumors, wherein excessive liquid is accumulated in enterocoelia, and the malignant ascites is one of the advanced emergencies of cancers, and the malignant ascites are generally caused by ovarian cancer, cervical cancer, endometrial cancer, digestive tract tumor, lymphoma, breast cancer, peritoneal mesothelioma and the like.

B. Subjects

The subject suitable for the treatment and/or prevention method of the invention includes mammal, which comprises but not limited to human and non-human mammal, optionally, the subject is human. In the context, the terms "subject" and "patient" can be used interchangeably. In some embodiments, the subject with tumors is the subject previously diagnosed with tumors such as malignant tumors.

In some embodiments, the subjects include but not limited to a subject with tumors such as malignant tumors that are not capable of being resected, a subject with tumors such as malignant tumors that are capable of being resected, a subject with cancers, a subject with metastasized tumors such as metastasized malignant tumors, and/or a subject with pleural effusion, ascites and/or pericardial effusion such as malignant pleural effusion, malignant ascites and/or malignant pericardial effusion. In some embodiments, the tumor is optionally resected by a surgical resection. In some embodiments, the subjects suffered from solid tumors. In some embodiments, the solid tumors are capable of being resected or are not capable of being resected, such as solid tumors that are capable of being resected or are not capable of being resected surgically. In some embodiments, the solid tumors that are capable of being resected or are not capable of being resected, such as solid tumors that are capable of being resected or are not capable of being resected surgically, are advanced, or stage III or stage IV solid tumors. In some embodiments, the subjects are the subjects with or without indications for cancers or tumors surgery such as lung cancers surgery. In some embodiments, the solid tumors are solid tumors with or without indications for surgery such as indications for tumor surgery. In some embodiments, the solid tumors with or without indications for surgery such as indications for tumor surgery, are advanced, or stage III or stage IV solid tumors. In some embodiments, the solid tumors are lung cancers.

As used herein, the term "indication for surgery" or "indicated for surgery" or "appropriate for surgery" refers to a surgical method which is employed when a disease is in accordance with the standard specified by treatment routine and cannot be cured by a non-surgical method and the surgical method can be employed for being helpful for the treatment of the disease. In some embodiments, the cancers without indications or not indicated for surgery include: (1) non-solid tumors or systematic tumors, such as leukemia, malignant lymphoma, bone tumor and the like; (2) cancers with extensive systematic metastases for which surgical treatment is of no value; (3) cancers at a position which is difficult for surgical resection, such as nasopharyngeal carcinoma, upper esophageal carcinoma, radix linguae carcinoma and the like; (4) cancers which easily metastasize at a very early stage, such as undifferentiated small cell lung cancer, so that surgical resection is generally not suggested; and (5) cancers with carcinoma cells which infiltrate into surrounding tissues while growing, have unclear boundary and cannot be completely resected by surgery, such as tonsil carcinoma, pancreas carcinoma and the like. In some embodiments, the solid tumors without indications or not indicated for surgery include: (1) systematic solid tumors such as bone tumor and the like; (2) solid tumors with extensive systematic metastases for which surgical treatment is of no value; (3) solid tumors at a position which is difficult for surgical resection, such as nasopharyngeal carcinoma, upper esophageal carcinoma, radix linguae carcinoma and the like; (4) solid tumors which easily metastasize at a very early stage, such as undifferentiated small cell lung cancer; and (5) solid tumors with carcinoma cells which infiltrate into surrounding tissues while growing, have unclear boundary and cannot be completely resected by surgery, such as tonsil carcinoma, pancreas carcinoma and the like.

As used herein, the term "tumors that are capable of being resected" are tumors which are limited to primary organs and are suitable for surgical therapy, such as malignant tumors. A subject with tumors such as malignant tumors that are not capable of being resected also includes a subject with tumors such as malignant tumors that are not capable of being resected surgically. Such surgery can include surgical procedures, minimally invasive operation and the like. In a specific embodiment, the subject with tumors such as malignant tumors that are capable of being resected includes a subject with tumors such as malignant tumors which can be resected surgically.

In some embodiments, the subjects include but not limited to early cancer patients, medium-term and advanced cancer patients, optionally medium-term or advanced cancer patients. As used herein, the term "early cancer" includes cancer in situ and stage I cancer, the term "medium-term cancer" includes stage II and stage III cancers, and the term "advanced cancer" refers to metastatic cancers with extensive infiltration in situ or with metastises at remote organs, such as stage IV cancer. In some embodiments, the subjects include but not limited to stage 0, I, II, III or IV cancer patients, optionally stage III or stage IV cancer patients; and the subjects with metastasized tumors such as metastasized malignant tumors includes but not limited to subjects with tumors such as malignant tumors which are metastasized in situ or in the distance. It should be understood that when the tumor or cancer is referred to as stage 0, I, II, III, or IV tumor or cancer, the stages of the tumor or cancer is defined by the TNM staging method well known in the art (see AJCC Cancer Staging Manual (Sixth Edition), Greene, F. L. et al. editor. LIAONING SCIENCE AND TECHNOLOGY PUBLISHING HOUSE, August 2005). For example, in the TNM staging method, the Stage 0 means $T_0N_0M_0$; the Stage Ia means $T_1N_0M_0$; the Stage Ib means $T_2N_0M_0$; the Stage IIa means $T_1N_1M_0$; the Stage IIb means $T_2N_1M_0$ and $T_3N_0M_0$; the Stage IIIa stage means $T_3N_1M_0$ and $T_{1-3}N_2M_0$; the Stage IIIb means any T, $N_3$ and $M_0$, T4, and any N and $M_0$; and Stage IV means any T, and any N and $M_1$. In some embodiments, the subjects are medium-term, advanced, or Stage III or Stage IV cancer patients. In some embodiments, the subjects are advanced, or Stage III or Stage IV cancer patients.

In some embodiments, the subjects with malignant pleural effusion, malignant ascites and/or malignant pericardial effusion include the subjects with malignant pleural effusion, malignant ascites and/or malignant pericardial effusion caused by cancers such as advanced, or Stage III or Stage IV cancers. In one embodiment, the cancers are lung cancers.

In some embodiments, the subjects suffered from tumors which can be lung tumors, such as lung cancers. In one embodiment, the subjects can be lung cancer patients, such as patients of lung cancer that is not capable of being resected surgically, the medium-term and advanced lung cancer patients, the Stage 0, I or II lung cancer patients, or Stage III or IV lung cancer patients, and the metastasized lung cancer patients or the lung cancer patients with malignant pleural effusion, malignant ascites and/or malignant pericardial effusion. In one embodiment, the lung cancer patients include but not limited to small cell lung cancer patients and non-small cell lung cancer patients.

C. Combination Therapy

In some embodiments of the method of the invention, other therapies or drugs can be administered to the subject before, simultaneously, and/or after administration of the present recombinant interferon. In some embodiments, the therapies are optionally anti-cancer therapies, and the drugs are optionally anti-tumor drugs. As used herein, the term "administration" refers to giving a substance to achieve the therapeutic purposes. As used herein, the term "combination therapy" refers to employing two or more treatment means for the subjects in the process of the treatment period, such as employing the present recombinant interferon and extra treatment means. The extra treatment means can be employed for the subjects before, simultaneously, and/or after administration of the present recombinant interferon. As used herein, the term "anti-cancer therapy" refers to a useful therapy in the cancer treatment.

In some embodiments, the other anti-cancer therapies include but not limited to chemotherapy, radiotherapy, surgical therapy, interventional therapy, biotherapy, gene therapy, ablation therapy, immune therapy, targeted therapy, traditional Chinese medicine therapy and any combination thereof. The other anti-cancer therapies can be easily determined by the person skilled in the art. In some embodiments, the other anti-cancer therapies are optionally chemotherapy, radiotherapy, surgical therapy, targeted therapy and/or biotherapy. In some embodiments, the other anti-cancer therapies are optionally chemotherapy and/or radiotherapy.

As used herein, the term "chemotherapy" refers to a drug therapy affecting cell growth and cell division, namely, the drug therapy is taken as a cell proliferation inhibitor or is used for inducing cell death (cell apoptosis). Compared with normal cells, cancer cells grow and divide uncontrollably so that the chemotherapy should be more effective to the cancer cells. In a specific embodiment, chemotherapy includes arterial infusion chemotherapy and embolism-form chemotherapy. In a specific embodiment, for different cancers, the chemotherapy can be the common first-line chemotherapy for the cancers. For example, chemotherapeutic drugs used in the first-line chemotherapy for treating lung cancer include but not limited to platinum compounds such as Cisplatin.

The chemotherapeutic drugs used in the chemotherapy for the cancers in the invention include but not limited to alkylating agents such as nitrogen mustards including but not limited to chlormethine hydrochloride, chlorambucil, phenylalanine mustard, chlornaphazine, estramustine, cyclophosphamide, ifosfamide, Mechlorethamine, mustron, Melphalan, novembichin, phenesterin, Prednimustine, Trofosfamide and Uramustine; ethyleneimines and methyl melamines including but not limited triethylenemelamine, Thiotepa, MST-16, altretamine, triethylene melamine, triethylene phosphamide, triethylene Thiophosphoramide and trimethylol melamine; sulfoacid alkyl esters including but not limited to busulfan, improsulfan and piposulfan; and nitrosoureas including but not limited to carmustine, Semustine, Streptozotocin, chlorozotocin, Fotemustine, Lomustine, Nimustine and Ranimustine; antimetabolites such as anti-folate antimetabolite including but not limited to methopterin (MTX), trimethyl-oxy quinazoline, dimethyl folate, pteropterin, trimetrexate, leucovorin and Pemetrexed (Alimta); pyrimidine antimetabolites including 5-fluorouracil (5-FU), floxuridine, ftorafur (Tegafur), Capecitabine (Xeloda), Ancitabine, Carmofur, di-deoxyuridine, Doxifluridine and enocitabine; cytidines antimetabolites including but not limited to cytarabine, Azacytidine, ancitabine and Gemcitabine (Gemzar); purines antimetabolites including but not limited to 6-mercaptopurine, 6-thioguanine, deoxycoformycin, Fludarabine and thiamiprine; plant-origin anti-tumor drugs such as Vinca Alkaloids including but not limited to vinblastine, vindesine, vincristine, vindesine, Vinorelbine, vinblastine sulfate, vincristine sulfate, Vinorelbine Tartrate and Vinflunine; Harringtonine and Homoharringtonine; Indirubin and analogue thereof including but not limited to N-methyllisoinidog-tin; etoposide drugs including but not limited to Teniposide (VM-26) and Etoposide (VP-16); Camptotheca and Camptothecin compounds including but not limited to Camptothecin, Topotecan (TFT) and Irinotecan (CPT-11); Paclitaxel compound including but not limited to Paclitaxel (Paclitaxel Liposome For Injection), Docetaxel (Docetaxel Injection, Taxotere) and paclitaxel liposome; antitumor antibiotics such as anthracyclines including but not limited to daunorubicin, adriamycin, aclacinomycin A, Epirubicin, mitoxantrone and marcellomycin; Glycopeptides including but not limited to bleomycin, tallysomycin, Leroymycin, pepreomycin and Pingyangmycin; actinomycins including but not limited to actinomycin C, actinomycin D, aurantin and dactinomycin; glucosides including but not limited to mithramycin, chromomycin A3 and Olivomycin; mitomycins including but not limited to mitomycin C; and Streptozotocin; the platinum compounds include but not limited to Spiroplatin, Cisplatin, Carboplatin, Nedaplatin, oxaliplatin, Lobaplatin, JM-216, Ring Platinum, SKI2053R, L-NDDP and TRK-710; retinoid compounds include but not limited to all-trans retinoic acid and 13-cis-retinoic acid; hormones include androgens including but not limited to Testosterone Propionate, Methyltestosterone, Fluoxymesterone, durabolin, calusterone, propionicacid methyl androstane pregnanolone, epithioandrostanol, mepitiostane and testolactone; antiandrogens including but not limited to flutamide, Nilutamide, Bicalutamide (Casodex), Goserelin, Leuprorelin and Androcur; estrogens including but not limited to diethylstilbestrol, estradiol and ethinyloestradiol; estrogen receptor blocker and composite drug formed by transplanting estrogen, including but not limited to Tamoxifen, Toremifene, Anastrozole and Exemestane; progesterones including but not limited to Methylhydroxyprogesterone and Megestrol Acetate; Gonadotropin releasing hormone analogues including but not limited to Leuprorelin, Gonadorelin and Dingsi-relin and naphthoxypropyl-relin; adrenocortical hormone including but not limited to metacortandracin (prednisone) and dexamethasone (DXM); adrenal-cortex selective damaging agent including but not limited to Mitotane; thyroid hormones including but not limited to thyroxine; and others including but not limited to Bacillus Calmette Guerin (BCG), Asparaginase, hydroxycarbamide, Ibenzmethyzin and Dacarbazine (DTIC); and pharmaceutically acceptable salts, acids or derivatives of any above substance.

In some embodiments, chemotherapy protocols used for treating cancers such as lung cancers in the invention include but not limited to a CMC protocol (cyclohexyl nitrosourea, cyclophosphamide and Methotrexate), an EP protocol (etoposide and Cisplatin), an IVP protocol (ifosfamide, vindesine and Cisplatin), an ICE protocol (ifosfamide, Cisplatin and etoposide), a NIP protocol (Navelbine, ifosfamide and Cisplatin), a Paclitaxel+DDP/CBP protocol (Paclitaxel and Cisplatin/carboplatin), a docetaxel+DDP/CBP protocol (docetaxel and Cisplatin/carboplatin), a topotecan+DDP protocol (topotecan and Cisplatin), an IP protocol (Irinotecan and carboplatin), a MVP protocol (mitomycin, vindesine and Cisplatin), a NP protocol (Navelbine and Cisplatin), a docetaxel protocol, a GEM+DDP (GP) protocol or GEM+CBP protocol (Gemzar and Cisplatin/carboplatin) and the like (see Lung Oncology Phymatology, First Edition, September 2008, Liao, M. L. editor, Shanghai Scientific and Technical Publisher, pages 323-326).

In addition, other chemotherapy protocols used for treating tumors such as cancers in the invention include but not limited to an FOLFOX protocol (see *Newest Chemotherapy Development of Malignant Tumors*, July, 2009, chief editor: Zheng Cuiping, Beijing: People's Military Medical Press, 1031), a DP protocol (see *Newest Chemotherapy Development of Malignant Tumors*, July, 2009, chief editor: Zheng Cuiping, Beijing: People's Military Medical Press, 232), a CHOPE protocol, a MTX protocol, a GCE protocol, an ESAP protocol, a CMOP protocol, a CHOP protocol (see *Practical Anti-tumor Pharmacotherapeutics, 2002*, chief editor: Liu Xinchun etc., Beijing: People's Medical Publishing House, 1031), a bleomycin+CHOP+Methotrexate protocol, a GP+Endostar protocol, a GP-T2 protocol, a TP protocol (see *Practical Anti-tumor Pharmacotherapeutics, 2002*, chief editor: Liu Xinchun etc., Beijing: People's Medical Publishing House, 668 and 744), a Cisplatin+mitomycin protocol and the like.

As used herein, the term "radiotherapy" refers to employing high-energy radiation for treating tumors such as cancers. The radiotherapy includes external radiation such as external radiotherapy from a linear accelerator, and brachytherapy for which radioactive sources are placed near the surface of the human body or in the body cavity. In the radiotherapy of the invention, the radioactive sources include but not limited to $\alpha$, $\beta$ and $\gamma$ rays generated by radioactive nuclides, and electron beams, proton beams. Neutron beams, $-\pi$ meson beams and other heavy particle beams generated by various accelerators. The radioactive nuclides include but not limited to $^{137}$Cs, $^{60}$Co, $^{131}$I, $^{125}$I, $^{32}$P, $^{198}$Au, $^{192}$Ir, $^{90}$Y, $^{186}$Re and $^{109}$Pd. Such radioactive sources can perform radiation in vitro and/or in vivo.

It should be understood that many methods known in the art can be used for determining the accumulation and duration of the radiotherapy. The typical radiotherapy is employed as one-time administration, and the usual dose is in the range of about 1 to about 200 grays/day, such as about 2 to about 150 grays/day, about 5 to about 100 grays/day, about 10 to about 70 grays/day, about 10 to about 50 grays/day and the like. In one embodiment, the radiotherapy used in the invention includes but not limited to two-dimensional conventional radiotherapy, three-dimensional conformal radiotherapy (3D-CRT), proton radiotherapy, brachytherapy, intensity modulated radiotherapy (IMRT), stereotactic radiotherapy (SRT), respiratory gating four-dimensional radiotherapy (4DRT) and gamma knife therapy, such as systematic gamma knife therapy and head gamma knife therapy.

As used herein, the term "targeted therapy" refers to a therapy aiming at identifying specific target molecules which can be, for example, play a role in tumorigenesis or tumor proliferation or cell repairing. Such identification may be, for example, lead to the combination between the targeted therapy and the target molecules, and can enhance or reduce the activity of the target molecules. Drugs used for the targeted therapy includes antibodies, in particular to monoclonal antibodies and small molecule drugs. Potential targets include EGFR receptors, which playing a role in vasculogenesis, VEGFA ligands, which being important in vasculogenesis, or PARP1, which being important in cell repairing, because the tumors with cancer gene defect can be more sensitive to the chemical therapy due to the suppression to the PARP1.

In the targeted therapy of the present invention, the targeted drug includes but not limited to an anti-angiogenesis drug, Kinase inhibitor, pan Kinase inhibitor or growth factor inhibitor. The anti-angiogenesis drug includes but not limited to EGF inhibitor, EGFR inhibitor, VEGF inhibitor, VEGFR inhibitor, TIE2 inhibitor, IGF1R inhibitor, COX-II (cyclo-oxygenase-II) inhibitor, MMP-2 (matrix metalloproteinase-2) inhibitor and MMP-9 (matrix metalloproteinase-9) inhibitor. A targeted drug that can be used herein includes but not limited to at least one of: Gefitinib (Iressa), Erlotinib (TARCEVA®), Lapatinib (GSK572016), Vatalanib (PTK787), Imatinib (GLEEEVEC®), Dasatinib (Sprycel), Sunitinib (SUTENT®), Nilotinib (Tasigna), Semaxanib (SU5416), Pazopanib (GW-786034), Erbitux (IMC-C225), Panitumumab (Vectibix), Trastuzumab (Herceptin), Recombinant Human Endostatin (Endostar), Sorafenib (NEXAVAR®), Bevacizumab (Avastin), Alemtuzumab (Campath), Gemtuzumab (Mylotarg), ibritumomab tiuxetan (Zevalin), tositumomab (Bexxar), Affinitak (LY90003/ISI3521), Farnesyltransferase inhibitors, Tipifanib, Lonafanib, BMS214-662, R115777 (Zarnestra), SCH-66336 (Sarasar), L-778,123, ZD6474 (ZACTIMA®), AZD2171, OSI-7904, ZD6126 (ANG453), ZD1839, AMG706, AG013736, MLN-518, CEP-701, PKC-412, VELCADE, XL880 and CHIR-265. In some embodiments, the targeted drug in the targeted therapy used for treating cancers such as lung cancers in the invention includes but not limited to Gefitinib (Iressa), Erlotinib (TARCEVA®), and Recombinant Human Endostatin (Endostar).

The dose and duration of the drugs and/or the radioactive sources used in the chemical therapy, radiotherapy and/or targeted therapy can be easily determined by skilled physicians according to the experience and the practical situations of patients such as age, weight, general health state, gender, diet, administration time, drug interaction and illness severity.

As used herein, the term "surgical therapy" refers to an invasive cancer therapy aiming at physically eliminating cancer cells. The surgical therapy includes, for example, tumor resection and lymph node dissection.

As used herein, the term "gene therapy" refers to a therapy by delivering recombinant genetic materials by virus or non-virus carriers ex vivo or in vivo so as to treat or prevent diseases or medical conditions, such as cancers.

As used herein, the term "ablation therapy" refers to a well known tissue damage method, such as high-temperature ablation such as radio frequency, microwave and laser ablation, low-temperature ablation such as cryocare knife cryotherapy, chemical ablation, radioactive ablation and the like.

As used herein, the term "immunotherapy" refers to a treatment strategy which is employed for regulating the immune system so as to prevent and/or treat specific diseases such as cancers. For example, vaccination is one immunotherapy. The vaccine used in the present immunotherapy includes but limited to ALLOVECTIN® vaccine, LEUVECTIN® vaccine, VAXID® vaccine and the like.

As used herein, the term "interventional therapy" refers to a treatment method with smallest trauma for performing local treatment to the lesion under the condition that the lesion is not operated through tiny channels made on the skin or original channels of the human body under the guidance of imaging equipment (such as a Digital Subtraction Angiography, a perspective machine, CT, MR and B ultrasonic). When being used for treating the tumors, the interventional therapy includes but not limited to transcatheter arterial chemoembolization, arterial infusion chemotherapy, high-temperature ablation such as radio frequency, microwave and laser ablation, low-temperature ablation such as cryocare knife cryotherapy, chemical ablation, radioactive ablation, gene drug arterial infusion, stent implantation and the like.

As used herein, the term "biotherapy" refers to all treatment methods employing modern biotechnologies and the products (small molecule compounds, polypeptide, polysaccharide, protein, cells, tissues, genes, RNAs and the like) thereof. When being used for treating the tumors, the biotherapy can directly or indirectly mediate anti-tumor and tumor-killing effects. The biotherapy used for treating the tumors includes but not limited to the application of non-specific immunologic stimulant, Biological Response Modifier (BRM), a tumor cell factor treatment and immunological effect cell treatments such as NK cell anti-tumor therapy, biology supporting therapy, tissue and cell transplanting therapy and the like.

As used herein, the term "traditional Chinese medicine therapy" refers to all methods employing the traditional Chinese medicine and drugs guided by Chinese medicine theories for treating diseases such as cancers.

In addition, other anti-tumor drugs which can be administered together with the present recombinant interferon include but not limited to biological agents used in the biotherapy such as tumor necrosis factors including TNF-$\alpha$ or TNF-$\beta$ and the like; interferon such as interferon $\alpha$ including interferon $\alpha$-1a, interferon $\alpha$-1b, interferon $\alpha$-2a, interferon $\alpha$-2b and the like, interferon $\beta$ including interferon $\beta$-1a, interferon $\beta$-1b and the like, interferon $\gamma$ including interferon $\gamma$-1b and the like, consensus interferon such as interferon$\alpha$-con1, long-acting interferon such as PEGylation interferon, fusion protein of interferon and albumin, and fusion protein of interferon and IgG Fc fragment; colony stimulating factors (CSF) such as macrophage-colony stimulating factor (M-CSF), granulocyte-macrophage (GM-CSF) and granulocyte-colony stimulating factor (G-CSF); interleukin (IL) such as IL-1, IL-1$\alpha$, IL-2, IL-3, IL-4, IL-5, IL-6, IL-7, IL-8, IL-9, IL-10, IL-11, IL-12, and Thymosin; antisense oligonucleotide, especially those for inhibition of the expression of genes (such as PKC-$\alpha$, Raf and H-Ras) in signaling pathway involved in the proliferation of adherent cells; siRNA and the like.

D. Pharmaceutical Composition and Administration Route

The present recombinant interferon can be incorporated into pharmaceutical compositions, so as to be administered to subjects. Generally, the pharmaceutical composition comprises the present recombinant interferon and pharmaceutically acceptable carriers. The "pharmaceutically acceptable carrier" herein includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the present recombinant interferon.

The pharmaceutical compositions of the invention may be in a variety of forms. These include, for example, liquid, semi-solid and solid dosage forms, such as liquid solutions (e.g., injectable and infusible solutions), dispersions or suspensions, aqueous solutions, tablets, capsules, oral solutions, patchs, sprays, suppositorys, powders and lyophilized powders. The form appropriate for use depends on the intended mode of administration and therapeutic application. Typical pharmaceutical compositions are in the form of injectables or infusible solutions, lyophilized powders, sprays, and aqueous solutions.

The pharmaceutical composition can be prepared by any well known method in the pharmaceutical field with reference to: Gilman, etc., (editor) 1990, *The Pharmacological Bases of Therapeutics*, the 8$^{th}$ version, Pergamon Press; A. Gennaro (editor), *Remington's Pharmaceutical Sciences*, the 18$^{th}$ version, 1990, Mack Publishing Co., Easton, Pennsylvania; Avis, etc., (editor) 1993, *Pharmaceutical Dosage Forms: Parenteral Medications* Dekker, New York; Lieberman, etc., (editor) 1990, *Pharmaceutical Dosage Forms: Tablets* Dekker, New York; and Lieberman, etc., (editor) 1990, *Pharmaceutical Dosage Forms: Disperse Systems* Dekker, New York.

The present recombinant interferon can be administered to the subjects through at least one of: systemic administration, topical administration, and local administration. As used herein, the term "systemic administration" refers to a mode for administering compositions or drugs to a subject, in a manner that leads to systemic circulation of the drugs or compositions in the subject, such as the spreading or distribution of the administered compositions or drugs to all parts of the body. Examples of systemic administration include, but are not limited to: intravenous injection, intra-arterial injection, intramuscular injection, subcutaneous injection, intra-lymphatic injection, oral administration, and the like.

As used herein, the term "local administration" refers to administering a composition or drug into a limited or partial anatomy space. Examples of local administration include but are not limited to: intratumoral, intra-lymph node, intrapleural space, intraperitoneal cavity and the like.

As used herein, the term "topical administration" refers to administering a drug or composition on the surface of skin or mucous membrane. For example, topical administration includes but is not limited to spraying the drug or composition onto the skin of a subject.

In some embodiments, the present recombinant interferon can be administered to the subject by at least one administration route, the administration route comprises but not limited to: oral, rectal, sublingual, intravenous, intra-arterial, intramuscular, subcutaneous, intra-bone, intracutaneous, intra-articular, intraperitoneal, intrathecal, intracerebral, vaginal, percutaneous, transdermal, epidermal, transmucosal, transocular, pulmonary, nasal, abdominal, intrapleural, intraventricular, pericardial, inhalation, intratumoral, uterine, infiltration, and intravesical administration. In some embodiments, the present recombinant interferon can be administered to the subject by injection route, such as subcutaneous, intramuscular, intravenous, intra-arterial, intracerebral, intraperitoneal and/or intratumoral injection. In some embodiments, the present recombinant interferon can be administered to the subject by inhalation, such as pulmonary inhalation and nasal inhalation. In some embodiments, the inhalation can be dry powder inhalation and/or aerosol inhalation. In some embodiments, the present recombinant interferon can be administered to the subject by perfusion, such as intrapleural perfusion, abdominal perfusion, pericardial perfusion, uterine perfusion and/or intravesical perfusion. In some embodiments, the present recombinant interferon can be administered to lesion (such as the surfaces of skin and mucosa, superficial lymph nodes and/or subcutaneous tissue) by spray, such as percutaneous, epidermal, transdermal and/or transmucosal spray administration. In some embodiments, the infiltration administration includes pulmonary infiltration administration, percutaneous infiltration administration, epidermal infiltration administration, transmucosal infiltration administration, intrapleural infiltration administration, abdominal infiltration administration, uterine infiltration administration, vaginal infiltration administration, intravesical infiltration administration, pericardial infiltration administration and the like.

Injection/Perfusion Administration

The pharmaceutical compositions suitable for injection/perfusion include sterile aqueous solutions (where water soluble) or dispersions and sterile powders for the extemporaneous preparation of sterile injectable solutions or dispersion. In all cases, the composition must be sterile and should be fluid so as to be administered using a syringe. Such compositions should be stable during manufacture and storage and must be preserved against contamination from microorganisms such as bacteria and fungi. The carrier can be a solvent or dispersion medium containing, for example, water, ethanol, polyol (such as glycerol, propylene glycol, and liquid polyethylene glycol), and suitable mixtures. Various antibacterial and antifungal agents; for example, parabens, chlorobutanol, phenol, ascorbic acid, and thimerosal; isotonic agents; for example, sugars, polyalcohols such as manitol, sorbitol, and sodium chloride can be included in the composition. Compositions that can delay absorption include agents such as aluminum monostearate and gelatin.

Sterile injection/perfusion solutions can be prepared by incorporating the present recombinant interferon in the required amount in an appropriate solvent with one or a combination of ingredients as required, followed by sterilization. Generally, dispersions are prepared by incorporating the present recombinant interferon into a sterile vehicle that contains a basic dispersion medium, and the other required ingredients. Sterile powders for the preparation of sterile injection/perfusion solutions, methods of preparation include vacuum drying and freeze-drying that yield a powder containing the active ingredient and any desired ingredient from a sterile solutions.

Inhalation Administration

The present recombinant interferon can be delivered by any of a variety of inhalation devices know in the art for administration of a therapeutic agent by inhalation. These devices include metered dose inhalers, nebulizers, dry powder generators, sprayers, and the like. Other devices suitable for inhalation administration of the present recombinant interferon are also known in the art.

Metered dose inhalers like the Ventolin® metered dose inhaler, typically use a propellent gas and require actuation during inspiration (See, e.g., WO 94/16970, WO 98/35888). Dry powder inhalers like Turbuhaler™ (Astra), Rotahaler® (Glaxo), Diskus® (Glaxo), Spiros™ inhaler (Dura), devices marketed by Inhale Therapeutics, and the Spinhaler® powder inhaler (Fisons), use breath-actuation of a mixed powder (U.S. Pat. No. 4,668,218 Astra, EP 237507 Astra, WO 97/25086 Glaxo, WO 94/08552 Dura, U.S. Pat. No. 5,458, 135 Inhale, WO 94/06498 Fisons). Nebulizers like AERx™ Aradigm, the Ultravent® nebulizer (Mallinckrodt), the Acorn II® nebulizer (Marquest Medical Products) (U.S. Pat.

No. 5,404,871 Aradigm, WO 97/22376), and the AP-100200 type spray inhaler (Taiwan Albert incorporated company). Producing aerosols from solutions, while metered dose inhalers, dry powder inhalers, etc. generate small particle aerosols.

Optionally, the present recombinant interferon is delivered by a nebulizer. The inhalation devices for administering the present recombinant interferon have several desirable features. For example, delivery by the inhalation device is advantageously reliable, reproducible, and accurate. The inhalation device can optionally deliver small dry particles or aerosol, e.g., less than about 10 μm, for example about 0.5 μm to about 5 μm, for good respirability.

Spray Administration

A spray including the present recombinant interferon can be produced by forcing a suspension or solution of the recombinant interferon through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles delivered by a sprayer have a particle size less than about 10 μm, optionally, in the range of about 0.5 μm to about 5 μm.

Formulations of the present recombinant interferon suitable for use with a sprayer typically include ones at a concentration in a range of about 0.01 mg to about 5 mg, such as about 0.03 mg to about 2 mg, about 0.05 mg to about 1 mg, and about 0.1 mg to about 0.5 mg of the recombinant interferon per ml of solution. The formulation can include an excipient or agent for stabilization of the present recombinant interferon, such as a buffer, a reducing agent, a bulk protein, or a carbohydrate. Bulk proteins useful in formulating the recombinant interferon include albumin, protamine, or the like. Typical carbohydrates useful in formulating the recombinant interferon include sucrose, mannitol, lactose, trehalose, glucose, or the like. The present recombinant interferon formulation can also include a surfactant, which can reduce or prevent surface-induced aggregation of the recombinant interferon caused by atomization of the solution in forming an aerosol.

E. Administration Dosage and Administration Protocol

Effective amount of the present recombinant interferon can be administered to the subjects such as cancer subjects, and such effective amount can be a therapeutically effective amount or a prophylactically effective amount according to the method of the invention. As used herein, the term "effective amount" refers to an amount effective, at dosages and for periods of time necessary, to achieve the desired therapeutic or prophylactic result. A therapeutically effective amount of the present recombinant interferon may vary according to factors such as the disease state, age, sex, and weight of the individual, and the ability of the recombinant interferon to elicit a desired response in the individual. A therapeutically effective amount is also one in which any toxic or detrimental effects of the recombinant interferon are outweighed by the therapeutically beneficial effects. A "prophylactically effective amount" refers to an amount effective, at dosages and for periods of time necessary, to achieve the desired prophylactic result. Typically but no surely, since a prophylactic dose is used in subjects prior to or at an earlier stage of disease, the prophylactically effective amount will be less than the therapeutically effective amount.

The present recombinant interferon can be administered to the subjects such as the cancer subjects in different amounts of single doses. For example, the single doses of the present recombinant interferon can be in the range of about 2 µg to about 2000 µg, optionally about 4 µg to about 1500 µg, and further optionally about 9 µg to about 1000 µg. As used herein, the term "single dose" refers to an amount of drug which can be at administered one time, that can be therapeutically or prophylactically effective by itself or cumulatively with other single doses. Such administration includes systemic administration, local administration and/ or topical administration.

When the present recombinant interferon is systemically administered via injection administration (such as subcutaneous injection, intramuscular injection, intravenous injection, intra-arterial injection, intracerebral injection and/or intraperitoneal injection), the single dose of the recombinant interferon can be in the range of about 4 µg to about 70 µg, optionally, about 4 µg to about 50 µg, and further optionally, about 4 µg to about 30 µg, wherein the single dose can be about 4 µg, about 4.5 µg, about 5 µg, about 6 µg, about 7 µg, about 8 µg, about 9 µg, about 10 µg, about 11 µg, about 12 µg, about 13 µg, about 13.5 µg, about 14 µg, about 15 µg, about 16 µg, about 17 µg, about 18 µg, about 19 µg, about 20 µg, about 21 µg, about 22 µg, about 23 µg, about 24 µg, about 25 µg, about 25.5 µg, about 26 µg, about 27 µg, about 28 µg, about 29 µg, about 30 µg, about 31 µg, about 32 µg, about 33 µg, about 34 µg, about 35 µg, about 36 µg, about 37 µg, about 38 µg, about 39 µg, about 40 µg, about 41 µg, about 42 µg, about 43 µg, about 44 µg, about 45 µg, about 46 µg, about 47 µg, about 48 µg, about 49 µg, about 50 µg, about 51 µg, about 52 µg, about 53 µg, about 54 µg, about 55 µg, about 56 µg, about 57 µg, about 58 µg, about 59 µg, about 60 µg, about 61 µg, about 62 µg, about 63 µg, about 64 µg, about 65 µg, about 66 µg, about 67 µg, about 68 µg, about 69 µg, and about 70 µg.

When the present recombinant interferon is locally administered via injection administration (such as the intratumoral injection), the single dose of the recombinant interferon can be in a range of about 60 µg to about 600 µg, optionally, about 60 µg to about 500 µg, further optionally, about 80 µg to about 400 µg, and still further optionally, about 100 µg to about 250 µg, wherein the single dose can be about 60 µg, about 70 µg, about 80 µg, about 90 µg, about 100 µg, about 110 µg, about 120 µg, about 130 µg, about 140 µg, about 150 µg, about 160 µg, about 170 µg, about 180 µg, about 190 µg, about 200 µg, about 210 µg, about 220 µg, about 230 µg, about 240 µg, about 250 µg, about 260 µg, about 270 µg, about 280 µg, about 290 µg, about 300 µg, about 310 µg, about 320 µg, about 330 µg, about 340 µg, about 350 µg, about 360 µg, about 370 µg, about 380 µg, about 390 µg, about 400 µg, about 410 µg, about 420 µg, about 430 µg, about 440 µg, about 450 µg, about 460 µg, about 470 µg, about 480 µg, about 490 µg, about 500 µg, about 510 µg, about 520 µg, about 530 µg, about 540 µg, about 550 µg, about 560 µg, about 570 µg, about 580 µg, about 590 µg, and about 600 µg.

When the present recombinant interferon is administered through inhalation administration (such as pulmonary inhalation and nasal inhalation, including dry powder inhalation and aerosol inhalation), the single dose of the recombinant interferon can be in a range of about 100 µg to about 2000 µg, optionally, about 100 µg to about 1500 µg, further optionally, about 150 µg to about 800 µg, and still further optionally, about 200 µg to about 600 µg, wherein the single dose can be about 100 µg, about 110 µg, about 120 µg, about 130 µg, about 140 µg, about 150 µg, about 160 µg, about 170 µg, about 180 µg, about 190 µg, about 200 µg, about 210 µg, about 220 µg, about 230 µg, about 240 µg, about 250 µg, about 260 µg, about 270 µg, about 280 µg, about 290 µg, about 300 µg, about 310 µg, about 320 µg, about 330 µg, about 340 µg, about 350 µg, about 360 µg, about 370 µg, about 380 µg, about 390 µg, about 400 µg, about 410 µg, about 42 µg, about 430 µg, about 440 µg, about 450 µg, about 460 µg, about 470 µg, about 480 µg, about 490 µg, about 500 µg, about 510 µg, about 520 µg, about 530 µg, about 540 µg, about 550 µg, about 560 µg, about 570 µg, about 580 µg, about 590 µg, about 600 µg, about 610 µg, about 620 µg, about 630 µg, about 640 µg, about 650 µg, about 660 µg, about 670 µg, about 680 µg, about 690 µg, about 700 µg, about 710 µg, about 720 µg, about 730 µg, about 740 µg, about 750 µg, about 760 µg, about 770 µg, about 780 µg, about 790 µg, about 800 µg, about 810 µg, about 820 µg, about 830 µg, about 840 µg, about 850 µg, about 860 µg, about 870 µg, about 880 µg, about 890 µg, about 900 µg, about 910 µg, about 920 µg, about 930 µg, about 940 µg, about 950 µg, about 960 µg, about 970 µg, about 980 µg, about 990 µg, about 1000 µg, about 1100 µg, about 1200 µg, about 1300 µg, about 1400 µg, about 1500 µg, about 1600 µg, about 1700 µg, about 1800 µg, about 1900 µg, and about 2000 µg.

When the present recombinant interferon is administered through perfusion or infiltration administration (such as intrapleural perfusion, abdominal perfusion, pericardial perfusion, uterine perfusion and intravesical perfusion), the single dose of the recombinant interferon can be in a range of about 30 µg to about 2000 µg, optionally, about 100 µg to about 1500 µg, further optionally, about 150 µg to about 1000 µg, still optionally, about 200 µg to about 800 µg, and still further optionally, about 200 µg to about 400 µg, wherein the single dose can be about 30 µg, about 40 µg, about 50 µg, about 60 µg, about 70 µg, about 80 µg, about 90 µg, about 100 µg, about 110 µg, about 120 µg, about 130 µg, about 140 µg, about 150 µg, about 160 µg, about 170 µg, about 180 µg, about 190 µg, about 200 µg, about 210 µg, about 220 µg, about 230 µg, about 240 µg, about 250 µg, about 260 µg, about 270 µg, about 280 µg, about 290 µg, about 300 µg, about 310 µg, about 320 µg, about 330 µg, about 340 µg, about 350 µg, about 360 µg, about 370 µg, about 380 µg, about 390 µg, about 400 µg, about 410 µg, about 420 µg, about 430 µg, about 440 µg, about 450 µg, about 460 µg, about 470 µg, about 480 µg, about 490 µg, about 500 µg, about 510 µg, about 520 µg, about 530 µg, about 540 µg, about 550 µg, about 560 µg, about 570 µg, about 580 µg, about 590 µg, about 600 µg, about 610 µg, about 620 µg, about 630 µg, about 640 µg, about 650 µg, about 660 µg, about 670 µg, about 680 µg, about 690 µg, about 700 µg, about 710 µg, about 720 µg, about 730 µg, about 740 µg, about 750 µg, about 760 µg, about 770 µg, about 780 µg, about 790 µg, about 800 µg, about 810 µg, about 820 µg, about 830 µg, about 840 µg, about 850 µg, about 860 µg, about 870 µg, about 880 µg, about 890 µg, about 900 µg, about 910 µg, about 920 µg, about 930 µg, about 940 µg, about 950 µg, about 960 µg, about 970 µg, about 980 µg, about 990 µg, about 1000 µg, about 1100 µg, about 1200 µg, about 1300 µg, about 1400, about 1500 µg, about 1600 µg, about 1700 µg, about 1800 µg, about 1900 µg, and about 2000 µg.

When the present recombinant interferon is administered to the lesions (such as surfaces of the skin and the mucosa, superficial lymph nodes and/or subcutaneous tissue) by spray administration such as percutaneous spray, epidermal spray, transdermal spray, transmucosal spray, the single dose of the recombinant interferon can be in a range of about 6 µg to about 100 µg, optionally, about 10 µg to about 40 µg, and further optionally, about 20 µg to about 40 µg, wherein the single dose can be about 6 µg, about 7 µg, about 8 µg, about 9 µg, about 10 µg, about 11 µg, about 12 µg, about 13 µg, about 14 μg, about 15 μg, about 16 μg, about 17 μg, about 18 μg, about 19 μg, about 20 μg, about 21 μg, about 22 μg, about 23 μg, about 24 μg, about 25 μg, about 26 μg, about 27 μg, about 28 μg, about 29 μg, about 30 μg, about 31 μg, about 32 μg, about 33 μg, about 34 μg, about 35 μg, about 36 μg, about 37 μg, about 38 μg, about 39 μg, about 40 μg, about 41 μg, about 42 μg, about 43 μg, about 44 μg, about 45 μg, about 46 μg, about 47 μg, about 48 μg, about 49 μg, about 50 μg, about 51 μg, about 52 μg, about 53 μg, about 54 μg, about 55 μg, about 56 μg, about 57 μg, about 58 μg, about 59 μg, about 60 μg, about 61 μg, about 62 μg, about 63 μg, about 64 μg, about 65 μg, about 66 μg, about 67 μg, about 68 μg, about 69 μg, about 70 μg, about 71 μg, about 72 μg, about 73 μg, about 74 μg, about 75 μg, about 76 μg, about 77 μg, about 78 μg, about 79 μg, about 80 μg, about 81 μg, about 82 μg, about 83 μg, about 84 μg, about 85 μg, about 86 μg, about 87 μg, about 88 μg, about 89 μg, about 90 μg, about 91 μg, about 92 μg, about 93 μg, about 94 μg, about 95 μg, about 96 μg, about 97 μg, about 98 μg, about 99 μg, and about 100 μg.

The present recombinant interferon can be administered to the subjects through different administration protocols. For example, for the purpose of treatment, the present recombinant interferon can be administered to the subject about 1, 2, 3, 4, 5, 6, 7, 8, or more times per day, or the present recombinant interferon can be administered to the subject once at the time interval of every about 2, 3, 4, 5, 6, 7, 8, 9, 10, 11, 12, 13, 14, 15, 16, 17, 18, 19, 20, or 21 days, every month, every 2 months, or longer time. For the purpose of prevention, the present recombinant interferon can be administered to the subject once at the time interval of every about 1, 2, 3, 4, 5, 6, 7, 8, 9, or 10, every 2 weeks, every 3 weeks, every month, every 2 months, every 3 months, every half year, every 1 year, or a longer time.

The present recombinant interferon can be administered to the subjects in one or more treatment cycles. As used herein, the term "treatment cycle" refers to a biological or medical response time length reached by the present recombinant interferon or the pharmaceutical composition comprising the recombinant interferon, and explored for researchers, veterinarians, medical practitioners or other clinicians observed in tissues, systems, animals, individuals or human beings. The duration of such one treatment cycle is at least about 1 day, about 2 days, about 3 days, about 4 days, about 5 days, about 6 days, about 7 days, about 8 days, about 9 days, about 10 days, about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, or about 6 years and the like, or the duration can also be about 1 day to about 6 years, about 1 week to about 4 years, about 2 weeks to about 3 years, about 1 month to about 1 year, or about 2 months to about 9 months and the like. The present recombinant interferon can be administered for a long time, namely, namely, the lasting prolonged time in one treatment cycle includes over the life time of the subject so as to improve or control or limit the symptom of the subjects. In one treatment cycle, the present recombinant interferon can be administered to the subjects one or more times.

Alternatively, the present recombinant interferon can be administered to the subjects in more treatment cycles. For example, such treatment cycles can be 2, 3, 4, 5, 6, 7, 8, 9, 10, or more treatment cycles; and the duration of the treatment cycles can include over the life time of the subject. The time intervals (i.e. withdrawal period) of any two adjacent treatment cycles in all the treatment cycles can be the same or different, for example, the time interval can be at least about 2 days, about 3 days, about 4 days, about 5 days, about 6 days, about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, about 6 years and the like; and such time interval can also be about 2 days to about 6 years, about 4 days to about 3 years, about 1 week to about 1 year, about 2 months to about 9 months, or about 3 months to about 6 months and the like.

When the present recombinant interferon is administered for more times in one treatment cycle, the dose in every administration can be the same or different, for example, the present recombinant interferon is administered for one or more times in a lower dose, and then the present recombinant interferon is administered for one or more times in an increased or gradually-increased dose; or, the present recombinant interferon is administered for one or more times in a smaller dose, then the present recombinant interferon is administered for one or more times in an increased or gradually-increased dose, and the present recombinant interferon is administered for one or more times in a decreased or gradually-decreased dose; or, the present recombinant interferon is administered for one or more times in a larger dose, and then the present recombinant interferon is administered for one or more times in a decreased or gradually-decreased dose; or, the present recombinant interferon is administered for one or more times in a larger dose, then the present recombinant interferon is administered for one or more times in a decreased or gradually-decreased dose, and the present recombinant interferon is administered for one or more times in an increased or gradually-increased dose. In some embodiments, the smaller dose can be the induction dose.

Compared with the previously administered dose, the later increasingly administered dose can be about 110% to about 500%, including, for example about 110%, about 120%, about 130%, about 140%, about 150%, about 160%, about 170%, about 180%, about 190%, about 200%, about 220%, about 240%, about 260%, about 280%, about 300%, about 350%, about 400%, about 450% and about 500%, of the previously administered dose. Compared with the previously administered dose, the later gradually-increased administered dose can be about 110% to about 500% including, for example about 110%, about 120%, about 130%, about 140%, about 150%, about 160%, about 170%, about 180%, about 190%, about 200%, about 220%, about 240%, about 260%, about 280%, about 300%, about 350%, about 400%, about 450% and about 500%, of the previously administered dose sequentially. The gradually-increased dose can be increased by 1 time, 2 times, 3 times, 4 times, 5 times, 6 times, 7 times, 8 times, 9 times, 10 times, or more times, and then the last dose can be kept till the end of the treatment cycle.

Compared with the previously administered dose, the later decreasingly administered dose can be about 5% to about 99% including, for example, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and about 99%, of the previously administered dose. Compared with the previously administered dose, the later gradually-decreased administered dose can be about 5% to about 99% including, for example, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and 99%, of the previously administered dose sequentially. The gradually-decreased dose can be decreased by 1 time, 2 times, 3 times, 4 times, 5 times, 6 times, 7 times, 8 times, 9 times, 10 times, or more times, and then the last dose can be kept till the end of the treatment cycle.

In addition, when the present recombinant interferon is administered for one or more times in the same single dose in each of the treatment cycles, the single doses of the present recombinant interferon in two different treatment cycles can be the same or different. For example, the single dose can be gradually increased or decreased. Compared with the previously administered dose, the increasing or decreasing degree is as mentioned above.

In some embodiments, the gradually increasing or the gradually decreasing can be linear increasing or decreasing, for example, the first administered drug is 9 μg, then the later increased dose is 18 μg, 36 μg, 72 μg and the like sequentially, namely, the sequential increasing rate is 100%; or, the gradually increasing or the gradually decreasing can be non-linear increasing or decreasing, for example, the first administered drug is 9 μg, then the later increased dose can be 15 μg, 18 μg, 21 μg and the like, namely, compared with the previous administered drug, the drug increasing degree at every time can be different.

It should be noted that the administration dosage and the administration protocol can be changed reasonably by the person skilled in the art based on the teaching of the invention, with the type and severity of the disorder to be released, the subject, the administration methods and the like.

F. Specific Treatment Methods and Pharmaceutical Applications.

Specific treatment methods and pharmaceutical applications with use of the present recombinant interferon are provided herein.

In one aspect, the present invention provides a method for treating a tumor in a subject, comprising administering to the subject a recombinant interferon encoded by SEQ ID NO: 2.

In one embodiment, the present invention provides a method for treating tumor in a subject, comprising administering to the subject a recombinant interferon encoded by SEQ ID NO: 2, and at least one other anti-cancer therapy, wherein the at least one other anti-cancer therapy is administered to the subject before, simultaneously, and/or after administration of the recombinant interferon, and wherein the tumor is a cancer or solid tumor that is not indicated nor appropriate for surgery, or the tumor is a solid tumor that cannot be resected, and the combination of the recombinant interferon and the at least one other anti-cancer therapy eliminate the tumor or reduce the size of the tumor compared to the tumor before treatment.

In one embodiment, the present invention provides a method for preventing tumor recurrence and/or metastasis or prolonging or maintaining a tumor-free status in a subject with a tumor after at least one anti-cancer therapy, comprising administering to the subject a recombinant interferon encoded by SEQ ID NO: 2.

In one embodiment, the present invention provides a non-surgical method for eliminating a tumor in a subject or reducing the size of a tumor in a subject, comprising administering to the subject a recombinant interferon encoded by SEQ ID NO: 2.

In one embodiment, the present invention provides a method for eliminating or reducing the pleural effusion, ascites, and/or pericardial effusion in a subject with tumor, comprising administering to the subject a recombinant interferon encoded by SEQ ID NO: 2.

In one embodiment, the present invention provides a method for treating tumor in a subject, comprising topically or locally administering to the tumor lesions of the subject a recombinant interferon encoded by SEQ ID NO: 2.

In one embodiment, the present invention provides a method for eliminating or reducing metastatic tumor lesions in a subject, comprising topically or locally administering to the metastatic tumor lesions of the subject a recombinant interferon encoded by SEQ ID NO: 2.

In one embodiment, the present invention provides a method for eliminating or reducing the bone metastatic lesions of tumor in a subject, comprising administering to the subject a recombinant interferon encoded by SEQ ID NO: 2 by topical or local administration, wherein the topical or local administration comprises transdermal administration and/or infiltration administration, optionally, the recombinant interferon is administered to the bone metastatic lesions of tumor of the subject.

In one embodiment, the present invention provides a method for eliminating or reducing the bone lesions of tumor such as bone metastatic lesions of tumor, muscular lesions of tumor such as muscular metastatic lesions of tumor, subcutaneous tissue lesions of tumor such as subcutaneous tissue metastatic lesions of tumor, prostatic lesions of tumor such as prostatic metastatic lesions of tumor, and/or lymph node lesions of tumor such as lymph node metastatic lesions of tumor in a subject, comprising administering to the subject a recombinant interferon encoded by SEQ ID NO: 2 by any administration route through the skin, so that eliminating or reducing the bone lesions of tumor such as bone metastatic lesions of tumor, muscular lesions of tumor such as muscular metastatic lesions of tumor, subcutaneous tissue lesions of tumor such as subcutaneous tissue metastatic lesions of tumor, prostatic lesions of tumor such as prostatic metastatic lesions of tumor, and/or lymph node lesions of tumor such as lymph node metastatic lesions of tumor, optionally, the recombinant interferon is administered to the metastatic lesions of tumor of the subject.

In another aspect, the present invention provides a method for treating lung cancer in a subject, comprising administering to the subject a recombinant interferon encoded by SEQ ID NO: 2.

In one embodiment, the present invention provides a method for treating lung cancer in a subject, comprising administering to the subject a recombinant interferon encoded by SEQ ID NO: 2 and one or more chemotherapeutic drugs in two or more treatment cycles, and then administering to the subject a recombinant interferon encoded by SEQ ID NO: 2 and one or more targeted drugs in one or more treatment cycles.

In one embodiment, the present invention provides a method for treating lung cancer in a subject, comprising administering to the subject a recombinant interferon encoded by SEQ ID NO: 2 by subcutaneous administration and/or intramuscular administration, wherein the recombinant interferon is administered in an amount in a range of about 2 μg to about 70 μg, optionally about 4 μg to about 50 μg, further optionally about 4 μg to about 30 μg by one subcutaneous administration and/or intramuscular administration, the recombinant interferon is administered by subcutaneous administration and/or intramuscular administration once every about 1 to about 7 days, optionally every about 1 to about 2 days, lasting at least about 1 day, about 2 days, about 3 days, about 4 days, about 5 days, about 6 days, about 7 days, about 8 days, about 9 days, about 10 days, about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, or about 6 years and the like, or the recombinant interferon can be administered for a long time, including over the life time of the subject; or the duration can also be about 1 day to about 6 years, about 1 week to about 4 years, about 2 weeks to about 3 years, about 1 month to about 1 year, or about 2 months to about 9 months and the like.

In one embodiment, the present invention provides a method for treating lung cancer in a subject, comprising administering to the subject a recombinant interferon encoded by SEQ ID NO: 2 by subcutaneous administration and/or intramuscular administration, wherein the recombinant interferon is administered one or more times by subcutaneous administration and/or intramuscular administration at an induction dose in a range of about 2 μg to about 10 μg each time, optionally about 4 μg to about 10 μg each time, further optionally about 4.5 μg to about 9 μg each time, such as about 4.5 μg each time or about 9 μg each time, and then the recombinant interferon is administered more times by subcutaneous administration and/or intramuscular administration at a therapeutic dose in a range of about 10 μg to about 70 μg each time, optionally about 12 μg to about 50 μg each time, further optionally about 12 μg to about 30 μg each time.

In one embodiment, the present invention provides a method for treating cancer in a subject, wherein the cancer originates from lung cancer in the subject and metastasizes to brain, comprising administering to the subject a recombinant interferon encoded by SEQ ID NO: 2, wherein the recombinant interferon is administered one or more times by subcutaneous administration and/or intramuscular administration at an induction dose in a range of about 2 μg to about 10 μg each time, optionally about 4 μg to about 10 μg each time, further optionally about 4.5 μg to about 9 μg each time, such as about 4.5 μg each time or about 9 μg each time, and then the recombinant interferon is administered more times by subcutaneous administration and/or intramuscular administration at a therapeutic dose in a range of about 10 μg to about 70 μg each time, optionally about 12 μg to about 50 μg each time, further optionally about 12 μg to about 30 μg each time, and the recombinant interferon is administered to the subject by inhalation administration before, simultaneously, and/or after the subcutaneous administration and/or intramuscular administration, the recombinant interferon is administered in an amount in a range of about 100 μg to about 2000 μg, optionally about 100 μg to about 1500 μg, further optionally about 150 μg to about 800 μg, still further optionally about 200 μg to about 600 μg by one inhalation administration, and the recombinant interferon is administered by inhalation administration once every about 1 day to about 3 days, optionally every about 1 day.

In one embodiment, the present invention provides a method for treating cancer in a subject, wherein the cancer originates from lung cancer in the subject and metastasizes to bone or liver, comprising administering to the subject a recombinant interferon encoded by SEQ ID NO: 2, wherein the recombinant interferon is administered one or more times by subcutaneous administration and/or intramuscular administration at an induction dose in a range of about 2 μg to about 10 μg each time, optionally about 4 μg to about 10 μg each time, further optionally about 4.5 μg to about 9 μg each time, such as about 4.5 μg each time or about 9 μg each time, and then the recombinant interferon is administered more times by subcutaneous administration and/or intramuscular administration at a therapeutic dose of about 10 μg-about 70 μg each time, optionally about 12 μg to about 50 μg each time, further optionally about 12 μg to about 30 μg each time.

In one embodiment, the present invention provides a method for treating cancer in a subject, wherein the cancer originates from lung cancer in the subject and metastasizes to lymph nodes, comprising administering to the subject a recombinant interferon encoded by SEQ ID NO: 2, wherein the recombinant interferon is administered one or more times by subcutaneous administration and/or intramuscular administration at an induction dose in a range of about 2 μg to about 10 μg each time, optionally about 4 μg to about 10 μg each time, further optionally about 4.5 μg to about 9 μg each time, such as about 4.5 μg each time or about 9 μg each time, and then the recombinant interferon is administered more times by subcutaneous administration and/or intramuscular administration at a therapeutic dose of about 10 μg to about 70 μg each time, optionally about 12 μg to about 50 μg each time, further optionally about 12 μg to about 30 μg each time, and the recombinant interferon is administered to the tumor and/or the lymph nodes metastases by topical or local administration before, simultaneously, and/or after the subcutaneous administration and/or intramuscular administration.

In one embodiment, the present invention provides a method for treating lung cancer in a subject, wherein the subject has pleural effusion, ascites and/or pericardial effusion, comprising administering to the subject a recombinant interferon encoded by SEQ ID NO: 2 by topical or local administration.

In another aspect, the present invention provides uses of a recombinant interferon encoded by SEQ ID NO: 2 in preparation of drugs for treating tumors in a subject.

In one embodiment, the present invention provides uses of a recombinant interferon encoded by SEQ ID NO: 2 and other anti-tumor drugs in preparation of drugs for treating tumors in a subject.

In one embodiment, the present invention provides uses of a recombinant interferon encoded by SEQ ID NO: 2 in preparation of drugs for preventing tumor recurrence and/or metastasis after anti-tumor therapies in a subject.

In one embodiment, the present invention provides uses of a recombinant interferon encoded by SEQ ID NO: 2 in preparation of drugs for eliminating a tumor or reducing the size of a tumor in a subject by non-surgical method.

In one embodiment, the present invention provides uses of a recombinant interferon encoded by SEQ ID NO: 2 in preparation of drugs for eliminating or reducing pleural effusion, ascites, and/or pericardial effusion in a subject with tumor.

In one embodiment, the present invention provides a uses of a recombinant interferon encoded by SEQ ID NO: 2 in preparation of drugs for treating lung cancer in a subject.

In one embodiment, the present invention provides uses of a recombinant interferon encoded by SEQ ID NO: 2 in preparation of drugs for treating lung cancer in a subject in combination with chemotherapeutic drugs, targeted drugs.

In some embodiments, the subject is an early, medium-term, or advanced cancer patient, optionally, the subject is a medium-term, or advanced cancer patient, further optionally, the subject is an advanced cancer patient, such as an advanced lung cancer patient.

In some embodiments, the subject can be a stage 0, I, II, III, or IV cancer patient, optionally, the subject is an stage III or stage IV cancer patient, such as an stage III or stage IV lung cancer patient. Such cancer patient can be a patient with metastasized tumors, such as the tumors which are metastasized in situ or in the distance.

In some embodiments, the subject is a medium-term, advanced cancer patient, or stage III or stage IV cancer patient, optionally, the subject is an advanced, or stage III or stage IV cancer patient.

In some embodiments, the tumor is a cancer or a solid tumor with or without indications for surgery.

In some embodiments, the tumor in a subject is a tumor that is capable of being resected. In some embodiments, the tumor in a subject is a tumor that is not capable of being resected. In some embodiments, the surgeries include but not limited to surgical procedures.

In some embodiments, the subject is a subject with solid tumors.

In some embodiments, the solid tumor is a solid tumor that is capable of or is not capable of being resected.

In some embodiments, the solid tumor that is capable of or is not capable of being resected is an advanced solid tumor.

In some embodiments, the solid tumor is a solid tumor with or without indications for surgery, such as indications for tumor surgery.

In some embodiments, the solid tumor with or without indications for surgery such as indications for tumor surgery is an advanced, or stage III or stage IV solid tumor.

In some embodiments, the tumor is a solid tumor. The solid tumor comprises one or more of: lung cancer, liver cancer, hepatocellular carcinoma (HCC), esophageal cancer, cholangiocarcinoma, gallbladder carcinoma, stomach cancer, abdominal cancer, gastrointestinal cancer, gastric cancer, pancreatic cancer, renal cell carcinoma, renal cancer, bone cancer, breast cancer, ovarian cancer, uterine cancer, cervical cancer, endometrial cancer, colorectal cancer, colon cancer, rectal cancer, bladder cancer, superficial bladder cancer, prostate cancer, adrenal tumors, squamous cell carcinoma, neuroma, malignant neuroma, myoepithelial carcinoma, synovial sarcoma, rhabdomyosarcoma, gastrointestinal interstitial cell tumor, skin cancer, basal cell carcinoma, malignant melanoma, thyroid cancer, nasopharyngeal carcinoma, hemangioma, epidermoid carcinoma, head and neck cancer, glioma, or Kaposi's sarcoma; optionally, lung cancer; further optionally, the lung cancer comprises small cell lung cancer (SCLC), non small cell lung cancer (NSCLC), or both.

In some embodiments, the tumor is a non-solid tumor. The non-solid tumor comprises one or more of leukemia, acute leukemia, chronic leukemia, chronic myelocytic leukemia, acute myelogenous leukemia, chronic myelogenous leukemia, chronic lymphocytic leukemia, acute lymphoblastic leukemia, T-cell leukemia, hairy cell leukemia, polycythemia, myelodysplastic syndrome, multiple myeloma, lymphadenoma, Hodgkin's lymphoma, or Non-Hodgkin's lymphoma.

In some embodiments, the effective amount is a therapeutically effective amount or a prophylactically effective amount. In some embodiments, the present recombinant interferon can be administered to the subject in single dose of about 2 µg to about 2000 µg, optionally, about 4 µg to about 1500 µg, further optionally, about 9 µg to about 1000 µg, and still further optionally, about 9 µg to about 600 µg.

In certain embodiments, when the present recombinant interferon is administered by systemic administration, the therapeutically effective amount is about 2 µg to about 70 µg, optionally about 4 µg to about 50 µg, further optionally about 4 µg to about 30 µg, and still further optionally, about 9 µg to about 30 µg. In specific embodiments, when the present recombinant interferon is administered by systemic administration, the prophylactically effective amount is about 2 µg to about 70 µg, optionally about 4 µg to about 50 µg, further optionally about 4 µg to about 30 µg, and still further optionally, about 9 µg to about 30 µg.

In some embodiments, the present recombinant interferon and/or chemotherapeutic drugs, targeted drugs, biological drugs and the like combined with the present recombinant interferon can be administered to the subject by at least one of: systemic administration, topical administration, and local administration. In some embodiments, the present recombinant interferon and/or chemotherapeutic drugs, targeted drugs, biological drugs and the like combined with the present recombinant interferon can be administered to the subject by an administration route, the administration route comprises one or more of oral, rectal, sublingual, intravenous, intra-arterial, intramuscular, subcutaneous, intra-bone, intracutaneous, intra-articular, intraperitoneal, intrathecal, intracerebral, vaginal, percutaneous, transdermal, epidermal, transmucosal, transocular, pulmonary, nasal, abdominal, intrapleural, intraventricular, pericardial, inhalation, intratumoral, uterine, infiltration, or intravesical administration. In some specific embodiments, the present recombinant interferon and/or chemotherapeutic drugs, targeted drugs, biological drugs and the like combined with the present recombinant interferon can be administered to the subject by subcutaneous, intramuscular, inhalation, infiltration, intrapleural, abdominal, pericardial, intratumoral, spary administration or any combination thereof. In some embodiments, the present recombinant interferon and/or chemotherapeutic drugs, targeted drugs, biological drugs and the like combined with the present recombinant interferon can be administered to the subject by intramuscular and/or subcutaneous administration. In some embodiments, when the present recombinant interferon and/or chemotherapeutic drugs, targeted drugs, biological drugs and the like combined with the present recombinant are administered to the operative site, which can be administered to the subject by topical or local administration, such as infiltration, intrapleural, abdominal, pericardial, uterine, intravesical, intratumoral, pulmonary, nasal, percutaneous, transdermal, epidermal, and/or transmucosal administration.

In some embodiments, the present recombinant interferon and/or chemotherapeutic drugs, targeted drugs, biological drugs and the like combined with the present recombinant interferon can be administered to the subject by injection, such as subcutaneous, intramuscular, intravenous, intra-arterial, intracerebral, intraperitoneal, intratumoral, intra-articular, intrathecal and intra-bone injection and the like. In some embodiments, when administering by inhalation, the inhalation can be pulmonary and/or nasal inhalation. In some specific embodiments, the inhalation administration can be dry powder inhalation or aerosol inhalation. In some embodiments, when administering by intrapleural, abdominal, uterine, intravesical, pericardial administration, the present recombinant interferon and/or chemotherapeutic drugs, targeted drugs, biological drugs and the like combined with the present recombinant interferon can be administered to the subject by perfusion, such as intrapleural, abdominal, uterine, intravesical, and/or pericardial perfusion. In some embodiments, when administering by percutaneous, transdermal, epidermal or transmucosal administration, the present recombinant interferon and/or chemotherapeutic drugs, targeted drugs, biological drugs and the like combined with the present recombinant interferon can be further administered to the subject by spray, such as percutaneous, epidermal, transdermal and/or transmucosal spray.

When the present recombinant interferon is systemically administered via injection administration (such as subcutaneous injection, intramuscular injection), the single dose can be about 2 μg to about 70 μg, optionally about 4 μg to about 50 μg, and further optionally about 4 μg to about 30 μg, including but not limited to about 2 μg, about 3 μg, about 4 μg, about 4.5 μg, about 9 μg, about 13.5 μg, about 15 μg, about 18 μg, about 21 μg, about 25.5 μg, about 30 μg, about 40 μg, about 50 μg, about 60 μg, and about 70 μg. In some embodiments, the present recombinant interferon is administered by subcutaneous and/or intramuscular administration once every about 1 day to about 7 days, optionally once every about 1 day to about 2 days. In some embodiments, the injection lasts at least about 1 day, about 2 days, about 3 days, about 4 days, about 5 days, about 6 days, about 7 days, about 8 days, about 9 days, about 10 days, about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, about 6 years and the like, or the recombinant interferon can be administered for a long time, including over the life time of the subject; or the duration can also be about 1 day to about 6 years, about 1 week to about 4 years, about 2 weeks to about 3 years, about 1 month to about 1 year, or about 2 months to about 9 months and the like.

When the present recombinant interferon is locally administered via injection administration (such as the intratumoral injection), the single dose of the recombinant interferon can be in the range of about 60 μg to about 600 μg, optionally about 60 μg to about 500 μg, further optionally about 80 μg to about 400 μg, and still further optionally about 100 μg to about 250 μg. In some embodiments, the present recombinant interferon is administered via intratumoral administration once every about 1 day to about 10 days, optionally once every about 1 day to about 7 days such as every about 1, 2, 3, 4, 5, 6 or 7 days. In some embodiments, the intratumoral administration such as intratumoral injection lasts at least about 1 day, about 2 days, about 3 days, about 4 days, about 5 days, about 6 days, about 7 days, about 8 days, about 9 days, about 10 days, about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, about 6 years and the like, or the recombinant interferon can be administered for a long time, including over the life time of the subject; or the duration can also be about 1 day to about 6 years, about 1 week to about 4 years, about 2 weeks to about 3 years, about 1 month to about 1 year, or about 2 months to about 9 months and the like. In specific embodiments, when the present recombinant interferon is administered via intratumoral administration, the protocol of intratumoral administration is as follow: the recombinant interferon is administered by intratumoral injection once every about 1 day for about 4 to about 8 times, and then the recombinant interferon is administered by intratumoral injection once every about 3 days to about 5 days for about 4 to about 8 times, and then the recombinant interferon is administered by intratumoral injection once every about 7 days, the intratumoral administration is stopped when the tumor disappears or becomes too small to conduct the intratumoral injection, wherein the recombinant interferon is administered in an amount of about 60 μg to about 600 μg, optionally about 60 μg to about 500 μg, further optionally about 80 μg to about 400 μg, still further optionally about 100 μg to about 250 μg by once intratumoral injection.

When the present recombinant interferon is administered via inhalation (such as pulmonary and nasal inhalation, including dry powder inhalation and aerosol inhalation), the single dose of the recombinant interferon can be about 100 μg to about 2000 μg, optionally about 100 μg to about 1500 μg, further optionally about 150 μg to about 800 μg, and still further optionally about 200 μg to about 600 μg, including but not limited to about 100 μg, about 200 μg, about 300 μg, about 400 μg, about 500 μg, about 600 μg, about 700 μg, about 800 μg, about 900 μg and about 1000 μg. In some embodiments, the present recombinant interferon is administered via inhalation once every about 1 day to about 3 days, optionally every about 1 day. In some embodiments, the inhalation lasts at least about 1 day, about 2 days, about 3 days, about 4 days, about 5 days, about 6 days, about 7 days, about 8 days, about 9 days, about 10 days, about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, about 6 years and the like, or the recombinant interferon can be administered for a long time, including over the life time of the subject; or the duration can also be about 1 day to about 6 years, about 1 week to about 4 years, about 2 weeks to about 3 years, about 1 month to about 1 year, or about 2 months to about 9 months and the like.

When the present recombinant interferon is administered via perfusion (such as intrapleural, abdominal, uterine, intravesical, pericardial perfusion), the single dose of the recombinant interferon can be about 30 μg to about 2000 μg, optionally about 100 μg to about 1500 μg, further optionally about 150 to about 1000 μg, still optionally about 200 to about 800 μg, and still further optionally about 200 to about 400 μg. In some embodiments, the present recombinant interferon is administered via intrapleural, abdominal and/or pericardial administration once every about 1 day to about 10 days, optionally once every about 1 day to about 7 days such as every about 1, 2, 3, 4, 5, 6, or 7 days. In some embodiments, the perfusion lasts at least about 1 day, about 2 days, about 3 days, about 4 days, about 5 days, about 6 days, about 7 days, about 8 days, about 9 days, about 10 days, about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, about 6 years and the like, or the recombinant interferon can be administered for a long time, including over the life time of the subject; or the duration can also be about 1 day to about 6 years, about 1 week to about 4 years, about 2 weeks to about 3 years, about 1 month to about 1 year, or about 2 months to about 9 months and the like.

When the present recombinant interferon is administered to the lesions (such as the surfaces of skin and mucosa) by spray, such as percutaneous, epidermal, transdermal, transmucosal spray, the single dose of the recombinant interferon can be about 6 μg to about 100 μg, optionally about 10 μg to about 40 μg, and further optionally about 20 μg to about 40 μg. In some embodiments, the present recombinant interferon is administered by spray administration about 1 to about 6 times such as about 1, 2, 3, 4, 5, or 6 times per day. In some embodiments, the spray lasts at least about 1 day, about 2 days, about 3 days, about 4 days, about 5 days, about 6 days, about 7 days, about 8 days, about 9 days, about 10 days, about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, about 6 years and the like, or the recombinant interferon can be administered for a long time, including over the life time of the subject; or the duration can also be about 1 day to about 6 years, about 1 week to about 4 years, about 2 weeks to about 3 years, about 1 month to about 1 year, or about 2 months to about 9 months and the like.

In some embodiments, for the purpose of treatment, the present recombinant interferon can be administered to the subject about 1, 2, 3, 4, 5, 6, 7, 8, or more times per day, or the present recombinant interferon can be administered to the subject once at the time interval of every about 2, 3, 4, 5, 6, 7, 8, 9, 10, 11, 12, 13, 14, 15, 16, 17, 18, 19, 20, or 21 days, every month, every 2 months, or a longer time. In some embodiments, for the purpose of prevention, the present recombinant interferon can be administered to the subject once at the time interval of every about 1, 2, 3, 4, 5, 6, 7, 8, 9, or 10, every 2 weeks, every 3 weeks, every month, every 2 months, every 3 months, every half year, every 1 year, or a longer time.

In some embodiments, the present recombinant interferon is administered in one or more treatment cycles. Optionally, the more cycles can be 2, 3, 4, 5, 6, 7, 8, 9, 10, or more treatment cycles. In specific embodiments, duration of the one treatment cycle is at least about 1 day, about 2 days, about 3 days, about 4 days, about 5 days, about 6 days, about 7 days, about 8 days, about 9 days, about 10 days, about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, about 6 years and the like, or the duration can also be about 1 day to about 6 years, about 1 week to about 4 years, about 2 weeks to about 3 years, about 1 month to about 1 year, or about 2 months to about 9 months and the like. In specific embodiments, the present recombinant interferon can be administered for a long time, including over the life time of the subject, so as to improve or control or limit the symptom of the subjects.

In some embodiments, the present recombinant interferon could be administered in more treatment cycles. In certain embodiments, the treatment cycles are 2 or more treatment cycles. In specific embodiments, the duration of the multiple treatment cycles may include over the life time of the subject. In some embodiments, the time intervals of any two adjacent treatment cycles in all the treatment cycles can be the same or different. In specific embodiments, the time intervals can be at least about 2 days, about 3 days, about 4 days, about 5 days, about 6 days, about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, about 6 years and the like; or the time intervals can be about 2 days to about 6 years, about 4 days to about 3 years, about 1 weeks to about 1 years, about 2 months to about months, about 3 months to about 6 months and the like.

In some embodiments, when the present recombinant interferon is administered more times in one treatment cycle, the present recombinant interferon can be administered for one or more times in a smaller dose, then the present recombinant interferon is administered for one or more times in an increased or gradually-increased dose. In specific embodiments, when the present recombinant interferon is systemically administered via subcutaneous, intramuscular administration (such as subcutaneous, intramuscular injection), the present recombinant interferon can be administered once at a smaller dose such as about 4.5 μg or 9 μg, then the recombinant interferon can be administered for more times in an increased (such as to be about 15 μg, about 18 μg, about 21 μg) or gradually-increased dose. In embodiments, the present recombinant interferon is administered once every about 1 day to abut 2 days. In embodiments, the duration for administration of the present recombinant interferon is about 1 week to about 2 years, optionally about 2 weeks to about 1 year, or further optionally about 1 month to about 9 months, including about 2 months to about 6 months, or over the life time of the subject. In embodiments, the gradually-increased administered dose can be about 110% to about 500% of the previously administered dose sequentially. In embodiments, a smaller dose of the present recombinant interferon (such as about 4.5 μg or about 9 μg) can be administered, followed by about 12 μg to about 18 μg (such as about 13.5 μg, about 15 μg, about 18 μg), and then about 15 μg to about 30 μg (such as about 18 μg, about 21 μg, about 25.5 μg, about 30 μg), once every about 2 days, and for about 2 months to about 3 years, or over the life time of the subject.

In some embodiments, the recombinant interferon can be administered one or more times at an induction dose, and then one or more times at a therapeutic dose. In some embodiments, the induction dose is about 2 μg to about 10 μg each time, optionally about 4 μg to about 10 μg each time, further optionally about 4.5 μg to 9 μg each time, for example, about 4.5 μg each time or about 9 μg each time. In some embodiments, the therapeutic dose is about 10 μg to about 70 μg each time, optionally about 12 μg to about 50 μg each time, further optionally about 12 μg to about 30 μg each time. In some embodiments, the induction dose is about 4 μg to about 10 μg each time, and the therapeutic dose is about 12 μg to about 50 μg each time. In some embodiments, the induction dose is usually lower than the therapeutic dose. In some embodiments, the time interval between administration of the induction dose and the therapeutic dose is about 1 day to about 1 month, optionally about 1 day to 1 week, further optionally about 1 day to about 3 days, including, for example, about 1 day, about 2 days, about 3 days, about 4 days, about 5 days, about 6 days, about 7 days, about 8 days, about 9 days, about 10 days, about 1 week, about 2 weeks, about 3 weeks and about 1 month. In some embodiments, when the induction dose is administered more times, it is administered once every about 1 day to about 10 days, optionally every about 1 day to about 7 days, further optionally every about 1 day to about 2 days, including, for example every about 1, 2, 3, 4, 5, 6, 7, 8, 9, or 10 days. In some embodiments, when the therapeutic dose is administered more times, it is administered once every about 1 day to about 10 days, optionally every about 1 day to about 7 days, further optionally every about 1 day to about 2 days, including, for example, every about 1, 2, 3, 4, 5, 6, 7, 8, 9, or 10 days. In some embodiments, the total administration time of the induction and therapeutic dose should last at least about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year, about 2 years, about 3 years, about 4 years, about 5 years, about 6 years and the like, or the recombinant interferon can be administered for a long time, including over the life time of the subject.

In some embodiments, the treatment has reduced the tumor size of the subject, for example, by about 10%, about 20%, about 30%, about 40%, about 50%, about 60%, about 70%, about 80%, about 90%, about 95%, or about 100% or more, or even completely eliminate the tumor, according to the tumor size at the beginning of treatment. In some embodiments, the treatment has reduced the number of cancer cells in tumor, malignant pleural effusion, malignant ascites and/or malignant pericardial effusion of the subjects, for example, by about 10%, about 20%, about 30%, about 40%, about 50%, about 60%, about 70%, about 80%, about 90%, about 95%, about 100% or more, or even the number of cancer cells is zero, according to the number of cancer cells at the beginning of treatment. In some embodiments, the treatment has inhibited (including reduced to some degree and/or terminated) the infiltration of tumor cells into peripheral organs; inhibited or prevented tumor metastasis, such as the in-situ or distant metastasis of tumors, or micrometastasis of tumors; reduced the size of the lesions; brought about downstaging of tumor; and also inhibited or killed micrometastasis in the blood and lymphatic channels; thereby allowing complete resection of initially unresectable tumors or helping to resect tumor which is capable of being resected, such resection is for example a surgical resection. As for the method, it can be a "neoadjuvant method" or an "introducing method". As used herein, term "neoadjuvant method" or "introducing method" refers to a therapy given prior to surgery, the goal of the therapy is to reduce the size of the lesions, bring about downstaging of tumor, inhibit or kill micrometastases in the blood and lymphatic channels, reduce the tumor size thereby allowing more conveniently resect tumors or completely resect of initially unresectable tumors. In addition, the present recombinant interferon can be further administered to the subject to prevent recurrence and/or metastasis of the tumors after resection of the tumors.

In some embodiments, the method has reduced or eliminated malignant pleural effusion, malignant ascites and/or malignant pericardial effusion, for example, by about 10%, about 20%, about 30%, about 40%, about 50%, about 60%, about 70%, about 80%, about 90%, about 95%, about 100% or more, or even completely eliminated malignant pleural effusion, malignant ascites and/or malignant pericardial effusion, according to the volume of malignant pleural effusion, malignant ascites and/or malignant pericardial effusion at the beginning of treatment.

In some embodiments, the method for preventing recurrence of tumor has reduced the possibility of tumor recurrence after the subject with tumors received treatment. In some embodiments, the subject with tumors has been identified and treated prior to administration of the present recombinant interferon (rSIFN-co); such treatments may be the method with the present recombinant interferon, or one or more other different anti-cancer therapies such as chemotherapy, radiotherapy, surgical therapy, interventional therapy, biotherapy, gene therapy, ablation therapy, immunotherapy, targeted therapy, traditional Chinese medicine therapy or any combination thereof. The treatment results can be clinical or basic healing. In some embodiments, such preventive therapies can inhibit or eliminate possible micrometastasis in the blood channel and lymphatic channel, so as to prevent recurrence and/or metastasis of the tumor, such micrometastasis can or cannot be clinically detected.

In some embodiments, the present recombinant interferon could delay the growth of tumor in the subject, for example, by about 10%, about 20%, about 30%, about 40%, about 50%, about 60%, about 70%, about 80%, about 90%, about 95% or more, according to the tumor growth speed at the beginning of the treatment.

In some embodiments, the present recombinant interferon is administered to the subject as monotherapy. In some embodiments, further comprising one or more other anti-cancer therapies administered to the subject, optionally, other anti-cancer therapies are administered to the subject before, simultaneously, and/or after administration of the recombinant interferon. In some embodiments, the other anti-cancer therapies comprise one or more of: chemotherapy, radiotherapy, surgical therapy, interventional therapy, biotherapy, gene therapy, ablation therapy, immunotherapy, targeted therapy, and traditional Chinese medicine therapy. In certain embodiments, the other anti-cancer therapies comprise one or more of chemotherapy, radiotherapy, surgical therapy, targeted therapy, and biotherapy. In some embodiments, the other anti-cancer therapies comprise chemotherapy, radiotherapy, or both. In some embodiments, the other anti-cancer therapies comprise chemotherapy such as first-line chemotherapy, for example, chemotherapeutic drugs and/or chemotherapeutic protocols comprising platinum compounds, such as Cisplatin.

In some embodiments, when in the treatment for lung cancer, chemotherapeutic drugs used in the chemotherapy combined with the present recombinant interferon include but not limited to platinum compounds such as Cisplatin, Carboplatin, Eloxatin and the like; Paclitaxel compounds such as Docetaxel (Docetaxel Injection, Taxotere) and the like; cytidine antimetabolite such as Gemcitabine (Gemzar) and the like; antifolic antimetabolite such as Pemetrexed (Alimta) and the like; pyrimidine antimetabolite such as Capecitabine (Xeloda) and the like; as well as any combination of the chemotherapeutic agents. Or otherwise the following chemotherapy protocols are used, including but not limited to chemotherapy protocols containing platinum compounds, such as GP, TP, EP, GP-T2 protocols and the like. In specific embodiments, when in the treatment for lung cancer, the chemotherapy protocol applied in conjunction with the present recombinant interferon includes Cisplatin nebulized inhalation, Cisplatin pericardial perfusion and the like.

In some embodiments, when in the treatment for lung cancer, the targeted drugs used in the targeted therapy combined with the present recombinant interferon include but not limited to Gefitinib, Erlotinib and/or recombinant human endostatin and the like.

In some embodiments, when in the treatment for the lung cancer, other anti-cancer therapies applied in combination with the present recombinant interferon include any combination of the chemotherapeutic drugs/chemotherapy protocols and targeted drugs.

In specific embodiments, when in the treatment for the lung cancer, other anti-cancer therapies applied in combination with the present recombinant interferon include GP protocol combined with recombinant human endostatin, EP protocol combined with Cisplatin nebulized inhalation and the like.

In some embodiments, the method of the present invention is a non-surgical therapy.

G. Evaluation Standard of Curative Effect and Adverse Effect

The curative effect evaluation on the present recombinant interferon in the aspect of clinical treatment for tumors such as solid tumors adopts the Response Evaluation Criteria in Solid Tumors standard (RECIST standard) published in 1999 (see James, K. et al. J Natl Cancer Inst, 1999, 91, 523-528).

The tumor lesions are divided into measurable lesions and un-measurable lesions, wherein the measurable lesions are defined as target lesions; the longest diameter represents the size of each lesion; at most 5 lesions can be selected in each involved organ, the sum of the measured lesions of all the involved organ is not more than 10, and the sum of the longest diameters of all the lesions is the overall diameter of the target lesion. The un-measurable lesions are defined as non-target lesions, only the existence of the lesions are recorded and tracked, but the sizes of the lesions are not measured.

The curative effect evaluation standard of the target lesion is divided into 4 grades, the curative effect evaluation standard of the non-target lesion is divided into 3 grades, and the overall curative effect evaluation is obtained by combining the curative effects of the two kinds of lesions. It is specifically described as follows:

The curative effect evaluation standard of the target lesions: (1) CR (complete remission): all the target lesions disappear; (2) PR (partial remission): the overall diameter of the target lesions is decreased by more than 30%; (3) NC or SD (no change or stable disease): the target lesions are neither decreased to "PR" nor increased to "PD"; and (4) PD (progression disease): the overall diameter of the target lesions is increased by more than 20%, or one or more new lesions appear.

The curative effect evaluation standard of the non-target lesion: (1) CR: all the non-target lesions disappear, and the tumor marker level is normal; (2) IR (incomplete response)/SD: one or more non-target lesions is/are not changed, and/or the tumor markers exceed the normal limit; and (3) PD: one or more new lesions appear, and/or the non-target lesions are obviously developed.

The overall curative effect evaluation standard of solid tumors.

TABLE 1

The overall curative effect evaluation standard of solid tumors

| Target lesion | Non-target lesion | New lesion | Overall curative effect |
|---|---|---|---|
| CR | CR | No | CR |
| CR | IR/SD | No | PR |
| PR | Non-PD | No | PR |
| NC/SD | Non-PD | No | NC/SD |
| PD | Any | Yes or No | PD |
| Any | PD | Yes or No | PD |
| Any | Any | Yes | PD |

The adverse effect evaluation on the present recombinant interferon for clinical treatment for the tumors such as the solid tumors takes the reference to the "WHO" Toxicity Grading Standard.

Compared with the prior art, the recombinant interferon has the beneficial effects as follows:

The recombinant interferon rSIFN-co used in the present invention has obvious different structural features and physiological activities compared with the existing interferons such as INFERGEN® (interferon alfacon-1) of the US Amgen. On one hand, the recombinant interferon can be singly used and/or can be combined with radiotherapy, chemotherapy, biological agents, and/or targeted drugs and the like, so as to non-surgically eliminate or reduce the tumors of the solid tumor subjects, particularly advanced tumors; specifically, the recombinant interferon can eliminate or reduce the solid tumors without indications for surgery, particularly the advanced solid tumors without indications for surgery. On the other hand, the recombinant interferon can be singly administered through topical or local administration such as intratumoral injection/epidermal spray administration and the like, or through the combination of the topical or local administration together with the systemic administration (using the present recombinant interferon or radiotherapy/other anti-tumor drugs and the like), so as to non-surgically (namely, without surgery) eliminate or reduce the solid tumors. Further, the recombinant interferon has obvious effect in replacing the chemotherapy drugs for preventing post-surgery recurrence or metastasis of the tumors, particularly various metastatic lesions such as bone metastasis which cannot be eliminated by existing treatment means; however, drugs can be directly administered to the lesions by the present invention, especially by the topical or local administration, to obviously reduce or eliminate the tumors. In addition, the recombinant interferon can be singly administered through intrapleural or abdominal perfusion so as to for effectively eliminate or decrease malignant pleural effusion and/or malignant ascites.

Furthermore, cancer can be controlled by the rSIFN-co combination therapy. Firstly, the present recombinant interferon (rSIFN-co) has broad-spectrum anti-tumor effects, which is effective on both solid tumors and non-solid tumors while, at the same time, rSIFN-co has a good synergetic effect with existing treatment means such as surgical therapy, chemotherapy, radiotherapy, biotherapy and other anti-tumor drugs. Secondly, rSIFN-co has low toxicity which means no harm to normal cells has been observed when rSIFN-co is used in large doses. Thirdly, rSIFN-co is convenient to use and can be directly applied to tumors in any position. The rSIFN-co can be used by subcutaneous/intramuscular injection to control systemic progress of tumor, by intrapleural/abdominal perfusion to eliminate effusion and intrapleural/abdominal tumors, by topical or local injection to eliminate primary or metastatic tumors, and by infiltration (transdermal) administration to treat tumor lesions in bone, skin, muscle, prostate and the like; and rSIFN-co can also be administered by aerosol inhalation. According to above three advantages of rSIFN-co, effective rate of the combination therapy is no lower than 90%. With regard to early or medium-term cancer cases, rSIFN-co can be used after surgery to replace chemotherapy and effectively prevent recurrence and metastasis; with regard to advanced cancer cases or cancer cases without indications for therapy, rSIFN-co can be used to eliminate tumors without surgery; with regard to cases without indications for surgery, rSIFN-co can be used to transformed the cases into ones with indications for surgery, thereby creating surgical conditions. Therefore, we believe the rSIFN-co combination therapy is capable of curing cancer.

In one embodiment, the present invention provides a method for eliminating or reducing the malignant pleural effusion, malignant ascites, and/or malignant pericardial effusion in a subject with tumor, the method comprises administering to the subject a recombinant interferon encoded by SEQ ID NO: 2. In one embodiment, the tumor is a solid tumor.

In one embodiment, the recombinant interferon is administered to the subject by an administration route comprising one or more of: infiltration administration, intrapleural administration, abdominal administration, pericardial administration, thoracic administration and intraperitoneal administration. In one embodiment, the recombinant interferon is administered in an amount in a range of about 30 μg to about 2000 μg by one administration. In another embodiment, the recombinant interferon is additionally administered to the subject by systemic administration. In one embodiment, the subject is administered with at least one other anti-cancer drug. In another embodiment, the other anti-cancer drug is chemotherapeutic drug, targeted drug, or biological drug.

In one embodiment, the present invention provides a method for preventing tumor recurrence or metastasis, or prolonging or maintaining a tumor-free status in a subject with a tumor, the method comprises administering to the subject a recombinant interferon encoded by the nucleotide sequence SEQ ID NO: 2, and the subject has been treated with at least one anti-cancer therapy before the administration of said recombinant interferon.

In one embodiment, the anti-cancer therapy is chemotherapy, radiotherapy, surgical therapy, interventional therapy, biotherapy, gene therapy, ablation therapy, immunotherapy, targeted therapy, or traditional Chinese medicine therapy. In another embodiment, the recombinant interferon is administered to the subject in a single dose of the range of about 2 μg to about 2000 μg.

In one embodiment, the present invention provides a method for eliminating or reducing metastatic tumor lesion in a subject, the method comprises administering a recombinant interferon encoded by SEQ ID NO: 2 topically or locally to the tumor lesion. In one embodiment, the metastatic tumor lesion comprises at least one of a bone lesion, a muscular lesion, a subcutaneous tissue lesion, a prostatic lesion, and a lymph node lesion.

In one embodiment, the recombinant interferon is administered to the lesion by an administration route comprising at least one of infiltration administration, percutaneous administration, transdermal administration, epidermal administration and transmucosal administration. In another embodiment, the recombinant interferon is administered topically. In another embodiment, the recombinant interferon is further administered systemically.

In one embodiment, the present invention provides a non-surgical method for eliminating a tumor in a subject or reducing the size of a tumor in a subject, the method comprises administering to the subject a recombinant interferon encoded by SEQ ID NO: 2. In one embodiment, the tumor is a non-resectable tumor.

In one embodiment, the recombinant interferon is administered to the subject by at least one of systemic administration, local administration, and topical administration. In one embodiment, the local administration or topical administration comprises one or more of intratumoral administration and spray administration.

In one embodiment, the subject is administered at least one other anti-cancer therapy. In one embodiment, the anti-cancer therapy is chemotherapy, radiotherapy, surgical therapy, interventional therapy, biotherapy, gene therapy, ablation therapy, immunotherapy, targeted therapy, or traditional Chinese medicine therapy.

In one embodiment, the present invention provides a method for treating lung cancer in a subject, the method comprises administering to the subject a recombinant interferon encoded by SEQ ID NO: 2, and the recombinant interferon is administered to the subject by at least one of systemic administration, topical administration, and local administration.

In one embodiment, the recombinant interferon is administered systemically and via inhalation. In one embodiment, the systemic administration comprises at least one of subcutaneous administration and intramuscular administration, and inhalation comprises at least one of: pulmonary inhalation and nasal inhalation. In another embodiment, the recombinant interferon is administered locally by perfusion.

In one embodiment, the at least one other anti-cancer therapy is administered to the subject before, simultaneously, and/or after administration of the recombinant interferon.

The present invention will be specifically described in the following examples that are only used to elaborate the purpose but not to limit the scope of the present invention. The present invention can be modified without deviating from its scope. All publications, patents and patent applications that are referenced, the contents of which are hereby incorporated by reference into this application as every independent publication, patent and patent application are separately incorporated by reference into this application.

Informed Consent Forms have been signed by all patients involved in the following embodiments, and Confidentiality Agreements have been signed by and between the applicants and hospitals. At the same time, the test processes are conducted in accordance with the requirements set forth by Ethics Committee for Clinical Drug Trials.

Example 1: Preparation of the Composition of the Recombinant Interferon

Ingredients of Recombinant Interferon Freeze-Dried Injection (Freeze-Dried Powder)

| | |
|---|---|
| rSIFN-co stock solution solution of present invention | 34.5 μg/ml |
| pH 7.0 phosphate buffer (PB) | 10 mmol/L |
| Glycine | 0.4 mol/L |

Preparation procedures: raw materials were weighed by the ingredients and dissolved by sterile and pyrogen-free water for injected; then filtered by a membrane of 0.22 μm pore diameter for sterilization, and preserved at 6-10° C.; the materials were sampled for sterile and pyrogen inspections and then separately loaded in vials after qualified inspections, each with a single dose of 0.3-0.5. And then, the materials were put into freeze dryer for freezing and drying. Ingredients of Recombinant Interferon Water Solution Injection

| | |
|---|---|
| rSIFN-co stock solution of present invention | 34.5 μg/ml |
| pH 7.0 phosphate buffer (PB) | 25 mmol/L |
| sodium chloride | 0.4 mol/L |

Preparation procedures: raw materials were weighed by the ingredients and dissolved by sterile and pyrogen-free water for injection; then filtered by a membrane of 0.22 μm pore diameter for sterilization, and preserved at 6-10° C.; the materials were sampled for sterile and pyrogen inspections and then separately loaded in sealed containers after qualified inspections, each with a single dose of 0.3-0.5. And then, the finished product were preserved at 2-10° C. in dark places.

Ingredients of Recombinant Interferon Spray

The ingredient content percentages in the table below are based on weight percentages.

| | |
|---|---|
| EDTA | 0.01% |
| Tween 80 | 0.05% |
| Trisodium citrate | 10 mmol/L |
| Glycerol | 1.26% |
| Sodium chloride | 0.03% |
| Benzyl alcohol | 0.5% |
| Human albumin | 0.1% |
| Recombinant super-compound interferon | 10 µg/ml |

The preparation method refers to conventional preparation method of spray.

Preparation of Recombinant Interferon Inhalant

Conventional preparation methods of interferon inhalant were adopted. The recombinant interferon inhalant of the present invention was prepared according to conventional preparation methods of interferon inhalant.

Example 2: Clinical Data of Patients Treated by the Present Recombinant Interferon (58 Cases)

Following is a summary clinical treatment table (table 2) of 58 patients of various cancer types who have been treated by the present recombinant interferon until Jul. 1, 2012.

Table 2: Summary of Clinical Treatment of Multiple Types of Cancers in 58 Patients

TABLE 2

Summary of Clinical Treatment of Multiple Types of Cancers in 58 Patients

| Patient No. | Sex | Age | Diagnosed Condition(s) | Stage | Treatment prior to drug administration | Dosage regimens for Interferon | Regimens for Combined therapy | Treatment results | Total therapeutic effectiveness |
|---|---|---|---|---|---|---|---|---|---|
| 1 | Male | 53 | Non small cell lung cancer in right lung | IIIb | DP Regimen® was provided from October 14, Year 1 to November 25, Year 1: 75 mg of Taxotere and 75 mg of Cisplatin on Day 1. Two cycles of chemotherapy were performed in total, each lasting for 21 days. | The rSIFN-co therapy started in November, Year 1. Intramuscular injection of rSIFN-co was done once every other day: 9 μg for the 1st time, 15 μg for the 2nd time and 18 μg for the 3rd time and thereafter. Therapy continued till February, Year 3, during which rSIFN-co treatment had been stopped for 1 month in April, Year 2, leading to a total treatment duration of 15 months. | Radiotherapy③ (DT40Gy) on right lung and mediastinal lymph nodes started on December 2, Year 1 followed by X-knife therapy (DT20Gy) | Primary lesions on right pulmonary hilum disappeared and cured. | CR |
| 2 | Male | 40 | Non small cell lung adenocarcinoma | IV | Systematic chemotherapy began at January, Year 1: Taxotere and Carboplatin. One cycle of 21 days was provided. | The rSIFN-co therapy began on April 14, Year 1. Intramuscular injection of rSIFN-co was done once every other day: 9 μg for the 1st time, 15 μg for the 2nd time, 18 μg for the 3rd time and 21 μg for the 4th time and thereafter. Meanwhile, aerosol inhalation of rSIFN-co was done once every day: 300 μg for the 1st time, 500 μg for the 2nd time, 600 μg for the 3rd time and thereafter. Administration of rSIFN-co ended in April Year 2. | From April 20, Year 1 to September 3, Year 1, Endostar⑤ was administrated every day: 7.5 mg/m² per dose, $1.2 \times 10^5$ U/m². Four cycles were performed totally with each lasting for 14 days. Meanwhile, GP regimen was combined: 1600 mg of Gemcitabine on days 1 and 8 and 40 mg of Cisplatin on days 1–3. Four cycles were performed, each being 15 days. One intrapericardial infusion with Cisplatin (30 mg) was performed on July 19, Year 1. Aerosol inhalation of Cisplatin was added from December 23, Year 1 to January 14, Year 2: 10 mg/dose, 2 doses per day. The second course of Endostar treatment was provided from January 18, Year 2 to January 30, Year 2. | The size of the primary lesions on upper lobe of right lung reduced from about $10.2 \times 8.2 \times 7.7$ cm to $1.2 \times 1.4$ cm. Metastatic lesions in the right liver and multiple lymph nodes disappeared. The metastatic lesions on the two lungs decreased in size and the radioactive concentration/ accumulation decreased. | PR |

TABLE 2-continued

Summary of Clinical Treatment of Multiple Types of Cancers in 58 Patients

| Patient No. | Sex | Age | Diagnosed Condition(s) | Stage | Treatment prior to drug administration | Dosage regimens for Interferon | Regimens for Combined therapy | Treatment results | Total therapeutic effectiveness |
|---|---|---|---|---|---|---|---|---|---|
| | | | | | | | with same dosage. Chemotherapy using Pemetrexed⑥ proceeded from December 25, Year 1 to January 19, Year 2: iv. 500 mg/m², every 3 to 4 weeks. As none of the treatments had any obvious effect, the chemotherapy during February 15, Year 2 to April 25, Year 2 was replaced with DP regimen⑧ (75 mg/m² of Taxotere and 75 mg/m² of Cisplatin on day 1) in combination with administration with Tarceva (150 mg/day) for 4 cycles with 21 days per cycle. A Gamma knife therapy was performed on head on June 29, Year 2. | | |
| 3 | Female | 51 | Non small cell lung cancer | IV | | Treatment with rSIFN-co started on May 29, Year 1. Intramuscular injection of rSIFN-co was done once every other day: 9 μg for the 1st time, 18 μg for the 2nd time and 21 μg for the 3rd time and thereafter. Aerosol inhalation of rSIFN-co was simultaneously performed: 200 μg/every other day. From July 14, Year 1, 18 μg of rSIFN-co was used in intramuscular injection. Aerosol inhalation of 400 μg of rSIFN-co was simultaneously performed every other day. The administration continued for more than 3 months till September 16, Year 1. | During this period, Gamma knife radiotherapy for the brain lesions was conducted. | The primary lesion of about 5.1 × 3.2 cm on the upper lobe of right lung disappeared. The enlarged lymph nodes in the mediastinum and the metastatic lesions in the brain of about 3.7 × 2.6 cm basically disappeared. | CR |

TABLE 2-continued

Summary of Clinical Treatment of Multiple Types of Cancers in 58 Patients

| Patient No. | Sex | Age | Diagnosed Condition(s) | Stage | Treatment prior to drug administration | Dosage regimens for Interferon | Regimens for Combined therapy | Treatment results | Total therapeutic effectiveness |
|---|---|---|---|---|---|---|---|---|---|
| 4 | Male | 49 | Small cell lung cancer in right lung | IV | The first cycle of EP⑦ chemotherapy was conducted from March 25, Year 1 to Apr 9, Year 1: 100 mg of Etoposide and 30 mg of Cisplatin. | The treatment of rSIFN-co began on April 12, Year 1. Intramuscular injection was done once every other day: 9 μg for the 1st time, 15 μg for the 2nd time and 18 μg for the 3rd time and thereafter. Aerosol inhalation of rSIFN-co was performed once every other day: 0.5–2 ml/dose (200 μg/ml). From July 16, Year 1, 21 μg of rSIFN-co was used in intramuscular injection. Aerosol inhalation of rSIFN-co continued but the amount per dose was changed to 200 μg. The first cycle finished by the end of March Year 2 (lasting for almost 1 year). The administration of rSIFN-co was stopped for 1 month because Aerosol inhalation of Cisplatin (one dose per day and 10 mg per dose) was performed throughout September Year 1. The 2nd cycle of treatment proceeded from October 9, Year 2 to January 26, Year 3 during which 18 μg of rSIFN-co was intramuscularly injected every other day. | Five cycles of EP chemotherapy were conducted from March 25, Year 1 to September 10, Year 1 and the same regimen as mentioned above was used. An interventional cryoablation was conducted on the supraclavicular lesions on September 3, Year 2. From October Year 1, a 15-day regimen of aerosol inhalation of Cisplatin was added: 10 mg per dose, 1 dose per day. Two cycles were done, each lasting for 15 days. | A primary lesion of about 0.6 × 0.4 cm, on the apex of right lung disappeared. A lesion with a nodule of about 2.6 × 2.2 cm on the of right clavicle disappeared. Mutliple nodules appearing in neighboring areas of the mediastinal brachiocephalic trunk, right brachiocephalic veins, superior vena cava, and trachea, part of which fused and lesions of about 5.5 cm × 4.9 cm in size disappeared. | CR |
| 5 | Female | 42 | Metastatic moderately differentiated lung adenocarcinoma (in right humerus) | IV | A surgical repair of right humerus was performed on February 23, Year 1. After that surgery, patient was given 4 courses of DP⑧ chemotherapy: 75 mg of Taxotere and 75 mg of Cisplatin on day 1. | Treatment with rSIFN-co began on April 15, Year 1. Intramuscular injection was performed once every other day: 9 μg for the 1st time and 21 μg for the 2nd time and thereafter. The treatment was provided for a total of 3 months till September 15, Year 1, during which rSIFN-co administration was suspended for 1 month due to chemotherapy (the chemotherapy regimen shown below related to aerosol inhalation of Cisplatin) and for 1 month because of the patient's physical condition. Aerosol inhalation of rSIFN-co was added on September 16, Year 1: 1 ml (200 μg/ml) per day. Till February, Year 2, the co-administration regimen was provided for 5 months. | Aerosol inhalation of Cisplatin began on September 16, Year 1: 10 mg per dose and 2 doses per day. Eight cycles were conducted with each cycle being 15 days. | Radioactive concentrations at the primary lesion of right lung tumor, right humerus and the T6 vertebra evidently decreased. Metastatic lesions on pelvis and lumbar vertebrae as well as enlarged paratracheal | CR |

TABLE 2-continued

Summary of Clinical Treatment of Multiple Types of Cancers in 58 Patients

| Patient No. | Sex | Age | Diagnosed Condition(s) | Stage | Treatment prior to drug administration | Dosage regimens for Interferon | Regimens for Combined therapy | Treatment results | Total therapeutic effectiveness |
|---|---|---|---|---|---|---|---|---|---|
| | | | | | | From September 15, Year 2, intramuscular injection of 15 μg was provided every other day. | | lymph nodes disappeared. | |
| 6 | Male | 39 | Moderately-poorly differentiated adenocarcinoma in left lung | IV | The first cycle of GP Regimen⑨ began in September Year 1 with each cycle lasting for 21 days; 1000 mg/m² of Gemcitabine on day 1 and 8 and 75 mg/m² of Cisplatin on day 1. | Treatment with rSIFN-co began on October 12, Year 1 with aerosol inhalation of 600 μg every day. Intramuscular injection of rSIFN-co started on December 12, Year 1, once every other day: 9 μg for 1st time, 15 μg for 2nd time and 18 μg for 3rd time and thereafter. Local spraying on bone metastases began on March 12, Year 2: 70 μg–139 μg/does/site, 4–5 doses/day. | The second cycle of GP Regimen⑨ started on October 14, Year 1 (the regimen was exactly the same as mentioned above). Gefinitib was taken from November 24, Year 1: 1 pill/dose (250 mg/pill), 1 dose/day. | Primary lesion of about 9 × 3.5 cm in size at the left lung almost disappeared. Enlarged lymph nodes of about 1.0 cm × 0.7 cm at left segment of neck, nodules of about 1.2 cm × 0.8 cm at left supraclavicular fossa and nodules of about 1.4 cm × 1.1 cm at right and root segment of neck disappeared. Metastatic lesions on sternum disappeared; and metastatic lesions at right sternoclavicular joints, ribs and pelvis shrank and relieved to some extent. | CR |
| 7 | Female | 53 | Metastatic lung adenocarcinoma (lymph nodes at left clavicle) | IV | | Treatment with rSIFN-co began on July 31, Year 1. Intramuscular injection was done once every other day: 9 μg for 1st time, 18 μg for 2nd time and 21 μg for 3rd time and | Meanwhile, Iressa (Gefinitib)⑩ produced in India was administered in combination for 1 | Primary lesions in right lung and metastatic lesions in | PR |

TABLE 2-continued

Summary of Clinical Treatment of Multiple Types of Cancers in 58 Patients

| Patient No. | Sex | Age | Diagnosed Condition(s) | Stage | Treatment prior to drug administration | Dosage regimens for Interferon | Regimens for Combined therapy | Treatment results | Total therapeutic effectiveness |
|---|---|---|---|---|---|---|---|---|---|
| | | | | | | thereafter. Seventy-five times of intramuscular injection were done till January 2, Year 2 (totally 5 months). | year: 1 pill/dose (250 mg/pill), 1 dose/day. | both lungs and several bones shrank with radioactive concentration decreased; metastasis in liver disappeared. | |
| 8 | Female | 68 | Lung cancer in right lung | IV | | Treatment with rSIFN-co began on July 21, Year 1 Intramuscular injection was done once every other day: 9 μg for 1st time, 15 μg for 2nd time and 18 μg for 3rd time and thereafter. Meanwhile, aerosol inhalation of rSIFN-co of 600 μg was performed once a day. Administration of rSIFN-co continued for 3 months till October 31, Year 1. | Administration of Gefinitib (Iressa)⑩ was added in July Year 1: 250 mg/pill, 1 pill/dose, 1 dose/day. | Lesions of about 3.0 × 3.9 cm at the lower lobe of right lung, and metastatic lesions in left ilium disappeared basically. | CR |
| 9 | Male | 55 | Squamous cell carcinoma | IIb | | Treatment with rSIFN-co began on March 18, Year 1. Aerosol inhalation of rSIFN-co of 600 μg was performed once a day. A course completed till July 20, Year 1 (for 4 months) with 100 doses of aerosol inhalation done. | Four cycles of chemotherapy (GP regimen⑨) were performed with the first one beginning at April 12, Year 1 and each cycle lasting for 21 days: 1600 mg of Gemcitabine on days 1 and 8 and 40 mg of Cisplatin on days 1 and 3. Meanwhile, 3 cycles of Endostar⑥ administration were performed with 14 days as one cycle: 7.5 mg/m² (1.2 × 10⁵ U/m²) per dose, 1 dose/day. Second cycle of chemotherapy began on May 10, Year 1 with the same regimen. Third cycle of chemotherapy began | Primary lesions of about 3.3 × 2.4 × 2.0 cm in right lung basically disappeared and enlarged lymph nodes in right hilum of about 2.0 × 2.2 cm disappeared. | CR |

TABLE 2-continued

Summary of Clinical Treatment of Multiple Types of Cancers in 58 Patients

| Patient No. | Sex | Age | Diagnosed Condition(s) | Stage | Treatment prior to drug administration | Dosage regimens for Interferon | Regimens for Combined therapy | Treatment results | Total therapeutic effectiveness |
|---|---|---|---|---|---|---|---|---|---|
| | | | | | | | on June 7, Year 1 with the same regimen. Fourth cycle of chemotherapy began on July 7, Year 1 with the same regimen. Four cycles of chemotherapies were totally performed. | | |
| 10 | Female | 48 | Non small cell lung cancer in left lung | IIIb | | Treatment with rSIFN-co began on March 9, Year 1. Intramuscular injection of rSIFN-co was performed once every other day: 18 μg for 1st time, 21 μg for 2nd time and thereafter. Such administration continued for almost 1 year till March, Year 2. Intrapleural perfusion of rSIFN-co was done once every 8 days from April 29, Year 1: 9 μg × 4 vials for 1st and 2nd time and 9 μg × 5 vials for 3rd time. Three perfusions were provided totally. Four CT-guided interventional operations were performed in July and August Year 2. The rSIFN-co was injected into relatively large lesions in lungs and 21 μg × 10 vials were used each time. | | Primary lesions of about 2.0 × 2.0 cm in left lung basically disappeared and malignant pleural effusion disappeared. | CR |
| 11 | Male | 40 | Non-hodgkin lymphoma on mesenteric lymph nodes | IV | Chemotherapy was performed for 7 times (five times of CHOPE regimen and two times of MTX regimen) began on August, Year 1. Autologous stem cell transplantation was done in March Year 2. Chemotherapy were provided for 4 times (1 time of GCE regimen and 3 times of ESAP regimen) began on August, Year 2. The forth one ended on November 26, Year 2. Chemotherapy was | Treatment with rSIFN-co began on June 9, Year 3. An aerosol preparation of rSIFN-co (72 μg/ml) was sprayed onto the nasopharynx and Oral Cavity 2~3 times every day. Administration continued till August 27, Year 3 with 5 days of suspension because of chemotherapy (see chemotherapy described below). Local injections on lymph nodes in neck started on June 11, Year 3. Injection was performed every other day by injection at multiple sites in a quincunx: 15 μg × 10 vials per treatment. Two times later, local | Four cycles of CHOP[11] chemotherepy were provided from July Year 3 to November 28, Year 3 with each cycle lasting for 21 days. Radiotherapy began on June 11, Year 3 (scheduled for 25 times) and stopped on July 5, Year 3 as the patient was weak due to myelosuppression. | Soft tissure around nasopharynx and oropharynx with the thickest part of 3.0 cm entirely disappeared, and the largest fused lymph node among those at submaxillary | PR |

TABLE 2-continued

Summary of Clinical Treatment of Multiple Types of Cancers in 58 Patients

| Patient No. | Sex | Age | Diagnosed Condition(s) | Stage | Treatment prior to drug administration | Dosage regimens for Interferon | Regimens for Combined therapy | Treatment results | Total therapeutic effectiveness |
|---|---|---|---|---|---|---|---|---|---|
| | | | | | administered 6 times (3 times of large-dosed CHOPE regimen, 2 times of CMOP regimen and 1 time of a regimen of "bleomycin + CHOP[(11)] + Methotrexate") began on January, Year 3, in combination with stem cell therapy. | subcutaneous injection was performed every other day: 30 µg per treatment. Till August 27, Year 3 (more than 2 months), for a total of 10 times. | | region, neck and clavicular region shrank from 7.4 cm × 2.4 cm × 14.6 cm to 1.1 cm × 1.5 cm. | |
| 12 | Male | 67 | Non small cell lung adenocarcinoma in right lung | IIb | From August 16, Year 1, two cycles of GP regimen ⑨ were provided: 1000 mg/m² of Gemcitabine on day 1 and 8 and 75 mg/m² of Cisplatin on day 1. Intrathoracic injection of Cisplatin was also performed for 5 times. 1 dose every 7 days, 30-40 mg per dose. | Treatment with rSIFN-co began on November 10, Year 1. Intramuscular injection of rSIFN-co was provided once every two days: 9 µg for 1st time, 18 µg for 2nd time and 21 µg for 3rd time and thereafter. Administration lasted for almost 1 year till October 27, Year 2. | | The mass reduced from about 3.1 × 4.2 cm to 2.2 × 1.5 cm after 2 months' treatment, and the lesion further reduced in size after administration for 3 months. | PR |
| 13 | Male | 63 | Poorly differentiated adenocarcinoma (upper lobe of right lung) | IIIb | On October 15, Year 1, resection of upper lobe of right lung and lymph node dissection were done as well as wedge resection of nodules on lower lobe of right lung. | Treatment with rSIFN-co began on December 10, Year 1. Intramuscular injection of rSIFN-co was provided once every other days: 9 µg for 1st time, 21 µg for 2nd time and thereafter). The first course was finished on April 9, Year 2. The second course was performed from December Year 2 to July Year 3 during which intramuscular injection was done every other day with 21 µg per dose. The third course was performed from February 21, Year 4 to May 21, Year 4 during which intramuscular injection was done every other day with 18 µg per dose. | | After surgery on primary lesions, no tumor recurrence or metastasis occurred. | CR |
| 14 | Male | 44 | Non small cell lung cancer (poorly differentiated adenocarcinoma) | IIIb | Upper lobe of right lung was resected on October 20, Year 1. | Treatment of rSIFN-co began on November 6, Year 1. Intramuscular injection of rSIFN-co was administered once every other day: 18 µg for 1st time, 21 µg for 2nd time and thereafter. A first course of 6 months ended on May 10, Year 2. The second course started on March | | After surgery, no tumor recurrence or metastasis was found at primary lesions. | CR |

TABLE 2-continued

Summary of Clinical Treatment of Multiple Types of Cancers in 58 Patients

| Patient No. | Sex | Age | Diagnosed Condition(s) | Stage | Treatment prior to drug administration | Dosage regimens for Interferon | Regimens for Combined therapy | Treatment results | Total therapeutic effectiveness |
|---|---|---|---|---|---|---|---|---|---|
| | | | | | | 18, Year 3 and continued for the next following 3 months. Intramuscular injection of rSIFN-co was provided every other day with 15 μg per dose. Intramuscular injection of rSIFN-co and Aerosol inhalation were administered for 3 months from November Year 4. Intramuscular injection was done once every other day with 15 μg per dose. Aerosol inhalation was performed every day and a total of 300 μg was used for one day. | | | |
| 15 | Male | 68 | Lung cancer with systemic metastases | IV | Treatment with Gamma Knife was done under local anesthesia on April 27, Year 3. Sr-89 therapy was done by Nuclear Medicine Department on April 30, Year 3. Oral administration of Gefitinib (Iressa) was provided from December Year 1 to June Year 3: 1 dose/day, 1 pill/dose, 250 mg/pill. | Treatment of rSIFN-co began on June 25, Year 3. The rSIFN-co was injected into lymph nodes of groin Intramuscularly every day: 15 μg × 6 vials for 1st time, 15 μg × 8 vials for 2nd time and 15 μg × 10 vials for 3rd time and thereafter. Eleven injections were done till July 20, Year 3 (Severe diarrhea occurred after 3 injections and administration was stopped for 2 weeks; after that injection was performed every day and 8 injections in total were continuasly provided). Discontinuous local injection in lymph nodes were performed for 6 times from August 18, Year 3 toSeptember 16, Year 3: 15 μg × 10 vials for each time. Local injection in lymph nodes were performed every 3 days from October 8, Year 3 to October 12, Year 3: 15 μg × 10 vials for each time. | | Mass of about 11.3 × 4.9 cm in pelvic cavity reduced in size to 7.52 × 7.67 × 6.72 cm | PR |
| 16 | Female | 63 | Well to moderately differentiated adenocarcinoma was found in rectum and mucinous adenocarcinoma was found in | IIIb | Laparoscopic-assisted abdominal perineal radical resection of rectal cancer was done on May 16, Year 1. | Treatment of rSIFN-co began on May 23, Year 1. Intramuscular injection of rSIFN-co was provided once every other day: 21 μg for each time. The first course of 8 months ended on February Year 2. The second course was provided from January Year 3 to April Year 3. Intramuscular injection of rSIFN-co | | After surgery, no tumor recurrence or metastasis occurred at primary lesions. | CR |

TABLE 2-continued

Summary of Clinical Treatment of Multiple Types of Cancers in 58 Patients

| Patient No. | Sex | Age | Diagnosed Condition(s) | Stage | Treatment prior to drug administration | Dosage regimens for Interferon | Regimens for Combined therapy | Treatment results | Total therapeutic effectiveness |
|---|---|---|---|---|---|---|---|---|---|
|  |  |  | part of rectum. Cancer invaded into deep muscularis of intestinal wall and formed cancerous nodules in mesorectum. |  |  | was provided once every other day with 9 μg each time and continued for 3 months. The third course was administered from December Year 3 to March Year 4. Intramuscular injection was performed every other day with 15 μg each time. |  |  |  |
| 17 | Female | 25 | cervical cancer | Ib1 |  | Treatment of rSIFN-co began on May 14, Year 1. Intramuscular injection of rSIFN-co was provided once every other day: 9 μg for 1st time, 15 μg for 2nd time and 18 μg for 3rd time and thereafter. Meanwhile, uterine perfusion was done once a day: at 1000 μg per dose, for 2 hours. Uterine perfusion ended on June 28, Year 1 (lasted for more than 1 month) and intramuscular injection was stopped on September 12, Year 1 (lasted for 4 months). |  | Malignant cervical lesion disappeared, and test of high-risk HPV became negative. Also, no tumor cells were found in cervical smear. | CR |
| 18 | Male | 64 | Prostatic cancer | IV |  | Treatment of rSIFN-co began on November 15, Year 1. Intramuscular injection of rSIFN-co was provided once every other day: 9 μg for 1st time, 15 μg for 2nd time, 18 μg for 3rd time and 24 μg for 4th time and thereafter. Meanwhile, the drug was locally applied by spraying to the skin surface where prostate biopsy was done: 4–5 doses per day and at 70 μg~139 μg per dose. The amount of rSIFN-co to be intramuscularly injected changed to 21 μg from December 15, Year 1 to July 1, Year 2. | Radiotherapy on prostate (EBRT)[12] was performed for 38 times from December 5, Year 1 to February 26, Year 2. | Prostate of 4.7 × 3.5 × 5.6 cm reduced normal size; two lymph nodes in right ischiorectal fossa were eliminated; the posterior wall of fundus of urinary bladder, bilateral seminal vesicles and anterior rectal wall infected by lesions recovered; | CR |

TABLE 2-continued

Summary of Clinical Treatment of Multiple Types of Cancers in 58 Patients

| Patient No. | Sex | Age | Diagnosed Condition(s) | Stage | Treatment prior to drug administration | Dosage regimens for Interferon | Regimens for Combined therapy | Treatment results | Total therapeutic effectiveness |
|---|---|---|---|---|---|---|---|---|---|
| | | | | | | | | and the level of specific antigen of Prostatic cancer (PSA) become normal. | |
| 19 | Female | 43 | Melanoma of nose (after a surgery) combined with bone metastases at bilateral hip joints, bilateral femurs, bilateral humeri, ribs and bilateral shoulder joints. | IV | Two cycles were provided on October 30, Year 1 and November 30, Year 1: 15 mg of Endostar on day 1~10 and 200 mg of temozolomide on day 1~5, oral administration. Targeted radiotherapy (50Gy/25f) was done on November 2, Year 1 and the targets were right maxillary sinus + ¼ of the left maxillary sinus, bilateral ethmoid sinus, frontal sinus and the adjacent tissues of the right eyeball. Radiotherapy ended on December 7, Year 1. | Treatment of rSIFN-co began on December 21, Year 1. Intramuscular injection of rSIFN-co was provided once every other day: 9 µg for 1st time, 15 µg for 2nd time, 18 µg for 3rd time and thereafter. Meanwhile, the drug was locally applied by spraying onto the skin surface of the right shouder: 70 µg-139 µg/dose/site, 4-5 doses/day. Spraying was provided to skin surface of the left shoulder and other sites with bone metastasis began on Febnary 27, Year 2: 70 µg-139 µg/dose/site, 4-5 doses/day. | | Multiple enlarged lymph nodes at bilateral shoulder joints and axillae disappeared; recurrence and metastatic lesions at residual right sinus and nasal cavity after surgery as well as multiple abnormal signals at bilateral hip joints and upper parts of femora disappeared. | CR |
| 20 | Male | 40 | Lung cancer | IV | | Treatment by administering Recombinant super-compound interferon ("rSIFN-co") began on October 12, Year 1; Intramuscular injection once every other day: 9 µg for the 1st time, 15 µg for the 2nd time and 21 µg for the 3rd time and thereafter; Aerosol inhalation of 1 ml (200 µg/ml) daily began from December 28, Year 1; Aerosol inhalation of 1 ml (300 µg/ml) daily began from January 13, Year 2. | Chemotherapy was conducted 3 times: GP-T2 regimen (cisplatin day 1-4, gemcitabine day 1) from October 25, Year 1 to November 7, Year 1; (no "gemcitabine" was administered at day 8 due to the low white blood cell level of the patient). DDP40 mg on day 1 and day 2 plus MMC 10 mg chemotherapy 1 time, beginning | Primary lesions of the right lower lung was reduced; swollen lymph nodes within the mediastinum were eliminated; pleural effusion was subsided. | PR |

TABLE 2-continued

Summary of Clinical Treatment of Multiple Types of Cancers in 58 Patients

| Patient No. | Sex | Age | Diagnosed Condition(s) | Stage | Treatment prior to drug administration | Dosage regimens for Interferon | Regimens for Combined therapy | Treatment results | Total therapeutic effectiveness |
|---|---|---|---|---|---|---|---|---|---|
| | | | | | | | from November 26, Year 1. Administered DP regimen (Cisplatin 40 mg on day 1-2 and 30 mg on day 3, Docetaxel 120 mg day 1) from December 6, Year 1 to December 18, Year 1. | | |
| 21 | Female | 75 | Lung cancer with bone metastases | IIIb | Self-medication with traditional Chinese medicine ("TCM"), ganoderma lucidum extract, spore powder and Gefitinib. | Treatment by administering rSIFN-co began on March 10, Year 1; Intramuscular injection once every other day: 9 μg for the 1st time, 15 μg for the 2nd time, and 18 μg for the 3rd time and thereafter. From September 18, Year 1 to November 17, Year 1, discontinuous spray inhalation 1 ml each time (200 μg/ml). | Gefitinib. | Primary lesions of the right upper lung and swollen lymph nodes within the mediastinum were eliminated | CR |
| 22 | Male | 50 | Lung cancer with hepatic metastases | IIIa | 4 courses of "Paclitaxel + Carboplatin" chemotherapy began from October 3, Year 1. Argon-helium cryoablation surgery of the lower left lung cancer was performed on January 6, Year 2. Radiofrequency ablation of the liver metastases was performed on January 13, Year 2. | Intramuscular injection of 18 μg once every other day for two months from January 19, Year 2 followed by 21 μg every other day thereafter. | The 3rd radiofrequency ablation targeting liver metastases was performed on March 17, Year 2. Hepatic local perfusion of "Paclitaxel + Carboplatin" was performed on April 21, Year 2. | Primary lesions of the left lung was eliminated, while no apparent change in liver metastases was observed. | PR |
| 23 | Male | 57 | Lung adenocarcinoma in the left lung with metastases to the left pleura, mediastinal lymph nodes and bone | IV | One course of "PTX + DDP" chemotherapy began on September 9, Year 1; drip infusion of 4 mg of zoledronic acid to treat metastases to bone was administered on September 9, Year 1. The 2nd course of TP chemotherapy began on October 6, Year 1; | Treatment by administering rSIFN-co began on December 6, Year 1; Intramuscular injection once every other day: 9 μg for the 1st time and 2nd time, and 21 μg for the 3rd time and thereafter till February 15, Year 2. | | Primary lesions in the left lung and systemic multiple metastatic lesions were eliminated. | CR |

TABLE 2-continued

Summary of Clinical Treatment of Multiple Types of Cancers in 58 Patients

| Patient No. | Sex | Age | Diagnosed Condition(s) | Stage | Treatment prior to drug administration | Dosage regimens for Interferon | Regimens for Combined therapy | Treatment results | Total therapeutic effectiveness |
|---|---|---|---|---|---|---|---|---|---|
| 24 | Male | 73 | Lung cancer | IIIb | The 3rd course of chemotherapy of TP chemotherapy began on October 29, Year 1. | Treatment by administering rSIFN-co began on March 19, Year 1; Beginning from March 21, Year 1, intramuscular injection once every other day: 9 μg for the 1st time, 13.5 μg for the 2nd time and 21 μg for the 3rd time and thereafter; Intrapleural perfusion of 21 μg × 6 vials began from March 19, Year 1; Intrapleural perfusion of 21 μg × 8 vials was performed on March 25, Year 1; Intrapleural perfusion of 21 μg × 10 vials was performed on April 21, Year 1; Intrapleural perfusion of 21 μg × 10 vials was performed on April 30, Year 1; Intrapleural injection of 21 μg × 10 vials was performed on May 8, Year 1; Intrapleural perfusion of 21 μg × 12 vials was performed on May 15, Year 1. | | Pleural effusion was reduced. | PR |
| 25 | Male | 48 | Lung cancer | IIIa | | Treatment by administering rSIFN-co began on November 19, Year 1; Intramuscular injection once every other day: 9 μg from November 19, Year 1 to November 25, Year 1, and 21 μg from November 27, Year 1 to April 17, Year 2. | Radiotherapy (time and regimen unknown). | | PD |
| 26 | Female | 51 | lung cancer with brain metastases | IV | "Self-medication with Gefitinib" | Treatment by administering rSIFN-co began on December 18, Year 1; Discontinuous treatment by intramuscular injection once every other day: 21 μg, beginning December 18, Year 1 From May 7, Year 3 to January Year 4: intramuscular injection of 18 ug, every other day. From May 17, Year 3 to September 18, Year 3: spray inhalation 100 ug/day. From September 19, Year 3 to December 28, Year 3: spray inhalation 400 ug/day. | Erlotinib hydrochloride. | Brain metastases lesions were reduced, while no apparent change in primary lesions in the lungs was observed. | PR |

TABLE 2-continued

Summary of Clinical Treatment of Multiple Types of Cancers in 58 Patients

| Patient No. | Sex | Age | Diagnosed Condition(s) | Stage | Treatment prior to drug administration | Dosage regimens for Interferon | Regimens for Combined therapy | Treatment results | Total therapeutic effectiveness |
|---|---|---|---|---|---|---|---|---|---|
| | | | | | | From December 29, Year 3 to January, Year 4: spray inhalation 300 ug/day. | | | |
| 27 | Male | 46 | Metastases to both lungs after surgery of the cancer in left lung | IIb | Radical surgery of the cancer in left lung in May Year 1, followed by chemotherapy and radiotherapy (details unknown). | Treatment by administering rSIFN-co began on August 22, Year 2; Intramuscular injection once every other day: 9 μg for the 1st time, and 21 μg for the 2nd time and thereafter. | | | NC/SD |
| 28 | Male | 53 | Cancer in the right upper lung with intrapulmonary metastasis and metastases to the right thoracic cavity. | IIb | Wedge resection of the right upper lung via video assisted thoracoscopic surgery (VATS), pleural biopsy and pleural nodules burning were performed on January 20, Year 1. After 3 days, intrapleural perfusion of "Vivatuxin" to the right thoracic cavity was performed. | Treatment by administering rSIFN-co began on March 13, Year 1; Intramuscular injection once every other day: 9 μg for the 1st time, and 21 μg for the 2nd time and thereafter; nasal spray of aerosol, 3 times/day; Aerosol inhalation of 0.2 ml (1 mg/ml) once a day began July 27, Year 1. September 2, Year 1: intramuscular injection of 21 ug, every other day, spray inhalation 200 μg/day. October 15, Year 1: stopped using rSIFN-co. | | | NC/SD |
| 29 | Male | 76 | Lung cancer | IIIa | The right upper lung was resected on August 17, Year 1. | Treatment by administering rSIFN-co began on September 2 Year 1; Intramuscular injection once every other day: 9 μg for the 1st time, 18 μg for the 2nd time and thereafter till September 20, Year 1, 21 μg from November 22, Year 1 to April 27, Year 2; In combination with nasal spray of 40 μg/ml aerosol, 3 times/day from April 29, Year 2. | Radiofrequency ablation targeting lung was performed on March 11, Year 3. | | NC/SD |
| 30 | Male | 47 | Lung adenocarcinoma with brain metastases | IV | Whole brain radiotherapy 30GY/10FX (10 times) was performed in December Year 1. 4 courses of GP-T1 chemotherapy regimen (gemcitabine day 1 and day 8; DDP140 mg day 1) began on January 3, Year 2. Gefitinib was taken in March Year 2. | Treatment by administering rSIFN-co began on July 18, Year 2; Intramuscular injection of 21 μg once every other day in combination with aerosol inhalation of 1 ml (200 μg/ml) every day lasted for 8 months. | | Pulmonary nodules reduced (5 months later), brain lesions basically subsided (6 months later). | PR |

TABLE 2-continued

Summary of Clinical Treatment of Multiple Types of Cancers in 58 Patients

| Patient No. | Sex | Age | Diagnosed Condition(s) | Stage | Treatment prior to drug administration | Dosage regimens for Interferon | Regimens for Combined therapy | Treatment results | Total therapeutic effectiveness |
|---|---|---|---|---|---|---|---|---|---|
| 31 | Male | 71 | Right lung cancer with bone metastases | IV | | Treatment by administering rSIFN-co began on June 29, Year 1; Intramuscular injection once every other day: 9 μg for the 1st time, 13.5 μg for the 2nd time, and 18 μg for the 3rd time and thereafter; Aerosol spray of 20 μg/ml rSIFN-co to lymph nodes at nasal cavity and neck began on August 20, Year 1; Injection of 21 μg rSIFN-co every other day began on September 16, Year 1. | | | PD |
| 32 | Female | 69 | Lung cancer | IIb | Three chemotherapy treatments were performed in March, April and May of Year 1; Began taking Gefitinib on June 10, Year 1. | Treatment by administering rSIFN-co began on July 9, Year 2; Intramuscular injection once every other day: 9 μg for the 1st time, 13.5 μg for the 2nd time, and 18 μg for the 3rd time and thereafter; Aerosol inhalation of 300 μg per day. | Gefitinib. | Lung tumor shrunk, and swollen lymph nodes disappeared. | PR |
| 33 | Female | 75 | Lung cancer | IIIb | "Left lower lung lobectomy, lymph node dissection, resection of part of thoracic aortic adventitia via VATS" under general anesthesia were performed on December 24, Year 1. | Treatment by administering rSIFN-co began on September 22, Year 2; Intramuscular injection once every other day: 4.5 μg for the 1st time, 9 μg for the 2nd time, 13.5 μg for the 3rd time, and 18 μg for the 4th time and thereafter; Injection of 9 μg every other day from September 29, Year 2. Later changed to 2 times of injection per week. Perfusion of rSIFN-co at 21 μg × 5 vials once every 6-8 days began on September 22, Year 2, depending on the subject's pleural effusion level and tolerance. Perfusion of rSIFN-co at 21 μg × 6 to 8 or 10 vials once every 4 days began on October 21, Year 2, depending on the subject's pleural effusion level and tolerance. | | | PD |
| 34 | Male | 79 | Lung cancer with multiple metastases | IV | | Treatment by administering rSIFN-co began on October 12, Year 1; Intramuscular injection of 18 μg once every other day in combination with aerosol inhalation of 1 ml | Local brain radiotherapy was received 2 times in November Year 1; Treatment with | | NC/SD |

TABLE 2-continued

Summary of Clinical Treatment of Multiple Types of Cancers in 58 Patients

| Patient No. | Sex | Age | Diagnosed Condition(s) | Stage | Treatment prior to drug administration | Dosage regimens for Interferon | Regimens for Combined therapy | Treatment results | Total therapeutic effectiveness |
|---|---|---|---|---|---|---|---|---|---|
| 35 | Female | 29 | Lung adenocarcinoma with bone metastases | IV | Beginning on June 28, Year 1, 1 course of chemotherapy (Gemcitabine 1.6 g on day 1 and day 8 + Cisplatin 60 mg on day 1 and day 2). | (200 µg/ml) per day. Stopped using rSIFN in December, Year 1. Treatment by administering rSIFN-co began on July 1, Year 1; Intramuscular injection once every other day: 15 µg for the first time, 18 µg for the second time and thereafter, and in combination with aerosol inhalation at the same time, 1 time a day, 600 µg each time. | anti-cancer TCM began on mid-December Year 1. From July 18, Year 1 to October 9, Year 1: 3 courses of chemotherapy. GP chemotherapy regimen: Gemcitabine + Cisplatin. Radiofrequency ablation targeting lung was performed on December 18, Year 1. Beginning in December, Year 1, began discontinuous use of Gefitinib. | Shrinkage of the primary lesion on the dorsal segment of the lower lobe of the left lung was evident. | PR |
| 36 | Female | 73 | Ovarian cancer | IIIb | "Hysterectomy, bilateral Salpingo oophorectomy, omentectomy, superior end rectum resection, anastomosis, urinary bladder rupture repair and cytoreductive surgery" were performed on May 19, Year 1. | Treatment by administering rSIFN-co began on February 13, Year 2; Intramuscular injection once every other day: 9 µg for the first time, 15 µg for the second time, 18 µg for the third time and thereafter; Intramuscular injection of 21 µg every other day beginning from March 13, Year 2 until May 21, Year 2. | | The pleural effusion in left thoracic cavity was disappeared; the pleural effusion right thoracic cavity was reduced. | PR |
| 37 | Female | 46 | cervical cancer, after radiotherapy and chemotherapy | IV | Radiotherapy was performed in Year 1: DT 5040Gy each time for 56 times; Treatment with PF regimen and radiotherapy were performed in August Year 2; Chemotherapy by arterial infusion for cervical cancer was performed on August 13, Year 2, primary drugs administered: Paclitaxel liposome + Carboplatin. | Treatment by administering rSIFN-co began on November 30, Year 2; Intramuscular injection of 21 µg every other day. | | Size of cervical lesions were reduced from 64 × 58 mm to 52 × 40 mm; Swollen left inguinal lymph nodes were disappeared. | PR |

TABLE 2-continued

Summary of Clinical Treatment of Multiple Types of Cancers in 58 Patients

| Patient No. | Sex | Age | Diagnosed Condition(s) | Stage | Treatment prior to drug administration | Dosage regimens for Interferon | Regimens for Combined therapy | Treatment results | Total therapeutic effectiveness |
|---|---|---|---|---|---|---|---|---|---|
| 38 | Female | 31 | Uterine papillary serous carcinoma (UPSC) mixed with clear cell carcinoma | IV | | Treatment by administering rSIFN-co began on August 1, Year 1; Intramuscular injection of 18 µg every other day once a day for a week and once every 5 days thereafter at 1 ml (200 µg/ml) each time. | | | NC/SD |
| 39 | Female | 41 | Poorly differentiated cervical squamous cell carcinoma | Ib2 | Laparoscopic extensive total hysterectomy + pelvic abdominal aortic lymphadenectomy + bilateral ovarian suspension were performed on June 3, Year 1. Following surgery, 1 course of PT chemotherapy regimen was administered. | Treatment by administering rSIFN-co began on November 26, Year 1; Intramuscular injection once every other day: 9 µg for the first time, 15 µg for the second time and thereafter. Use of rSIFN for 6 months altogether. | NK cell therapy | High-risk human papillomavirus (HPV) changed from positive to negative. | CR |
| 40 | Female | 70 | Cancer of hepatic flexure of colon, with lung metastases after surgery | IV | Radical resection was performed on May 4, Year 1. Six chemotherapy treatments had been performed from May Year 1 to September Year 1, with the regimen of XELOX, capecitabine tablets 3000 mg, oral, d1-d14; oxaliplatin 200 mg, intravenous drip, d1. 1 course of chemotherapy treatment was performed from October 26, Year 2. Oxaliplatin 150 mg, intravenous drip, QD, d1; cetuximab 600 mg, intravenous drip, QD, d1; irinotecan 240 mg, intravenous drip, QD, d2; fluorouracil 2500 mg, continuous intravenous drip for 48 hours; TCM treatment had been performed from November Year 2 to August Year 3. | Treatment by administering rSIFN-co began on March 17, Year 4; Intramuscular injection once every other day: 9 µg for the first time, 21 µg for the second time and thereafter. | Radiofrequency ablation targeting right lung metastases was performed on March 28, Year 4; Argon-helium cryosurgery targeting the right upper lung metastases was performed on April 9, Year 4; the right arm plexus was found damaged after the surgery; Radiofrequency ablations targeting left lung metastases were performed 2 times on May 5, Year 4 and June 13, Year 4, respectively; The right lower lung metastases were treated by ion implantation on May 27, Year 4. 2 courses of chemotherapy in December Year 4: capecitabine tablets 3000 mg, oral, d1-d14. Systemic | | PD |

TABLE 2-continued

Summary of Clinical Treatment of Multiple Types of Cancers in 58 Patients

| Patient No. | Sex | Age | Diagnosed Condition(s) | Stage | Treatment prior to drug administration | Dosage regimens for Interferon | Regimens for Combined therapy | Treatment results | Total therapeutic effectiveness |
|---|---|---|---|---|---|---|---|---|---|
| | | | | | | | chemotherapy on March 9, Year 5, cetuximab + alimta. Avastin and NK cells were added for treatment on March 23, Year 5. Radiotherapy of hepatic metastases from April 21, Year 5 to May 19, Year 5. | | NC/SD |
| 41 | Male | 57 | Colon cancer with hepatic metastases | IV | Hepatic interventions were performed 2 times in August Year 1 and on September 12, Year 1, respectively. | Treatment by administering rSIFN-co began on September 30, Year 1; Intramuscular injection once every other day: 9 µg for the 1st time; 21 µg from October 2, Year 1 to December 10, Year 1; 21-25.5 µg from December 12, Year 1 to January 9, Year 2; 21 µg from January 11, Year 2 to July 17, Year 2; Injection into liver tumor: 21 µg × 5 vials on January 15, Year 2; 21 µg × 8 vials on January 22, Year 2 21 µg × 10 vials on February 1, Year 2. | | | |
| 42 | Female | 47 | cholangiocarcinoma with hepatic metastases after surgery | IV | Diagnosed with intrahepatic biliary cystadenocarcinoma on May 31, Year 1 and radical surgery of intrahepatic biliary cystadenocarcinoma was performed; Resection of right hepatic posterior lobe and caudate lobe mass + clearance of abdominal lymph node + I$^{125}$ ion implantation + abdominal drainage were performed on November 23, Year 2. | Treatment by administering rSIFN-co began on November 21, Year 2; Intramuscular injection once every other day: 9 µg for the 1st time; 18 µg for the 2nd time; 21 µg from February 27, Year 3 to July 5, Year 4; Administration was stopped for 3 months from May Year 3 to August Year 3. Started using recombinant super-compound interferon treatment again from June 5, Year 5. | Ovarian cancer surgery was performed on June 18, Year 3. | The volume of multiple space-occupying lesions of the right and left lobes of liver is significantly reduced and the number of the lesions is also reduced. | PR |

TABLE 2-continued

Summary of Clinical Treatment of Multiple Types of Cancers in 58 Patients

| Patient No. | Sex | Age | Diagnosed Condition(s) | Stage | Treatment prior to drug administration | Dosage regimens for Interferon | Regimens for Combined therapy | Treatment results | Total therapeutic effectiveness |
|---|---|---|---|---|---|---|---|---|---|
| 43 | Female | 50 | Intrahepatic cholangiocarcinoma with intrahepatic metastases | IV | Right half liver resection + cholecystectomy + abdominal lymphadenectomy were performed on November 8, Year 1. Transcatheter arterial chemoembolization (TACE) was performed on December 22, Year 1. The 2nd TACE on liver was performed on June 4, Year 2. Chemotherapy by continuous hepatic arterial infusion (cisplatin + epirubicin + 5 FM) was performed on July 2, Year 2. The 3rd TACE was performed on August 2, Year 2. Argon-helium cryoablation targeting multiple intrahepatic lesions was performed in September Year 2. The 2nd argon-helium cryoablation was performed on November 7, Year 2. | Treatment by administering rSIFN-co began on November 15, Year 2; Intramuscular injection of 9 μg once every other day; intramuscular injection of 21 μg every other day from November 21, Year 2 to May 20, Year 3. | | | PD |
| 44 | Male | 58 | Liver cancer with lung metastases | IV | Liver transplantation in Year 1. Wedge resection of left lung superior lobe masses was performed on July 6, Year 4. | Treatment by administering rSIFN-co began on September 5, Year 4; Intramuscular injection of 9 μg every other day from September 5, Year 4 to September 9, Year 4. Intramuscular injection of 18 μg every other day from September 11, Year 4 to October 23, Year 4. Intramuscular injection of 21 μg every other day from October 25, Year 4 to February 25, Year 5. | | | PD |

TABLE 2-continued

Summary of Clinical Treatment of Multiple Types of Cancers in 58 Patients

| Patient No. | Sex | Age | Diagnosed Condition(s) | Stage | Treatment prior to drug administration | Dosage regimens for Interferon | Regimens for Combined therapy | Treatment results | Total therapeutic effectiveness |
|---|---|---|---|---|---|---|---|---|---|
| 45 | Male | 40 | Liver cancer with intrahepatic metastases | IV | Hepatic arterial embolization was performed on August 9, Year 1. | Treatment by administering rSIFN-co began on August 21, Year 1, 1 time every other day; Intramuscular injection of 9 µg at the 1st time; Intramuscular injection of 18 µg from the 2nd time and thereafter; Intramuscular injection of 21 µg every other day from September 17, Year 1 to February 1, Year 2. | | The original massive primary space-occupying lesions of the left liver clearly shrunk; the swollen retroperitoneal or abdominal para-aortic lymph nodes were disappeared. | PR |
| 46 | Female | 37 | breast cancer with lymph node metastases after surgery | IIIc | Breast-conserving cancer surgery was performed on June 3, Year 1, with 1/11 axillary lymph nodes; 6 times of chemotherapy were performed after surgery (main drug: perarubicin); 33 times of radiotherapy were performed 1 month after the end of the chemotherapy. 4 times of "docetaxel + xeloda" chemotherapy were performed after another metastatic lymph node resection in January Year 2. | Treatment by administering rSIFN-co began on May 18, Year 2. Intramuscular injection of 18 µg every other day till September 16, Year 2. | | | PD |
| 47 | Female | 58 | breast cancer, recurrence after surgery | IV | Left mastectomy and lymphadenectomy were performed on December 26, Year 1 after 6 courses of chemotherapy beginning in July Year 1 (details unknow); Multiple courses of chemotherapy (details undknown) were performed after the mastectomy; Left pleural effusion appeared in July Year 2and was improved after 2 courses of chemotherapy with "paclitaxel." | Treatment by administering rSIFN-co began on February 5, Year 3: Intrapleural injection of 21 µg × (5 or 7 or 8 or 10 or 13 vials) each time from February 5, Year 3 to May 23, Year 3; Local injection to points of the left anterior chest wall 5 times from May 30, Year 3 to July 11, Year 3, 1 time/week, 21 µg × 8 vials each time; Intramuscular injection of 21 µg every other day from July 14, Year 3 to September 30, Year 3. | Oral administration of tamoxifen, exemestane (Italy), anastrozole tablets. Carboplatin combined with thoracic perfusion of rSIFN-co. | | PD |
| 48 | Female | 45 | Left breast cancer, after surgery | IIa | Left breast-conserving surgery with clearance of tumor cells plus right breast | Treatment by administering rSIFN-co began on March 5, Year 2, 1 time every other day: | | 2 years after left breast-conserving | CR |

TABLE 2-continued

Summary of Clinical Treatment of Multiple Types of Cancers in 58 Patients

| Patient No. | Sex | Age | Diagnosed Condition(s) | Stage | Treatment prior to drug administration | Dosage regimens for Interferon | Regimens for Combined therapy | Treatment results | Total therapeutic effectiveness |
|---|---|---|---|---|---|---|---|---|---|
| | | | | | lobectomy were performed on August 22, Year 1. | intramuscular injection of 9 μg at the 1st time, intramuscular injection of 15 μg at the 2nd time, intramuscular injection of 18 μg at the 3rd time, and intramuscular injection of 21 μg from the 4th time and thereafter; Intramuscular injection of 18 μg every other day from April 23, Year 3. Administration was stopped from June 26, Year 2 to April 20, Year 3. | | surgery, subcutaneous layers of both breasts were clear without any abnormalities; no defined mass was detected in both breasts. | |
| 49 | Female | 39 | Breast cancer, recurrence after surgery | IV | Radical surgery of right breast with clearance of cancer cells was performed in November Year 1, followed by chemotherapy (details unknown). | Treatment by administering rSIFN-co began on November 29, Year 2: Local injection, 4 times, 15 μg/× 6 vials each time, from November 29, Year 2 to December 20, Year 2; Intramuscular injection of 9 ug, every other day, from December 11, Year 2 to December 20, Year 2. Intramuscular injection of 21 μg every other day from January 31, Year 3 to April 22, Year 3. | | | NC/SD |
| 50 | Male | 64 | Gastric cancer, after radical surgery | IV | "Radical surgery of gastric cancer " was performed on March 15, Year 1. | Treatment by administering rSIFN-co began on April 14, Year 1, 1 time every other day: Intramuscular injection of 9 μg at the 1st time, Intramuscular injection of 18 μg from the 2nd time and thereafter. Intramuscular injection of 15 μg every other day from September 1, Year 1 to January 22, Year 2. Intramuscular injection of 21 μg every other day from January 24, Year 2 to August 29, Year 2. Administration was stopped for 2 months from September Year 2 to November Year 2. Intraperitoneal injection of 21 μg × (8-10 vials) each time to lesions in abdominal cavity under type-B ultrasound guidance from November 28, Year 2 to December 24, Year 2. Intramuscular injection of 21 ug, every other day, from November 13, Year 2 to March 16, Year 3. | | | PD |

TABLE 2-continued

Summary of Clinical Treatment of Multiple Types of Cancers in 58 Patients

| Patient No. | Sex | Age | Diagnosed Condition(s) | Stage | Treatment prior to drug administration | Dosage regimens for Interferon | Regimens for Combined therapy | Treatment results | Total therapeutic effectiveness |
|---|---|---|---|---|---|---|---|---|---|
| 51 | Male | 59 | Gastric cancer, with abdominal cavity metastases | IV | From October, Year 1 to May, Year 3, Chemotherapy was administered for 9 times (regimen unknown). | Treatment by administering rSIFN-co began on November 2, Year 3. Intraperitoneal perfusion, 1 time every other day: 15 μg × 8 vials at the 1st time, 15 μg × 12 vials at the 2nd time, 15 μg × 14 vials at the 3rd time, and 15 μg × 16 vials at the 4th time, total 4 times until November 10, Year 3. | | Ascites were significantly reduced; cancer cells in the ascites disappeared. | PR |
| 52 | Female | 73 | Pancreatic cancer | III | | Treatment by administering rSIFN-co began on December 27, Year 1. Intramuscular injection of 9 μg every other day. Intramuscular injection of 21 μg every other day from January 2, Year 2 to September 15, Year 2. | | Lesions in the portacaval space shrank. | PR |
| 53 | Male | 73 | prostate cancer with pelvic metastases | IV | Oral Casodex, zoladex and flutamide. Androgen deprevation was performed on January 16, Year 1. Radiofrequency ablation targeting a large pelvic lymph node was performed on June 26, Year 1. I-125 particle implantation was performed on July 18, Year 1. | Treatment by administering rSIFN-co began on November 30, Year 1, once every other day: Intramuscular injection of 9 μg at the 1st time; Intramuscular injection of 21 μg from the 2nd time and thereafter; Intraperitoneal perfusion, 7 times, 21 μg × 8 vials each time. | Casodex. Three-dimensional conformal radiotherapy was performed 24 times, beginning December 12, Year 1 (60Gy 2.5 × 24 times).. | Some of pelvic metastastic lesions were eliminated or shrank. | NC/SD |
| 54 | Female | 46 | Gastrointestinal stromal tumors | Ib | Duodenal tumorectomy was performed on July 13, Year 1. Radiotherapy was performed on November 16, Year 1 after duodenal surgery. | Treatment by administering rSIFN-co began on December Year 1. 1 time every other day: Intramuscular injection for 6 months 9 μg at the 1st time; 21 μg from the 2nd time and thereafter;. The 2nd treatment was received for 3 months from Year 3 to August Year 4. The 3rd treatment of rSIFN-co was received on September 26, Year 4. | | No signs of apparent tumor recurrence and metastasis were observed by imaging examination. | CR |
| 55 | Male | 16 | Embryonal rhabdomyosarcoma, with metastases after the surgery | IV | Beginning on July 29, Year 1: 4 courses of chemotherapy was administered (main drugs: epirubicin and oxaliplatin). On September 1, Year 1: Radiotherapy of the left upper chest was administered. | Treatment by administering rSIFN-co began on February 2, Year 2, once every other day: Intramuscular injection of 9 μg at the first time; intramuscular injection of 15 μg at the 2nd time and thereafter; Intramuscular injection of 18 μg every other day from April 21, Year 2 to May 19, Year 2. | | | PD |

TABLE 2-continued

Summary of Clinical Treatment of Multiple Types of Cancers in 58 Patients

| Patient No. | Sex | Age | Diagnosed Condition(s) | Stage | Treatment prior to drug administration | Dosage regimens for Interferon | Regimens for Combined therapy | Treatment results | Total therapeutic effectiveness |
|---|---|---|---|---|---|---|---|---|---|
| | | | | | | Intramuscular injection of 21 µg every other day from May 21, Year 2 to July 11, Year 2. Intramuscular injection of 9 µg every other day from July 13, Year 2 to November 5, Year 2. Intramuscular injection of 18 µg every other day from November 7, Year 2 to December 2, Year 2. Intramuscular injection of 21 µg every other day from December 4, Year 2 to March 25, Year 3. Lymph node and intratumoral injections, 4 times, 21 µg × 8 vials each time, from November 12, Year 2 to November 28, Year 2. | | | |
| 56 | Female | 17 | Lymphoma | III | | Treatment by administering rSIFN-co began on December 29, Year 1. Intramuscular injection of 21 µg every other day from February 24, Year 2 to April 22, Year 2; Intramuscular injection of 18 µg every other day from April 24, Year 2 to June 5, Year 2; Intratumoral injection in the neck, 1 time every other day, 21 µg × (8-10-12-12-13-15 vials) each time, from December 29, Year 1 to February 18, Year 2; 21 µg × 10 vials each time from March 24, Year 2; 9 µg × 20-23 vials each time from April 25, Year 2 to May 5, Year 2; 1 ml each time, 500 µg/ml from May 7, Year 2 to May 25, Year 2. | Chemotherapy was received twice after the Spring Festival of Year 2. Treatment was in combination with TCM with detoxifying function. | Lymphoma apparently shrank; breathing and eating functions returned to normal; the hearing of the right ear recovered from no hearing weak hearing. | PR |
| 57 | Female | 19 | malignant neuroma of the right hip, recurrence after surgery | IIIc | Surgeries were performed in January Year 1 and in September Year 1; postoperative radiotherapy and chemotherapy were received (details unknown). Radiotherapy and chemotherapy were received again in January Year 2 (details unknown). Recurrence in January Year 3. Radiotherapy and chemotherapy were | Treatment by administering rSIFN-co began on February 9, Year 4. Intramuscular injection of 21 µg every other day. Hip intratumoral injection every 2-3 days, 21 µg × 4 vials each time. | TCM | | NC/SD |

TABLE 2-continued

Summary of Clinical Treatment of Multiple Types of Cancers in 58 Patients

| Patient No. | Sex | Age | Diagnosed Condition(s) | Stage | Treatment prior to drug administration | Dosage regimens for Interferon | Regimens for Combined therapy | Treatment results | Total therapeutic effectiveness |
|---|---|---|---|---|---|---|---|---|---|
| | | | | | received again (details unknown). Recurrence in January Year 4; ultrasonic scalpel and TCM treatments were received. | | | | |
| 58 | Female | 61 | Metastatic poorly differentiated squamous cell carcinoma in the right chest, after surgery for | IIIa | Tumor resection in the right anterior chest wall was performed on June 11, Year1. | Treatment by administering rSIFN-co began on July 7, Year 1, intramuscular injection once time every other day: 9 μg at the 1st time, 21 μg from the 2nd time and thereafter, until January 6, Year 2 | Postoperative radiotherapy after surgery of metastatic cancer in the upper right chest wall was performed from July 7, Year 1 to August 8, Year 1. | | NC/SD |

Example 3: Clinical Data on Typical Patients Treated with the Recombinant Interferon of the Invention (19 Patients)

Clinical data collected until Jul. 1, 2012 of 19 patients treated with the recombinant interferon of the invention are provided below (Patients numbered by 1-19 correspond to Patients 1-19, respectively, in the "Summary of Clinical Treatment of Multiple Types of Cancers in 58 Patients" in aforementioned Table 2 of Example 2).

Patient 1. Non-Small-Cell Lung Cancer; the Primary Lesions in the Right Pulmonary Hilum and the Mediastinal Lymph Node Metastasis Disappeared after Treatment by Intramuscular Injection of Recombinant Super-Compound Interferon (rSIFN-co) in Combination with Radiotherapy.

Figure 3A:
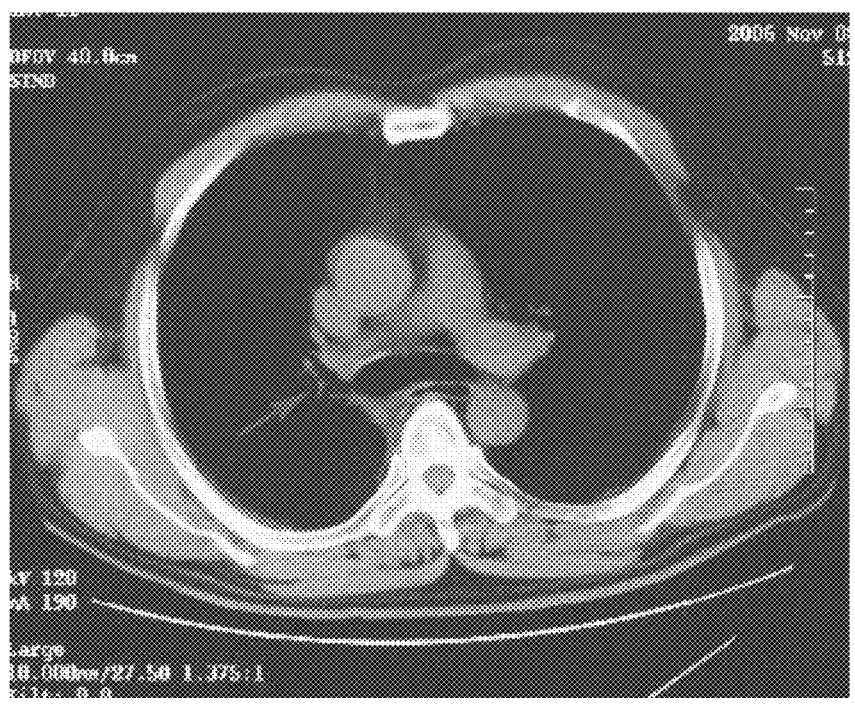
FIGS. 3A and 3B shows the treatment situation of patient 1, wherein an arrow in FIG. 3A shows state of the original lesion observed in a CT image on $8^{th}$ November, Year 2, after 12 months of medication; and an arrow in FIG. 3B shows state of the original lesion observed in a CT image on $1^{st}$ February, Year 3, after 15 months of medication, the year of the start of treatment being Year 1.
Figure 3B:
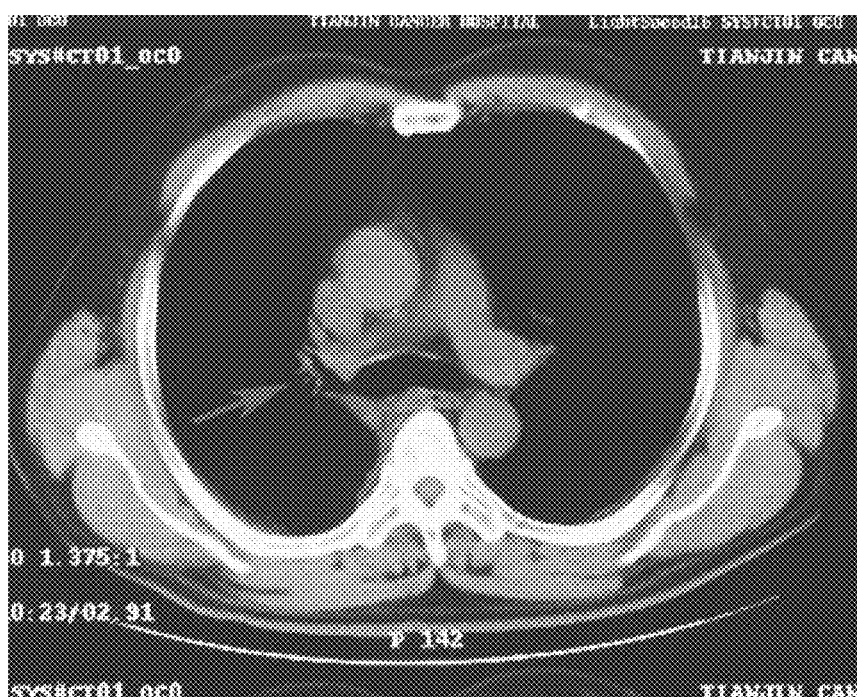

| Patient 1 | Gender: Male | Age: 53 |
|---|---|---|
| Pathological diagnosis: | Squamous cell carcinoma | |
| Clinical and pathological staging[1]: | $T_3N_2M_0$. IIIb | |
| Regimens before administration of rSIFN-co: | DP Regimen[8] was provided from October 14, Year 1 to November 25, Year 1: 75 mg of Taxotere and 75 mg of Cisplatin on Day 1. Two cycles of chemotherapy were performed in total, each lasting for 21 days. | |
| Regimens: administration of rSIFN-co combined with radiotherapy | The rSIFN-co therapy started in November, Year 1. Intramuscular injection of rSIFN-co was done once every other day: 9 µg for the 1st time, 15 µg for the 2nd time and 18 µg for the 3rd time and thereafter. Therapy continued till February, Year 3, during which rSIFN-co treatment had been stopped for 1 month in April, Year 2, leading to a total treatment duration of 15 months. Radiotherapy[3] (DT40Gy) on right lung and mediastinal lymph nodes started on December 2, Year 1 followed by X-knife therapy (DT20Gy) | |
| Response to rSIFN-co treatment: | CR[2] (primary lesions on right pulmonary hilum disappeared and cured) | |
| Survival time: | After about 80 months (from October Year 1~July Year 8), the patient remained alive and lived a normal life. No recurrence or metastasis was observed upon imaging examinations. | |
| Diagnostic imaging before administration of rSIFN-co: | CT scan on November 25, Year 1 after chemotherapy: The right main bronchus was obstructed by the invasive masses originated from right hilum, resulting in atelectasis of upper lobe of the right lung; multiple nodules occurred at the lower lobe of right lung. These signs indicated progression of tumor. The patient had breathing difficulty and breath sound disappeared. | |
| Diagnostic imaging after administration of rSIFN-co: | CT scans on January 4, Year 2: The masses at right hilum were reduced in size, relieving atelectasis at the upper lobe of the right lung. Part of mediastinal lymph nodes also decreased in size. CT scans on June 12, Year 2: The mediastinal lymph nodes continued to shrink and infiltration of right lung was absorbed. CT-scan on November 08, Year 2 (12 months after administration): Please refer to the location indicated by arrow in FIG. 3A where the lesions originally occurred. CT-scan on February 1, Year 3 (15 months after administration): Please refer to the location indicated by arrow in FIG. 3A where the lesions originally occurred. CT scan on October 19, Year 3: The blood vessels or lymph nodes on the right hilum were a little larger than normal and more infiltration on lower lobe of right lung was absorbed; other changes were not obvious. | |
| Description of FIGS. 3A-3B: | After 12 months of treatment, the lesions on the right lung were obviously reduced in size. After 15 months of rSIFN-co administration, progression or metastasis of lesions was not observed. | |

Patient 2. Non-Small-Cell Lung Adenocarcinoma with Systemic Metastases on Body Parts Including Bilateral Lungs, Liver and Lymph Nodes/Intramuscular Injection and Aerosol Inhalation of rSIFN-co Combined with Chemotherapy (GP Regimen) and Administration of Recombinant Human Endostatin (Endostar). After Treatment, the Primary Lesions in the Lungs Evidently Became Reduced in Size and the Metastatic Lesions Disappeared in the Liver and in Many of the Lymph Nodes.

5

Figure 4A:
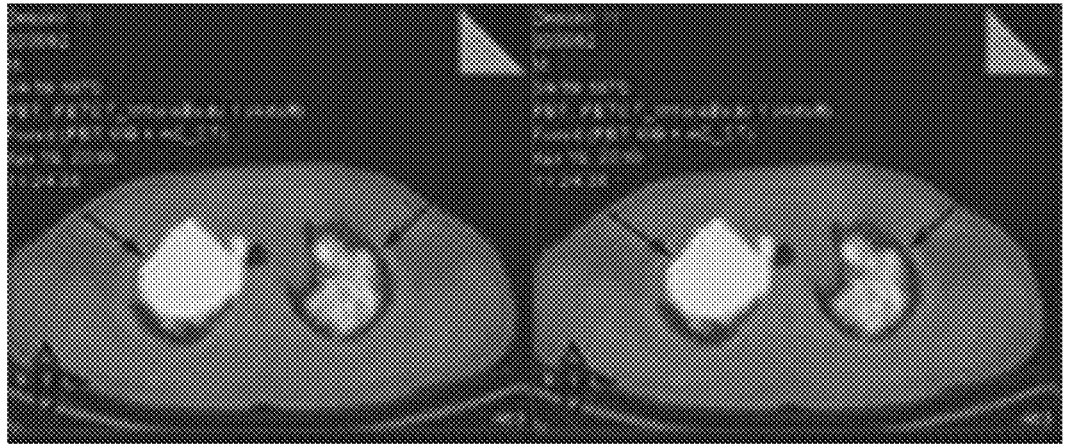
Figure 4B:
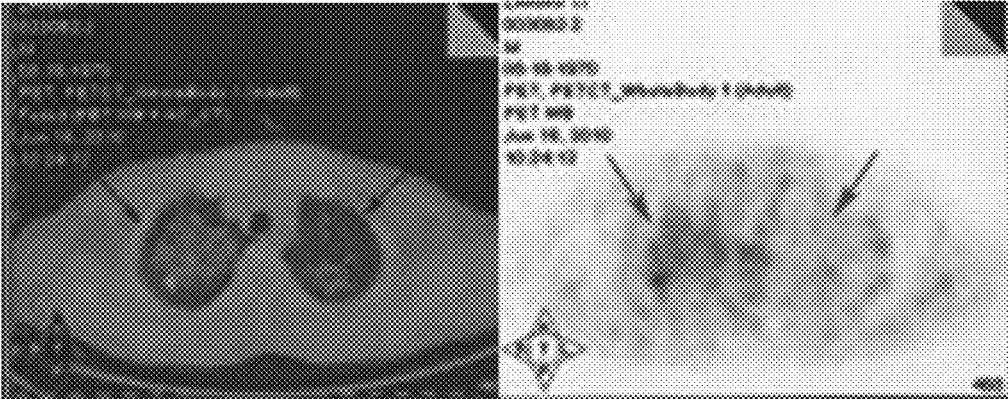

| Patient 2 | Gender: Male | Age: 40 |
|---|---|---|
| Pathological diagnosis: | Lung Adenocarcinoma | |
| Clinical and pathological staging[1]: | $T_3N_3M_1$. IV | |
| Regimens before administration of rSIFN-co: | Systematic chemotherapy began at January, Year 1: Taxotere and Carboplatin. One cycle of 21 days was provided. | |
| Regimens: administration of rSIFN-co combined with chemotherapy and other biotherapies | The rSIFN-co therapy began on April 14, Year 1. Intramuscular injection of rSIFN-co was done once every other day: 9 µg for the 1st time, 15 µg for the 2nd time, 18 µg for the 3rd time and 21 µg for the 4th time and thereafter. Meanwhile, aerosol inhalation of rSIFN-co was done once every day: 300 µg for the 1st time, 500 µg for the 2nd time, 600 µg for the 3rd time and thereafter. Administration of rSIFN-co ended in April Year 2. From April 20, Year 1 to September 3, Year 1, Endostar[5] was administrated every day: 7.5 mg/m² per dose, 1.2 × 10⁵ U/m². Four cycles were performed totally with each lasting for 14 days. Meanwhile, GP regimen was combined: 1600 mg of Gemcitabine on days 1 and 8 and 40 mg of Cisplatin on days 1~3. Four cycles were performed, each being 15 days. One intrapericardial infusion with Cisplatin (30 mg) was performed on July 19, Year 1. Aerosol inhalation of Cisplatin was added from December 23, Year 1 to January 14, Year 2: 10 mg/dose, 2 doses per day. The second course of Endostar treatment was provided from January 18, Year 2 to January 30, Year 2 with same dosage. Chemotherapy using Pemetrexed[6] proceeded from December 25, Year 1 to January 19, Year 2: iv. 500 mg/m², every 3 to 4 weeks. As none of the treatments had any obvious effect, the chemotherapy during February 15, Year 2 to April 25, Year 2 was replaced with DP regimen[8] (75 mg/m² of Taxotere and 75 mg/m² of Cisplatin on day 1) in combination with administration with Tarceva (150 mg/day) for 4 cycles with 21 days per cycle. A Gamma knife therapy was performed on head on June 29, Year 2. | |
| Response to rSIFN-co treatment: | PR[2] (the size of the primary lesions on upper lobe of right lung reduced from about 10.2 × 8.2 × 7.7 cm to 1.2 × 1.4 cm; metastatic lesions in the right liver and multiple lymph nodes disappeared; the metastatic lesions on the two lungs decreased in size and the radioactive concentration/accumulation decreased.) | |
| Survival: | About 18 months from start of this treatment: (January 20, Year 1 to August 3, Year 2) | |
| Diagnostic imaging before administration of rSIFN-co: | Diagnostic imaging after administration of rSIFN-co: | |
| PET/CT on April 19, Year 1 (see the lesions indicated by the arrow in FIG. 4A): | PET/CT on June 18, Year 1 (see the lesions indicated by arrow in FIG. 4B): | |
| 1. A mass shadow of was found in the upper lobe of right lung whose size was about 10.2 × 8.2 × 7.7 cm and CT value was about 38.8 Hu, indicating the existence of a central lung cancer; | 1. The size of primary mass in the upper lobe of right lung was 1.2 × 1.4 cm. Lesions shrank and radioactive concentration reduced significantly. The maximum SUV value was 2.9, and the average value was 2.1; | |
| 2. Multiple lymph node metastases were found at the right side of trachea, root of neck (right-side) and the nearby regions at the right-side of pancreas head,; size of the maximum lesions was about 1.4 × 1.1 cm. | 2. Multiple metastatic lesions of lymph nodes at the right side of trachea, root of neck (right-side) and the nearby regions beside the pancreas head had all disappeared; 3. Patches, flocculent shadows and reticular shadows were extensively distributed at other | |

-continued

| | |
|---|---|
| 3. A large quantity of miliary nodule shadows were diffusely distributed on both lungs with radioactive uptake increased. Diffuse metastases happened in both lungs. | parts of the lungs with slightly increased radioactive uptake. Space-occupying lesions and consolidation were not found. The size of lesions shrank evidently and the radioactive uptake reduced significantly. |
| 4. The maximum size of the metastatic lesions on the right lobe of liver is about 1.2 × 0.9 cm. | 4. Two metastatic lesions on the right lobe of the liver disappeared. |
| Description of FIGS. 4A-4B: | After 2 months' treatment, lesions on the upper lobes of both lungs evidently shrank or disappeared. |

Patient 3. Non-Small-Cell Lung Cancer with Brain Metastases/Intramuscular Injection and Aerosol Inhalation of rSIFN-co Combined with Gamma Knife Treatment. After the Treatment, Primary Lesions on Right Lung and Brain Metastatic Lesions were Cleared Up.

Figure 5A:
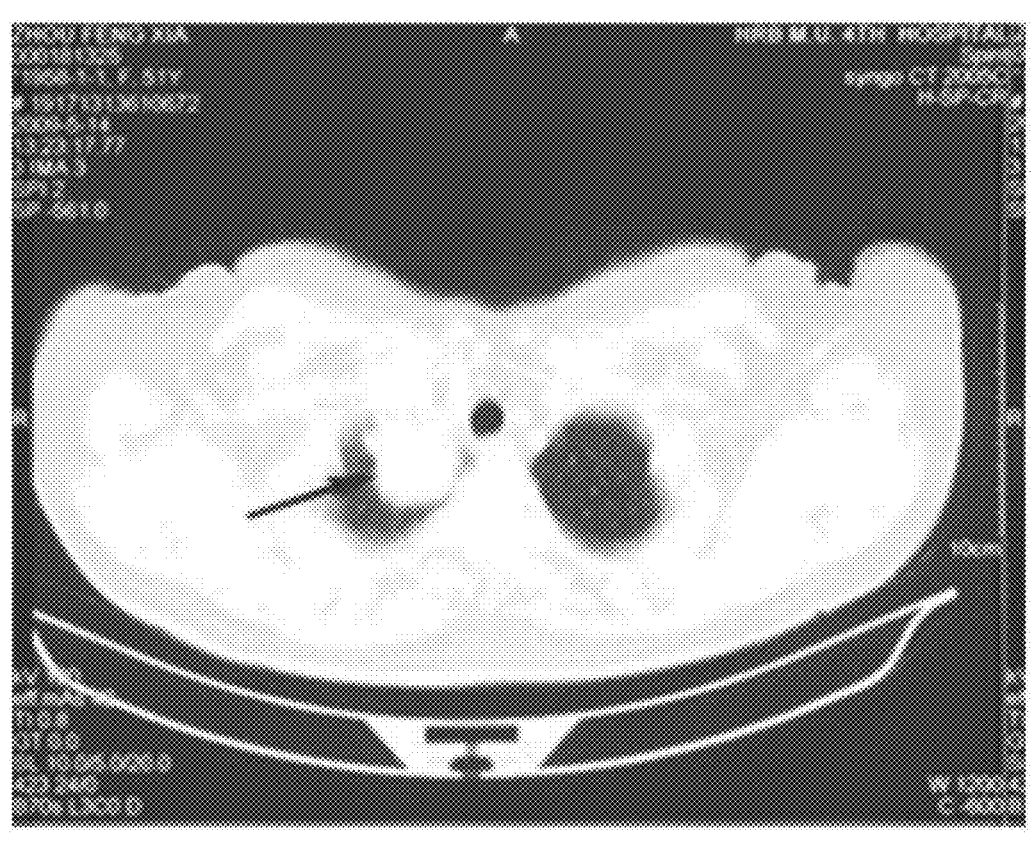
Figure 5B:
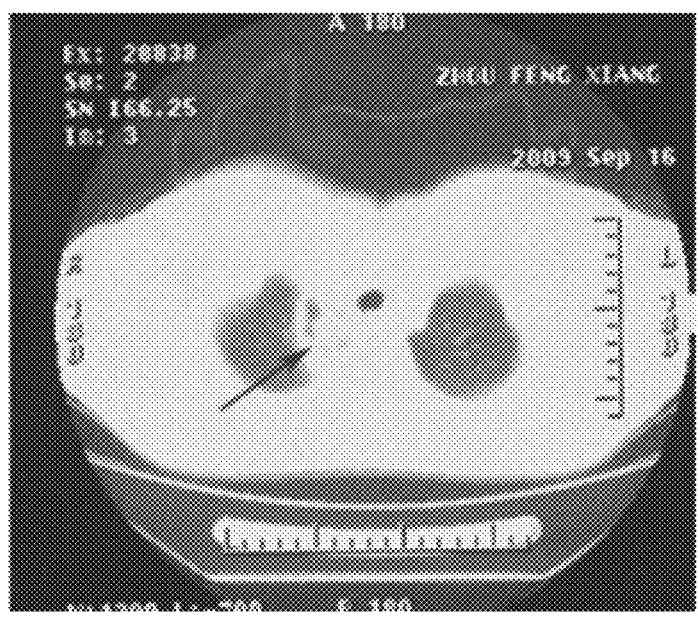
Figure 6A:
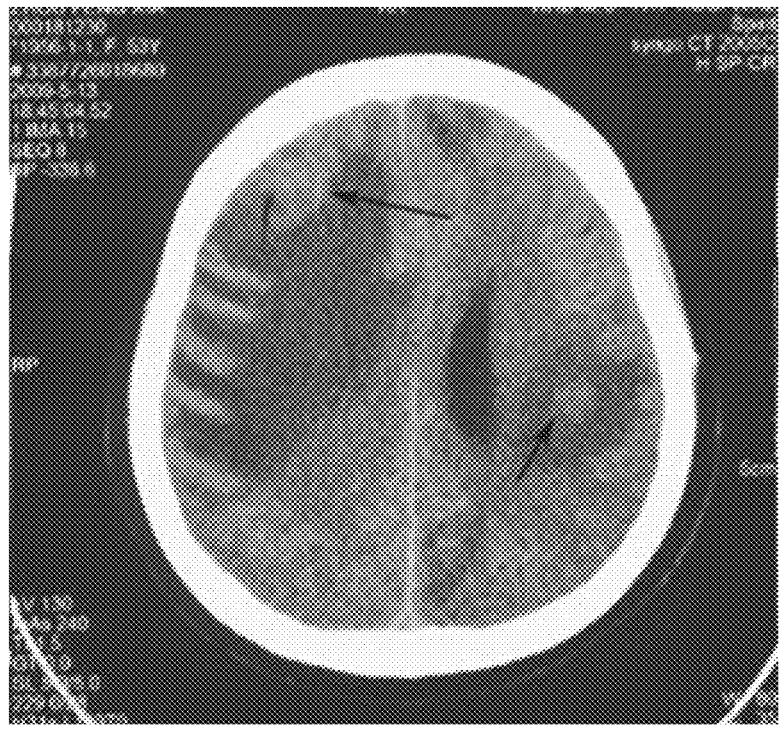
Figure 6B:
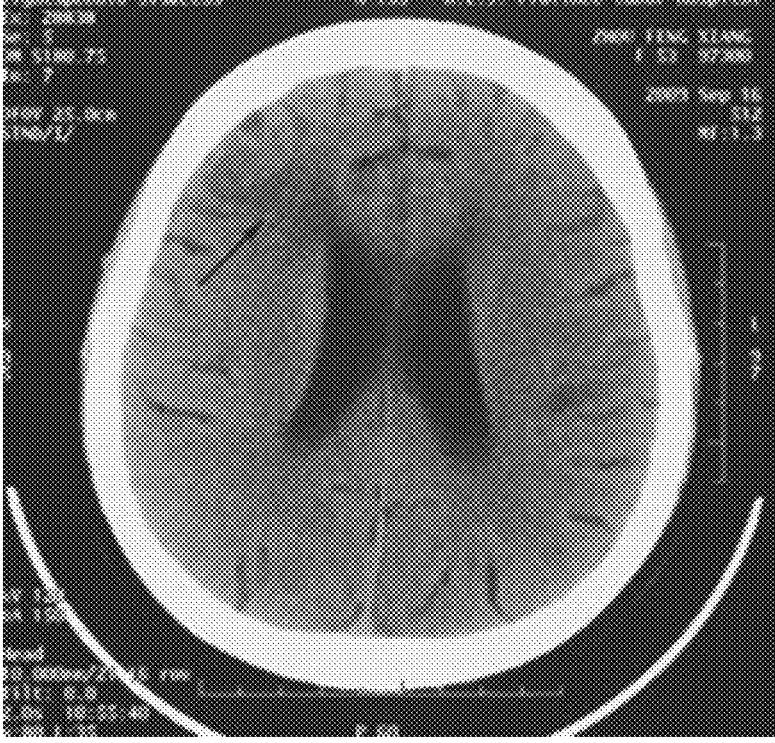
Figure 7A:
Figure 7B:
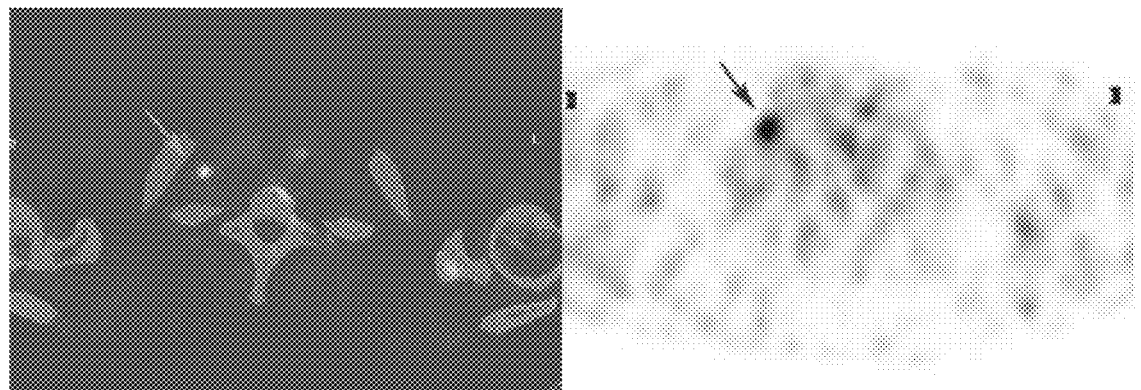
Figure 8A:
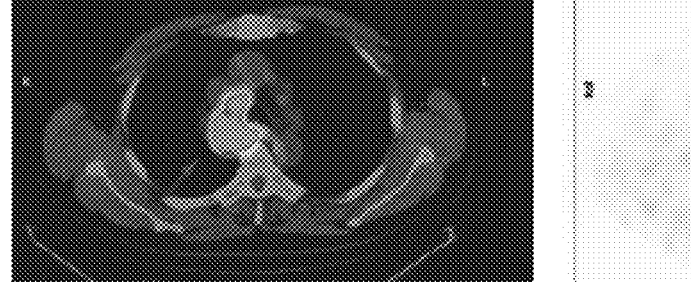
Figure 8A:
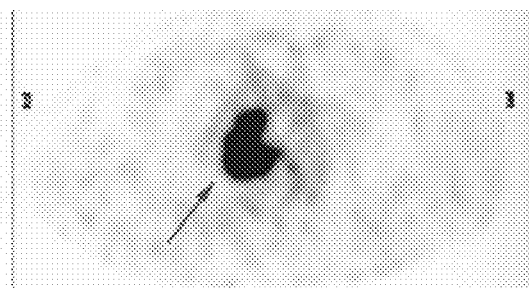
Figure 8B:
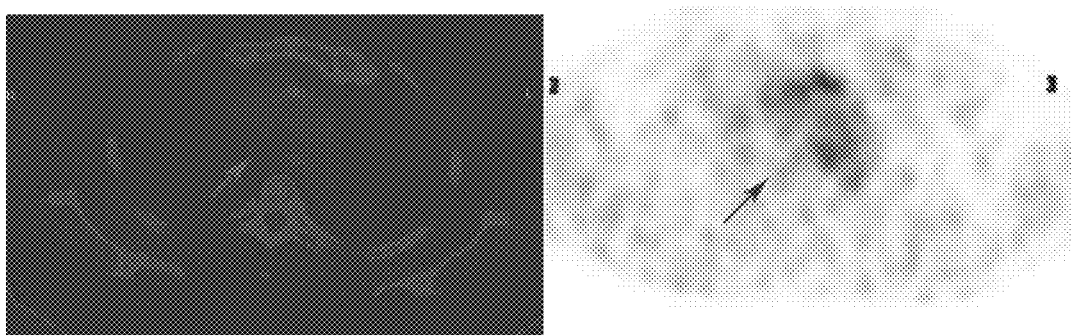

| Patient 3 | Gender: Female | Age: 51 |
|---|---|---|
| Pathological diagnosis: | None | |
| Clinical and pathological staging[1]: | $T_2N_2M_1$. IV | |
| Regimens before administration of rSIFN-co: | None | |
| Regimens: administration of rSIFN-co combined with Gamma knife treatment | Treatment with rSIFN-co started on May 29, Year 1. Intramuscular injection of rSIFN-co was done once every other day: 9 µg for the 1st time, 18 µg for the 2nd time and 21 µg for the 3rd time and thereafter. Aerosol inhalation of rSIFN-co was simultaneously performed: 200 µg/every other day. | |
| | From July 14, Year 1, 18 µg of rSIFN-co was used in intramuscular injection. Aerosol inhalation of 400 µg of rSIFN-co was simultaneously performed every other day. | |
| | The administration continued for more than 3 months till September 16, Year 1. | |
| | During this period, Gamma knife radiotherapy for the brain lesions was conducted. | |
| Response to rSIFN-co treatment: | CR[2] (the primary lesion of about 5.1 × 3.2 cm on the upper lobe of right lung disappeared; the enlarged lymph nodes in the mediastinum and the metastatic lesions in the brain of about 3.7 × 2.6 cm basically disappeared.) | |
| Survival: | About 13 months from start of the treatment (from May Year 1 to June Year 2) | |
| Diagnostic imaging before administration of rSIFN-co: | Diagnostic imaging after administration of rSIFN-co: | |
| Lung CT scans on May 14, Year 1 (see the lesions indicated by arrow in FIG. 5A): | CT scans on September 16, Year 1 for brain (FIG. 6B) and chest (FIG. 5B): | |
| An irregular soft-tissue density shadow of about 5.1 × 3.2 cm was found at the apex of right lung, which had an obscure boundary and connected to anterior pleural membrane. Enlarged lymph nodes were found in neighboring mediastinum. Diagnostic imaging showed that it was a space-occupying lesion in the apex of right lung. | 1. Irregular increased density shadows were found at upper lobe of right lung near mediastinum, suggesting the possible occurrence of inflammation in the right lung. The thorax was symmetrical, and the perivascular space in mediastinum was clear with no enlarged lymph node found. (See the original location of the lesions indicated by arrow in FIG. 5B) | |
| Brain CT scans on May 14, Year 1 (see the lesions indicated by arrow in FIG. 6A): Multiple hybrid-density shadows were found at frontal lobe, temporal lobe and parietal lobe of both sides, which were surrounded by low density shadows especially on the right side. The lateral ventricle was pressed to be narrower and the midline structure was shifted leftwards. The pathline of the lesions at the right frontal lobe was about 3.7 × 2.6 cm. | 2. Irregular low-density shadows could be seen in the right frontal lobe and left temporal lobe. The anterior horn of right lateral ventricle was narrowed. Cerebral fissures and sulcus were not widened and the midline structure was centered. (See the original location of the lesions indicated by arrow in FIG. 6B) | |
| Description of FIGS. 5A-5B: | After 3-month of treatment, the mass at the apex of right lung completely disappeared. | |
| Description of FIGS. 6A-6B: | After treatment, the metastatic brain lesions disappeared. | |

Patient 4. Small-Cell Lung Cancer with Metastases in the Mediastinal Lymph Nodes and Clavicles/Intramuscular Injection and Aerosol Inhalation of rSIFN-co Combined with Chemotherapy (Aerosol Inhalation of Cisplatin and EP Regimen) and Interventional Therapy for Supraclavicular Lesions. After the Treatment, Primary Lesions in the Right Lung and Metastases in Mediastinal Lymph Nodes and Clavicles Cleared Up.

| Patient 4 | Gender: Male | Age: 49 |
|---|---|---|

| | |
|---|---|
| Pathological diagnosis: | Small-cell lung cancer |
| Clinical and pathological staging①: | $T_4N_3M_1$. IV |
| Regimes before administration of rSIFN-co: | The first cycle of EP⑦ chemotherapy was conducted from March 25, Year 1 to Apr 9, Year 1: 100 mg of Etoposide and 30 mg of Cisplatin. |
| Regimes: administration of rSIFN-co combined with chemotherapy and interventional therapy | The treatment of rSIFN-co began on April 12, Year 1. Intramuscular injection was done once every other day: 9 µg for the 1st time, 15 µg for the 2nd time and 18 µg for the 3rd time and thereafter. Aerosol inhalation of rSIFN-co was performed once every other day: 0.5~2 ml/dose (200 µg/ml). From July 16, Year 1, 21 µg of rSIFN-co was used in intramuscular injection. Aerosol inhalation of rSIFN-co continued but the amount per dose was changed to 200 µg. The first cycle finished by the end of March Year 2 (lasting for almost 1 year). The administration of rSIFN-co was stopped for 1 month because Aerosol inhalation of Cisplatin (one dose per day and 10 mg per dose) was performed throughout September Year 1. The 2nd cycle of treatment proceeded from October 9, Year 2 to January 26, Year 3 during which 18 µg of rSIFN-co was intramuscularly injected every other day. Five cycles of EP chemotherapy were conducted from March 25, Year 1 to September 10, Year 1 and the same regimen as mentioned above was used. An interventional cryoablation was conducted on the supraclavicular lesions on September 3, Year 2. From October Year 1, a 15-day regimen of aerosol inhalation of Cisplatin was added: 10 mg per dose, 1 dose per day. Two cycles were done, each lasting for 15 days. |
| Response to rSIFN-co treatment: | CR② (a primary lesion of about 0.6 × 0.4 cm, on the apex of right lung disappeared.; a lesion with a nodule of about 2.6 × 2.2 cm on the of right clavicle disappeared; Mutilple nodules appearing in neighboring areas of the mediastinal brachiocephalic trunk, right brachiocephalic veins, superior vena cava, and trachea, part of which fused and lesions of about 5.5 cm × 4.9 cm in size disappeared.) |
| Survival: | After about 39 months (from March 23, Year 1 to July Year 4), the patient remained alive and had a normal life. No recurrence or metastasis was observed upon imaging. |
| Diagnostic imaging before administration of rSIFN-co: | Diagnostic imaging after administration of rSIFN-co: |
| PET/CT scans on April 8, Year 1 (see the lesions indicated by arrows in FIG. 7A-8A) after the chemotherapy: | PET/CT scans on December 24, Year 1 (see the original lesion locations indicated by arrows in FIG. 7A-8A): |
| 1. One nodule with coarse edge and slight lobulated appearance was found at the apex of right lung (diameter: 0.6 × 0.4 cm). PET showed abnormal radioactive concentration and the SUV value was 4.1. | 1. The nodule at the apex of right lung were not obviously shown; |
| 2. Nodules of about 2.6 × 2.2 cm were observed at right clavicle, the boundaries of which were obscure. PET showed abnormal radioactive concentration and the SUV value was 9.1. | 2. The nodules on right clavicle were significantly downsized. PET showed abnormal radioactive concentration with a SUV value of 4.7; |
| 3. Multiple nodules of about 5.5 cm × 4.9 cm appeared around the mediastinal brachiocephalic trunk, right brachiocephalic veins, superior vena cava, and trachea. The boundaries of these nodules were not distinct | 3. The nodules around the mediastinal brachiocephalic trunk, right brachiocephalic veins, and trachea were not clearly observed. superior vena cava; |
| | 4. Multiple nodules were found around the superior vena cava. PET did not show an obvious radioactive concentration, indicating the suppression on the lesions' metabolism. |
| | PET/CT scans on July 26, Year 3: |

-continued

| | |
|---|---|
| and some were partially fused together. PET showed abnormal radioactive concentration and the SUV value was 11.5). Metastasis of lymph nodes should be taken into account.<br>4. The superior vena cava could not be excluded. | 1. Streaky shadows were found in the upper lobe of right lung while patchy shadows were found in dorsal segment of lower lobe. PET scan did not show obvious radioactive concentration;<br>2. After cryotherapy was conducted for the right supraclavicular metastasis, no obvious nodules or masses were found in the right clavicle and PET image did not show obvious radioactive concentration. PET scans on other parts showed similar metabolic images as before.<br>PET/CT on February 7, Year 4 (after treatment of "small-cell cancer of right lung" and compared to PET/CT scans taken on July 26, Year 3):<br>1. The posterior wall of left nasopharynx was thickened slightly and PET imaging showed radioactive concentration, suggesting the possible occurrence of an inflammatory lesion;<br>2. Multiple nodules were at deep cervical and submentum and PET imaging did not show abnormal radioactive concentration, suggesting the possible occurrence of inflammatory hyperplasia of lymph nodes;<br>3. The wall of greater gastric curvature was slightly thickened and PET imaging did not show radioactive concentration. Inflammatory lesion could be taken into consideration;<br>4. PET/CT scans on other parts did not show significant changes. |
| Description of FIGS. 7A-7B: | After 8 months of treatment, the lesions on the apex of the right lung disappeared. |
| Description of FIGS. 8A-8B: | After 8 months of treatment, the metastatic lesions in mediastinum disappeared. |

Patient 5. Non-Small-Cell Lung Cancer with Metastases to the Right Humerus, after Surgeries/Intramuscular Injection and Aerosol Inhalation of rSIFN-co Combined with Chemotherapy (Aerosol Inhalation of Cisplatin). After Treatment, the Metastatic Lesions in Right Lung Hilum, Paratracheal Lymph Nodes and Several Sites of Spinal Metastases Disappeared.

| Patient 5 | Gender: Female | Age: 42 |
|---|---|---|
| Pathological diagnosis[①]: | Metastatic adenocarcinoma (in right humerus) (moderately differentiated adenocarcinoma) | |
| Clinical and pathological staging[①]: | $T_2N_2M_1$. IV | |
| Regimes before administration of rSIFN-co: | A surgical repair of right humerus was performed on February 23, Year 1.<br>After that surgery, patient was given 4 courses of DP[⑧] chemotherapy: 75 mg of Taxotere and 75 mg of Cisplatin on day 1. | |
| Regimes: administration of rSIFN-co combined with chemotherapy | Treatment with rSIFN-co began on April 15, Year 1. Intramuscular injection was performed once every other day: 9 μg for the 1st time and 21 μg for the 2nd time and thereafter.<br>The treatment was provided for a total of 3 months till September 15, Year 1, during which rSIFN-co administration was suspended for 1 month due to chemotherapy (the chemotherapy regimen shown below related to aerosol inhalation of Cisplatin) and for 1 month because of the patient's physical condition.<br>Aerosol inhalation of rSIFN-co was added on September 16, Year 1: 1 ml (200 μg/ml) per day. Till February, Year 2, the co-administration regimen was provided for 5 months.<br>From September 15, Year 2, intramuscular injection of 15 μg was provided every other day.<br>Aerosol inhalation of Cisplatin began on September 16, Year 1: 10 mg per dose and 2 doses per day. Eight cycles were conducted with each cycle being 15 days. | |

-continued

Figure 9A:
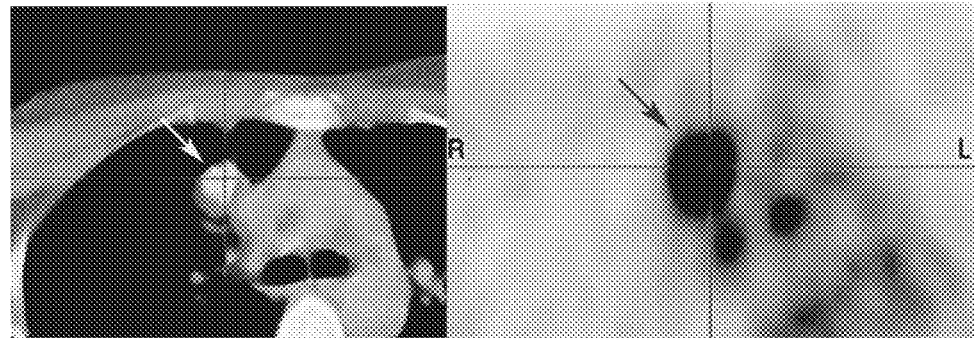
Figure 9B:
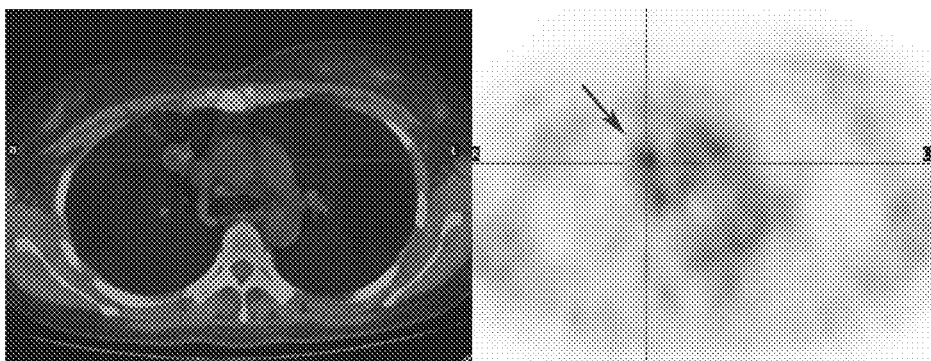
Figure 10A:
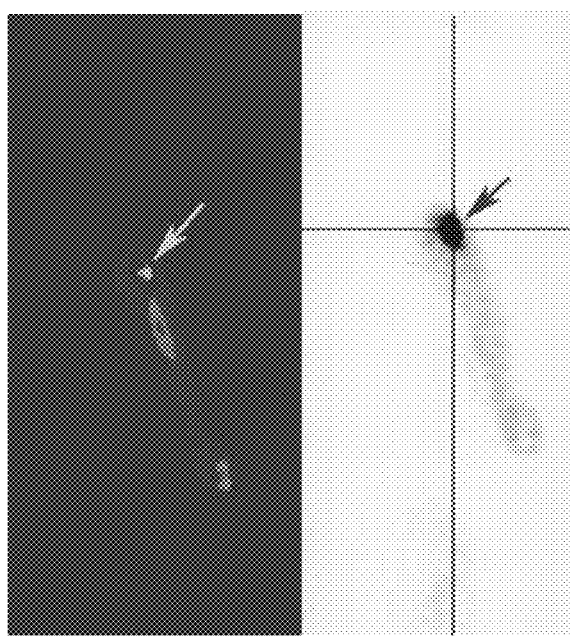
Figure 10B:
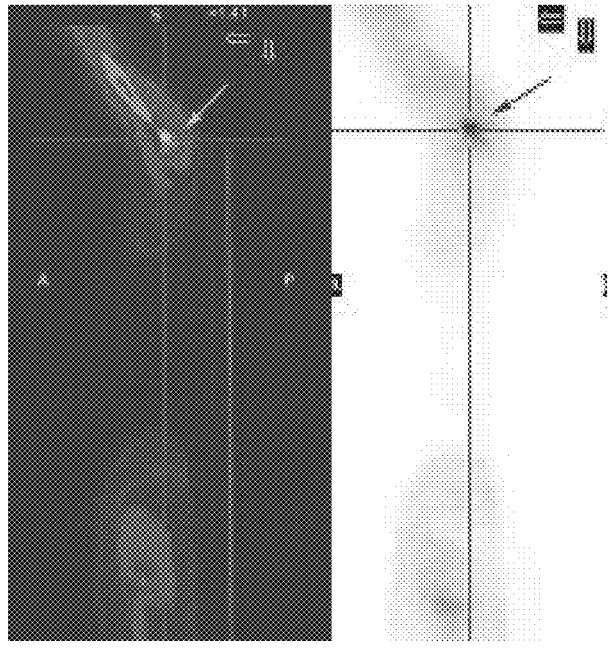
Figure 11A:
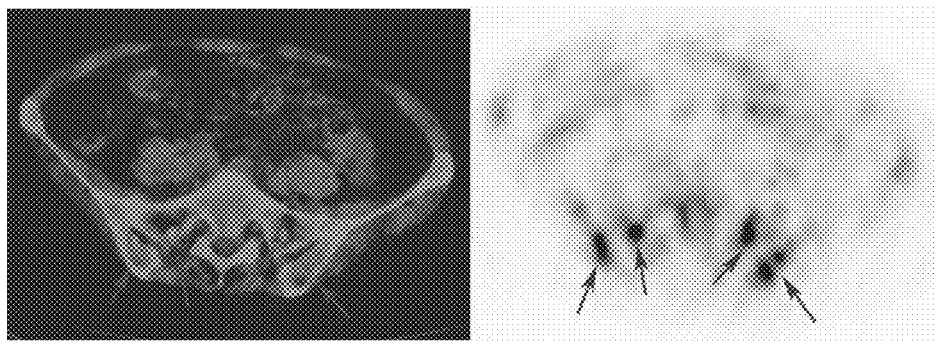
Figure 11B:
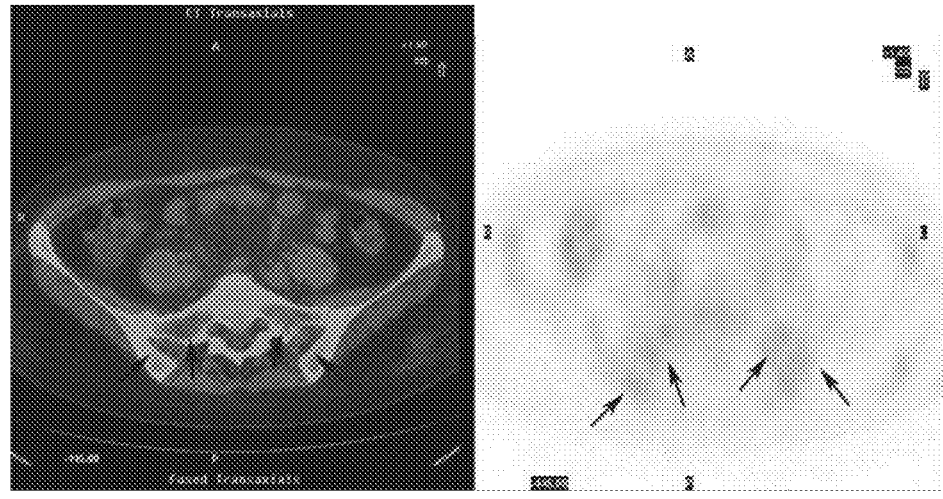

| Response to rSIFN-co treatment: | CR② (radioactive concentrations at the primary lesion of right lung tumor, right humerus and the T6 vertebra evidently decreased. Metastatic lesions on pelvis and lumbar vertebrae as well as enlarged paratracheal lymph nodes disappeared.) |
| Survival: | After about 40 months (February Year 1 to July Year 4), the patient remained alive with a normal life. No recurrence or metastasis was observed upon imaging. |
| Diagnostic imaging before administration of rSIFN-co: PET/CT scans on February 26, Year 1 after surgery (See lesions indicated by arrows in FIG. 9A-11A): 1. A circular nodule shadow of about 24 mm × 19 mm × 18 mm was found at the front end of right lung' upper lobe. 2. Metastases happened to the right upper lung hilum and lymph nodes on anterior tracheal space. Metastatic lesions were also observed at right humerus. 3. Accumulated lesions on the right upper humerus were found which was considered as changes during the recovery phase after the surgery. 4. Increased radionuclide metabolism was observed at chest, lumbar and bilateral ilia. Multiple bone metastases probably happened. 5. Tiny nodular shadows of 2 mm were found on the posterior portion of the upper lobe of right lung, which was recommended to be continually observed. CT scans on April 13, Year 1 after chemotherapy: Cancer on upper portion of right lung, tiny nodules on right lung, circumscribed pleural thickening and enlarged mediastinal lymph nodes were found. The results suggested that the chemotherapy was not effective and the lesions had progressed. | Diagnostic imaging after administration of rSIFN-co: PET/CT scans on March 2, Year 2 (see original locations of lesions indicated by arrows in FIG. 9B-11B): 1. The mass on the soft tissue of anterior segment of upper lobe of right lung did not change in shape, size and density. The extent of radionuclide metabolism decreased (SUVmax reduced from 9.5 to 1.7); 2. The glucose metabolism of lymph nodes on anterior tracheal space became normal and calcified lymph nodes at right upper lung hilum showed a mild radioactive concentration. 3. The radioactive concentration at upper segment of right humerus and T6 vertebra reduced (SUVmax decreased from 6.3 and 3.8 to 2.9 and 1.7, respectively); 4. No abnormal distribution of radionuclide was obviously found in lumbar, sacrum and pelvis. 5. Tiny modules were almost the same as seen before in lateral segment of middle lobe of right lung and the lateral basal segment of lower lobe of left lung. No radionuclide was abnormally distributed. |
| Description of FIGS. 9A-9B: | After treatment, the radionuclide metabolism reduced significantly in the primary lesions of right lung. |
| Description of FIGS. 10A-10B: | The radioactive concentration of the lesions at upper segment of right humerus decreased. |
| Description of FIGS. 11A-11B: | Metastatic lesions on pelvis disappeared. |

Patient 6. Non-Small-Cell Lung Cancer with Multiple Lymph Node Metastases in Mediastinum, Left Segment of Neck, Right and Root Segment of Neck, Left Supraclavicular Fossa; Left-Sided Pleural Effusion; Multiple Bone Metastases in Vertebral Column, Bilateral Ribs, Right Clavicle Joint, Sternum and Left Sacrum, and Obvious Generalized Pain/Intramuscular Injection, Aerosol Inhalation and Local Spraying of rSIFN-co Combined with Chemotherapy (GP Regimen) and Gefinitib (Iressa) Therapy. After the Treatment, Primary Lesions on Left Lung Disappeared and Metastatic Lesions Around the Body Shrank. Further, Generalized Pain was Relieved.

| Patient 6 | Gender: Male | Age: 39 |
| --- | --- | --- |
| Pathological diagnosis: Clinical and pathological staging①: Regimens before administration of rSIFN-co: | Moderately-poorly differentiated adenocarcinoma $T_4N_3M_{1b}$. IV The first cycle of GP Regimen⑨ began in September Year 1 with each cycle lasting for 21 days: 1000 mg/m² of Gemcitabine on day 1 and 8 and 75 mg/m² of Cisplatin on day 1. | |
| Regimens: administration of rSIFN-co combined with chemotherapy and other biological therapies | Treatment with rSIFN-co began on October 12, Year 1 with aerosol inhalation of 600 μg every day. Intramuscular injection of rSIFN-co started on December 12, Year 1, once every other day: 9 μg for 1st time, 15 μg for 2nd time and 18 μg for 3rd time and thereafter. Focal spraying on bone metastases began on March 12, Year 2: 70 μg~139 μg/does/site, 4~5 doses/day. | |

-continued

Figure 12A:
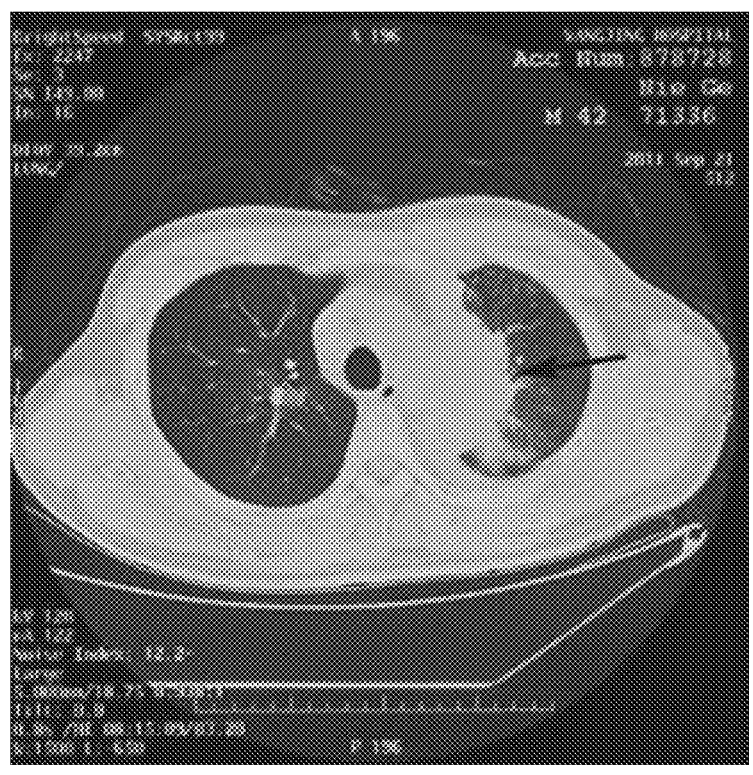
Figure 12B:
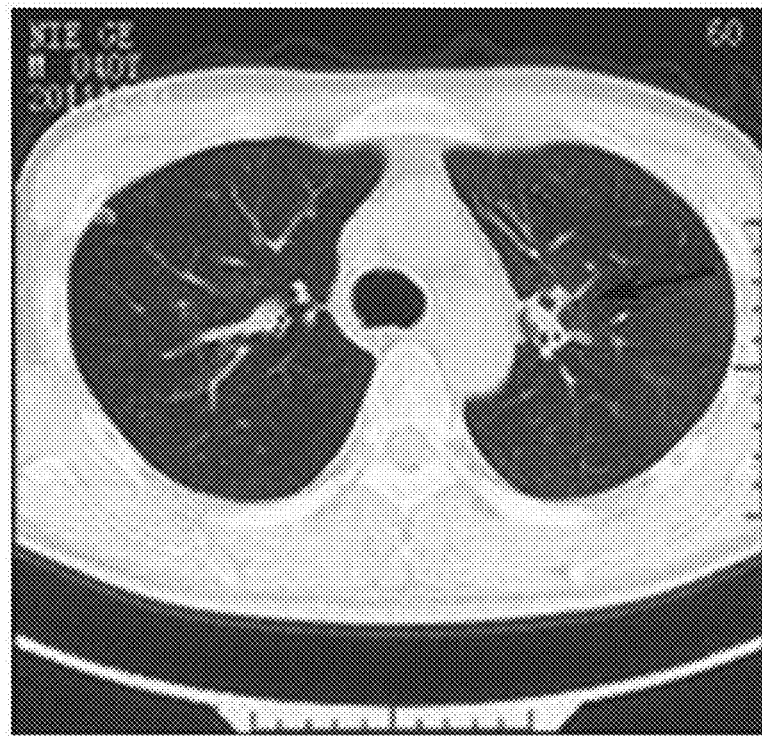

| | |
|---|---|
| | The second cycle of GP Regimen[9] started on October 14, Year 1 (the regimen was exactly the same as mentioned above). Gefinitib was taken from November 24, Year 1: 1 pill/dose (250 mg/pill), 1 dose/day. |
| Response to rSIFN-co treatment: | CR[2] (primary lesion of about 9 × 3.5 cm in size at the left lung almost disappeared; enlarged lymph nodes of about 1.0 cm × 0.7 cm at left segment of neck, nodules of about 1.2 cm × 0.8 cm at left supraclavicular fossa and nodules of about 1.4 cm × 1.1 cm at right and root segment of neck disappeared; metastatic lesions on sternum disappeared; and metastatic lesions at right sternoclavicular joints, ribs and pelvis shrank and relieved to some extent.) |
| Survival: | After 10 months (from September 27, Year 1 to July Year 2), the patient remained alive and had a normal life. Further, his condition was stable. |
| Diagnostic imaging before administration of rSIFN-co: | Diagnostic imaging after administration of rSIFN-co: |
| Chest CT scans on September 21, Year 1 (see primary lesions indicated by arrows in FIG. 12A): | CT scans on November 15, Year 1: |
| A blocky shadow (9 × 3.5 cm) of high density was found around left mediastinum and CT value was 39 Hu. The boundaries between this shadow and part of great vessels in mediastinum superius, left hilum and left posterior pleura were obscure. Patchy shadow of inflammatory exudation with high density could be seen in lung. Enlarged lymph nodes were found in mediastinum. A few patchy shadows with high density were seen inhomogeneous in upper segment of right lung, boundaries of which were clear. Arched effusions were found on left posterior side. | Shadows of soft tissues of about 3.6 × 4.2 cm were found; sheet-like density shadows were scattered and had obscure boundaries; no enlarged lymph nodes were seen in the mediastinum (the original ones disappeared). CT scans on December 12, Year 1 (see original locations of lesions indicated by arrows in FIG. 12B): Sheet-like and single-sheet-like shadows with increased density were scattered in both lungs. The boundaries were obscure and two hila were not larger. The tracheas were clear and no enlarged lymph nodes were seen in the mediastinum. Pneumonia of both lungs might happen. |
| Diagnosis conclusion: lung cancer in left mediastinum combined with pleural effusion and obstructive pneumonia; multiple patchy shadows were present in hilum, suggesting the possible occurrence of metastases. | Bone scans on December 6, Year 1: Multiple spot-like, mass-like and sheet-like shadows with abnormal radioactive concentration could be seen in right sternoclavicular joints, ribs, spinal column and pelvis. Radioactive distributions in other parts were basically uniform and symmetrical. |
| Color Doppler ultrasound on September 30, Year 1: | Diagnosis conclusion: systemic bone metastases shrank in size and were relieved to some extent than before. |
| Multiple hypoechoic nodules were at left segment of neck, which had clear boundaries and had no hilum of lymph nodes. The big hypoechoic nodule was 1.0 cm × 0.7 cm in size. One hypoechoic nodule of about 1.2 cm × 0.8 cm was at left supraclavicular fossa. It had clear boundary but had no hilum of lymph node. One hypoechoic nodule of about 1.4 cm × 1.1 cm was at root segment of neck on the right side. It had clear boundary but had no hilum of lymph node. | PET/CT scans on December 29, Year 1: A nodule with diameter of about 8 mm was observed at the apex of left lung and radioactive distribution was slightly increased. Patchy shadows with slightly higher (than normal) density and fabric lesions were found in surrounding area of lung and the radioactive distribution was slight increased. Scattered, patchy shadows with slightly higher density were found in both lungs and the radioactive distribution was not obviously abnormal. |
| Diagnosis conclusion: hypoechoic nodules were found at left segment of neck, left supraclavicular fossa and root segment of neck on the right side. | Conclusion: 1. After treatment, no obvious increase of FDG metabolism was found on at lesions of the apex of left lung, suggesting the inactivation of most tumor cells; 2. Asymmetric hyperosteogeny was found in whole body and FDG metabolism in some lesions was inhomogeneous with a few increased. |
| Bone scans on September 29, Year 1: Multiple lesions with radioactive concentrations were found in spinal column, bilateral ribs, right-sided sternoclavicular joints, sternum, left-sided sacroiliac joints and left-sided ilium. Conclusion: Systemic bone lesions with radioactive concentration were found, suggesting the possible occurrence of systemic bone metastases. | |
| Description of FIGS. 12A-12B: | After treatment of 2 months, lesions in the left lung disappeared. |

Patient 7. Non-Small-Cell Lung Cancer with Metastases in Both Lungs, Both Livers and Bones of Whole Body/ Intramuscular Injection and Aerosol Inhalation of rSIFN-co Combined with Administration of Gefinitib (Iressa). After Treatment, Metastases Disappeared or Shrank in Lungs and Several Bones, and Metastatic Lesions of Lymph Nodes Disappeared in Liver and Mediastinum.

Figure 13A:
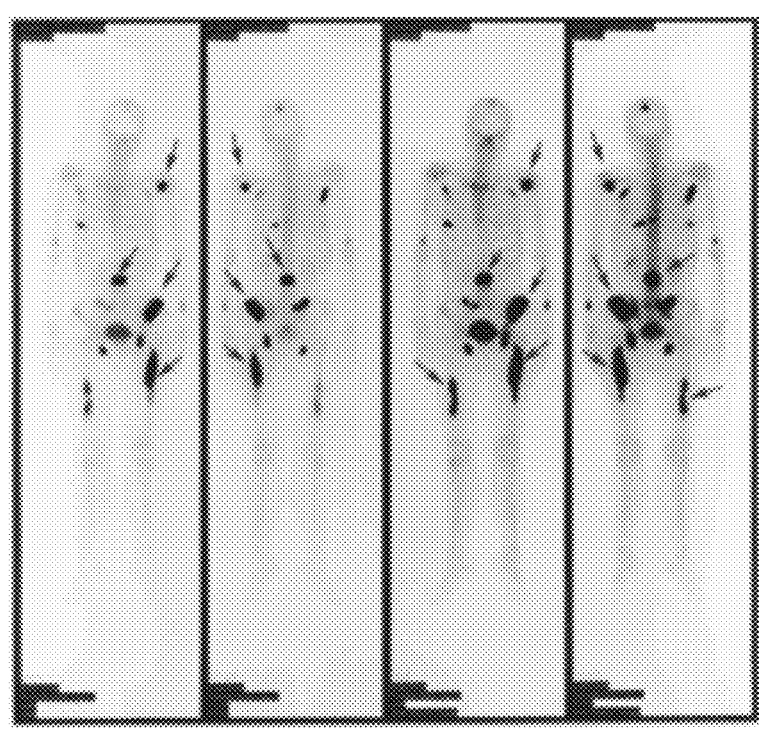
Figure 13B:
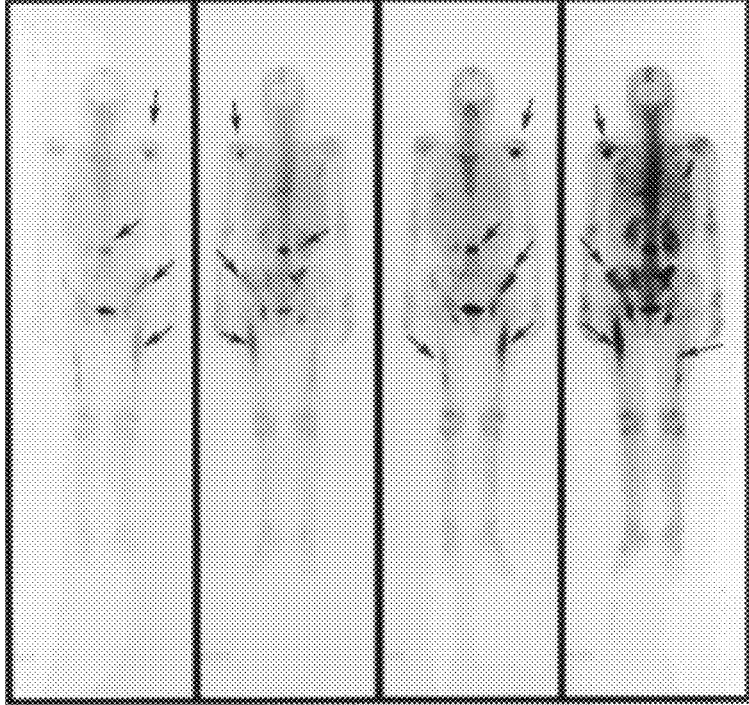
Figure 14A:
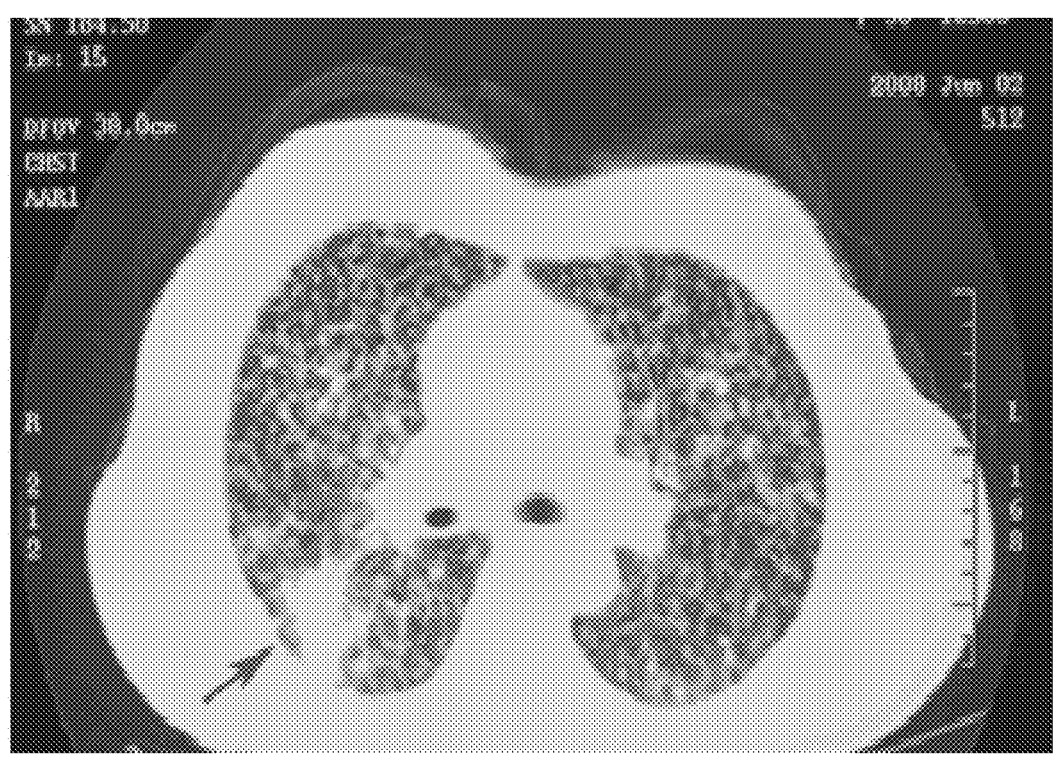
Figure 14B:
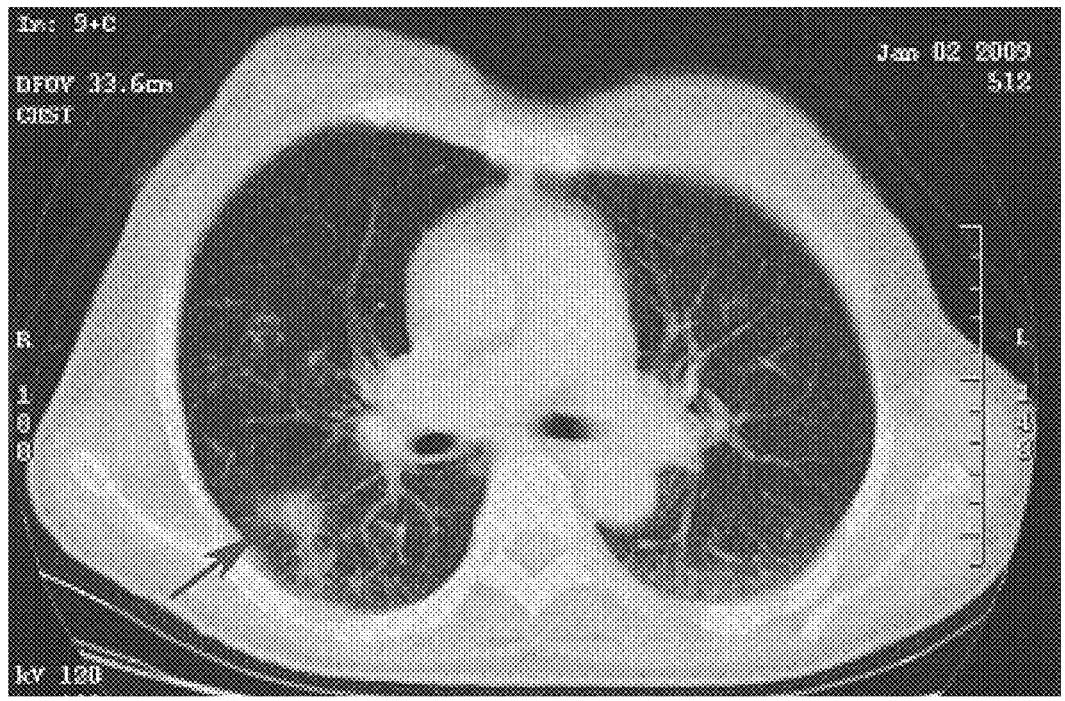

| Patient 7 | Gender: Female | Age: 53 |
|---|---|---|
| Pathological diagnosis: | metastatic adenocarcinoma (lymph nodes at left clavicle) | |
| Clinical and pathological staging[1]: | $T_4N_3M_1$. IV | |
| Regimens before administration of rSIFN-co: | None | |
| Regimens: administration of rSIFN-co combined with administration of other biological agents | Treatment with rSIFN-co began on July 31, Year 1. Intramuscular injection was done once every other day: 9 µg for $1^{st}$ time, 18 µg for 2nd time and 21 µg for $3^{rd}$ time and thereafter. Seventy-five times of intramuscular injection were done till January 2, Year 2 (totally 5 months). Meanwhile, Iressa (Gefinitib)[10] produced in India was administered in combination for 1 year: 1 pill/dose (250 mg/pill), 1 dose/day. | |
| Response to rSIFN-co treatment: | PR[2] (primary lesions in right lung and metastatic lesions in both lungs and several bones shrank with radioactive concentration decreased; metastasis in liver disappeared.) | |
| Survival: | About 28 months (From June 9, Year 1 to October 15, Year 3) | |
| Diagnostic imaging before administration of rSIFN-co: CT scans on June 26, Year 1: 1. Sheet-like lesions with radioactive concentration could be found in the upper lobe of right lung and multiple lesions at nodules were found in both lungs; shadows with radioactive concentration could be found in liver and lumbar, suggesting the happening of metastases. 2. Bone scans all over the body showed metastatic lesions were widely spread (parietal bone, left shoulder joint, both shoulder blades and bilateral ribs) (See lesions indicated by arrows in FIG. 13A). CT imaging on July 2, Year 1: see lesions indicated by arrows in FIG. 14A. | Diagnostic imaging after administration of rSIFN-co: CT scans on October 22, Year 1 (See original locations for lesions indicated by arrows in FIG. 13B): 1. Lung cancer with metastases in two lungs and liver (recovered compared with previous CT scan); 2. Bone scans showed that metastatic lesions were widely spread in bones all over the body (slightly recovered compared with previous CT scan). CT scans on January 2, Year 2 (see original locations of lesions indicated by arrows in FIG. 14B): 1. The disease was diagnosed as lung cancer in July. Specifically, patchy nodular lesions in the lower lobe of right lung and circumjacent spot-like shadows with high density were seen. Condition was improved as compared with previous CT scans. 2. The size and shape of liver were normal. Density of liver is even and no focal density abnormality was found. CT scans on March 3, Year 2: Compared with the imaging on October 22, Year 1, no new lesion was found and partial sclerotin radiation was reduced. Multiple bone metastases existed with lung cancer, but improved after treatment. | |
| Description of FIGS. 13A-13B: | After treatment, systemic metastatic lesions at bones partially disappeared or shrank. | |
| Description of FIGS. 14A-14B: | After treatment, metastatic lesions in both lungs disappeared and lesions in right lung evidently shrank. | |

Patient 8. Non-Small-Cell Lung Cancer with Bone Metastases/Intramuscular Injection and Aerosol Inhalation of rSIFN-co Combined with Administration of Gefinitib (Iressa). After Treatment, the Metastatic Lesions in the Lungs Disappeared and the Primary Lesions in Right Lung Shrank Evidently.

| Patient 8 | Gender: Female | Age: 68 |
|---|---|---|
| Clinical and pathological staging[1]: | $T_4N_2M_1$. IV | |
| Regimens before administration of rSIFN-co: | None | |

-continued

Figure 15A:
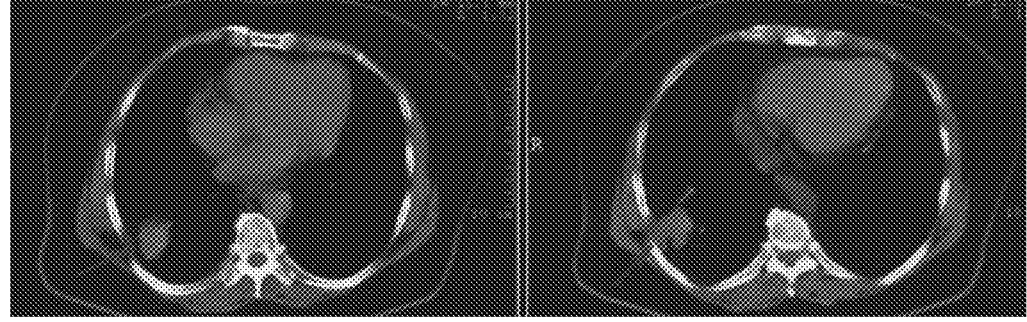
Figure 15B:
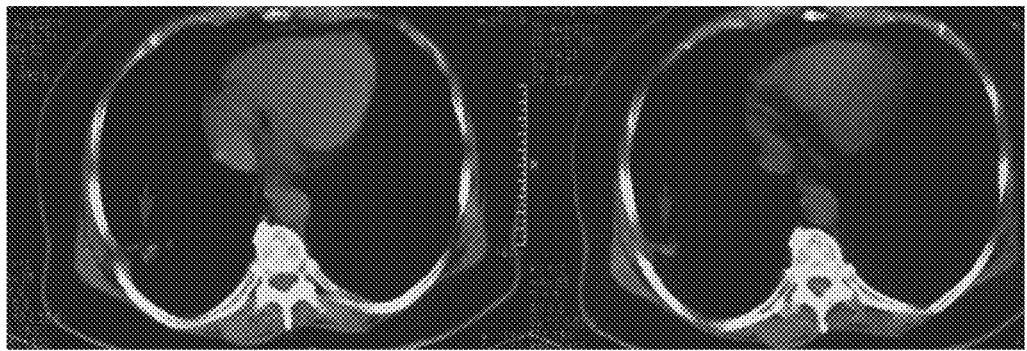
Figure 16A:
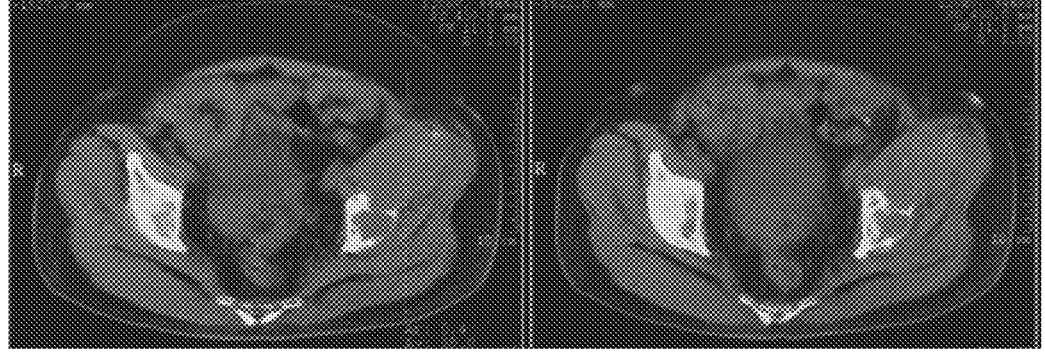
Figure 16B:
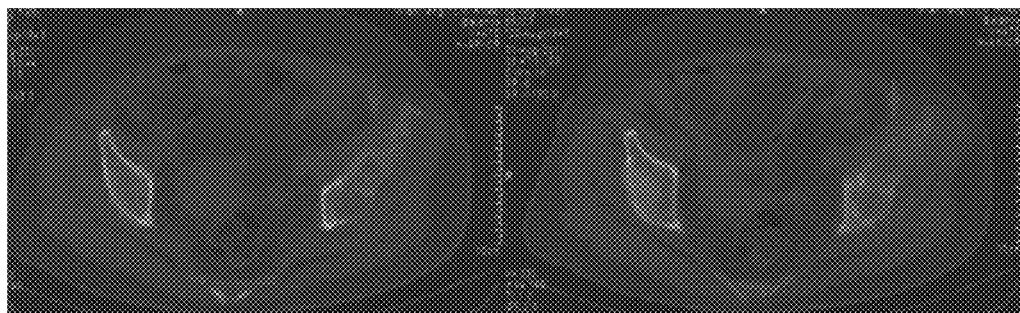

| Regimens: administration of rSIFN-co combined with other biological therapies | Treatment with rSIFN-co began on July 21, Year 1 Intramuscular injection was done once every other day: 9 μg for 1st time, 15 μg for 2nd time and 18 μg for 3rd time and thereafter. Meanwhile, aerosol inhalation of rSIFN-co of 600 μg was performed once a day. Administration of rSIFN-co continued for 3 months till October 31, Year 1. Administration of Gefinitib (Iressa) ® was added in July Year 1: 250 mg/pill, 1 pill/dose, 1 dose/day. |
| Response to rSIFN-co treatment: | CR② (lesions of about 3.0 × 3.9 cm at the lower lobe of right lung, and metastatic lesions in left ilium disappeared basically.) |
| Survival: | After about 12 months (from June 15, Year 1 to July Year 2), the patient remained alive and had stable conditions. |
| Diagnostic imaging before administration of rSIFN-co: | Diagnostic imaging after administration of rSIFN-co: |
| CT scans on July 17, Year 1 (see lesions indicated by arrows in FIG. 15A): The thorax was symmetrical. The lung markings increased and disorganized and transmittance of lung field was low. Spot-like and reticular density shadows were diffusely distributed in bilateral lungs. A density shadow of soft tissue mass (3.0 × 3.9 cm) was found in lower lobe of right lung. The shadow had obscure and irregular boundary and had burrs and spinous protuberance at the border. CT imaging on July 17, Year 1: See lesions shown in FIG. 16A. | CT scans on August 20, Year 1 (see original locations of lesions in FIG. 15B-16B): The lesions in the lower lobe of right lung and metastatic lesions in left Ilium were evidently absorbed and shrank after one-month therapy. CT scans on October 10, Year 1: Thorax was symmetrical and barrel shaped. The lung markings increased and disordered and transmittance of lung field was elevated. Lesions on the lower lobe of right lung were obviously absorbed and shrank, and spot-like calcified shadows were in the lesions; the diffusely distributed spot-like density shadows in both lungs were further absorbed and patchy calcified shadows were found in right hilum. Mediastinal lymph nodes were seen and calcified shadows of lymph nodes were found below carina. |
| Description of FIGS. 15A-15B: | After treatment, lesions in the lower lobe of right lung was evidently absorbed and shrunk. |
| Description of FIGS. 16A-16B: | After treatment, metastatic lesions in left ilium was evidently absorbed and shrunk. |

Patient 9. Non-Small-Cell Lung Squamous Cell Carcinoma/Aerosol Inhalation of rSIFN-co Combined with Chemotherapy (GP Regimen) and Administration of Recombinant Human Endostatin (Endostar). After Treatment, Masses of Soft Tissue at Hilum of Lower Lobe of Right Lung Evidently Shrank and Enlarged Lymph Nodes at Right Lung Hilum Disappeared.

| Patient 9 | Gender: Male | Age: 55 |
|---|---|---|
| Pathological diagnosis : | Squamous cell carcinoma | |
| Clinical and pathological staging①: | $T_2N_1M_0$. IIb | |
| Regimens before administration of rSIFN-co: | None | |
| Regimens: rSIFN-co combined with chemotherapy. | Treatment with rSIFN-co began on March 18, Year 1. Aerosol inhalation of rSIFN-co of 600 μg was performed once a day. A course completed till July 20, Year 1 (for 4 months) with 100 doses of aerosol inhalation done. Four cycles of chemotherapy (GP regimen⑨) were performed with the first one beginning at April 12, Year 1 and each cycle lasting for 21 days: 1600 mg of Gemcitabine on days 1 and 8 and 40 mg of Cisplatin on days 1 and 3. Meanwhile, 3 cycles of Endostar⑤ administration were performed with 14 days as one cycle: 7.5 mg/m² (1.2 × 10⁵ U/m²) per dose, 1 dose/day. Second cycle of chemotherapy began on May 10, Year 1 with the same regimen. Third cycle of chemotherapy began on June 7, Year 1 with the same regimen. Fourth cycle of chemotherapy began on July 7, Year 1 with the same regimen. Four cycles of chemotherapies were totally performed. | |

-continued

Figure 17A:
Figure 17B:
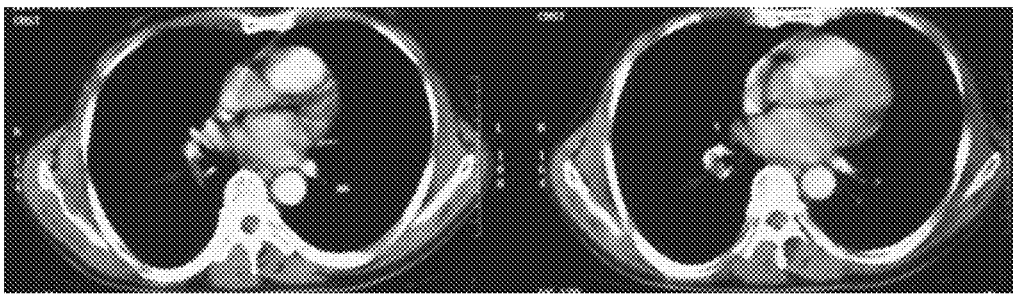

| Response to rSIFN-co treatment: | CR[2] (primary lesions of about 3.3 × 2.4 × 2.0 cm in right lung basically disappeared and enlarged lymph nodes in right hilum of about 2.0 × 2.2 cm disappeared.) |
| Survival: | After 16 months (from March 1, Year 1 to July Year 2), the patient remained alive and had normal life. His condition was stable. |
| Diagnostic imaging before administration of rSIFN-co: | Diagnostic imaging after administration of rSIFN-co: |
| CT scans on February 28, Year 1: see the size of lesions indicated by arrows in FIG. 17A. | CT scans on May 23, Year 1: 1. Irregular tissue shadows were seen in right hilum and masses shrank. Spot-like calcified lesions were at right hilum. |
| Chest PET/CT scans on March 18, Year 1: 1. Soft tissue nodules of about 3.3 × 2.4 × 2.0 cm with obscure boundary from neighboring hilum and extremely high radioactive uptake (SUVmax = 10.2) was observed at opening segment of bronchus on lower lobe of right lung. 2. Enlarged lymph nodes of about 2.0 × 2.2 cm was observed at right hilum with increased radioactive uptake (SUVmax = 6.6.) | 2. The enlarged lymph nodes at right hilum shrank. CT scans on July 18, Year 1 (see size of tumors indicated by arrows in FIG. 17B): Several density shadows of soft tissue could be found at the right lower hilum. Enhancement could be observed after enhancement scan. Spot-like calcified lesions could be found at right hilum; mediastinum was centered with no obvious shadows of enlarged lymph nodes |
| Description of FIGS. 17A-17B: | After treatment of 4 months, soft tissue masses at hilum of lower lobe of right lung evidently shrank. |

25

Patient 10. Non-Small-Cell Lung Cancer with Metastases in Lung and Pleura; Pleural Effusion/Intramuscular Injection of rSIFN-co Alone or Intrapleural Perfusion of rSIFN-co Alone. After Treatment, Primary Lesions on the Apical Segment of Upper Lobe of Left Lung were Cleared Up and 30 Metastatic Lesions on Lingual Segment of Left Lung Shrank.

| Patient 10 | Gender: Female | Age: 48 |
|---|---|---|

Figure 19A:
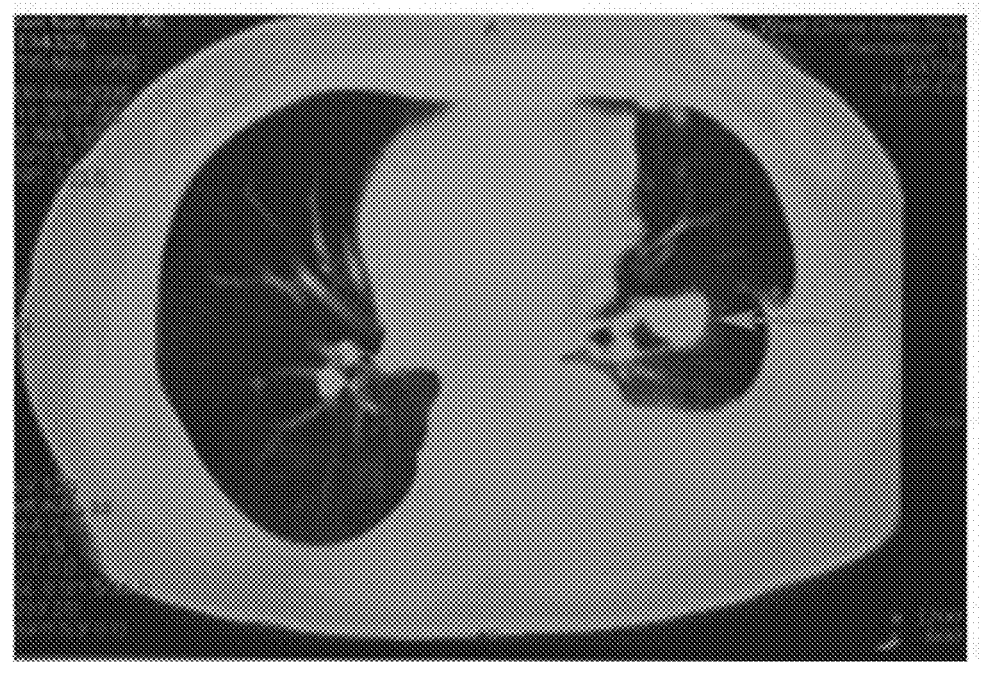
Figure 19B:
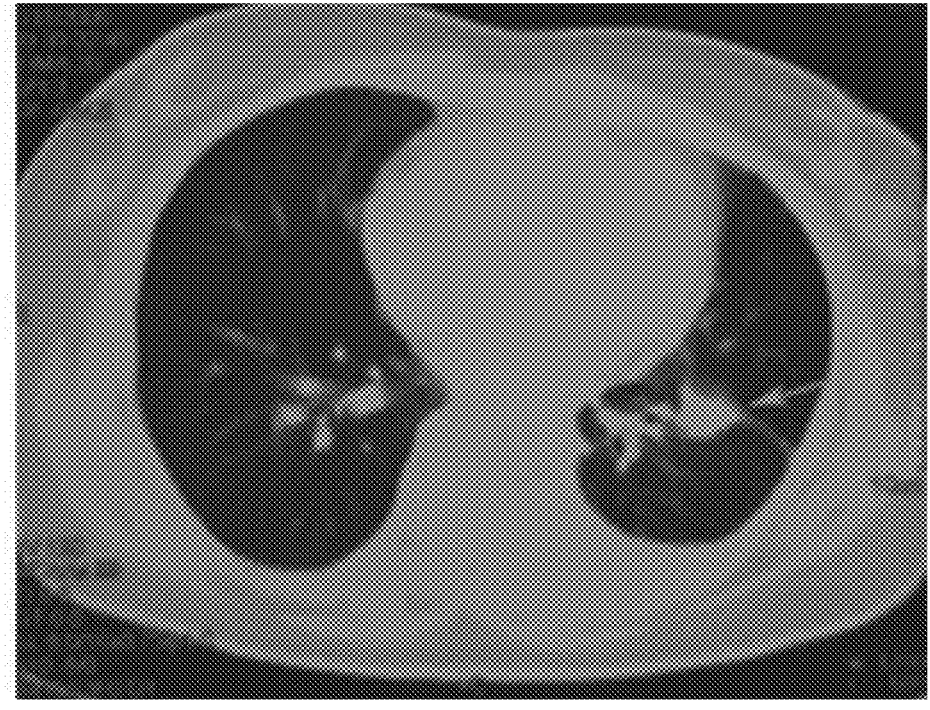

| Clinical and pathological staging[1]: | $T_4N_0M_0$. IIIb |
| Regimens before administration of rSIFN-co: | None |
| Regimens: administration of rSIFN-co alone | Treatment with rSIFN-co began on March 9, Year 1. Intramuscular injection of rSIFN-co was performed once every other day: 18 μg for 1st time, 21 μg for 2nd time and thereafter. Such administration continued for almost 1 year till March, Year 2. Intrapleural perfusion of rSIFN-co was done once every 8 days from April 29, Year 1: 9 μg × 4 vials for 1st and 2nd time and 9 μg × 5 vials for 3rd time. Three perfusions were provided totally. Four CT-guided interventional operations were performed in July and August Year 2. The rSIFN-co was injected into relatively large lesions in lungs and 21 μg × 10 vials were used each time. |
| Response to rSIFN-co treatment: | CR[2] (primary lesions of about 2.0 × 2.0 cm in left lung basically disappeared and malignant pleural effusion disappeared.) |
| Survival: | Patient died after about 19 months later due to renal and hepatic failure caused by traditional Chinese medicine (from February 22, Year 1 to October Year 2). |
| Cytological diagnosis before administration of rSIFN-co: | Cytological diagnosis after administration of rSIFN-co: |
| Pleural fluid smear (March 2, Year 1): poorly differentiated cancer cells were found. | Pleural fluid smear and cell mass (September 18, Year 1): Lymphocytes, neutrophils and necrotic materials were found, no tumor cells was found. |
| Diagnostic imaging before administration of rSIFN-co : | Diagnostic imaging after administration of rSIFN-co: |
| Chest CT scans on February 23, Year 1: 1. A mass of 2.0 × 2.0 cm was found at apical segment of the upper lobe of the left lung, suggesting the possible occurrence of lung cancer. | CT scans on August 1, Year 1 (see original locations of lesions indicated by arrows in FIG. 19B): 1. After treatment on left lung, small nodular shadows in the posterior segment of upper lobe of |

-continued

| | |
|---|---|
| 2. Multiple nodular lesions were seen in the upper lobe of left lung, indicating the possibility of metastases happening.<br>3. Pleural effusion was observed in left thoracic cavity.<br>CT imaging on March 6, Year 1:<br>See lesions indicated by arrows in FIG. 19A.<br>Description of FIG. 18:<br><br>Description of FIGS. 19A-19B: | left lung were completely absorbed and dissipated.<br>2. Nodular lesions in the lingual segment of left lung were absorbed and shrunken.<br>3. Left-sided pleural effusion was evidently reduced and streaky nodular lesions on the left pleura were evidently absorbed and relieved.<br><br>After treatment, pleural effusion was reduced evidently.<br>After treatment, lesions in left lung shrank obviously and pleural effusion was evidently reduced. |

Patient 11. Non-Hodgkin Lymphoma/Aerosol Inhalation (Though Nasopharynx and Oral Cavity) of rSIFN-co and Local Injection into Enlarged Lymph Nodes at Neck Combined with Radiotherapy. After Local Administration, Lesions in the Nasal Cavity, Oropharynx, Neck and Submaxillary Region Disappeared or Shrank.

Figure 20:
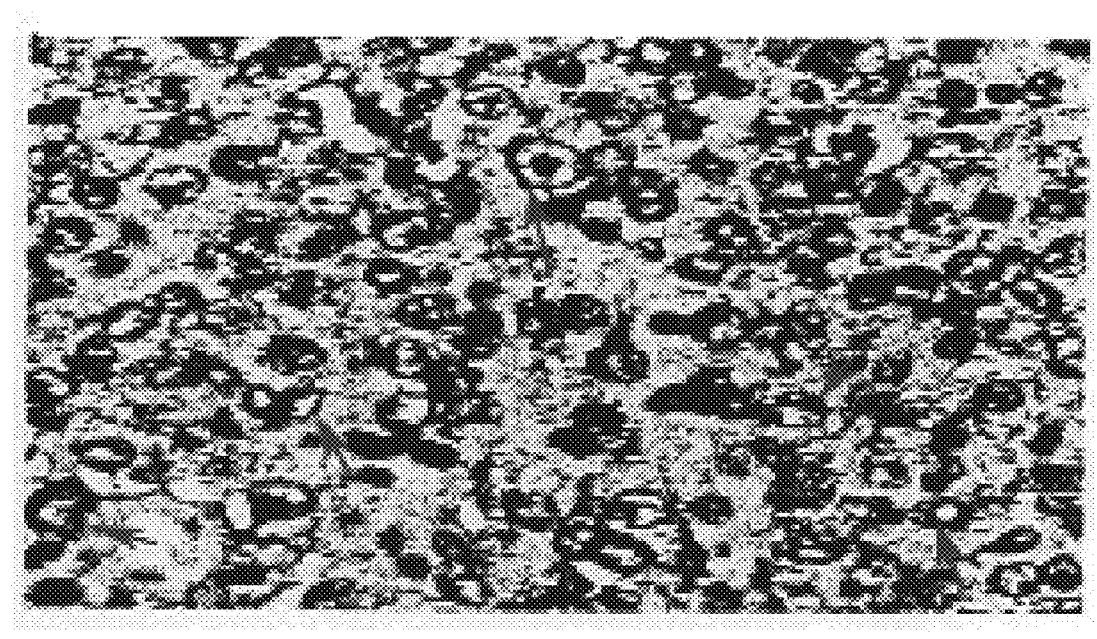

| Patient 11 | Gender: Male | Age: 40 |
|---|---|---|
| Pathological diagnosis: | Non-hodgkin lymphoma on mesenteric lymph nodes | |
| Clinical and pathological staging[1]: | IV | |
| Immunohistochemical examination: | Non-Hodgkin malignant lymphoma (B-cell-originated) (see tumor cells shown by arrows in FIG. 20) | |
| Regimens before administration of rSIFN-co: | Chemotherapy was performed for 7 times (five times of CHOPE regimen and two times of MTX regimen) began on August, Year 1.<br>Autologous stem cell transplantation was done in March Year 2.<br>Chemotherapy were provided for 4 times (1 time of GCE regimen and 3 times of ESAP regimen) began on August, Year 2. The forth one ended on November 26, Year 2.<br>Chemotherapy was administered 6 times (3 times of large-dosed CHOPE regimen, 2 times of CMOP regimen and 1 time of a regimen of "bleomycin + CHOP[11] + Methotrexate") began on January, Year 3, in combination with stem cell therapy. | |
| Regimens: rSIFN-co combined with chemotherapy and radiotherapy | Treatment with rSIFN-co began on June 9, Year 3. An aerosol preparation of rSIFN-co (72 µg/ml) was sprayed onto the nasopharynx and Oral Cavity 2~3 times every day. Administration continued till August 27, Year 3 with 5 days of suspension because of chemotherapy (see chemotherapy describebd below).<br>Local injections on lymph nodes in neck started on June 11, Year 3. Injection was performed every other day by injection at multiple sites in a quincunx: 15 µg × 10 vials per treatment. Two times later, local subcutaneous injection was performed every other day: 30 µg per treatment. Till August 27, Year 3 (more than 2 months), for a total of 10 times.<br>Four cycles of CHOP[11] chemotharepy were provided from July Year 3 to November 28, Year 3 with each cycle lasting for 21 days.<br>Radiotherapy began on June 11, Year 3 (scheduled for 25 times) and stopped on July 5, Year 3 as the patient was weak due to myelosuppression. | |
| Response to rSIFN-co treatment: | PR[2] (soft tissure around nasopharynx and oropharynx with the thickest part of 3.0 cm entirely disappeared, and the largest fused lymph node among those at submaxillary region, neck and clavicular region shrank from 7.4 cm × 2.4 cm × 14.6 cm to 1.1 cm × 1.5 cm.) | |
| Survival: | about 32 months (August 2, Year 1 to April 17, Year 4) | |

US 12,636,347 B2

149                                                                    150

-continued

Figure 21A:
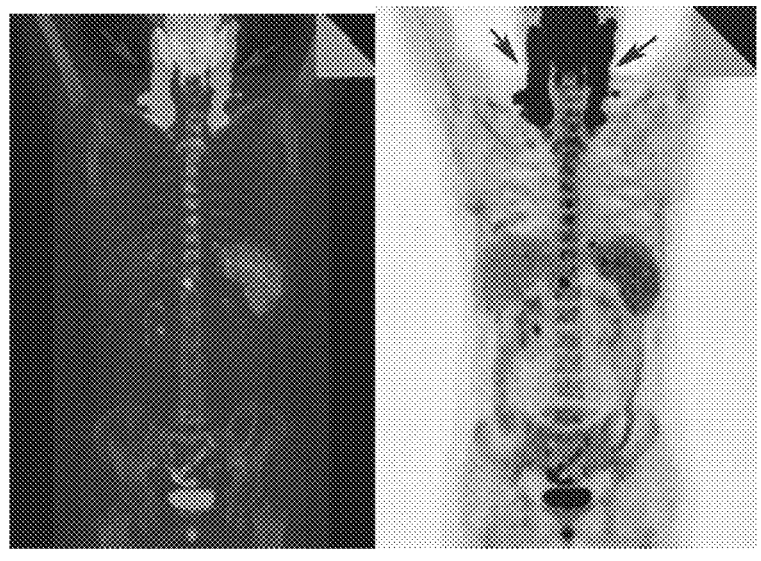
Figure 21B:
Figure 22A:
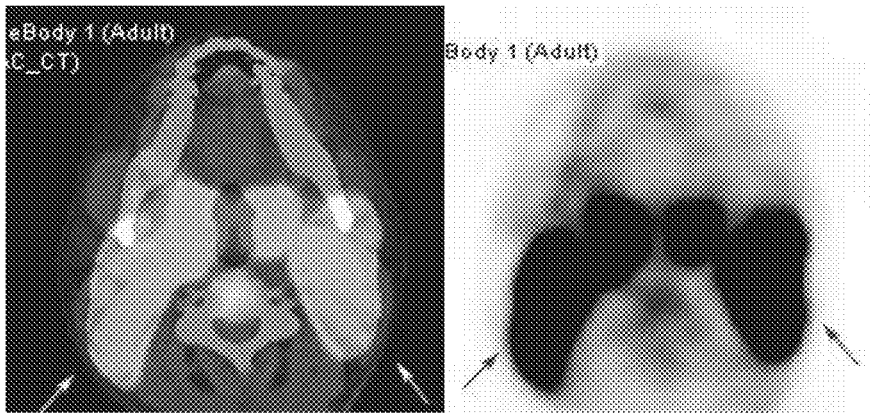
Figure 22B:
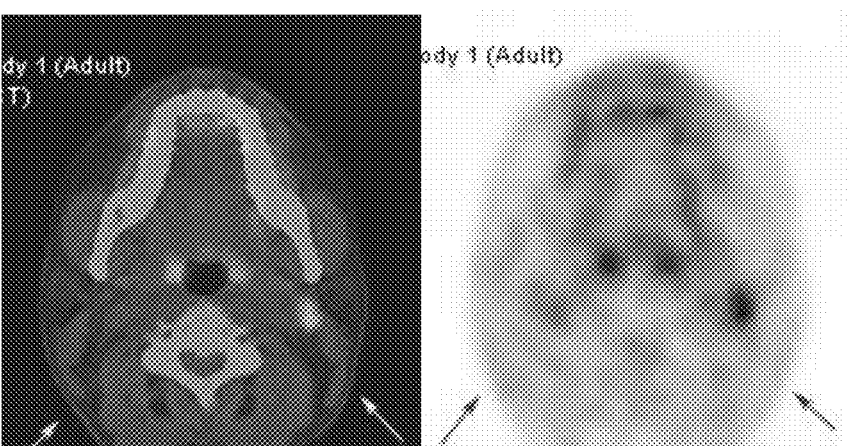
Figure 23A:
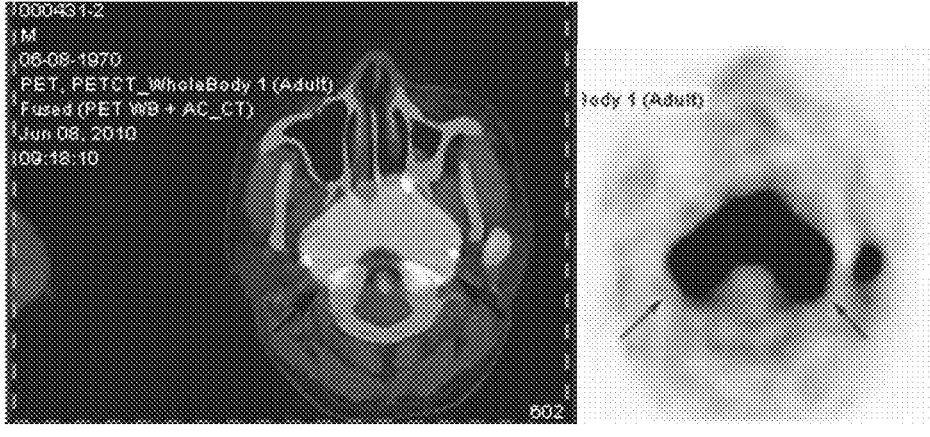
Figure 23B:
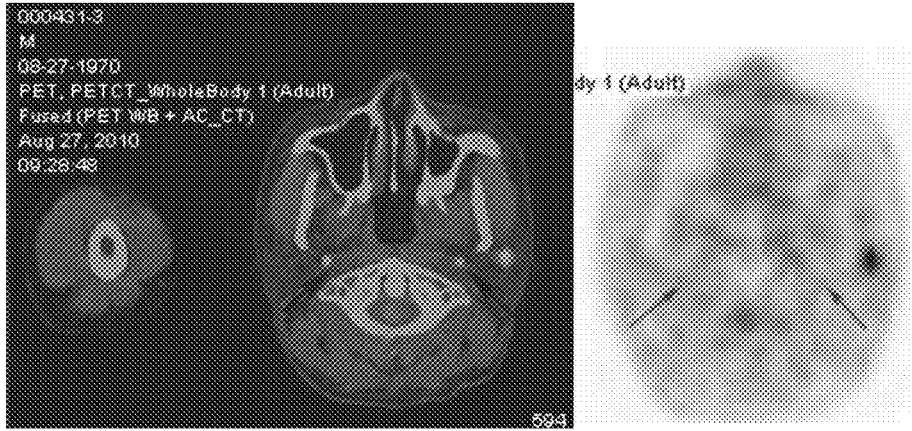

| Diagnostic imaging before administration of rSIFN-co: | Diagnostic imaging after administration of rSIFN-co: |
|---|---|
| PET/CT scans on July 8, Year 3 (see the lesions indicated by arrows in FIG. 21A-23A): | PET/CT scans on August 27, Year 3 (see original locations of lesions indicated by arrows in FIG. 21B-23B): |
| 1. Nasopharyngeal cavity and oropharyngeal cavity become significantly narrower; surrounding soft tissues were thickened with the thickest part of 3.0 cm; and choanae was blocked. | 1. The thickening of soft tissue at nasopharyngeal cavity and oropharyngeal cavity disappeared, and radioactive uptake was significantly reduced. |
| 2. A large number of lymph nodes were enlarged and fused at bilateral submaxillay, neck and supraclavicular and infraclavicular regions with the biggest of about 7.4 cm × 2.4 cm × 14.6 cm. | 2. The number, volume and radioactive uptake of enlarged fused lymph nodes at bilateral mandible, neck and supraclavicular and infraclavicular region reduced as compared to the previous examination. Only two slightly bigger lymph nodes of about 1.1 cm × 1.5 cm with elevated radioactive uptake were seen in the left submaxillay. |
| Description of FIGS. 21A-21B: | After treatment, a large number of primary enlarged lymph nodes at neck disappeared. |
| Description of FIGS. 22A-22B: | After treatment, primary lesions at bilateral mandible disappeared. |
| Description of FIGS. 23A-23B: | After treatment, primary lesions at pharyngeal disappeared. |

Patient 12. Non-Small-Cell Lung Cancer with Metastasis in Pleura/Intramuscular Injection of rSIFN-co. After Treatment, Lesions on Lower Lobe of Right Lung Evidently Shrank.

| Patient 12 | Gender: Male | Age: 67 |
|---|---|---|

Figure 24A:
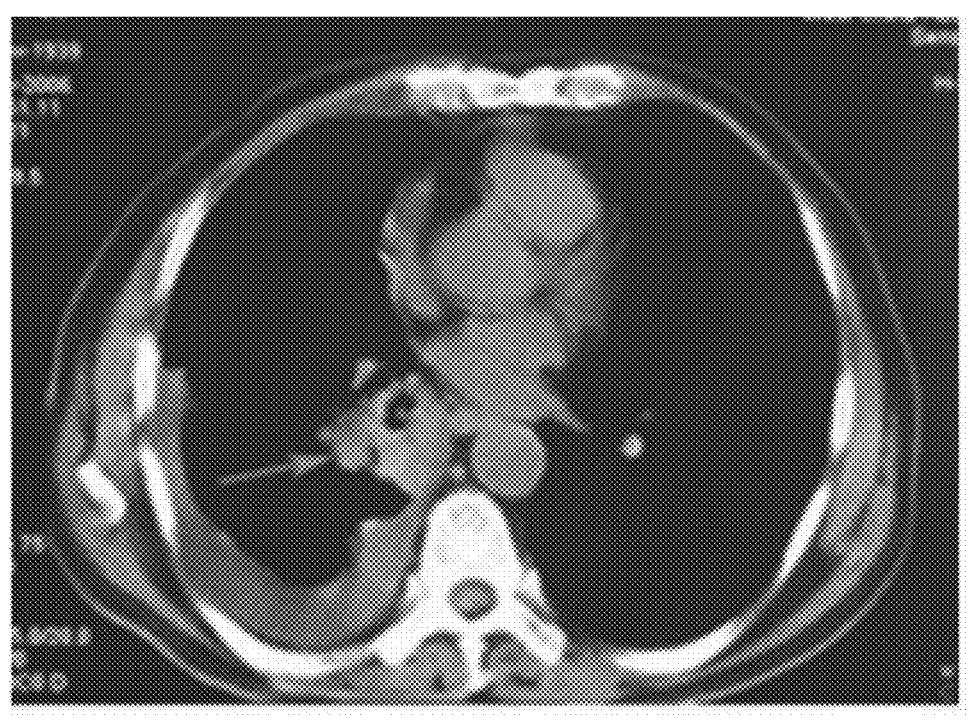
Figure 24B:
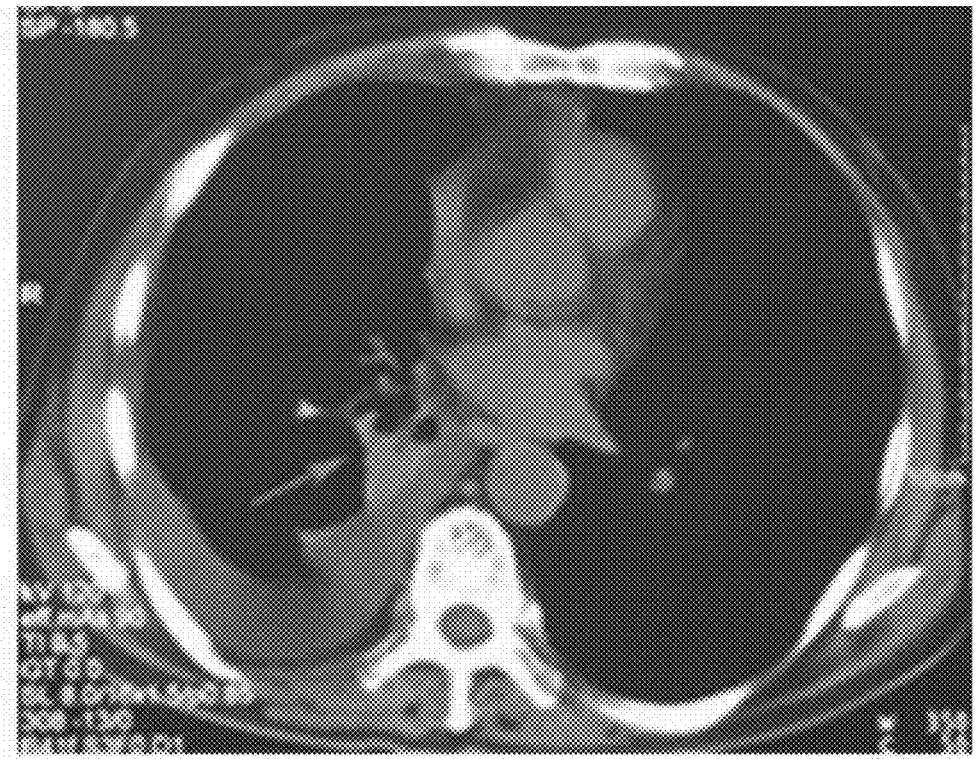

| Cytologic diagnosis: | Lung adenocarcinoma |
|---|---|
| Clinical and pathological staging[1]: | $T_3N_0M_0$. II b |
| Regimens before administration of rSIFN-co: | From August 16, Year 1, two cycles of GP regimen[9] were provided: 1000 mg/m² of Gemcitabine on day 1 and 8 and 75 mg/m² of Cisplatin on day 1. Intrathoracic injection of Cisplatin was also performed for 5 times. 1 dose every 7 days, 30-40 mg per dose. |
| Regimens: administration of rSIFN-co alone | Treatment with rSIFN-co began on November 10, Year 1. Intramuscular injection of rSIFN-co was provided once every two days: 9 µg for 1st time, 18 µg for 2nd time and 21 µg for 3rd time and thereafter. Administration lasted for almost 1 year till October 27, Year 2. |
| Response to rSIFN-co treatment: | PR[2](the mass reduced from about 3.1 × 4.2 cm to 2.2 × 1.5 cm after 2 months' treatment, and the lesion further reduced in size after administration for 3 months.) |
| Survival: | about 28 months (from Augugst 11, Year 1 to Year 4) |
| Diagnostic imaging before administration of rSIFN-co: | Diagnostic imaging after administration of rSIFN-co: |
| Chest CT scans on October 10, Year 1 after chemotherapy: | CT scans on January 10, Year 2: |
| A shadow of tumor mass of about 3.1 × 4.2 cm was found at opening segment of bronchus on lower lobe of right lung, probably to be central type lung cancer. Right-sided pneumothorax occurred. | The mass was about 2.2 × 1.5 cm on lower segment of right hilum which was significantly smaller than before. |
| Lung tissue was compressed by about 10% in size and not much pleural effusion were seen in right-sided thoracic cavity. | CT scans on February 12, Year 2 (see original locations of lesions indicated by arrows in FIG. 24B): After 3 months' treatment, the mass on lower segment of right hilum evidently shrank. |
| CT imaging on November 15, Year 1 when administration was newly conducted: | CT scans on October 23, Year 2: Masses were seen at dorsal segment of lower lobe of right lung. Not much effusion was in right thoracic cavity and right pleura was thicker. There was not much changes compared with the previous CT. |
| see lesions nidicated by arrows in FIG. 24A). | |
| Description of FIGS. 24A-24B: | After treatment of nearly 3 months', masses on lower segment of right hilum had significantly shrunk. |

Patient 13. Non-Small-Cell Lung Cancer, after Surgeries/ Intramuscular Injection of rSIFN-co Alone. After the Treatment, No Tumor Recurrence or Metastasis was Found in Right Lung and the Whole Body.

Figure 25A:
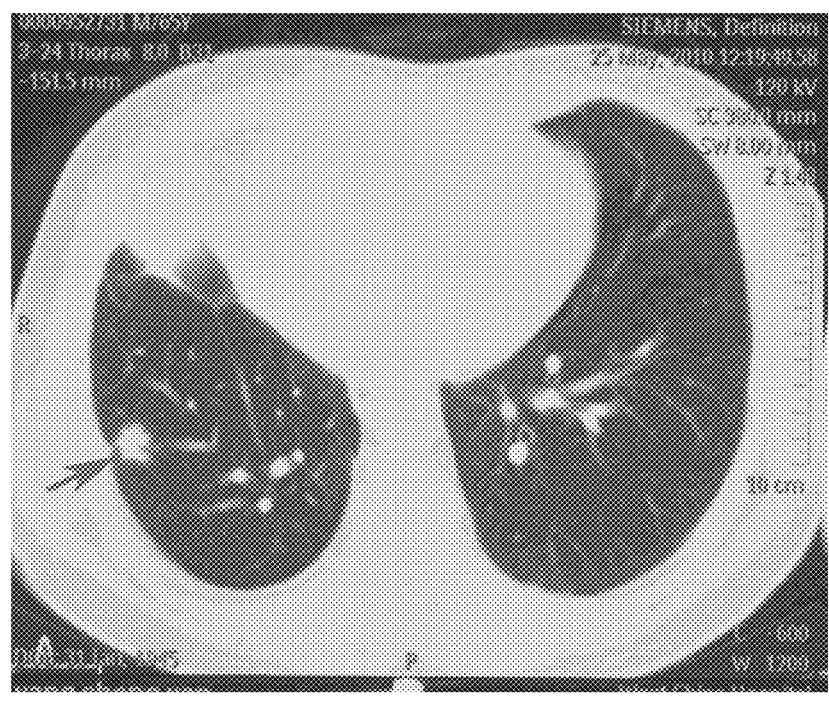
Figure 25B:
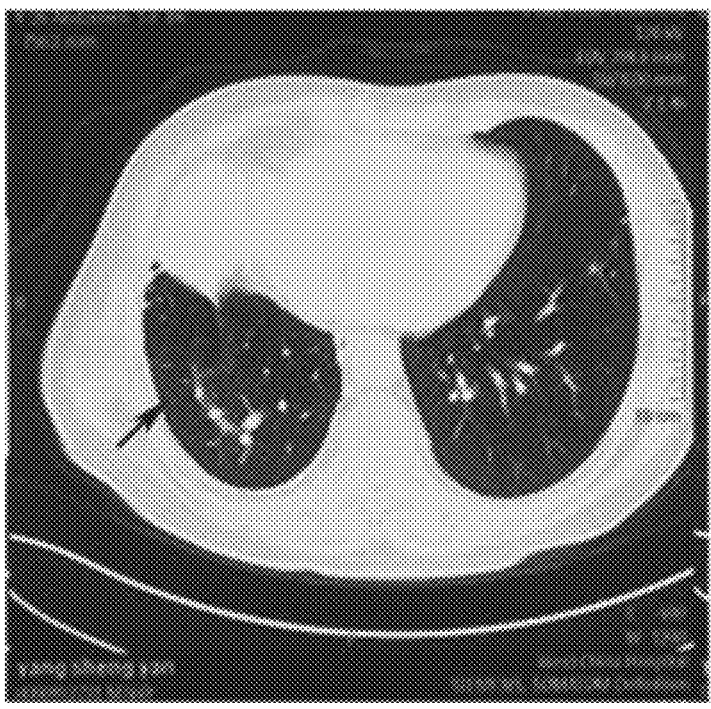

| Patient 13 | Gender: Male | Age: 63 |
|---|---|---|
| Pathological diagnosis: | poorly differentiated adenocarcinoma (upper lobe of right lung) | |
| Clinical and pathological staging[1]: | $T_4N_2M_0$. IIIb | |
| Regimens before administration of rSIFN-co: | On October 15, Year 1, resection of upper lobe of right lung and lymph node dissection were done as well as wedge resection of nodules on lower lobe of right lung. | |
| Postoperative pathology report: | Poorly differentiated adenocarcinoma occured on upper lobe of right lung; the tumor was 4.5 × 4.5 × 4 cm in size and grew to regions below visceral pleura. Poorly differentiated adenocarcinoma was found in two suture zones on nodules of dorsal and lower segment of lungs with diameters of 0.8 cm and 1.2 cm. (lymph nodes): metastasis was found in: "Group 2" (1/8), group 4 (2/4), and Group 10 (1/2). | |
| Regimens: treatment with rSIFN-co alone | Treatment with rSIFN-co began on December 10, Year 1. Intramuscular injection of rSIFN-co was provided once every other days: 9 µg for 1st time, 21 µg for 2nd time and thereafter). The first course was finished on April 9, Year 2. The second course was performed from December Year 2 to July Year 3 during which intramuscular injection was done every other day with 21 µg per dose. The third course was performed from February 21, Year 4 to May 21, Year 4 during which intramuscular injection was done every other day with 18 µg per dose. | |
| Response to rSIFN-co: | CR[2] (After surgery on primary lesions, no tumor recurrence or metastasis occurred.) | |
| Survival: | After 45 months (from September 13, Year 1 to July Year 5), the patient remained alive and had normal life. No recurrence or metastases was observed on imaging test. | |
| Diagnostic imaging before administration of rSIFN-co: | Diagnostic imaging after administration of rSIFN-co: CT scans on May 25, Year 3: see the suspicious lesion at lower lobe of right lung indicated by arrows in FIG. 25A. Chest CT scans on February 11, Year 4: 1. After surgery on the lung cance in upper lobe of right lung, no recurrence signs were found in bronchial stump. 2. Compared with previous CT, no significant change was found in the irregular nodular shadow of 1.6 cm on lateral basal segment of lower lobe of right lung. Chest CT scans on January 2, Year 5 (see original location of the suspicious lesion at lower lobe of right lung indicated by arrow in FIG. 25B): 1. After surgery on lung cancer of upper lobe of right lung: no recurrence signs were found in bronchial stump compared to CT scans on February 11, Year 4; nodules in lateral basal segment of the lower lobe of right lung was not found. 2. Inflammatory lesions were scattered in residue of right lung; the right-sided pleura was slightly thickened. | |
| Description of FIGS. 25A-25B: | After treatment, the space occupying at lower lobe of right lung disappeared and no tumor recurrence or metastasis was found. | |

Patient 14. Non-Small-Cell Lung Adenocarcinoma, after Surgery/Intramuscular Injection of rSIFN-co Alone. After the Treatment, No Tumor Recurrence and Metastasis was Found.

Figure 26A:
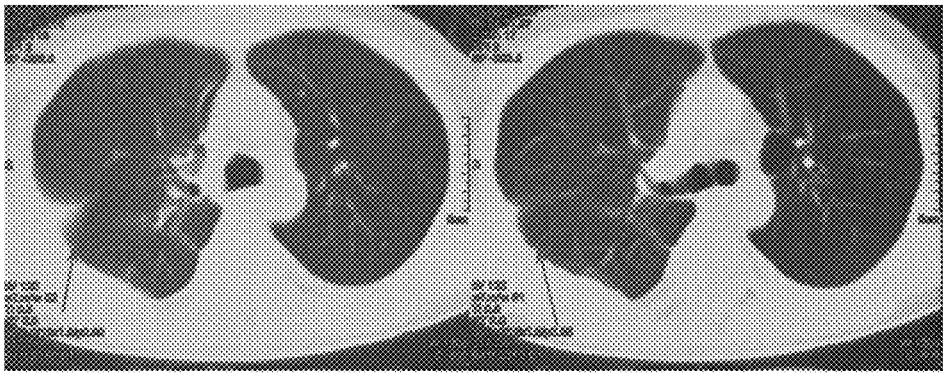
Figure 26B:
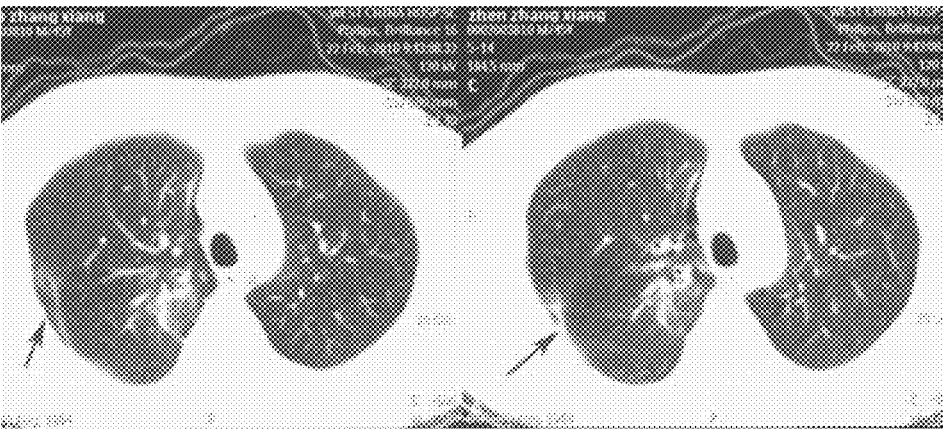

| Patient 14 | Gender: Male | Age: 44 |
| --- | --- | --- |
| Pathological diagnosis: | Poorly differentiated adenocarcinoma | |
| Clinical and pathological staging[1]: | $T_4N_3M_0$, IIIb | |
| Regimens before administration of rSIFN-co: | Upper lobe of right lung was resected on October 20, Year 1. | |
| Postoperative pathology report: | Examination on October 27, Year 1: (masses at upper lobe of the right lung) part of lung tissue was resected. Alveolar epithelium hyperplasia and chronic inflammatory cell infiltration were observed under microscope. Fibroplasia happened at the side of pleura with collagenization. Focal hemorrhage and necrosis were also observed while poorly differentiated adenocarcinoma was found. Immunohistochemistry of the cancer tissue showed CK7(+), P63(−)and TTF1(−). | |
| Regimens: administration of rSIFN-co alone | Treatment of rSIFN-co began on November 6, Year 1. Intramuscular injection of rSIFN-co was administered once every other day: 18 µg for 1st time, 21 µg for 2nd time and thereafter. A first course of 6 months ended on May 10, Year 2. The second course started on March 18, Year 3 and continued for the next following 3 months. Intramuscular injection of rSIFN-co was provided every other day with 15 µg per dose. Intramuscular injection of rSIFN-co and Aerosol inhalation were administered for 3 months from November Year 4. Intramuscular injection was done once every other day with 15 µg per dose. Aerosol inhalation was performed every day and a total of 300 µg was used for one day. | |
| Response to rSIFN-co treatment: | CR[2] (after surgery, no tumor recurrence or metastasis was found at primary lesions.) | |
| Survival: | After about 44 months (from October 14, Year 1 to July Year 5), the patient remained alive and had a normal life. No initial recurrence or metastases was observed upon imaging. | |
| Diagnostic imaging before administration of rSIFN-co: | Diagnostic imaging after administration of rSIFN-co: | |
| Chest CT scans on October 13, Year 1: Peripheral lung cancer was found in posterior segment of right upper lobe; the tumor of about 4.0 × 2.9 cm in size grew into posterosuperior segment of right-sided pleura and implantation metastasis happened at right-sided pleura; not much pleural effusion occurred in thoracic cavity. CT scans on November 13, Year 1, when drug use was just started (after surgery): See the surgical site of primary lesion indicated by arrows in FIG. 26A | CT scans on February 22, Year 3 (see the original surgical site indicated by arrow in FIG. 26b): High-density stripe-like shadows were found in residual part of upper lobe of right lung and local bronchiectasia happened, which were mainly postoperative changes. No significant change was found in lesions as compared with previous CT. | |
| Description of FIGS. 26A-26B: | After treatment, no tumor recurrence and metastasis was found in residual end of right lung and the neighering regions. | |

Patient 15. Non-Small-Cell Lung Cancer with Systemic Metastases, Local Injection of rSIFN-co into Enlarged Lymph Nodes in Groin. After Local Injections, Metastatic Lesions in the Lymph Nodes in Pelvic Cavity and Inguinal Area were Cleared Up or Shrank.

| Patient 15 | Gender: Male | Age: 68 |
| --- | --- | --- |
| Pathological diagnosis: | none | |
| Clinical and pathological staging[1]: | $T_4N_3M_1$. IV | |
| Regimens before administration of rSIFN-co: | Treatment with Gamma Knife was done under local anesthesia on April 27, Year 3. | |

-continued

Figure 27A:
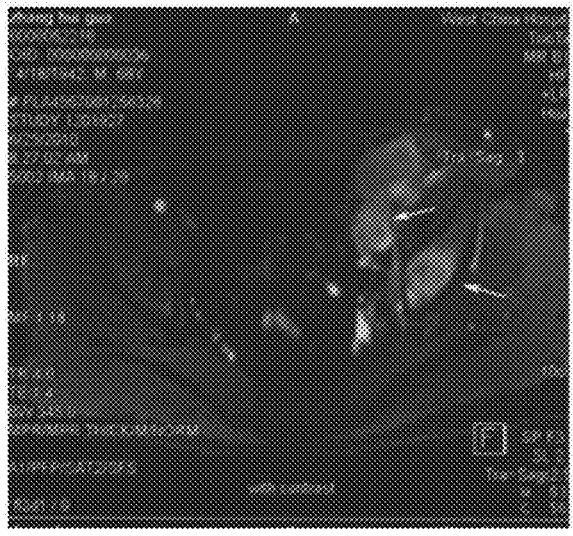
Figure 27B:
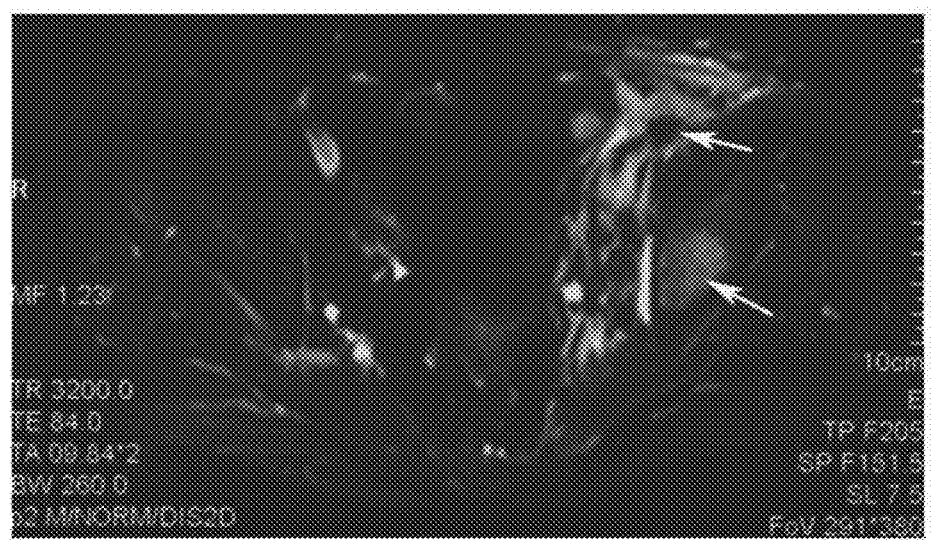

| | |
|---|---|
| | Sr-89 therapy was done by Nuclear Medicine Department on April 30, Year 3. Oral administration of Gefitinib (Iressa) was provided from December Year 1 to June Year 3: 1 dose/day, 1 pill/dose, 250 mg/pill. |
| Regimens: administration of rSIFN-co alone | Treatment of rSIFN-co began on June 25, Year 3. The rSIFN-co was injected into lymph nodes of groin Intramuscularly every day: 15 μg × 6 vials for 1st time, 15 μg × 8 vials for 2nd time and 15 μg × 10 vials for 3rd time and thereafter. Eleven injections were done till July 20, Year 3 (Severe diarrhea occurred after 3 injections and administration was stopped for 2 weeks; after that injection was performed every day and 8 injections in total were continuasly provided). Discontinuous local injection in lymph nodes were performed for 6 times from August 18, Year 3 toSeptember 16, Year 3: 15 μg × 10 vials for each time. Local injection in lymph nodes were performed every 3 days from October 8, Year 3 to October 12, Year 3: 15 μg × 10 vials for each time. |
| Response to rSIFN-co treatment: | PR② (mass of about 11.3 × 4.9 cm in pelvic cavity reduced in size to 7.52 × 7.67 × 6.72 cm). |
| Survival: | about 24 months (from December Year 1 to December 13, Year 3) |
| Diagnostic imaging before administration of rSIFN-co: MRI of pelvic cavity on June 6, Year 3 (see lesions indicated by arrows in FIG. 27A): Bone distruction was found at left ilium, sacroiliac joint, left-sided corpora ossis pubis, superior ramus of pubis and femoral head with slightly longer T1 and slightly longer T2 signal. The left gluteus minimus, obturator internus and obturator externus, musculus adductor magnus and longus, and rectus femoris were involved and the fascia was obviously swollen. Irregular mass of about 11.3 cm × 4.9 cm with slightly longer T2 signal were seen at acetabular plane in left pelvis which was slightly enhanced after reinforcement. | Diagnostic imaging after administration of rSIFN-co: MRI of pelvic cavity on July 28, Year 3 (see original locations of lesions indicated by arrows in FIG. 27B): Bone destruction at left pubis was replaced by shadow of soft tissue with long T2 signal and fused into block with the swollen soft tissue of pelvic wall within a range of 7.52 cm × 7.67 cm × 6.72 cm. Left acetabulum, ala of ilium, obturator internus and obturator externus, vastus medialis and soft tissue in groin were involved. |
| Description of FIGS. 27A-27B: | After 1 month's treatment, the enlarged lymph nodes in pelvis and groin disappeared or shrank. |

Patient 16. Rectal Cancer, after a Surgery/Intramuscular Injection of rSIFN-co Alone. After the Treatment, No Tumor Recurrence or Metastasis was Found.

Figure 28:
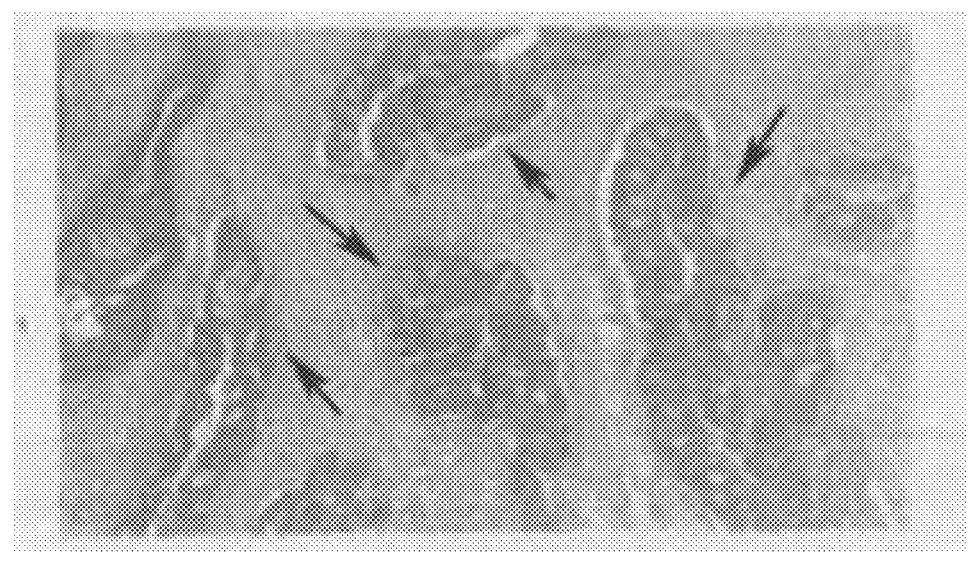
FIG. 28 shows a pathological diagnosis of patient 16, and an arrow shows adenocarcinoma cells.
Figure 28:

| Patient 16 | Gender: Female | Age: 63 |
|---|---|---|
| Pathological diagnosis: | Well to moderately differentiated adenocarcinoma was found in rectum and mucinous adenocarcinoma was found in part of rectum. Cancer invaded into deep muscularis of intestinal wall and formed cancerous nodules in mesorectum (see the cancer cells indicated by arrows in FIG. 28) | |
| Clinical and pathological staging①: | $T_4N_1M_x$. IIIb | |
| Regimens before administration of rSIFN-co: | Laparoscopic-assisted abdominal perineal radical resection of rectal cancer was done on May 16, Year 1. | |
| Regimens: administration of rSIFN-co alone | Treatment of rSIFN-co began on May 23, Year 1. Intramuscular injection of rSIFN-co was provided once every other day: 21 μg for each time. The first course of 8 months ended on February Year 2. The second course was provided from January Year 3 to April Year 3. Intramuscular injection of rSIFN-co was provided once every other day with 9 μg each time and continued for 3 months. | |

-continued

Figure 29A:
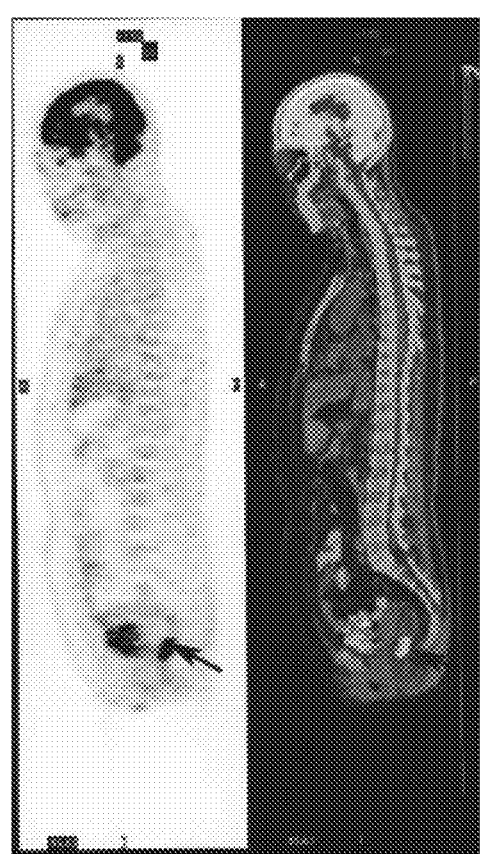
Figure 29B:
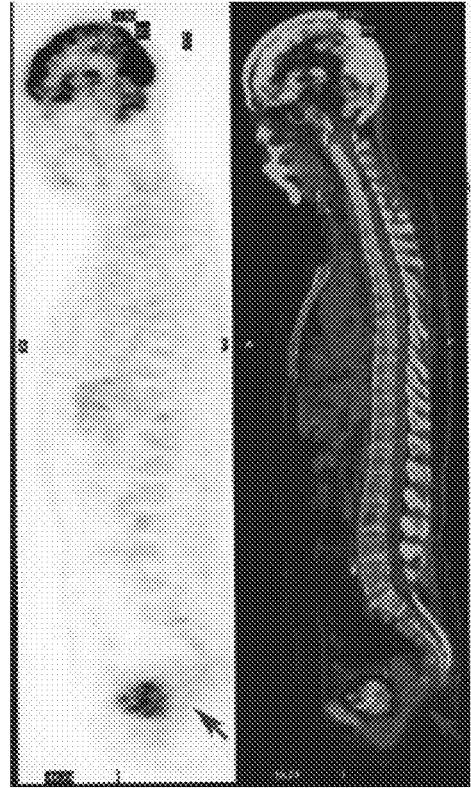

| | |
|---|---|
| | The third course was administered from December Year 3 to March Year 4. Intramuscular injection was performed every other day with 15 µg each time. |
| Response to rSIFN-co treatment: | CR② (after surgery, no tumor recurrence or metastasis occurred at primary lesions.) |
| Survival: | After about 49 months (from May Year 1 to July Year 5), the patient remained alive. No recurrence or metastases was observed upon imaging. |
| Diagnostic imaging before administration of rSIFN-co: | Diagnostic imaging after administration of rSIFN-co: |
| PET/CT scans on April 30, Year 1 (see primary lesions indicated by arrows in FIG. 29A): | PET/CT scans on June 17, Year 3 (see the original location of lesions indicated by arrows in FIG. 29B): |
| 1. Mass with high metabolic rate was seen in rectum combined with intestinal wall thickened, suggesting the posibility of malignant tumor happening (rectal cancer or lymphoma). | No signs were found on recurrence of primary lesions or systemic metastases. PET/CT scans on March 3, Year 4: |
| 2. A nodular lesion of high metabolic rate was found beside the left-sided external iliac vessels in pelvic cavity, suggesting the possible occurrence of lymphatic metastasis. No signs of malignant tumor were found in pelvic cavity, other parts and retroperitoneum. | 1. After surgery on rectal cancer, no signs of malignant tumor were found in colorectum and the artificial fistula in lower segment of left-sided abdomen. 2. Two slightly enlarged lymph nodes beside the left-sided external iliac vessels and great vessel in pelvic cavity and metabolism was not increased. It might be caused by inflammation of lymph nodes in view of sevel inmaging examination (It can be seen that the enlarged lymph nodes were not metastatic lesions.). |
| Description of FIGS. 29A-29B: | During 25 months after surgery, no recurrence or systemic metastasis occurred in the cured primary lesions. |

Patient 17. In Situ Cervical Cancer In Situ/Intramuscular Injection of rSIFN-co Alone or Uterine Perfusion of rSIFN-co Alone. After Treatment, Cervical Tumor was Basically Inhibited and Test of High-Risk HPV Became Negative. Also, No Tumor Cells were Found in Cervical Smear.

| Patient 17 | Gender: Female | Age: 25 |
|---|---|---|
| Cytologic diagnosis: | Cervical smear on May 11, Year 1 showed high-grade intraepithelial lesion. | |
| Clinical and pathological staging①: | Ib1 | |
| Regimens before administration of rSIFN-co: | none | |
| Regimens: administration of rSIFN-co alone | Treatment of rSIFN-co began on May 14, Year 1. Intramuscular injection of rSIFN-co was provided once every other day: 9 µg for 1st time, 15 µg for 2nd time and 18 µg for 3rd time and thereafter. Meanwhile, uterine perfusion was done once a day: at 1000 µg per dose, for 2 hours. Uterine perfusion ended on June 28, Year 1 (lasted for more than 1 month) and intramuscular injection was stopped on September 12, Year 1 (lasted for 4 months). | |
| Response to rSIFN-co treatmenr: | CR② (malignant cervical lesion disappeared, and test of high-risk HPV became negative. Also, no tumor cells were found in cervical smear.) | |
| Survival: | After about 26 months (from May 5, Year 1 to July Year 3), the patient remained alive and had normal life. No recurrence or metastases was observed upon imaging. | |
| Pathological diagnosis before administration of rSIFN-co: | Pathological diagnosis after administration of rSIFN-co: | |
| On May 5, Year 1, cervical intraepithelial lesion of grade II~III was seen with glands involved. | Chronic endocervicitis was found on June 24, Year 1. | |
| Viral diagnosis (HC2HPV DNA) before administration of rSIFN-co: | Viral diagnosis (HC2HPV DNA) after administration of rSIFN-co | |
| April 14, Year 1, High-risk subtypes (15 kinds): positive- HPV16 | June 25, Year 1: RLU/CO 0.23 (negative) | |
| Diagnostic imaging before administration of rSIFN-co: | Diagnostic imaging after administration of rSIFN-co: | |
| PET/CT scans on May 14, Year 1: | PET/CT scans on November 8, Year 1: | |
| 1. Cervical hypertrophy was found and FDG metabolism was slightly increased, | The FDG metabolism in the cervix significantly reduced, indicating that the tumor activity was | |

-continued

| | |
|---|---|
| suggesting the possible occurrence of low-grade malignant lesion. 2. No metastatic lesion was found in pelvic cavity and pelvic wall. | locally inhibited; FDG metabolism was inhomogeneous and obscure, indicating that inflammatory change might happen. |

Patient 18. Prostatic Cancer/Intramuscular Injection of rSIFN-co and Local Spraying (to Skin Surface where Prostate Biopsy was Done) of rSIFN-co Combined with Local Radiotherapy. After Treatment, the Prostate Tumor and Two Lymph Nodes in Right-Sided Ischiorectal Fossa were Eliminated; the Posterior Wall of Fundus of Urinary Bladder, Bilateral Seminal Vesicles and Anterior Rectal Wall Infected by Lesions Recovered; and the Level of Tumor Marker (PSA) Become Normal.

| Patient 18 | Gender: Male      Age: 64 |
|---|---|
| Pathological diagnosis: | Adenocarcinoma was found in the 1st-10th prostate biopsy. |
| Clinical and pathological staging[1]: | $T_4N_1M_0$. IV |
| Regimens before administration of rSIFN-co: | none |
| Regimens: administration of rSIFN-co combined with radiotherapy | Treatment of rSIFN-co began on November 15, Year 1. Intramuscular injection of rSIFN-co was provided once every other day: 9 μg for 1st time, 15 μg for 2nd time, 18 μg for 3rd time and 24 μg for 4th time and thereafter. Meanwhile, the drug was locally applied by spraying to the skin surface where prostate biopsy was done: 4~5 doses per day and at 70 μg~139 μg per dose. The amount of rSIFN-co to be intramuscularly injected changed to 21 μg from December 15, Year 1 to July 1, Year 2. Radiotherapy on prostate (EBRT)[12] was performed for 38 times from December 5, Year 1 to February 26, Year 2. |
| Response to rSIFN-co treatment: | CR[2] (prostate of 4.7 × 3.5 × 5.6 cm reduced normal size; two lymph nodes in right ischiorectal fossa were eliminated; the posterior wall of fundus of urinary bladder, bilateral seminal vesicles and anterior rectal wall infected by lesions recovered; and the level of specific antigen of Prostatic cancer (PSA) become normal.) |
| Survival: | After about 8 months (from November 11, Year 1 to July Year 2), the patient remained alive. |
| Level of specific antigen of Prostatic cancer (PSA) before administration of rSIFN-co: | Level of specific antigen of Prostatic cancer (PSA) after administration of rSIFN-co: |
| Examination on November 2, Year 1: | Examination on March 7, Year 2: |
| Total specific antigen of Prostatic cancer (T-PSA): 23.090 ng/ml (reference value < 3 ng/ml) Free PSA (F-PSA): 1.850 ng/ml (reference value < 0.75 ng/ml) Ratio of antigen of Prostatic cancer (F-PSA/PSA): 8.01% (reference value 25~100) | Total specific antigen of Prostatic cancer (T-PSA):: 0.006 ng/ml (reference value < 3) Free PSA (F-PSA): <0.010 ng/ml (reference value < 0.75 ng/ml) |
| Diagnostic imaging before administration of rSIFN-co: | Diagnostic imaging after administration of rSIFN-co: |
| MRI scans on November 4, Year 1: | MRI (March 31, Year 2): |
| 1. Prostate was significantly enlarged and irregular mass shadows of about 4.7 × 4.3 × 5.6 cm in size were formed with obscure border and inhomogeneous signals. Inhomogeneous reinforcement happened in enhanced scan. All these suggested the occurrence of prostatic cancer. | 1. The prostate was smaller in size and left posterior part protruded slightly. No obvious abnormality was found in each imaging sequence signal. 2. Bladder wall was inhomogeneously thickened: inflammation? 3. No effusion and enlarged lymph nodes were found in pelvic cavity. |

2. Two lymph nodes in right-sided
ischiorectal fossa were found with
diameter of about 1 cm, suggesting the
occurrence of metastasis.
3. The posterior wall of fundus of
urinary bladder, bilateral seminal
vesicles and anterior rectal wall might be
invaded.

Patient 19. Melanoma of Nose (after a Surgery) Combined with Bone Metastases at Bilateral Hip Joints, Bilateral Femurs, Bilateral Humeri, Ribs and Bilateral Shoulder Joints/Intramuscular Injection of rSIFN-co and Local Spraying of rSIFN-co on Lesions. After Treatment, Multiple Enlarged Lymph Nodes at Bilateral Shoulder Joints and Subaxillary were Cleared Up as Well as Recurrence and Metastases at Bilateral Hip Joints, Upper Femur, Residual Right Paranasal Sinuses and Nasal Cavity after Surgery.

| Patient 19 | Gender: Female | Age: 43 |
|---|---|---|
| Pathological diagnosis: | | Tumors were found in the neoplasma inside the right maxillary sinus. Malignant melanoma was proved by immunohistochemistry: (HMB45 (part+), MART1 (−), S100 (−), CD63 (+), NSE (−), PCK (−), EMA (+), CD56 (−) and KI671 25%). |
| Clinical and pathological staging ①: | | $pT_3NxM_1$. IV |
| Regimens before administration of rSIFN-co: | | Two cycles were provided on October 30, Year 1 and November 30, Year 1: 15 mg of Endostar on day 1~10 and 200 mg of temozolomide on day 1~5, oral administration. Targeted radiotherapy (50Gy/25f) was done on November 2, Year 1 and the targets were right maxillary sinus + ¼ of the left maxillary sinus, bilateral ethmoid sinus, frontal sinus and the adjacent tissues of the right eyeball. Radiotherapy ended on December 7, Year 1. |
| Regimens: administration of rSIFN-co alone | | Treatment of rSIFN-co began on December 21, Year 1. Intramuscular injection of rSIFN-co was provided once every other day: 9 μg for 1st time, 15 μg for 2nd time, 18 μg for 3rd time and thereafter. Meanwhile, the drug was locally applied by spraying onto the skin surface of the right shouder: 70 μg-139 μg/dose/site, 4-5 doses/day. Spraying was provided to skin surface of the left shoulder and other sites with bone metastasis began on February 27, Year 2: 70 μg-139 μg/dose/site, 4-5 doses/day. |
| Response to rSIFN-co treatment: | | CR② (Multiple enlarged lymph nodes at bilateral shoulder joints and axillae disappeared; recurrence and metastatic lesions at residual right sinus and nasal cavity after surgery as well as multiple abnormal signals at bilateral hip joints and upper parts of femora disappeared.) |
| Survival: | | After about 11 months (from August Year 1 to July Year 2), the patient remained alive. |
| Diagnostic imaging before administration of rSIFN-co: | | Diagnostic imaging after administration of rSIFN-co: |
| MRI of paranasal sinus on December 8, Year 1: | | MRI of shoulder joint on May 2, Year 2: |
| 1. Compared with the previous imaging (taken on October 26, Year 1, after surgery in right sinus and nasal cavity), soft tissues surrounding residual cavity were thickened and intensification was apparent, suggesting recurrence. | | No obvious bone destruction was found at left shoulder. Spot-like shadows with long T2 and long T1 signals were seen in humeral head, mostly small cystic lesions. Pelvis MRI on May 2, Year 2: Long T1 and long T2 signals changed at upper branch of the left pubis and signals were intensified significantly as shown in the intensified image. No obvious abnormality |
| 2. Several lymph nodes at the neck were enlarged. | | |

-continued

3. Hypertrophy was found at left-sided inferior nasal concha and inflammation was seen at left maxillary sinus, sphenoid sinus and ethmoid sinus.
4. Otitis media and mastoiditis was observed at right side..
MRI scans of hip joint on December 8, Year 1: Lesions with long T1 and long T2 signal were seen at left acetabulum. And lesions extended to left ischium, High signals with significant enhancement in fat suppression sequences were found. Lesions with significantly intensified long T1 and long T2 signals were seen at lower portions of bilateral ilia and right anterior acetabulum,.
Conclusion: multiple lesions were found in the bone mass of bilateral hip joints and bone metastasis probably happened.
MRI of shoulder joint on December 8, Year 1: Sheet-like shadows with long T1 and long T2 signals, inhomogeneous enhancement and obscure boundaries were found at bilateral acromial ends of clavicles, right glenoid cavity of scapula, bone surrounding bilateral scapula, upper parts of bilateral humeri and ribs. Multiple lymph nodes were found at bilateral axillae with part enlarged. Conclusion: multiple metastases of bilateral shoulder joints and axillae happened.

was seen in remaining part of the pelvis. Brain MRI on May 2, Year 2:
1. No intracranial abnormality; 2. Bilateral otitis media and mastoiditis; 3. Nasal conchae of middle and lower segments at right side were missing and inner wall of maxillary sinus at right side was missing, leading to an empty cavity formed by connecting sinus cavity and nasal cavity; 4. Left maxillary sinusitis; 5. Sphenoid sinusitis and frontal sinusitis.
MRI of lumbar, head and shoulder joint on June 26, Year 2:
1. Fat deposition was found on lumbar 2 from the back with the remaining corpus vertebrae and intervertebral disc being normal;
2. Intracranial brain tissue was normal;
3. The lack of nasal conchae at right nasal cavity and inner wall of the right maxillary sinus was as shown above;
4 Bilateral ethmoiditis and sphenoid sinusitis, and bilateral mastoiditis were found;
5. No further enlargement was found at the lymph nodes on either side of the neck;
6. Femoral heads of bilateral shoulder joints were normal.

Example 4: Data of Clinical Effectiveness of rSIFN-co of the Present Invention In the following tables, the number listed before the brackets represents the number of patients conforming to the condition described in that row and column; the number between each pair of parenthesis represents the number as a percentage of all the patients listed in either that column or that row; finally, II/III/IV between parentheses represent cancer staging. The cancer staging was made in accordance with *AJCC Cancer Staging Manual (6th Edition)*/Edited by F. L. Greene, D. L. Page and I.D. Fleming etc. Shenyang: Liaoning Science and Technology Press, 2005.8.

TABLE 3

Efficacy of rSIFN-co administration on lung cancer at different stages

| Tumor staging | CR | PR | NC/SD | PD | Total |
|---|---|---|---|---|---|
| II | 1(20.00%) | 2(40.00%) | 2(40.00%) | 0(0.00) | 5 |
| III | 5(50.00%) | 2(20.00%) | 1(10.00%) | 2(20.00%) | 10 |
| IV | 6(40.00%) | 7(46.67%) | 1(6.67%) | 1(6.67%) | 15 |
| Total | 12(40.00%) | 11(36.67%) | 4(13.33%) | 3(10.00%) | 30 |

Note:
for detailed regimens, refer to those described in example 2.

TABLE 4

Efficacy of rSIFN-co administration on lung cancer after or without surgery*

| Group | CR | PR | NC/SD | PD | Total |
|---|---|---|---|---|---|
| After surgery | 2(33.33%) (III/IV) | 0(0.00%) | 3(50.00%) (II/III/IV) | 1(16.67%) (III) | 6 |

TABLE 4-continued

Efficacy of rSIFN-co administration on lung cancer after or without surgery*

| Group | CR | PR | NC/SD | PD | Total |
|---|---|---|---|---|---|
| Without surgery | 10(41.67%) (II/III/IV) | 11(45.83%) (II/III/IV) | 1(4.17%) (IV) | 2(8.33%) (III/IV) | 24 |
| Total | 12(40.00%) | 11(36.67%) | 4(13.33%) | 3(10.00%) | 30 |

Note:
for detailed regimens, refer to those described in example 2.
*In this table, surgery does not include cryoablation or radiofrequency ablation.

TABLE 5

Efficacy of administration provided in different ways on lung cancer

| Way to administer | CR | PR | NC/SD | PD | Total |
|---|---|---|---|---|---|
| Systemic administration | 4(44.44%) (III/IV) | 3(33.33%) (II/III) | 1(11.11%) (II) | 1(11.11%) (III) | 9 |
| Systemic + local | 6(33.33%) (III/IV) | 7(38.89%) (II/III/IV) | 3(16.67%) (II/III/IV) | 2(11.11%) (III/IV) | 18 |
| Local | 2(66.67%) (II /III/IV) | 1(33.33%) (IV) | 0(00.00%) | 0(00.00%) | 3 |
| Total | 12(40.00%) | 11(36.67%) | 4(13.33%) | 3(10.00%) | 30 |

Note:
systemic administration refers to intramuscular or subcutaneous administration; local administration refers to aerosol inhalation and spraying on skin surface; refer to those described in example 2 for detailed regimens.

TABLE 6

Efficacy of rSIFN-co administration on lung cancer with different durations

| Medication duration (month(s)) | CR | PR | NC/SD | PD | Total |
|---|---|---|---|---|---|
| <3 | 1(50.00%) (IV) | 0(00.00%) | 1(50.00%) (IV) | 0(00.00%) | 2 |
| 3~6 | 3(50.00%) (IV) | 3(50.00%) (III/IV) | 0(00.00%) | 0(00.00%) | 6 |
| 7~12 | 2(20.00%) (III) | 4(40.00%) (II/IV) | 2(20.00%) (II) | 2(20.00%) (III/IV) | 10 |
| >12 | 6(50.00%) (II/III/IV) | 4(33.33%) (III/IV) | 1(8.33%) (III) | 1(8.33%) (III) | 12 |
| Total | 12(40.00%) | 11(36.67%) | 4(13.33%) | 3(10.00%) | 30 |

Note:

for detailed regimens, refer to those described in example 2.

TABLE 7

Efficacy of drug combination on lung cancer

| drug combination | CR | PR | NC/SD | PD | Total |
|---|---|---|---|---|---|
| Yes | 8(42.11%) (II/III/IV) | 7(36.84%) (III/IV) | 3(15.79%) (II/III/IV) | 1(5.26%) (III) | 19 |
| No | 4(36.36%) (III/IV) | 4(36.36%) (II/III/IV) | 1(9.09%) (II) | 2(18.18%) (III/IV) | 11 |
| Total | 12(40.00%) | 11(36.67%) | 4(13.33%) | 3(10.00%) | 30 |

Note:

drug combination or combined therapy includes: chemotherapy, radiotherapy, radiofrequency ablation, biological medicine and traditional Chinese medicine, but excludes surgery; for detailed regimens, refer to those described in example 2.

TABLE 8

Efficacy of administration on lung cancer with/without metastasis

| Metastasis | CR | PR | NC/PD | PD | Total |
|---|---|---|---|---|---|
| Yes | 11(44.00%) (II/III/IV) | 9(36.00%) (II/IIII/IV) | 4(16.00%) (II/IIII/IV) | 1(4.00%) (IV) | 25 |

TABLE 8-continued

Efficacy of administration on lung cancer with/without metastasis

| Metastasis | CR | PR | NC/PD | PD | Total |
|---|---|---|---|---|---|
| No | 1(20.00%) (III) | 2(40.00%) (II/III) | 0(0.00%) | 2(40.00%) (III) | 5 |
| Total | 12(40.00%) | 11(36.67%) | 4(13.33%) | 3(10.00%) | 30 |

Note:

for detailed regimens, refer to those described in example 2.

TABLE 9

Efficacy of rSIFN-co administration on tumor of different stages

| Tumor staging | CR | PR | NC/SD | PD | Total |
|---|---|---|---|---|---|
| I | 3(100.00%) | 0(0.00%) | 0(0.00%) | 0(0.00%) | 3 |
| II | 2(33.33%) | 2(33.33%) | 2(33.33%) | 0(0.00) | 6 |
| III | 6(35.29%) | 5(29.41%) | 3(17.64%) | 3(17.64%) | 17 |
| IV | 8(25.00%) | 12(37.50%) | 5(15.62%) | 7(21.88%) | 32 |
| Total | 19(32.76%) | 19(32.76%) | 10(17.24%) | 10(17.24%) | 58 |

Note:

for detailed regimens, refer to those described in example 2, wherein:

Tumor of stage I includes: cervical cancer, gastrointestinal stromal tumor;

Tumor of stage II includes: lung cancer, breast cancer;

Tumor of stage III includes: lung cancer, ovarian cancer, cervical cancer, rectal cancer, breast cancer, pancreatic cancer, lymphoma, malignant neuroma and metastatic poorly differentiated squamous carcinoma;

Tumor of stage IV includes: lung cancer, cervical cancer, endometrial or uterine papillary serous carcinoma with hybrid clear-cell carcinoma, colon cancer, cholangiocarcinoma, including cholangioadenocarcinoma, liver cancer including hepatocellular carcinoma, breast cancer, gastric cancer, prostate cancer, embryonal rhabdomyosarcoma, malignant melanoma and lymphoma, including Non-Hodgkin's lymphoma.

TABLE 10

Efficacy of rSIFN-co administration on tumor after or without surgery

| Group | CR | PR | NC/SD | PD | Total |
|---|---|---|---|---|---|
| After surgery | 8(32.00%) | 2(8.00%) | 7(28.00%) | 8(32.00%) | 25 |
| Without surgery | 11(33.33%) | 17(51.52%) | 3(9.09%) | 2(6.06%) | 33 |
| Total | 19(32.76%) | 19(32.76%) | 10(17.24%) | 10(17.24%) | 58 |

Note:

for detailed regimens, refer to those described in example 2.

TABLE 11

Efficacy of administration provided in different ways

| Way to administrate | CR | PR | NC/SD | PD | Total |
|---|---|---|---|---|---|
| Systemic | 8(34.78%) | 8(34.78%) | 2(8.70%) | 5(21.74%) | 23 |
| Systemic + local | 10(32.26%) | 8(25.81%) | 8(25.81%) | 5(16.13%) | 31 |
| Local | 1(25.00%) | 3(75.00%) | 0(00.00%) | 0(00.00%) | 4 |
| Total | 19(32.76%) | 19(32.76%) | 10(17.24%) | 10(17.24%) | 58 |

Note:

for detailed regimens, refer to those described in example 2.

TABLE 12

Efficacy of rSIFN-co administration with different durations

| Medication duration (month(s)) | CR | PR | NC/PD | PD | Total |
|---|---|---|---|---|---|
| <3 | 2(40.00%) | 1(20.00%) | 2(40.00%) | 0(00.00%) | 5 |
| 3~6 | 4(25.00%) | 6(37.50%) | 3(18.75%) | 3(18.75%) | 16 |
| 7~12 | 3(18.75%) | 6(37.50%) | 3(18.75%) | 4(25.00%) | 16 |
| >12 | 10(47.62%) | 6(28.57%) | 2(9.52%) | 3(14.29%) | 21 |
| Total | 19(32.76%) | 19(32.76%) | 10(17.24%) | 10(17.24%) | 58 |

Note:
for detailed regimens, refer to those described in example 2.

TABLE 13

Efficacy of drug combination

| drug combination | CR | PR | NC/PD | PD | Total |
|---|---|---|---|---|---|
| Yes | 10(34.48%) | 10(34.48%) | 6(20.69%) | 3(10.34%) | 29 |
| No | 9(31.03%) | 9(31.03%) | 4(13.79%) | 7(24.14%) | 29 |
| Total | 19(32.76%) | 19(32.76%) | 10(17.24%) | 10(17.24%) | 58 |

Note:
combined medication includes: chemotherapy, radiotherapy, radiofrequency ablation, biological medicine and traditional Chinese medicine; for detailed regimens, refer to those described in example 2.

TABLE 14

Efficacy of administration on tumor with/without metastasis

| Metastasis | CR | PR | NC/SD | PD | Total |
|---|---|---|---|---|---|
| Yes | 14(29.79%) | 16(34.04%) | 9(19.15%) | 8(17.02%) | 47 |
| No | 5(45.45%) | 3(27.27%) | 1(9.09%) | 2(18.18%) | 11 |
| Total | 19(32.76%) | 19(32.76%) | 10(17.24%) | 10(17.24%) | 58 |

Note:
for detailed regimens, refer to those described in example 2.

TABLE 15

Patients in Complete Remission (CR) up until the date of last count.

| Patient No. | Cancer | Cell type | Stage | Staging | Therapies | Re-sponse | rSIFN-co Tx Duration (months) | rSIFN-co admin | Amount of rSIFN-co per dose |
|---|---|---|---|---|---|---|---|---|---|
| 1 | NSCLC | sqamous cell carcinoma | IIIb | $T_3N_2M_0$ | prior CTx, rSIFN-co + RTx | CR | 15 | im, qod | 9 ug, 15 ug, 18 ug |
| 3 | NSCLC | lung adenocarcinoma | IV | $T_2N_2M_1$ | rSIFN-co + RTx | CR | 3+ | im, qod + inhalation qod | 9 ug, 18 ug, 21 ug, 200 ug, 400 ug |
| 4 | SCLC | | IV | $T_4N_3M_1$ | prior CTx, rSIFN-co + CTx + cryoablation | CR | 16+ | im, qod + inhalation qod | 9 ug, 15 ug, 18 ug, 200 ug, 21 ug, 100 ug-400 ug |
| 5 | NSCLC | moderately differentiated adenocarcinoma | IV | $T_2N_2M_1$ | prior CTx, rSIFN-co + CTx | CR | 8+ | im, qod + inhalation qd | 9 ug, 21 ug, 200 ug, 15 ug |
| 6 | NSCLC | moderately to poorly differentiated adenocarcinoma | IV | $T_4N_3M_{1b}$ | prior CTx, rSIFN-co + CTx + Gefinitib (Iressa) | CR | 5+ | im, qod + inhalation qd + spraying qd 4-5x/day | 600 ug, 9 ug, 15 ug, 18 ug, 70 ug-139 ug |
| 8 | NSCLC | | IV | $T_4N_2M_1$ | rSIFN-co + Iressa | CR | 3 | im, qod + inhalation qd | 9 ug, 15 ug, 18 ug, 600 ug |

TABLE 15-continued

Patients in Complete Remission (CR) up until the date of last count.

| Patient No. | Cancer | Cell type | Stage | Staging | Therapies | Re-sponse | rSIFN-co Tx Duration (months) | rSIFN-co admin | Amount of rSIFN-co per dose |
|---|---|---|---|---|---|---|---|---|---|
| 9 | NSCLC | squamous cell carcinoma | IIb | $T_2N_1M_0$ | rSIFN-co + CTx + Endostar | CR | 4 | inhalation, qd | 600 ug |
| 10 | NSCLC | | IIIb | $T_4N_0M_0$ | rSIFN-co | CR | 15 | im, qod + thoracic perfusion every 7 days + intralesion | 18 ug, 21 ug, 36 ug, 45 ug, 2100 ug |
| 13 | NSCLC | poorly differentiated adenocarcinoma | IIIb | $T_4N_2M_0$ | prior surgery, rSIFN-co | CR | 15 | im, qod | 9 ug, 21 ug, 18 ug |
| 14 | NSCLC | poorly differentiated adenocarcinoma | IIIb | $T_4N_3M_0$ | prior surgery, rSIFN-co | CR | 12 | im, qod + inhalation qd | 18 ug, 21 ug, 15 ug, 300 ug |
| 16 | rectum | moderately differentiated adenocarcinoma | IIIb | $T_4N_1Mx$ | prior surgery, rSIFN-co | CR | 15 | im, qod | 21 ug, 9 ug, 15 ug |
| 17 | uterine cervical | squamous intraepithelial lesion | 1b1 | no metastasis | rSIFN-co | CR | 4 | im, qod + uterine perfusion, qd | 9 ug, 15 ug, 18 g, 1000 ug |
| 18 | prostate | adenocarcinoma | IV | $T_4N_1M_0$ | rSIFN-co + RTx | CR | | im, qod + spray topically, qd, 4-5x/day | 9 ug, 15 ug, 18 ug, 24 ug, 70 ug-139 ug, 21 ug |
| 19 | malignant melanoma | melanoma | IV | $pT_3N_xM_1$ | Prior Endostar + CTx + RTx, rSIFN-co | CR | | im, qod + spray topically, qd, 4-5x/day | 9 ug, 15 ug, 18 ug, 70 ug-139 ug |
| 21 | lung | | IIIb | metastasis to bone | Prior TCM + Iressa, rSIFN-co + Iressa | CR | | im, qod | 9 ug, 15 ug, 18 g |
| 23 | lung | adenocarcinoma | IV | metastasis to pleural cavity, mediastinal lymph nodes & bone | prior CTx + rSIFN-co | CR | 2 | im, qod | 9 ug, 21 ug |
| 39 | cervical | poorly differentiated squamous cell carcinoma | Ib2 | | prior surgery + CTx, rSIFN-co + NK cell Tx | CR | 6 | im, qod | 9 ug, 15 ug |
| 48 | breast | | IIa | | prior surgery, rSIFN-co | CR | 4+ | im, qod | 9 ug, 15 ug, 18 ug, 21 ug |
| 54 | GI | | Ib | | prior surgery + RTx, rSIFN-co | CR | 9+ | im, qod | 9 ug, 21 ug |

TABLE 16

Patients in Partial Remission (PR) up until the date of last count.

| Patient No. | Cancer | Cell type | Stage | Staging | Therapies | Re-sponse | rSIFN-co Tx Duration (months) | rSIFN-co admin | Amount of rSIFN-co per dose |
|---|---|---|---|---|---|---|---|---|---|
| 2 | NSCLC | lung adenocarcinoma | IV | $T_3N_3M_1$ | prior CTx, rSIFN-co + Endostar + CTx | PR | 12 | im, qod + inhalation, qd | 9 ug, 15 ug, 18 ug, 21 ug, 300 ug, 500 ug, 600 ug |
| 7 | NSCLC | lung adenocarcinoma | IV | $T_4N_3M_1$ | rSIFN-co + Iressa | PR | 5 | im, qod | 9 ug, 18 ug, 21 ug |
| 11 | Non-Hodgkin lymphoma | | IV | | prior CTx, prior stem cell Tx, rSIFN-co + CTx + RTx | PR | 4.5 | inhalation, qd, 2-3x/day + intralesion, qod + s.c., qod | 72 ug/ml, 150 ug, 30 ug |

TABLE 16-continued

Patients in Partial Remission (PR) up until the date of last count.

| Patient No. | Cancer | Cell type | Stage | Staging | Therapies | Response | rSIFN-co Tx Duration (months) | rSIFN-co admin | Amount of rSIFN-co per dose |
|---|---|---|---|---|---|---|---|---|---|
| 12 | NSCLC | lung adenocarcinoma | IIb | $T_3N_0M_0$ | prior CTx, rSIFN-co | PR | 12 | im, qod | 9 ug, 18 ug, 21 ug |
| 15 | NSCLC | | IV | $T_4N_3M_1$ | prior RTx + Iressa, rSIFN-co | PR | 1.5+ | inj into part of inguinal LN, qd | 90 ug, 120 ug, 150 ug |
| 20 | lung | | IV | | rSIFN-co + CTx | PR | 3+ | im, qod + inhalation, qd | 9 ug, 15 ug, 21 ug, 200 ug, 300 ug |
| 22 | lung | | IIIa | liver mets | prior CTx + RFA, rSIFN-co | PR | 2+ | im, qod | 18 ug, 21 ug |
| 24 | lung | | IIIb | | rrSIFN-co-co | PR | 2 | im, qod + intrapleural injection | 9 ug, 13.5 ug, 21 ug, 126 ug, 168 ug, 210 ug, 252 ug |
| 26 | lung | | IV | brain mets | prior Iressa, rSIFN-co + Iressa | PR | 24+ | im, qod + inhalation qd | 21 ug, 18 ug, 100 ug, 300 ug, 400 ug |
| 30 | lung | adenocarcinoma | IV | brain mets | prior RTx + CTx, rSIFN-co | PR | | im, qod + inhalation, qd | 21 ug, 200 ug |
| 32 | lung | | IIb | | prior CTx + Gefitinib, rSIFN-co + Gefitinib | PR | | im, qod + inhalation, qd | 9 ug, 13.5 ug, 18 ug, 300 ug |
| 35 | lung | adenocarcinoma | IV | | prior CTx, rSIFN-co + CTx + RFA | PR | | im, qod + inhalation, qd | 15 ug, 18 ug, 600 ug |
| 36 | ovarian | | IIIb | | prior surgery, rSIFN-co | PR | 3+ | im, , qod | 9 ug, 15 ug, 18 ug, 21 ug |
| 37 | cervical | | IV | | prior RTx + CTx, rSIFN-co | PR | | im, , qod | 21 ug |
| 42 | Cholangio-adenocarcinoma | | IV | liver mets | prior surgery + RTx, rSIFN-co + surgery | PR | 18+ | im, , qod | 9 ug, 18 ug, 21 ug |
| 45 | HCC | | IV | intrahepatic mets | prior surgery, rSIFN-co | PR | 5.5+ | im, , qod | 9 ug, 18 ug, 21 ug |
| 51 | gastric | | IV | abdominal mets | prior CTx, rSIFN-co | PR | 8 days | intraperitoneal perfusion, qod | 120 ug, 180 ug, 210 ug, 240 ug |
| 52 | pancreatic | | III | | rSIFN-co | PR | 9 | im, qod | 9 ug, 21 ug |
| 56 | lymphoma | | III | | rSIFN-co + CTx + TCM | PR | 6 | im, qod + intratumoral injection | 21 ug, 18 ug, 168 ug, 210 ug, 252 ug, 273 ug, 315 ug, 180 ug, 189 ug, 198 ug, 207 ug, 500 ug |

TABLE 17

Patients with No Change (NC) or Stable Disease (SD) up until the date of last count.

| Patient No. | Cancer | Cell type | Stage | Metastases | Therapies | Response | rSIFN-co Tx Duration (months) | rSIFN-co admiin | Amount of rSIFN-co per dose |
|---|---|---|---|---|---|---|---|---|---|
| 27 | lung | | IIb | lung mets | prior surgery + CTx + RTx, rSIFN-co | NC/SD | | im, qod | 9 ug, 21 ug |
| 28 | lung | | IIb | lung + intrapleural cavity mets | prior surgery + Vivatuxin, rSIFN-co | NC/SD | 7 | im, qod + nasal spray, tid + inhalation, qd | 9 ug, 21 ug, 200 ug |
| 29 | lung | | IIIa | | prior surgery + radioimmunotherapy, rSIFN-co + radiofrequency ablation (RFA) | NC/SD | 5.5+ | im, qod + nasal spray, tid | 9 ug, 18 ug, 21 ug |
| 34 | lung | | IV | multiple mets | rSIFN-co + RTx + TCM | NC/SD | 2 | im, qod + inhalation, qd | 18 ug, 200 ug |
| 38 | uterine papillary serous adenocarcinoma | mixed with clear cell carcinoma | IV | | rSIFN-co | NC/SD | | im, qod + uterine drip, qd, then once every 5 days | 18 ug, 200 ug |

TABLE 17-continued

Patients with No Change (NC) or Stable Disease (SD) up until the date of last count.

| Patient No. | Cancer | Cell type | Stage | Metastases | Therapies | Re-sponse | rSIFN-co Tx Duration (months) | rSIFN-co admiin | Amount of rSIFN-co per dose |
|---|---|---|---|---|---|---|---|---|---|
| 41 | colonic carcinoma | | IV | liver mets | prior surgery, rSIFN-co | NC/SD | 4+ | im, qod, intratumor injection | 9 ug, 21 ug, 21-25.5 ug, 105 ug, 168 ug, 210 ug |
| 49 | breast | recurrence after breast surgery | IV | | prior surgery + CTx, rSIFN-co | NC/SD | 5 | local injection + im, qod | 90 ug, 21 ug., 9 ug |
| 53 | prostate | | IV | | prior antiandrogen + hormone + RFA + radioactive seeds, rSIFN-co + RTx | NC/SD | | im, qod, intraperitoneal injection | 9 ug, 21 ug, 168 ug |
| 57 | neuroma | recurrence after surgery | IIIc | | Prior surgery + CTx + TCM, rSIFN-co | NC/SD | | im, qod + intratumoral | 21 ug, 84 ug |
| 58 | poorly differentiated squamous cell carcinoma in right chest | | IIIa | | prior surgery, rSIFN-co | NC/SD | 6 | im, qod | 9 ug, 21 ug |

TABLE 18

Patients with Progressive Disease (PD) up until the date of last count.

| Patient No. | Cancer | Stage | Metastases | Therapies | Re-sponse | rSIFN-co Tx Duration (in months) | rSIFN-co admin | Amount of rSIFN-co per dose |
|---|---|---|---|---|---|---|---|---|
| 25 | lung | IIIa | | rSIFN-co + RTx | PD | 5 | im, qod | 9 ug, 21 ug |
| 31 | lung | IV | bone metastasis | rSIFN-co | PD | 3+ | im, qod; spray | 9 ug, 13.5 ug, 18 ug, 20 ug/ml, 21 ug |
| 33 | lung | IIIb | | prior sugery, rSIFN-co | PD | 1+ | im, qod; im, twice a week; pleural perfusion | 4.5 ug, 9 ug, 13.5 ug, 18 ug, 105 ug, 126 ug, 147 ug, 168 ug, 189 ug, 210 ug |
| 40 | colon | IV | lung metastasis | prior surgery + CTx + TCM, rSIFN-co + RFA + CTx + RTx | PD | | im, qod | 9 ug, 21 ug |
| 43 | intrahepatic cholangiocarcinoma | IV | liver metastasis | prior sugery + CTx, rSIFN-co + surgery | PD | 6 | im, qod | 9 ug, 21 ug |
| 44 | hepatocellular carcinoma | IV | lung metastasis | prior surgery, rSIFN-co | PD | 5.5+ | im, qod | 9 ug, 18 ug, 21 ug |
| 46 | breast | IIIc | LN metastasis | prior surgery + CTx + RTx, rSIFN-co | PD | 4 | im, qod | 18 ug |
| 47 | breast | IV | | prior surgery + CTx, rSIFN-co | PD | 7.5+ | intrapleural injection; local injection, once a week; im, qod | 105 ug, 147 ug, 168 ug, 210 ug, 273 ug, 21 ug |
| 50 | gastric | IV | | prior surgery, rSIFN-co | PD | 20.5 | im, qod; intraperitoneal injection | 9 ug, 18 ug, 15 ug, 21 ug, 168 ug, 189 ug, 210 ug |
| 55 | embryonal rhabdomyosarcoma | IV | metastasis | prior surgery + CTx + RTx, rSIFN-co | PD | 13 | im, qod; lymph node injection, intratumor injection | 9 ug, 15 ug, 18 ug, 21 ug, 168 ug |

What is claimed is:

1. A method for eliminating or reducing bone metastatic lesions of a tumor in a subject, comprising administering to the subject a recombinant interferon encoded by SEQ ID NO: 2 via intramuscular or inhalation administration, wherein the tumor is a lung cancer.

2. The method of claim 1, wherein the lung cancer comprises at least one of: small cell lung cancer (SCLC), non-small cell lung cancer (NSCLC), lung adenocarcinoma, and lung squamous cell carcinoma.

3. The method of claim 1, wherein the lung cancer in the subject comprises a metastasized tumor.

4. The method of claim 1, wherein the administration is performed with a pharmaceutically acceptable carrier and according to a dosing schedule effective to reduce bone metastatic lesions.

5. The method of claim 1, wherein the metastasized tumor comprises brain metastatic tumor or bone metastatic tumor.

6. The method of claim 1, wherein the subject is administered at least one other anti-cancer therapy.

7. The method of claim 6, wherein said other anti-Cancer therapy is selected from the group consisting of chemotherapy, radiotherapy, surgical therapy, interventional therapy, biotherapy, gene therapy, ablation therapy, immunotherapy, targeted therapy, and traditional Chinese medicine therapy.

8. The method of claim 1, wherein the subject is an early, medium-term, or advanced cancer patient, optionally, the subject is a medium-term, or advanced cancer patient, further optionally, the subject is an advanced cancer patient.

9. The method of claim 1, wherein the subject is a stage 0, I, II, III, or IV cancer patient, optionally, the subject is a stage III or stage IV cancer patient.

10. The method of claim 1, wherein the tumor is a cancer or a solid tumor that is indicated of appropriate for surgery.

11. The method of claim 1, wherein the tumor is a cancer a solid tumor that is not indicated nor appropriate for surgery.

12. The method of claim 1, wherein the tumor is a tumor that is capable of being resected.

13. The method of claim 1, wherein the tumor is a tumor that is not capable of being resected.

14. The method of claim 1, wherein the tumor is resected by a surgical resection.

15. A method for eliminating or reducing bone metastatic lesions of a tumor in a subject, comprising administering to the subject a recombinant interferon encoded by SEQ ID NO: 2 via intramuscular administration in an amount in a range of about 2 μg to about 70 μg by one intramuscular administration, wherein the tumor is a lung cancer.

16. The wherein the lung method of claim 15, cancer comprises at least one of: small cell lung cancer (SCLC), non-small cell lung cancer (NSCLC), lung adenocarcinoma, and lung squamous cell carcinoma.

17. The method of claim 15, wherein the subject is administered at least one other anti-cancer therapy.

18. A method for eliminating or reducing bone metastatic lesions of a tumor in a subject, comprising administering to the subject a recombinant interferon encoded by SEQ ID NO: 2 via intramuscular administration in an amount in a range of about 100 μg to about 2000 μg by one intramuscular administration, wherein the tumor is a lung cancer.

19. The method of claim 18, wherein the lung cancer comprises at least one of: small cell lung cancer (SCLC), non-small cell lung cancer (NSCLC), lung adenocarcinoma, and lung squamous cell carcinoma.

20. The method of claim 18, wherein the subject administered at least one other anti-cancer therapy.

* * * * *